United States Patent
Attar et al.

(10) Patent No.: US 12,018,289 B2
(45) Date of Patent: Jun. 25, 2024

(54) VACCINES BASED ON MUTANT CALR AND JAK2 AND THEIR USES

(71) Applicant: Janssen Biotech, Inc., Horsham, PA (US)

(72) Inventors: Ricardo Attar, Lawrenceville, NJ (US); Jason Dehart, San Diego, CA (US); Selina Khan, Leiden (NL); Vinod Krishna, Philadelphia, PA (US); Jenifer Lum, Castro Valley, CA (US); Christian Maine, San Diego, CA (US); Barbara Sanders, Amsterdam (NL); Manuel Alejandro Sepulveda, West Windsor, NJ (US); Patrick Wilkinson, Collegeville, PA (US); Roland Zahn, Rijnsburg (NL)

(73) Assignee: Janssen Biotech, Inc., Horsham, PA (US)

(*) Notice: Subject to any disclaimer, the term of this patent is extended or adjusted under 35 U.S.C. 154(b) by 292 days.

(21) Appl. No.: 17/097,458

(22) Filed: Nov. 13, 2020

(65) Prior Publication Data

US 2021/0222133 A1 Jul. 22, 2021

Related U.S. Application Data

(60) Provisional application No. 62/936,846, filed on Nov. 18, 2019, provisional application No. 62/936,841, filed on Nov. 18, 2019.

(51) Int. Cl.
| | |
|---|---|
| *C12N 7/00* | (2006.01) |
| *A61K 39/00* | (2006.01) |
| *A61K 45/06* | (2006.01) |
| *C12N 15/86* | (2006.01) |

(52) U.S. Cl.
CPC ............... *C12N 7/00* (2013.01); *A61K 45/06* (2013.01); *C12N 15/86* (2013.01); *A61K 2039/505* (2013.01); *C12N 2750/14111* (2013.01)

(58) Field of Classification Search
None
See application file for complete search history.

(56) References Cited

U.S. PATENT DOCUMENTS

| | | |
|---|---|---|
| 1,051,266 A | 1/1913 | Rockwood |
| 4,235,871 A | 11/1980 | Papahadjopoulos et al. |
| 4,501,728 A | 2/1985 | Geho et al. |
| 4,603,112 A | 7/1986 | Paoletti et al. |
| 4,769,330 A | 9/1988 | Paoletti et al. |
| 4,772,848 A | 9/1988 | Hummel |
| 4,837,028 A | 6/1989 | Allen |
| 5,100,587 A | 3/1992 | Clough et al. |
| 5,179,993 A | 1/1993 | Bak et al. |
| 5,185,146 A | 2/1993 | Altenburger |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,559,099 A | 9/1996 | Wickham et al. |
| 5,571,698 A | 11/1996 | Ladner et al. |
| 5,580,717 A | 12/1996 | Dower et al. |
| 5,595,897 A | 1/1997 | Midoux et al. |
| 5,744,166 A | 4/1998 | Lisbeth |
| 5,747,323 A | 5/1998 | Darlix et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,885,793 A | 3/1999 | Griffiths et al. |
| 5,891,690 A | 4/1999 | Massie |
| 5,965,541 A | 10/1999 | Wickham et al. |
| 5,969,108 A | 10/1999 | Mccafferty et al. |
| 5,972,707 A | 10/1999 | Roy et al. |
| 5,976,567 A | 11/1999 | Wheeler et al. |
| 5,981,225 A | 11/1999 | Kochanek et al. |
| 5,981,501 A | 11/1999 | Wheeler et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,025,337 A | 2/2000 | Truong et al. |

(Continued)

FOREIGN PATENT DOCUMENTS

| | | |
|---|---|---|
| EP | 0901463 A1 | 3/1999 |
| EP | 0919627 A2 | 6/1999 |

(Continued)

OTHER PUBLICATIONS

Holman et al. Viral Vectors. Vaccines for Biodefense and Emerging and Neglected Diseases (2009) 7: 77-91. (Year: 2009).*
Lim et al. Frequent CALR exon 9 alterations in JAK2 V617F-mutated essential thrombocythemia detected by high-resolution melting analysis. Blood Cancer Journal (2015) 5: 1-4. (Year: 2015).*
Ljungberg et al. Self-replicating alphavirus RNA vaccines. Expert Review of Vaccines (2015) 14: 177-194. (Year: 2015).*
Khan et al. Immunoinformatics approaches to explore Helicobacter Pylori proteome (Virulence Factors) to design B and T cell multi-epitope subunit vaccine. Scientific Reports (2019) 9: 1-13. (Year: 2019).*
Anonymous: "CALR Exon 9 Mutant Peptide Vaccine to Patients With CALR-mutant Myeloproliferative Neoplasms: NCT03566446", Retrieved from https://clinicaltrials.gov/ct2/show/NCT03566446, Jun. 25, 2018, pp. 1-5.

(Continued)

*Primary Examiner* — Allison M Fox
*Assistant Examiner* — Alyssa G Weston
(74) *Attorney, Agent, or Firm* — BakerHostetler

(57) ABSTRACT

Provided are vaccines, polypeptides and polynucleotides based on mutant CALR and JAK2 sequences, vectors, host cells, viruses, and methods of making and using them. The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises a plurality of administrations of any of the compositions comprising polynucleotides, polypeptides or vectors disclosed herein.

26 Claims, 26 Drawing Sheets

Specification includes a Sequence Listing.

(56) References Cited

U.S. PATENT DOCUMENTS

| | | |
|---|---|---|
| 6,040,174 A | 3/2000 | Imler et al. |
| 6,113,913 A | 9/2000 | Brough et al. |
| 6,150,584 A | 11/2000 | Kucherlapati et al. |
| 6,172,197 B1 | 1/2001 | Mccafferty et al. |
| 6,207,195 B1 | 3/2001 | Walsh et al. |
| 6,218,370 B1 | 4/2001 | Bischoff et al. |
| 6,348,584 B1 | 2/2002 | Hodgson et al. |
| 6,440,442 B1 | 8/2002 | Ehrhard et al. |
| 6,521,404 B1 | 2/2003 | Griffiths et al. |
| 6,534,484 B1 | 3/2003 | Wheeler et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,586,410 B1 | 7/2003 | Wheeler et al. |
| 6,593,081 B1 | 7/2003 | Griffiths et al. |
| 6,673,901 B2 | 1/2004 | Koide |
| 6,815,432 B2 | 11/2004 | Wheeler et al. |
| 6,818,749 B1 | 11/2004 | Kashmiri et al. |
| 7,270,811 B2 | 9/2007 | Bout et al. |
| 7,329,731 B2 | 2/2008 | Jakobsen et al. |
| 7,569,664 B2 | 8/2009 | Jakobsen et al. |
| 7,709,226 B2 | 5/2010 | Foote |
| 7,781,199 B2 | 8/2010 | Vainchenker et al. |
| 8,007,781 B2 | 8/2011 | Wu et al. |
| 8,163,293 B2 | 4/2012 | Chaplin |
| 8,268,329 B2 | 9/2012 | Chaplin et al. |
| 8,313,740 B2 | 11/2012 | Delcayre et al. |
| 8,377,688 B2 | 2/2013 | Delcayre et al. |
| 8,394,385 B2 | 3/2013 | Hausmann et al. |
| 8,748,356 B2 | 6/2014 | Raghunathan |
| 8,940,290 B2 | 1/2015 | Roy et al. |
| 9,133,264 B2 | 9/2015 | Blankenstein et al. |
| 9,371,570 B2 | 6/2016 | Kralovics et al. |
| 9,593,077 B2 | 3/2017 | Payne et al. |
| 9,617,560 B2 | 4/2017 | Brough et al. |
| 9,624,292 B2 | 4/2017 | Voss et al. |
| 9,750,801 B2 | 9/2017 | Barouch et al. |
| 9,790,256 B2 | 10/2017 | Bunnik et al. |
| 9,884,075 B2 | 2/2018 | Bethune et al. |
| 10,010,592 B2 | 7/2018 | Thess et al. |
| 10,035,832 B2 | 7/2018 | Schlom et al. |
| 10,350,275 B2 | 7/2019 | Aguilar-Cordova |
| 10,441,643 B2 | 10/2019 | Pulido et al. |
| 10,512,662 B2 | 12/2019 | Deng et al. |
| 10,532,067 B2 | 1/2020 | Geall et al. |
| 10,548,930 B2 | 2/2020 | Deng et al. |
| 10,640,786 B2 | 5/2020 | Barry et al. |
| 10,736,962 B2 | 8/2020 | Deng et al. |
| 10,781,169 B2 | 9/2020 | Payne et al. |
| 10,973,892 B2 | 4/2021 | Lauterbach et al. |
| 2001/0049136 A1 | 12/2001 | Imler et al. |
| 2010/0216708 A1 | 8/2010 | Jacobs et al. |
| 2010/0255056 A1 | 10/2010 | Jacobs et al. |
| 2010/0261620 A1 | 10/2010 | Almagro et al. |
| 2015/0079091 A1 | 3/2015 | Kralovics et al. |
| 2016/0130319 A1 | 5/2016 | Li |
| 2016/0271239 A1 | 9/2016 | Mandl et al. |
| 2017/0106065 A1 | 4/2017 | Foy et al. |
| 2017/0266270 A1 | 9/2017 | Mandl et al. |
| 2018/0000912 A1 | 1/2018 | Meruelo et al. |
| 2018/0028626 A1 | 2/2018 | Slos et al. |
| 2018/0064803 A1 | 3/2018 | Tomaka et al. |
| 2018/0104359 A1 | 4/2018 | Kamrud |
| 2018/0171340 A1 | 6/2018 | Kamrud et al. |
| 2018/0251852 A1 | 9/2018 | Kralovics et al. |
| 2018/0311269 A1 | 11/2018 | Lobb et al. |
| 2018/0340944 A1 | 11/2018 | Han et al. |
| 2019/0000948 A1 | 1/2019 | Mccurry et al. |
| 2019/0093085 A1 | 3/2019 | Tufaro et al. |
| 2019/0328857 A1 | 10/2019 | Andersen et al. |
| 2019/0343942 A1 | 11/2019 | Fotin-Mleczek et al. |
| 2019/0350993 A1 | 11/2019 | Cai |
| 2019/0351040 A1 | 11/2019 | Valiante et al. |
| 2020/0061174 A1 | 2/2020 | Kalla et al. |
| 2020/0121774 A1 | 4/2020 | Harris et al. |
| 2020/0138923 A1 | 5/2020 | Silvestre et al. |
| 2020/0148742 A1 | 5/2020 | Grandi et al. |
| 2020/0171151 A1 | 6/2020 | Yeung |
| 2020/0197500 A1 | 6/2020 | Blair et al. |
| 2020/0239906 A1 | 7/2020 | Roeth et al. |
| 2020/0299725 A1 | 9/2020 | Beissert et al. |
| 2020/0306352 A1 | 10/2020 | Hochrein et al. |
| 2020/0330534 A1 | 10/2020 | Delgoffe et al. |
| 2020/0339959 A1 | 10/2020 | Merghoub et al. |
| 2021/0015878 A1 | 1/2021 | Larson et al. |
| 2021/0046130 A1 | 2/2021 | Jia et al. |

FOREIGN PATENT DOCUMENTS

| | | |
|---|---|---|
| EP | 1230354 A2 | 8/2002 |
| EP | 3494985 A1 | 6/2019 |
| EP | 3721899 A1 | 10/2020 |
| JP | 2016-537012 A | 12/2016 |
| JP | 2019-517544 A | 6/2019 |
| WO | 88/01649 A1 | 3/1988 |
| WO | 90/04036 A1 | 4/1990 |
| WO | 90/07861 A1 | 7/1990 |
| WO | 92/01047 A1 | 1/1992 |
| WO | 92/22653 A1 | 12/1992 |
| WO | 94/13804 A1 | 6/1994 |
| WO | 95/01447 A1 | 1/1995 |
| WO | 95/24221 A1 | 9/1995 |
| WO | 96/02655 A1 | 2/1996 |
| WO | 96/17070 A1 | 6/1996 |
| WO | 96/19240 A1 | 6/1996 |
| WO | 96/27677 A2 | 9/1996 |
| WO | 96/40964 A2 | 12/1996 |
| WO | 97/04119 A1 | 2/1997 |
| WO | 97/35996 A1 | 10/1997 |
| WO | 98/00524 A1 | 1/1998 |
| WO | 98/26048 A1 | 6/1998 |
| WO | 98/34910 A1 | 8/1998 |
| WO | 98/37916 A1 | 9/1998 |
| WO | 98/39411 A1 | 9/1998 |
| WO | 98/44001 A1 | 10/1998 |
| WO | 99/45962 A1 | 9/1999 |
| WO | 00/50573 A1 | 8/2000 |
| WO | 2000/070071 A1 | 11/2000 |
| WO | 01/30382 A1 | 5/2001 |
| WO | 01/30847 A1 | 5/2001 |
| WO | 01/36615 A2 | 5/2001 |
| WO | 02/12281 A2 | 2/2002 |
| WO | 2002/043478 A2 | 6/2002 |
| WO | 2002/066630 A1 | 8/2002 |
| WO | 2004/044176 A2 | 5/2004 |
| WO | 2005/046621 A2 | 5/2005 |
| WO | 2005/048957 A2 | 6/2005 |
| WO | 2005/051991 A2 | 6/2005 |
| WO | 2005/071093 A2 | 8/2005 |
| WO | 2007/047653 A2 | 4/2007 |
| WO | 2007/101792 A1 | 9/2007 |
| WO | 2007/104792 A2 | 9/2007 |
| WO | 2009/006479 A2 | 1/2009 |
| WO | 2009/065546 A1 | 5/2009 |
| WO | 2009/127060 A1 | 10/2009 |
| WO | 2010/086189 A2 | 8/2010 |
| WO | 2010/132867 A1 | 11/2010 |
| WO | 2011/068810 A1 | 6/2011 |
| WO | 2012/006369 A2 | 1/2012 |
| WO | 2012/006372 A1 | 1/2012 |
| WO | 2012/006376 A2 | 1/2012 |
| WO | 2012/006378 A1 | 1/2012 |
| WO | 2012/030901 A1 | 3/2012 |
| WO | 2012/031043 A1 | 3/2012 |
| WO | 2012/089225 A1 | 7/2012 |
| WO | 2012/089338 A1 | 7/2012 |
| WO | 2012/172277 A1 | 12/2012 |
| WO | 2013/006825 A1 | 1/2013 |
| WO | 2013/006838 A1 | 1/2013 |
| WO | 2013/006842 A2 | 1/2013 |
| WO | 2013/033563 A1 | 3/2013 |
| WO | 2013/116778 A2 | 8/2013 |
| WO | 2014/127917 A1 | 8/2014 |
| WO | 2015/036599 A1 | 3/2015 |

(56) References Cited

FOREIGN PATENT DOCUMENTS

| | | |
|---|---|---|
| WO | 2015/069571 A1 | 5/2015 |
| WO | 2015/069770 A1 | 5/2015 |
| WO | 2015/077624 A1 | 5/2015 |
| WO | 2015/078856 A1 | 6/2015 |
| WO | 2015/123496 A1 | 8/2015 |
| WO | 2015/164674 A1 | 10/2015 |
| WO | 2015/175334 A2 | 11/2015 |
| WO | 2015/175340 A1 | 11/2015 |
| WO | 2015/176033 A1 | 11/2015 |
| WO | 2015/192068 A1 | 12/2015 |
| WO | 2016/046357 A1 | 3/2016 |
| WO | 2016/087514 A1 | 6/2016 |
| WO | 2016/128542 A1 | 8/2016 |
| WO | 2016/170176 A1 | 10/2016 |
| WO | 2016/184822 A1 | 11/2016 |
| WO | 2016/197067 A1 | 12/2016 |
| WO | 2016/203025 A1 | 12/2016 |
| WO | 2017/020026 A1 | 2/2017 |
| WO | 2017/070110 A1 | 4/2017 |
| WO | 2017/070618 A1 | 4/2017 |
| WO | 2017/095486 A1 | 6/2017 |
| WO | 2017/095487 A1 | 6/2017 |
| WO | 2017/147554 A2 | 8/2017 |
| WO | 2017/180770 A1 | 10/2017 |
| WO | 2017/201325 A1 | 11/2017 |
| WO | 2017/201350 A1 | 11/2017 |
| WO | 2017/201352 A1 | 11/2017 |
| WO | 2017/205810 A1 | 11/2017 |
| WO | 2017/211371 A2 | 12/2017 |
| WO | 2017/220499 A1 | 12/2017 |
| WO | 2018/014008 A1 | 1/2018 |
| WO | 2018/033254 A2 | 2/2018 |
| WO | 2018/046803 A1 | 3/2018 |
| WO | 2018/075235 A1 | 4/2018 |
| WO | 2018/081480 A1 | 5/2018 |
| WO | 2018/093907 A1 | 5/2018 |
| WO | 2018/098362 A1 | 5/2018 |
| WO | 2018/106615 A2 | 6/2018 |
| WO | 2018/107011 A1 | 6/2018 |
| WO | 2018/144082 A1 | 8/2018 |
| WO | 2018/146205 A1 | 8/2018 |
| WO | 2018/148381 A1 | 8/2018 |
| WO | 2018/161092 A1 | 9/2018 |
| WO | 2018/167320 A1 | 9/2018 |
| WO | 2018/187356 A2 | 10/2018 |
| WO | 2019/008111 A1 | 1/2019 |
| WO | 2019/012082 A1 | 1/2019 |
| WO | 2019/012091 A1 | 1/2019 |
| WO | 2019/023566 A1 | 1/2019 |
| WO | 2019/046377 A1 | 3/2019 |
| WO | 2019/086615 A1 | 5/2019 |
| WO | 2019/094396 A1 | 5/2019 |
| WO | 2019/115816 A1 | 6/2019 |
| WO | 2019/134048 A1 | 7/2019 |
| WO | 2019/135086 A1 | 7/2019 |
| WO | 2019/143949 A2 | 7/2019 |
| WO | 2019/147925 A1 | 8/2019 |
| WO | 2019/152922 A1 | 8/2019 |
| WO | 2019/191780 A1 | 10/2019 |
| WO | 2019/213550 A1 | 11/2019 |
| WO | 2019/219851 A1 | 11/2019 |
| WO | 2019/226939 A1 | 11/2019 |
| WO | 2019/226941 A1 | 11/2019 |
| WO | 2019/232103 A1 | 12/2019 |
| WO | 2020/003126 A1 | 1/2020 |
| WO | 2020/014539 A1 | 1/2020 |
| WO | 2020/025642 A1 | 2/2020 |
| WO | 2020/056424 A1 | 3/2020 |
| WO | 2020/070303 A1 | 4/2020 |
| WO | 2020/072371 A1 | 4/2020 |
| WO | 2020/073045 A1 | 4/2020 |
| WO | 2020/079234 A1 | 4/2020 |
| WO | 2020/096640 A2 | 5/2020 |
| WO | 2020/097291 A1 | 5/2020 |
| WO | 2020/097393 A1 | 5/2020 |
| WO | 2020/099614 A1 | 5/2020 |
| WO | 2020/104531 A1 | 5/2020 |
| WO | 2020/121273 A1 | 6/2020 |
| WO | 2020/123912 A1 | 6/2020 |
| WO | 2020/131586 A2 | 6/2020 |
| WO | 2020/143634 A1 | 7/2020 |
| WO | 2020/150152 A1 | 7/2020 |
| WO | 2020/154189 A1 | 7/2020 |
| WO | 2020/205412 A1 | 10/2020 |
| WO | 2020/243719 A1 | 12/2020 |
| WO | 2020/247547 A1 | 12/2020 |

OTHER PUBLICATIONS

Holmstrom et al., "High frequencies of circulating memory T cells specific for calreticulin exon 9 mutations in healthy individuals", Blood Cancer Journal, vol. 9, No. 2, Jan. 17, 2019, 14 Pages.

Masarova et al., "The Rationale for Immunotherapy in Myeloproliferative Neoplasms", Current Hematologic Malignancy Reports, Current Science Inc., Philadelphia, PA, us, vol. 14, No. 4, Jun. 21, 2019, pp. 310-327.

Ahl et al., "Enhancement of the in vivo circulation lifetime of L-a-distearoylphosphatidylcholine liposomes: importance of liposomal aggregation versus complement opsonization", Biochim. Biophys. Acta, 1997, 1329, 370-382.

Akimaru et al., "Formulation and antitumor efficacy of Liposomal-Caprylated-TNF-Sam2", Cytokines Mol. Ther., 1995, 1, 197-210.

Altschul et al., "BLAST—(see, for example), in Basic Local Alignment Search Tool", J. Mol. Biol., 1993, 215, 403-410.

Alving et al., "Liposomes as Carriers of Peptide Antigens: Induction of antibodies and Cytototic T Lymphocytes to Conjugated and Unconjugated Peptides", Immunol. Rev., 1995, 145, 5-31.

Balligand et al., "Pathologic activation of thrombopoietin receptor and JAK2-STAT5 pathway by frameshift mutants of mouse calreticulin", Leukemia, Aug., 2016, 30(8), 1775-1778.

Behr et al., "Efficient gene transfer into mammalian primary endocrine cells with lipopolyamine-coated DNA", Proc. Natl. Acad. Sci. USA, 1989, 86, 6982-6986.

Bozkus et al., "Immune Checkpoint Blockade Enhances Shared Neoantigen-Induced T-cell Immunity Directed against Mutated Calreticulin in Myeloproliferative Neoplasms", Cancer Discov. 2019 9, 1192-1207.

Chachoua et al., "Thrombopoietin receptor activation by myeloproliferative neoplasm associated calreticulin mutants", Blood, Mar. 10, 2016, 127(10), 1325-1335.

Danos et al., "Safe and efficient generation of recombinant retroviruses with amphotropic and ecotropic host ranges", Proc. Natl. Acad. Sci. USA, 1988, 85, 6460.

Felgner et al., "Cationic Lipid-Mediated Transfection in Mammalian Cells: Lipofection", Methods, 1993, 5, 63-68.

Felgner et al., "Lipofection: A highly efficient, lipid-mediated DNA-transfection procedure", Proc. Natl. Acad. Sci. USA, 1987, 84, 7413-7417.

Gao et al., "A Novel Cationic Reagent for Efficient Transfection of Mammalian Cells", Biochemical and Biophysical Research Comms., 1991, 179, 280-285.

Geall et al., "Nonviral delivery of self-amplifying RNA vaccines", PNAS, 2012, 109, 14604-14609.

Gilboa et al., "Retroviral Gene Transfer: Applications to Human Therapy", Adv. Exp. Med. Biol., 1988, 241, 29-33.

Goding, "Monoclonal Antibodies: Principles and Practice", Academic Press, 1986, 59-103.

Gorchakov et al., "A new role for ns polyprotein cleavage in Sindbis virus replication", J. Virol., 2008, 82(13), 6218-6231.

Haensler et al., "Polyamidoamine Cascade Polymers Mediate Efficient Transfection of Cells in Culture", Bioconjugate Chem., 1993, 4, 372-379.

Handlos et al., "Therapeutic Cancer Vaccination With a Peptide Derived From the Calreticulin Exon 9 Mutations Induces Strong Cellular Immune Responses in Patients With CALR-Mutant Chronic Myeloproliferative Neoplasms", Front. 2021 Oncol. 11:637420.

(56) References Cited

OTHER PUBLICATIONS

Holmström et al., "The CALR exon 9 mutations are shared neoantigens in patients with CALR mutant chronic myeloproliferative neoplasms", Leukemia, Dec. 2016, 30(12), 2413-2416.

Holmström et al., "The calreticulin (CALR) exon 9 mutations are promising targets for cancer immune therapy". Leukemia, Feb. 2018, 32(2), 429-437.

Holmström et al., "The JAK2V617F mutation is a target for specific T cells in the JAK2V617F-positive myeloproliferative neoplasms", Leukemia, Feb. 2017, 31(2), 495-498.

Hosse et al., "A New Generation of Protein Display Scaffolds for Molecular Recognition", Protein Sci., 2006, 15, 14-27.

Juliano, "The effect of Particle size and change on the clearance rates of liposomes and liposome encapsulated Drugs", Biochem. Biophys. Res. Commun., 1975, 63, 651-658.

Kim et al., "Enhancement of protein expression by alphavirus replicons by designing self-replicating subgenomic RNAs", PNAS, 2014, 111, 10708-10713.

Klampfl et al., "Somatic mutations of calreticulin in myeloproliferative neoplasms", New Engl. J. Med., Dec. 19, 2013, 369(25), 2379-2390.

Kohler et al., "Continuous Cultures of Fused Cells Secreting Antibody of Predefined Specificity", Nature, 1975, 256, 495.

Krougliak et al., "Development of Cell Lines Capable of Complementing E1, E4 and protein 1x defective adenovirus type 5 mutants", Human Gene Ther., 1995, 6, 1575-1586.

Lacout et al., "Expression in murine hematopoietic cells leads to MPD mimicking human PV with secondary myelofibrosis", Blood, Sep. 1, 2006, 108(5), 1652-1660.

Lopata et al., "High level trasient expression of a chloramphenicol acetyl transferase gene by DEAE-dextran mediated DNA transfection coupled with a dimethyl sulfoxide or glycerol shock treatment", Nucleic Acid Res., 1984, 12, 5707-5717.

Lusky et al., "In Vitro and In Vivo Biology of Recombinant Adenovirus Vectors with E1, E1/E2A, or E1/E4 Deleted", J. Virol., 1998, 72, 2022-2032.

Markowitz et al., "Construction of use of a safe and efficient amphotropic packaging cell line", Virol., 1988, 167, 400-406.

Mayr et al., "Vaccination against pox diseases under immunosuppressive conditions", Dev. Biol. Stand., 1978, 41, 225-234.

McLachlan et al., "Evaluation in vitro and in vivo of cationic liposome-expression construct complexes for cystic fibrosis gene therapy", Gene Therapy, 1995, 2, 614-622.

Meisinger-Henschel et al., "Genomic sequence of chorioallantois vaccinia virus Ankara, the ancestor of modified vaccinia virus Ankara", J. Gen. Virol., 2007, 88, 3249-3259.

Meyer, H. et al., "Mapping of deletions in the genome of the highly attenuated vaccinia virus MVA and their influence on virulence", J. Gen. Virol. 72, 1991, 1031-1038.

Miller et al., "Improved Retroviral Vectors for Gene Transfer and Expression", BioTechniques, 1989, 7, 980-990.

Nicaise et al., "Affinity Transfer by CDR Grafting on a Nonimmunoglobulin Scaffold", Protein Sci., 2004, 13, 1882-1891.

Nygren et al., "Scaffolds for Engineering Novel Binding Sites in Proteins", Curr. Opin. Struc. Biol., 1997, 7, 463-469.

Padlan, "A Possible Procedure for reducing the Immunogenicity of antibody Variable Domains while Preserving their Ligand-Binding Properties", Mol. Immunol., 1991, 28, 489-499.

Piccini et al., "[34] Vaccinia Virus as an Expression Vector", Methods of Enzymology, 1987, 153, 545-563.

Skerra, "Alternative Non-Antibody Scaffolds for Molecular Recognition", Curr. Opin. Biotechnol., 2007, 18, 295-304.

Sun et al., "An enhanced immune response against G250, induced by a heterologous DNA prime-protein boost vaccination, using polyethyleneimine as a DNA vaccine adjuvant", Mol. Med. Rep., 2014, 10(5), 2657-2662.

Szoka, "Comparative Properties and Methods of Preparation of Lipid Vesicles (Liposomes)l", Ann. Rev. Biophys. Bioeng., 1980, 9, 467-508.

Toribio et al., "An RNA trapping mechanism in Alphavirus mRNA promotes ribosome stalling and translation initiation", Nucleic Acids Res., May 19, 2016, 44(9), 4368-4380.

Vainchenker et al., "JAK/STAT signaling in hematological malignancies", Oncogene, May 23, 2013, 32(21), 2601-2613.

Ventoso, "Adaptive Changes in Alphavirus mRNA Translation Allowed Colonization of Vertebrate Hosts", J. Virol., Sep. 2012, vol. 86, 9484-9494.

Wang, et al., "A Packaging cell line for propagation of recombinant adenovirus vectors containing two lethal gene-region deletions", Gene Ther., 1995, 2, 775-783.

Yeh et al., "Efficient Dual Transcomplementation of Adenovirus E1 and E4 Regions from a 293-Derived Cell Line Expressing a Minimal E4 Functional Unit", J. Virol., 1996, 70, 559-565.

Graham et al., Characteristics of a Human Cell Line Transformed by DNA from Human Adenovirus Type 5, Gen. Virol., 1977, 36, 59-72.

Spivak, "The chronic myeloproliferative disorders: clonality and clinical heterogeneity", Semin Hematol., 2004, vol. 41, Suppl. 3, pp. 1-5.

Swerdlow et al., "WHO Classification of Tumours of Haematopoietic and Lymphoid Tissues", Lyon, France: IARC, 2008, pp. 885-887.

Talpaz et al., "A Newly Approved Treatment For Patients With Myeloproliferative Neoplasmassociated Myelofibrosis", Leukemia, 2021, vol. 35, pp. 1-17.

Tapia et al., "Use of ChAd3-EBO-Z Ebola Virus Vaccine In Malian And US Adults And Boosting Of Malian Adults With MVA-BN-Filo: A Phase 1, Single-Blind, Randomised Trial, A Phase 1b, Open-Label And Double-Blind, Dose-Escalation Trial, And A Nested, Randomised, Double-Blind, Placebo-Controlled Trial", Lancet Infect Dis., 2016, vol. 16, No. 1, pp. 31-42.

Taylor et al., "Mechanisms of Immune Suppression By Interleukin-10 And Transforming Growth Factor-Beta: The Role Of T Regulatory Cells", Immunology, 2006, vol. 117, No. 4, pp. 433-442.

Tefferi et al., "MIPSS70+ Version 2.0: Mutation And Karyotype-Enhanced International Prognostic Scoring System For Primary Myelofibrosis", J Clin Oncol., 2018, vol. 36, pp. 1769-1770.

Tefferi et al., "Revised Cytogenetic Risk Stratification In Primary Myelofibrosis: Analysis Based On 1002 Informative Patients", Leukemia, 2018, vol. 32, pp. 1189-1199.

Tefferi et al., "Revised response criteria for myelofibrosis: International Working Group-Myeloproliferative Neoplasms Research and Treatment (IWG-MRT) and European LeukemiaNet (ELN) consensus report", Blood, 2013, vol. 122, No. 8, pp. 1395-1398.

Tefferi, "Primary Myelofibrosis: 2017 Update On Diagnosis, Risk-Stratification, And Management", Am J Hematol., 2016, vol. 91, No. 12, pp. 1262-1271.

Verstovsek et al., "A Double-Blind, Placebo-Controlled Trial Of Ruxolitinib For Myelofibrosis", N Engl J Med., 2012, vol. 366, No. 9, pp. 799-807.

Vinay et al., "Immune Evasion In Cancer: Mechanistic Basis And Therapeutic Strategies", Semin Cancer Biol., 2015, 35 Suppl, pp. S185-S198.

Yetter et al., "Estimating Splenic Volume: Sonographic Measurements Correlated with Helical CT Determination", AJR Am J Roentgenol., 2003, vol. 181, No. 6, pp. 1615-1620.

Zeidan et al., "A Multi-center Phase I Trial of Ipilimumab in Patients with Myelodysplastic Syndromes following Hypomethylating Agent Failure", Clin Cancer Res., 2018, vol. 24, No. 15, pp. 3519-3527.

Zhao et al., "Safety and Efficacy of Therapeutic Cancer Vaccines Alone or in Combination with Immune Checkpoint Inhibitors in Cancer Treatment", Front Pharmacol., 2019, vol. 10, No. 1184, pp. 1-11.

Amato et al., "Evaluation of MVA-5T4 As A Novel Immunotherapeutic Vaccine In Colorectal, Renal And Prostate Cancer", Future Oncol., 2012, vol. 8, No. 3, pp. 231-237.

Arber et al., "The 2016 Revision To The World Health Organization Classification Of Myeloid Neoplasms And Acute Leukemia", Blood, 2016, vol. 127, No. 20, pp. 2391-2405.

Barbui et al., "Survival And Disease Progression In Essential Thrombocythemia Are Significantly Influenced By Accurate Morphologic Diagnosis: An International Study", J Clin Oncol., 2011, vol. 29, No. 23, pp. 3179-3184.

(56) References Cited

OTHER PUBLICATIONS

Barosi et al., "International Working Group For Myelofibrosis Research And Treatment (IWGMRT). Proposed Criteria For The Diagnosis Of Post-Polycythemia Vera And Post-Essential Thrombocythemia Myelofibrosis: A Consensus Statement From The International Working Group For Myelofibrosis Research And Treatment", Leukemia, 2008, vol. 22, No. 2, pp. 437-438.
Barosi et al., "Revised Response Criteria For Polycythemia Vera And Essential Thrombocythemia: An ELN And IWG-MRT Consensus Project", Blood, 2013, vol. 121, No. 23, pp. 4778-4781.
Bendjama et al., "Modified Vaccinia Virus Ankara-Based Vaccines In The Era Of Personalized Immunotherapy Of Cancer", Hum Vaccin Immunother., 2017, vol. 13, No. 9, pp. 1997-2003.
Brahmer et al., "Society For Immunotherapy Of Cancer (SITC) Clinical Practice Guideline On Immune Checkpoint Inhibitor-Related Adverse Events", J Immunother Cancer, Jun. 2021, vol. 9, No. 6, e00243, pp. 1-33.
Cervantes et al., "Three-Year Efficacy, Safety, And Survival Findings From Comfortii, A Phase 3 Study Comparing Ruxolitinib With Best Available Therapy For Myelofibrosis", Blood, 2013, vol. 122, No. 25, pp. 4047-4053.
Chamanza et al., "Incidences and Range of Spontaneous Findings in Control Cynomolgus Monkeys (*Macaca fascicularis*) Used in Toxicity Studies", Toxicol Pathol., 2010, vol. 38, No. 4, pp. 642-657.
ClinicalTrials.gov. NCT04041310: Nous-209 genetic vaccine for the treatment of microsatellite unstable solid tumors. https://clinicaltrials.gov/ct2/show/NCT04041310. Accessed Mar. 19, 2021.
Colby et al., "Safety And Immunogenicity Of Ad26 And MVA Vaccines In Acutely Treated HIV And Effect On Viral Rebound After Antiretroviral Therapy Interruption", Nat Med., 2020, vol. 26, No. 4, pp. 498-501.
Demaria et al., "Phase 1 Open-Label Trial Of Intravenous Administration Of MVA-BN-brachyury-TRICOM Vaccine In Patients With Advanced Cancer", J. Immunother Cancer, Sep. 2021, vol. 9, No. 9, e003238, pp. 1-12.
Emanuel et al., "Myeloproliferative Neoplasm (MPN) Symptom Assessment Form Total Symptom Score: Prospective International Assessment Of An Abbreviated Symptom Burden Scoring System Among Patients With Mpns", J Clin. Oncol., 2012, vol. 30, No. 33, pp. 4098-4103.
Excler et al., "HIV-1 Vaccines: Challenges And New Perspectives", Hum Vaccin Immunother, 2014, vol. 10, No. 6, pp. 1734-1746.
Expert Hematology Panel (EHP), "Guidance from the Expert Hematology Panel (EHP) on Covid-19 Vaccine-induced Immune Thrombocytopenia and Thrombosis (VITT)", Updated Guidance on Management. Version 2.2, Issued Aug. 31, 2021. https://b-s-h.org.uk/media/20499/guidance-version-22-20210903.pdf. Accessed Nov. 29, 2021.
Gangat et al., "DIPSS Plus: A Refined Dynamic International Prognostic Scoring System For Primary Myelofibrosis That Incorporates Prognostic Information From Karyotype, Platelet Count, And Transfusion Status", J. Clin. Oncol., 2011, vol. 29, pp. 392-397.
Garcia et al., "Safety and Efficacy of Decitabine Plus Ipilimumab in Relapsed or Refractory MDS/AML in the Post-BMT or Transplant Naïve Settings", Blood, 2020, vol. 136, No. S1, pp. 15-17.
Garcia-Manero et al., "A Phase II Study of Nivolumab or Ipilimumab with or without Azacitidine for Patients with Myelodysplastic Syndrome (MDS)", Blood, 2018, vol. 132, Supplement 1, 465, pp. 1-4.
Grauslund et al., "Therapeutic Cancer Vaccination with a Peptide Derived From the Calreticulin Exon 9 Mutations Induces Strong Cellular Immune Responses in Patients With CALR-Mutant Chronic Myeloproliferative Neoplasms", Front Oncol. 2021, vol. 11, No. 637420, pp. 1-17.
Guglielmelli et al., "MIPSS-70: Mutation-Enhanced International Prognostic Score System for Transplantation-Age Patients with Primary Myelofibrosis", J. Clin. Oncol., 2018, vol. 36, pp. 310-318.
Gulley et al., "Phase III Trial of PROSTVAC in Asymptomatic or Minimally Symptomatic Metastatic Castration-Resistant Prostate Cancer", J Clin Oncol., 2019, vol. 37, No. 13, pp. 1051-1061.
Guo et al., "Vaccinia virus-mediated cancer immunotherapy: cancer vaccines and oncolytics", J Immunother Cancer, 2019, vol. 7, No. 6, pp. 1-21.
Gwaltney et al., "Development Of A Harmonized Patient-Reported Outcome Questionnaire To Assess Myelofibrosis Symptoms In Clinical Trials", Leuk Res. 2017, vol. 59, pp. 26-31.
Harrison et al., "Long-term findings from Comfort-II, A Phase 3 Study Of Ruxolitinib Vs Best Available Therapy For Myelofibrosis", Leukemia, 2016, vol. 30, No. 8, pp. 1701-1707.
Hodge et al., "Multiple Costimulatory Modalities Enhance CTL Avidity", J Immunol., 2005, vol. 174, No. 10, pp. 5994-6004.
Kantoff et al., "Sipuleucel-T immunotherapy for castration-resistant prostate cancer", N. England J. Med., 2010, vol. 363, No. 5, pp. 411-422.
Larkin et al., "Combined nivolumab and ipilimumab or monotherapy in untreated melanoma", N. Engl. J. Med., 2015, vol. 373, No. 1, pp. 23-34.
Levey et al., "Using standardized serum creatinine values in the modification of diet in renal disease study equation for estimating glomerular filtration rate", Ann Intern Med., 2006, vol. 145, No. 4, pp. 247-254.
Liu et al., "Bayesian optimal interval designs for phase I clinical trials", J R Stat Soc Ser C Appl Stat., 2015, vol. 64, No. 3, pp. 507-523.
Mendonca et al., "Adenoviral vector vaccine platforms in the SARS-CoV-2 pandemic", NPJ Vaccines, 2021, vol. 6, No. 97, pp. 1-14.
Mesa et al., "Comparison of placebo and best available therapy for the treatment of myelofibrosis in the phase 3 Comfort studies", Haematologica, 2014, vol. 99, No. 2, pp. 292-298.
Mesa et al., Myeloproliferative Neoplasms, Version 2.2017, Journal of the National Comprehensive Cancer Network, vol. 14, No. 12, Dec. 2016, pp. 1572-1611.
Meyer et al., "Mapping of deletions in the genome of the highly attenuated vaccinia virus MVA and their influence on virulence", J. Gen. Virol., 1991, pp. 1031-1038.
Mosteller, "Simplified calculation of body-surface area", N. England J. Med., 1987, vol. 317, No. 17, pp. 1098-1098.
Mudireddy et al., "Prefibrotic versus overtly fibrotic primary myelofibrosis: clinical, cytogenetic, molecular and prognostic comparisons", Br J Haematol, 2018, vol. 182, pp. 594-597.
Newberry et al., "Clonal evolution and outcomes in myelofibrosis after ruxolitinib discontinuation", Blood, 2017, vol. 130, No. 9, pp. 1125-1131.
Oken et al., "Toxicity and response criteria of the Eastern Cooperative Oncology Group", Am J Clin Oncol., 1982, vol. 5, No. 6, pp. 649-655.
Overman et al., Initial Results from a Phase I Study of NOUS-209, an Off-the-Shelf Viral Vectored Immunotherapy Encoding 209 Shared Frame Shift Peptide Neoantigens, with Pembrolizumab, for the Treatment of Tumors with a Deficiency in Mismatch Repair/Microsatellite Instability. Abstract 1004P presented at European Society for Medical Oncology (ESMO) 2021.
Passamonti et al., "A clinical-molecular prognostic model to predict survival in patients with post polycythemia vera and post essential thrombocythemia myelofibrosis", Leukemia, 2017, vol. 31, pp. 2726-2731.
Passamonti et al., "A dynamic prognostic model to predict survival in primary myelofibrosis: a study by the IWG-MRT (International Working Group for Myeloproliferative Neoplasms Research and Treatment)", Blood, 2010, vol. 115, No. 9, pp. 1703-1708.
Porpaczy et al., "Aggressive B-cell lymphomas in patients with myelofibrosis receiving JAK1/2 inhibitor therapy", Blood, 2018, 132(7), 694-706.
Rahja et al., "Gastrointestinal adverse events associated with immune checkpoint inhibitor therapy", Gastroenterol Rep (Oxf)., 2019, vol. 8, No. 1, pp. 25-30.
Rocha et al., "Pedroto I. Management of Gastrointestinal Toxicity from Immune Checkpoint Inhibitor", Port J Gastroenterol., 2019, vol. 26, pp. 268-274.
Sadoff et al., "Interim Results of a Phase 1-2a Trial of Ad26.COV2.S Covid19 Vaccine", N. England J. Med., 2021, vol. 384, No. 19, pp. 1824-1835.

(56) References Cited

OTHER PUBLICATIONS

Sato et al., "Histopathology of incidental findings in cynomolgus monkeys (*Macaca fascicularis*) used in toxicity studies", J. Toxicol Pathol., 2012, vol. 25, No. 1, pp. 63-101.
Schieber et al., "Myelofibrosis in 2019: moving beyond JAK2 inhibition", Blood Cancer J., 2019, vol. 9, No. 9, 74.
Selby et al., "Preclinical Development of Ipilimumab and Nivolumab Combination Immunotherapy: Mouse Tumor Models, In Vitro Functional Studies, and Cynomolgus Macaque Toxicology", PLoS One, 2016, vol. 11, No. 9, e0161779.
Sharma et al., "The future of immune checkpoint therapy", Science, 2015, vol. 348, No. 6230, pp. 56-61.
Shaw et al., "Immunology of Adenoviral Vectors in Cancer Therapy", Mol Ther Methods Clin Dev., 2019, vol. 15, pp. 418-429.
Singh et al., "Development of PROSTVAC immunotherapy in prostate cancer", Future Oncol., 2015, vol. 11, No. 15, pp. 2137-2148.

* cited by examiner

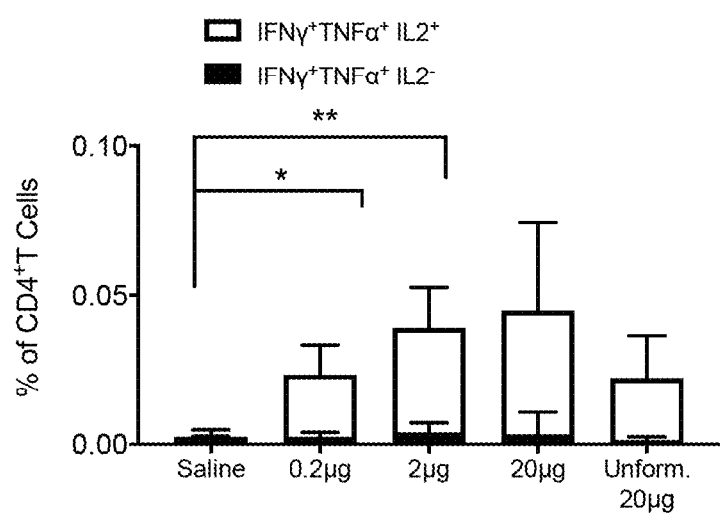

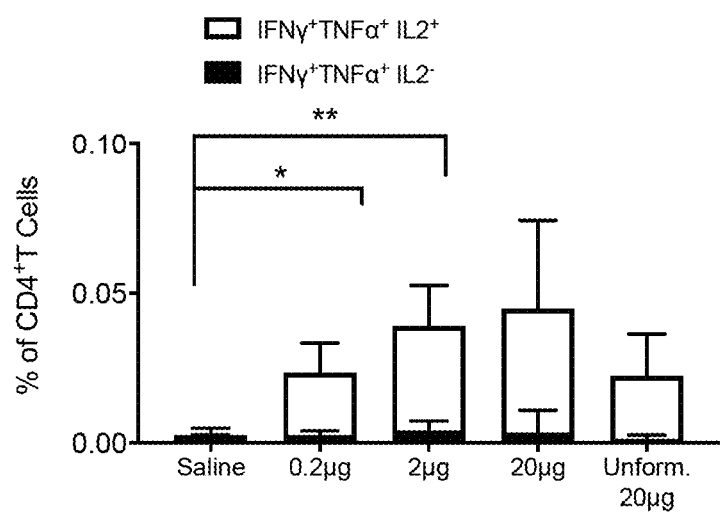

SEQUENCE LISTING

<160> NUMBER OF SEQ ID NOS: 59

<210> SEQ ID NO 1
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Lys Asp Lys Gln Asp Glu Glu Gln Arg Thr Arg Arg Met Met Arg
1               5                   10                  15

Thr Lys Met Arg Met Arg Arg Met Arg Arg Thr Arg Arg Lys Met Arg

```
                    20                  25                  30

Arg Lys Met Ser Pro Ala Arg Pro Arg Thr Ser Cys Arg Glu Ala Cys
        35                  40                  45

Leu Gln Gly Trp Thr Glu
    50
```

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Glu Glu Ala Glu Asp Asn Cys Arg Arg Met Met Arg Thr Lys
1               5                   10
```

<210> SEQ ID NO 3
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Lys Asp Lys Gln Asp Glu Glu Gln Arg Thr Arg Arg Met Met Arg
1               5                   10                  15

Thr Lys Met Arg Met Arg Arg Met Arg Arg Thr Arg Arg Lys Met Arg
            20                  25                  30

Arg Lys Met Ser Pro Ala Arg Pro Arg Thr Ser Cys Arg Glu Ala Cys
        35                  40                  45

Leu Gln Gly Trp Thr Glu Ala Ala Tyr Glu Glu Ala Glu Asp Asn Cys
    50                  55                  60

Arg Arg Met Met Arg Thr Lys
65                  70
```

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Lys Leu Ser His Lys His Leu Val Leu Asn Tyr Gly Val Cys Phe Cys
1               5                   10                  15

Gly Asp Glu Asn Ile Leu Val Gln Glu Phe Val Lys Phe Gly
            20                  25                  30
```

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Val Leu Asn Tyr Gly Val Cys Phe Cys
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Cys Gly Asp Glu Asn Ile Leu Val
1               5

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Asn Tyr Gly Val Cys Phe Cys Ala Ala Tyr Phe Cys Gly Asp
1               5                   10                  15

Glu Asn Ile Leu Val
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ala Cys Pro Gly Phe Leu Trp Ala Leu Val Ile Ser Thr Cys Leu
1               5                   10                  15

Glu Phe Ser Met Ala
            20

<210> SEQ ID NO 9
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Cys Pro Gly Phe Leu Trp Ala Leu Val Ile Ser Thr Cys Leu
1               5                   10                  15

Glu Phe Ser Met Ala Met Lys Asp Lys Gln Asp Glu Gln Arg Thr
            20                  25                  30

Arg Arg Met Met Arg Thr Lys Met Arg Met Arg Met Arg Met Arg Thr
            35                  40                  45

Arg Arg Lys Met Arg Arg Lys Met Ser Pro Ala Arg Pro Arg Thr Ser
        50                  55                  60

Cys Arg Glu Ala Cys Leu Gln Gly Trp Thr Glu Ala Ala Tyr Glu Glu
65                  70                  75                  80

Ala Glu Asp Asn Cys Arg Arg Met Met Arg Thr Lys
                85                  90

<210> SEQ ID NO 10
```

```
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Cys Pro Gly Phe Leu Trp Ala Leu Val Ile Ser Thr Cys Leu
1               5                   10                  15

Glu Phe Ser Met Ala Met Lys Asp Lys Gln Asp Glu Glu Gln Arg Thr
            20                  25                  30

Arg Arg Met Met Arg Thr Lys Met Arg Met Arg Arg Met Arg Arg Thr
        35                  40                  45

Arg Arg Lys Met Arg Arg Lys Met Ser Pro Ala Arg Pro Arg Thr Ser
    50                  55                  60

Cys Arg Glu Ala Cys Leu Gln Gly Trp Thr Glu Ala Ala Tyr Glu Glu
65                  70                  75                  80

Ala Glu Asp Asn Cys Arg Arg Met Met Arg Thr Lys Ala Ala Tyr Val
                85                  90                  95

Leu Asn Tyr Gly Val Cys Phe Cys Ala Ala Tyr Phe Cys Gly Asp Glu
            100                 105                 110

Asn Ile Leu Val
        115

<210> SEQ ID NO 11
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Cys Pro Gly Phe Leu Trp Ala Leu Val Ile Ser Thr Cys Leu
1               5                   10                  15

Glu Phe Ser Met Ala Met Lys Asp Lys Gln Asp Glu Glu Gln Arg Thr
            20                  25                  30

Arg Arg Met Met Arg Thr Lys Met Arg Met Arg Arg Met Arg Arg Thr
        35                  40                  45

Arg Arg Lys Met Arg Arg Lys Met Ser Pro Ala Arg Pro Arg Thr Ser
    50                  55                  60

Cys Arg Glu Ala Cys Leu Gln Gly Trp Thr Glu Ala Ala Tyr Glu Glu
65                  70                  75                  80

Ala Glu Asp Asn Cys Arg Arg Met Met Arg Thr Lys Ala Ala Tyr Lys
                85                  90                  95

Leu Ser His Lys His Leu Val Leu Asn Tyr Gly Val Cys Phe Cys Gly
            100                 105                 110

Asp Glu Asn Ile Leu Val Gln Glu Phe Val Lys Phe Gly
        115                 120                 125

<210> SEQ ID NO 12
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Met Lys Asp Lys Gln Asp Glu Glu Gln Arg Thr Arg Arg Met Met Arg
1               5                   10                  15

Thr Lys Met Arg Met Arg Met Arg Arg Thr Arg Arg Lys Met Arg
            20                  25                  30

Arg Lys Met Ser Pro Ala Arg Pro Arg Thr Ser Cys Arg Glu Ala Cys
            35                  40                  45

Leu Gln Gly Trp Thr Glu Ala Ala Tyr Glu Glu Ala Glu Asp Asn Cys
            50                  55                  60

Arg Arg Met Met Arg Thr Lys Ala Ala Tyr Val Leu Asn Tyr Gly Val
65                  70                  75                  80

Cys Phe Cys Ala Ala Tyr Phe Cys Gly Asp Glu Asn Ile Leu Val
                85                  90                  95
```

<210> SEQ ID NO 13
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Lys Asp Lys Gln Asp Glu Glu Gln Arg Thr Arg Arg Met Met Arg
1               5                   10                  15

Thr Lys Met Arg Met Arg Met Arg Arg Thr Arg Arg Lys Met Arg
            20                  25                  30

Arg Lys Met Ser Pro Ala Arg Pro Arg Thr Ser Cys Arg Glu Ala Cys
            35                  40                  45

Leu Gln Gly Trp Thr Glu Ala Ala Tyr Glu Glu Ala Glu Asp Asn Cys
            50                  55                  60

Arg Arg Met Met Arg Thr Lys Ala Ala Tyr Lys Leu Ser His Lys His
65                  70                  75                  80

Leu Val Leu Asn Tyr Gly Val Cys Phe Cys Gly Asp Glu Asn Ile Leu
                85                  90                  95

Val Gln Glu Phe Val Lys Phe Gly
            100
```

<210> SEQ ID NO 14
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
            50                  55                  60

Ser Thr Leu His Leu Val Leu Arg Leu Arg Gly Val Arg Lys Asp Lys
65                  70                  75                  80

Gln Asp Glu Glu Gln Arg Thr Arg Arg Met Met Arg Thr Lys Met Arg
                85                  90                  95
```

Met Arg Arg Met Arg Arg Thr Arg Arg Lys Met Arg Lys Met Ser
            100                 105                 110

Pro Ala Arg Pro Arg Thr Ser Cys Arg Glu Ala Cys Leu Gln Gly Trp
        115                 120                 125

Thr Glu Ala Ala Tyr Glu Glu Ala Glu Asp Asn Cys Arg Arg Met Met
    130                 135                 140

Arg Thr Lys Ala Ala Tyr Val Leu Asn Tyr Gly Val Cys Phe Cys Ala
145                 150                 155                 160

Ala Tyr Phe Cys Gly Asp Glu Asn Ile Leu Val
                165                 170

<210> SEQ ID NO 15
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Val Arg Lys Asp Lys
65                  70                  75                  80

Gln Asp Glu Glu Gln Arg Thr Arg Arg Met Met Arg Thr Lys Met Arg
                85                  90                  95

Met Arg Arg Met Arg Arg Thr Arg Arg Lys Met Arg Lys Met Ser
            100                 105                 110

Pro Ala Arg Pro Arg Thr Ser Cys Arg Glu Ala Cys Leu Gln Gly Trp
        115                 120                 125

Thr Glu Ala Ala Tyr Glu Glu Ala Glu Asp Asn Cys Arg Arg Met Met
    130                 135                 140

Arg Thr Lys Ala Ala Tyr Lys Leu Ser His Lys His Leu Val Leu Asn
145                 150                 155                 160

Tyr Gly Val Cys Phe Cys Gly Asp Glu Asn Ile Leu Val Gln Glu Phe
                165                 170                 175

Val Lys Phe Gly
            180

<210> SEQ ID NO 16
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggcatgcc caggcttcct gtgggccctg gtcatcagca cctgtctgga gttttccatg      60
gccatgaagg acaagcagga tgaggagcag cggacccgga gaatgatgag acaaagatg     120 cgcatgaggc gcatgcggag aacaaggcgc aagatgcgga gaaagatgtc tccagcaagg    180
cctagaacca gctgcaggga ggcatgtctg cagggatgga cagaggcagc atacgaggag    240
gcagaggaca actgcaggcg catgatgagg accaag                              276

<210> SEQ ID NO 17
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggcatgcc caggcttcct gtgggccctg gtcatcagca cctgtctgga gttttccatg    60
gccatgaagg acaagcagga tgaggagcag cggacccgga gaatgatgag gacaaagatg   120
cgcatgaggc gcatgcggag aacaaggcgc aagatgcgga gaaagatgtc tccagcaagg   180
cctagaacca gctgcaggga ggcatgtctg cagggatgga cagaggcagc atacgaggag   240
gcagaggaca actgcaggcg catgatgagg accaaggccg cctacgtgct gaattatggc   300
gtgtgcttct gtgccgccta ttttgtggc gatgagaaca tcctggtg                 348

<210> SEQ ID NO 18
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggcatgcc caggcttcct gtgggccctg gtcatcagca cctgtctgga gttttccatg    60
gccatgaagg acaagcagga tgaggagcag cggacccgga gaatgatgag gacaaagatg   120
cgcatgaggc gcatgcggag aacaaggcgc aagatgcgga gaaagatgtc tccagcaagg   180
cctagaacca gctgcaggga ggcatgtctg cagggatgga cagaggcagc atacgaggag   240
gcagaggaca actgcaggcg catgatgagg accaaggccg cctacaagct gagccacaag   300
cacctggtgc tgaactatgg cgtgtgcttc tgtggcgatg agaatatcct ggtgcaggag   360
ttcgtgaagt ttggc                                                    375

<210> SEQ ID NO 19
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgaaggaca agcaggatga ggagcagcgg acccggagaa tgatgaggac aaagatgcgc    60
atgaggcgca tgcggagaac aaggcgcaag atgcggagaa agatgtctcc agcaaggcct   120
agaaccagct gcagggaggc atgtctgcag ggatggacag aggcagcata cgaggaggca   180
gaggacaact gcaggcgcat gatgaggacc aaggccgcct acgtgctgaa ttatggcgtg   240
tgcttctgtg ccgcctattt tgtggcgat gagaacatcc tggtg                    285

<210> SEQ ID NO 20
<211> LENGTH: 312
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 20
atgaaggaca agcaggatga ggagcagcgg acccggagaa tgatgaggac aaagatgcgc      60
atgaggcgca tgcggagaac aaggcgcaag atgcggagaa agatgtctcc agcaaggcct     120
agaaccagct gcagggaggc atgtctgcag ggatggacag aggcagcata cgaggaggca     180
gaggacaact gcaggcgcat gatgaggacc aaggccgcct acaagctgag ccacaagcac     240
ctggtgctga actatggcgt gtgcttctgt ggcgatgaga atatcctggt gcaggagttc     300
gtgaagtttg gc                                                         312

<210> SEQ ID NO 21
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgcagatct tcgtgaagac cctgacaggc aagaccatca cactggaggt ggagccctcc      60
gacaccatcg agaacgtgaa ggccaagatc caggacaagg agggcatccc ccctgatcag     120
cagcggctga tctttgccgg caagcagctg gaggacggca gaaccctgtc tgattacaat     180
atccagaagg agagcacact gcacctggtg ctgcggctga gaggcgtgag gaaggacaag     240
caggatgagg agcagcgcac ccggagaatg atgcggacaa agatgagaat gaggcgcatg     300
cggagaacca ggcgcaagat gcggagaaag atgagcccag caaggccacg cacctcctgc     360
agggaggcat gtctgcaggg atggacagag gcagcctatg aggaggccga ggacaactgc     420
aggcgcatga tgcggacaaa ggccgcctac gtgctgaatt atggcgtgtg cttctgtgcc     480
gcctattttt gtggcgatga gaacatcctg gtg                                  513

<210> SEQ ID NO 22
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgcagatct tcgtgaagac cctgacaggc aagaccatca cactggaggt ggagccctcc      60
gacaccatcg agaacgtgaa ggccaagatc caggacaagg agggcatccc ccctgatcag     120
cagcggctga tctttgccgg caagcagctg gaggacggca gaaccctgtc tgattacaat     180
atccagaagg agagcacact gcacctggtg ctgcggctga gaggcgtgag gaaggacaag     240
caggatgagg agcagcgcac ccggagaatg atgcggacaa agatgagaat gaggcgcatg     300
cggagaacca ggcgcaagat gcggagaaag atgagcccag caaggccacg cacctcctgc     360
agggaggcat gtctgcaggg atggacagag gcagcctatg aggaggccga ggacaactgc     420
aggcgcatga tgcggacaaa ggccgcctac aagctgtctc acaagcacct ggtgctgaac     480
tatggcgtgt gcttctgtgg cgatgagaat atcctggtgc aggagttcgt gaagtttggc     540
tgataa                                                                546

<210> SEQ ID NO 23
```

<211> LENGTH: 1417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
tcaatattgg ccattagcca tattattcat tggttatata gcataaatca atattggcta      60
ttggccattg catacgttgt atccatatca taatatgtac atttatattg gctcatgtcc     120
aacattaccg ccatgttgac attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca atagggactt tccattgacg tcaatgggtg gagtatttac ggtaaactgc     360
ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca gtctccacc ccattgacgt      600
caatgggagt ttgttttggc accaaaatca acgggacttt ccaaaatgtc gtaacaactc     660
cgccccattg acgcaaatgg gcggtaggcg tgtacggtgg gaggtctata taagcagagc     720
tctccctatc agtgataga g atctccctat cagtgataga gatcgtcgac gagctcgttt     780
agtgaaccgt cagatcgcct ggagacgcca tccacgctgt tttgacctcc atagaagaca     840
ccgggaccga tccagcctcc gcggccggga acggtgcatt ggatctagag ccaccatggc     900
atgcccaggc ttcctgtggg ccctggtcat cagcacctgt ctggagttt ccatggccat      960
gaaggacaag caggatgagg agcagcggac ccggagaatg atgaggacaa agatgcgcat    1020
gaggcgcatg cggagaacaa ggcgcaagat gcggagaaag atgtctccag caaggcctag    1080
aaccagctgc agggaggcat gtctgcaggg atggacagag gcagcatacg aggaggcaga    1140
ggacaactgc aggcgcatga tgaggaccaa ggccgcctac aagctgagcc acaagcacct    1200
ggtgctgaac tatggcgtgt gcttctgtgg cgatgagaat atcctggtgc aggagttcgt    1260
gaagtttggc tgataaggta ccatccgaac ttgtttattg cagcttataa tggttacaaa    1320
taaagcaata gcatcacaaa tttcacaaat aaagcatttt tttcactgca ttctagttgt    1380
ggtttgtcca aactcatcaa tgtatcttat catgtct                              1417
```

<210> SEQ ID NO 24
<211> LENGTH: 1390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
tcaatattgg ccattagcca tattattcat tggttatata gcataaatca atattggcta      60
ttggccattg catacgttgt atccatatca taatatgtac atttatattg gctcatgtcc     120
aacattaccg ccatgttgac attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca atagggactt tccattgacg tcaatgggtg gagtatttac ggtaaactgc     360
```

```
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tctccctatc agtgatagag atctccctat cagtgataga gatcgtcgac gagctcgttt    780
agtgaaccgt cagatcgcct ggagacgcca tccacgctgt tttgacctcc atagaagaca    840
ccgggaccga tccagcctcc gcggccggga acggtgcatt ggatctagag ccaccatggc    900
atgcccaggc ttcctgtggg ccctggtcat cagcacctgt ctggagtttt ccatggccat    960
gaaggacaag caggatgagg agcagcggac ccggagaatg atgaggacaa agatgcgcat   1020
gaggcgcatg cggagaacaa ggcgcaagat gcggagaaag atgtctccag caaggcctag   1080
aaccagctgc agggaggcat gtctgcaggg atggacagag gcagcatacg aggaggcaga   1140
ggacaactgc aggcgcatga tgaggaccaa ggccgcctac gtgctgaatt atggcgtgtg   1200
cttctgtgcc gcctattttt gtggcgatga gaacatcctg gtgtgataag gtaccatccg   1260
aacttgttta ttgcagctta taatggttac aaataaagca atagcatcac aaatttcaca   1320
aataaagcat ttttttcact gcattctagt tgtggtttgt ccaaactcat caatgtatct   1380
tatcatgtct                                                           1390

<210> SEQ ID NO 25
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gatcactaat tccaaaccca cccgcttttt atagtaagtt tttcacccat aaataataaa     60
tacaataatt aatttctcgt aaaagtagaa aatatattct aatttattgc acggtaagga    120
agtagaatca taaagaacag tgacggatcc cgcgacttcg ccgccatggg ccagaaggaa    180
cagattcata cgcttcagaa aaattctgaa cgaatgtcaa agcaattgac acgaagttct    240
caggcagtaa tgaaggacaa acaagacgaa gaacaacgaa ctaggcggat gatgaggact    300
aagatgagga tgcggaggat gagacggacg cgacgcaaga tgcgccggaa aatgtctccc    360
gcccggccaa ggacgtcttg tcgggaagcc tgtttgcagg gctggaccga agcagcttac    420
gaagaagcag aagacaattg tcggcgaatg atgagaacga aggctgctta cgtgcttaac    480
tatggagtgt gcttctgcgc tgcctatttc tgcggagatg agaacattct ggtgtagtaa    540
aggcgcgcc                                                            549

<210> SEQ ID NO 26
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
```

```
atgggccaga aggaacagat tcatacgctt cagaaaaatt ctgaacgaat gtcaaagcaa    60
ttgacacgaa gttctcaggc agtaatgaag gacaaacaag acgaagaaca acgaactagg   120
cggatgatga ggactaagat gaggatgcgg aggatgagac ggacgcgacg caagatgcgc   180
cggaaaatgt ctcccgcccg gccaaggacg tcttgtcggg aagcctgttt gcagggctgg   240
accgaagcag cttacgaaga agcagaagac aattgtcggc gaatgatgag aacgaaggct   300
gcttacgtgc ttaactatgg agtgtgcttc tgcgctgcct atttctgcgg agatgagaac   360
attctggtg                                                          369
```

<210> SEQ ID NO 27
<211> LENGTH: 284
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 27

```
atgaaggaca acaagacga agaacaacga actaggcgga tgatgaggac taagatgagg    60
atgcggagga tgagacggac gcgacgcaag atgcgccgga aaatgtctcc cgcccggcca   120
aggacgtctt gtcgggaagc ctgtttgcag gctggaccg aagcagctta cgaagaagca   180
gaagacaatt gtcggcgaat gatgagaacg aaggctgctt acgtgcttaa ctatggagtg   240
tgcttctgcg ctgcctattt ctgcggagat gagaacattc tggt                   284
```

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 28

Phe Cys Gly Asp Glu Asn Ile Leu Val Ala Ala Tyr Phe Cys Gly Asp
1               5                   10                  15

Glu Asn Ile Leu Val
            20

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 29

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val
            20                  25

<210> SEQ ID NO 30
<211> LENGTH: 84
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 30

```
atgggccaga aggaacagat tcatacgctt cagaaaaatt ctgaacgaat gtcaaagcaa      60
ttgacacgaa gttctcaggc agta                                            84
```

<210> SEQ ID NO 31
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Met Lys Asp Lys
            20                  25                  30

Gln Asp Glu Glu Gln Arg Thr Arg Arg Met Met Arg Thr Lys Met Arg
        35                  40                  45

Met Arg Arg Met Arg Arg Thr Arg Arg Lys Met Arg Arg Lys Met Ser
    50                  55                  60

Pro Ala Arg Pro Arg Thr Ser Cys Arg Glu Ala Cys Leu Gln Gly Trp
65                  70                  75                  80

Thr Glu Ala Ala Tyr Glu Glu Ala Glu Asp Asn Cys Arg Arg Met Met
                85                  90                  95

Arg Thr Lys Ala Ala Tyr Val Leu Asn Tyr Gly Val Cys Phe Cys Ala
            100                 105                 110

Ala Tyr Phe Cys Gly Asp Glu Asn Ile Leu Val
        115                 120

<210> SEQ ID NO 32
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gatcactaat tccaaaccca cccgcttttt atagtaagtt tttcacccat aaataataaa      60
tacaataatt aatttctcgt aaaagtagaa aatatattct aatttattgc acggtaagga     120
agtagaatca taaagaacag tgacggatc                                      149
```

<210> SEQ ID NO 33
<211> LENGTH: 10712
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
taatacgact cactatagat aggcggcgca tgagagaagc ccagaccaat tacctaccca      60
aataggagaa agttcacgtt gacatcgagg aagacagccc attcctcaga gctttgcagc     120
ggagcttccc gcagtttgag gtagaagcca agcaggtcac tgataatgac catgctaatg     180
ccagagcgtt ttcgcatctg gcttcaaaac tgatcgaaac ggaggtggac ccatccgaca     240
cgatccttga cattggaata gtcagcatag tacatttcat ctgactaata ctacaacacc     300
accaccatga atagaggatt ctttaacatg ctcggccgcc gccccttccc ggcccccact     360
```

```
gccatgtgga ggccgcggag aaggaggcag gcggccccgg gaagcggagc tactaacttc    420
agcctgctga agcaggctgg agacgtggag agaaccctg dacctgagaa agttcacgtt    480
gacatcgagg aagacagccc attcctcaga gctttgcagc ggagcttccc gcagtttgag    540
gtagaagcca agcaggtcac tgataatgac catgctaatg ccagagcgtt ttcgcatctg    600
gcttcaaaac tgatcgaaac ggaggtggac ccatccgaca cgatccttga cattggaagt    660
gcgcccgccc gcagaatgta ttctaagcac aagtatcatt gtatctgtcc gatgagatgt    720
gcggaagatc cggacagatt gtataagtat gcaactaagc tgaagaaaaa ctgtaaggaa    780
ataactgata aggaattgga caagaaaatg aaggagctcg ccgccgtcat gagcgaccct    840
gacctggaaa ctgagactat gtgcctccac gacgacgagt cgtgtcgcta cgaagggcaa    900
gtcgctgttt accaggatgt atacgcggtt gacggaccga caagtctcta tcaccaagcc    960
aataagggag ttagagtcgc ctactggata ggctttgaca ccacccctt tatgtttaag    1020 aacttggctg gagcatatcc atcatactct accaactggg ccgacgaaac cgtgttaacg    1080
gctcgtaaca taggcctatg cagctctgac gttatggagc ggtcacgtag agggatgtcc    1140
attcttagaa agaagtattt gaaaccatcc aacaatgttc tattctctgt tggctcgacc    1200
atctaccacg agaagaggga cttactgagg agctggcacc tgccgtctgt atttcactta    1260
cgtggcaagc aaaattacac atgtcggtgt gagactatag ttagttgcga cgggtacgtc    1320
gttaaaagaa tagctatcag tccaggcctg tatgggaagc cttcaggcta tgctgctacg    1380
atgcaccgcg agggattctt gtgctgcaaa gtgacagaca cattgaacgg ggagagggtc    1440
tcttttcccg tgtgcacgta tgtgccagct acattgtgtg accaaatgac tggcatactg    1500
gcaacagatg tcagtgcgga cgacgcgcaa aaactgctgg ttgggctcaa ccagcgtata    1560
gtcgtcaacg gtcgcaccca gagaaacacc aataccatga aaaattacct tttgccccgta    1620 gtggcccagg catttgctag gtgggcaaag gaatataagg aagatcaaga agatgaaagg    1680
ccactaggac tacgagatag acagttagtc atggggtgtt gttgggcttt tagaaggcac    1740
aagataacat ctatttataa gcgcccggat acccaaacca tcatcaaagt gaacagcgat    1800
ttccactcat tcgtgctgcc caggataggc agtaacacat tggagatcgg gctgagaaca    1860
agaatcagga aaatgttaga ggagcacaag gagccgtcac ctctcattac cgccgaggac    1920
gtacaagaag ctaagtgcgc agccgatgag gctaaggagg tgcgtgaagc cgaggagttg    1980
cgcgcagctc taccacctt ggcagctgat gttgaggagc ccactctgga agccgatgtc    2040
gacttgatgt tacaagaggc tggggccggc tcagtggaga cacctcgtgg cttgataaag    2100
gttaccagct acgatggcga ggacaagatc ggctcttacg ctgtgctttc tccgcaggct    2160
gtactcaaga gtgaaaaatt atcttgcatc cacctctcg ctgaacaagt catagtgata    2220
acacactctg gccgaaaagg gcgttatgcc gtggaaccat accatggtaa agtagtggtg    2280
ccagagggac atgcaatacc cgtccaggac tttcaagctc tgagtgaaag tgccaccatt    2340
gtgtacaacg aacgtgagtt cgtaaacagg tacctgcacc atattgccac acatggagga    2400
gcgctgaaca ctgatgaaga atattacaaa actgtcaagc ccagcgagca cgacggcgaa    2460
tacctgtacg acatcgacag gaaacagtgc gtcaagaaag aactagtcac tgggctaggg    2520
ctcacaggcg agctggtgga tcctcccttc catgaattcg cctacgagag tctgagaaca    2580
cgaccagccg ctccttacca agtaccaacc atagggtgt atggcgtgcc aggatcaggc    2640
aagtctggca tcattaaaag cgcagtcacc aaaaaagatc tagtggtgag cgccaagaaa    2700
```

```
gaaaactgtg cagaaattat aagggacgtc aagaaaatga aagggctgga cgtcaatgcc    2760
agaactgtgg actcagtgct cttgaatgga tgcaaacacc ccgtagagac cctgtatatt    2820
gacgaagctt ttgcttgtca tgcaggtact ctcagagcgc tcatagccat tataagacct    2880
aaaaaggcag tgctctgcgg ggatcccaaa cagtgcggtt tttttaacat gatgtgcctg    2940
aaagtgcatt ttaaccacga gatttgcaca caagtcttcc acaaaagcat ctctcgccgt    3000
tgcactaaat ctgtgacttc ggtcgtctca accttgtttt acgacaaaaa aatgagaacg    3060
acgaatccga aagagactaa gattgtgatt gacactaccg gcagtaccaa acctaagcag    3120
gacgatctca ttctcacttg tttcagaggg tgggtgaagc agttgcaaat agattacaaa    3180
ggcaacgaaa taatgacggc agctgcctct caagggctga cccgtaaagg tgtgtatgcc    3240
gttcggtaca aggtgaatga aaatcctctg tacgcaccca cctctgaaca tgtgaacgtc    3300
ctactgaccc gcacggagga ccgcatcgtg tggaaaacac tagccggcga cccatggata    3360
aaaacactga ctgccaagta ccctgggaat ttcactgcca cgatagagga gtggcaagca    3420
gagcatgatg ccatcatgag gcacatcttg agagaccgg  accctaccga cgtcttccag    3480
aataaggcaa acgtgtgttg ggccaaggct ttagtgccgg tgctgaagac cgctggcata    3540
gacatgacca ctgaacaatg gaacactgtg gattattttg aaacggacaa agctcactca    3600
gcagagatag tattgaacca actatgcgtg aggttctttg gactcgatct ggactccggt    3660
ctattttctg cacccactgt tccgttatcc attaggaata atcactggga taactccccg    3720
tcgcctaaca tgtacgggct gaataaagaa gtggtccgtc agctctctcg caggtaccca    3780
caactgcctc gggcagttgc cactggaaga gtctatgaca tgaacactgg tacactgcgc    3840
aattatgatc cgcgcataaa cctagtacct gtaaacagaa gactgcctca tgctttagtc    3900
ctccaccata atgaacaccc acagagtgac ttttcttcat tcgtcagcaa attgaagggc    3960
agaactgtcc tggtggtcgg ggaaaagttg tccgtcccag gcaaaatggt tgactggttg    4020
tcagaccggc ctgaggctac cttcagagct cggctggatt taggcatccc aggtgatgtg    4080
cccaaatatg acataatatt tgttaatgtg aggacccccat ataaatacca tcactatcag    4140
cagtgtgaag accatgccat taagcttagc atgttgacca agaaagcttg tctgcatctg    4200
aatcccggcg gaacctgtgt cagcataggt tatggttacg ctgacagggc cagcgaaagc    4260
atcattggtg ctatagcgcg gcagttcaag ttttcccggg tatgcaaacc gaaatcctca    4320
cttgaagaga cggaagttct gtttgtattc attgggtacg atcgcaaggc ccgtacgcac    4380
aatccttaca agctttcatc aaccttgacc aacatttata caggttccag actccacgaa    4440
gccggatgtg caccctcata tcatgtggtg cgaggggata ttgccacggc caccgaagga    4500
gtgattataa atgctgctaa cagcaaagga caacctggcg gaggggtgtg cggagcgctg    4560
tataagaaat ccccggaaag cttcgattta cagccgatcg aagtaggaaa agcgcgactg    4620
gtcaaaggtg cagctaaaca tatcattcat gccgtaggac caaacttcaa caaagtttcg    4680
gaggttgaag gtgacaaaca gttggcagag gcttatgagt ccatcgctaa gattgtcaac    4740
gataacaatt acaagtcagt agcgattcca ctgttgtcca ccggcatctt ttccgggaac    4800
aaagatcgac taaccaatc  attgaaccat ttgctgacag ctttagacac cactgatgca    4860
gatgtagcca tatactgcag ggacaagaaa tgggaaatga ctctcaagga agcagtggct    4920
aggagagaag cagtggagga gatatgcata tccgacgact cttcagtgac agaacctgat    4980
gcagagctgt gagggtgca  tccgaagagt tctttggctg gaaggaaggg ctacagcaca    5040
agcgatggca aaactttctc atatttggaa gggaccaagt ttcaccaggc ggccaaggat    5100
```

```
atagcagaaa ttaatgccat gtggcccgtt gcaacggagg ccaatgagca ggtatgcatg    5160
tatatcctcg gagaaagcat gagcagtatt aggtcgaaat gccccgtcga agagtcggaa    5220
gcctccacac cacctagcac gctgccttgc ttgtgcatcc atgccatgac tccagaaaga    5280
gtacagcgcc taaaagcctc acgtccagaa caaattactg tgtgctcatc ctttccattg    5340
ccgaagtata gaatcactgg tgtgcagaag atccaatgct cccagcctat attgttctca    5400
ccgaaagtgc ctgcgtatat tcatccaagg aagtatctcg tggaaacacc accggtagac    5460
gagactccgg agccatcggc agagaaccaa tccacagagg ggacacctga caaccacca    5520 cttataaccg aggatgagac caggactaga acgcctgagc cgatcatcat cgaagaggaa    5580
gaagaggata gcataagttt gctgtcagat ggcccgaccc accaggtgct gcaagtcgag    5640
gcagacattc acgggccgcc ctctgtatct agctcatcct ggtccattcc tcatgcatcc    5700
gactttgatg tggacagttt atccatactt gacaccctgg agggagctag cgtgaccagc    5760
ggggcaacgt cagccgagac taactcttac ttcgcaaaga gtatggagtt tctggcgcga    5820
ccggtgcctg cgcctcgaac agtattcagg aaccctccac atcccgctcc gcgcacaaga    5880
acaccgtcac ttgcacccag cagggcctgc tcgagaacca gcctagtttc cacccccgcca   5940 ggcgtgaata gggtgatcac tagagaggag ctcgaggcgc ttaccccgtc acgcactcct    6000
agcaggtcgg tctcgagaac cagcctggtc tccaacccgc caggcgtaaa tagggtgatt    6060
acaagagagg agtttgaggc gttcgtagca caacaacaat gacggtttga tgcgggtgca    6120
tacatctttt cctccgacac cggtcaaggg catttacaac aaaaatcagt aaggcaaacg    6180
gtgctatccg aagtggtgtt ggagaggacc gaattggaga tttcgtatgc cccgcgcctc    6240
gaccaagaaa aagaagaatt actacgcaag aaattacagt taaatcccac acctgctaac    6300
agaagcagat accagtccag gaaggtggag aacatgaaag ccataacagc tagacgtatt    6360
ctgcaaggcc tagggcatta tttgaaggca gaaggaaaag tggagtgcta ccgaaccctg    6420
catcctgttc ctttgtattc atctagtgtg aaccgtgcct tttcaagccc caaggtcgca    6480
gtggaagcct gtaacgccat gttgaaagag aactttccga ctgtggcttc ttactgtatt    6540
attccagagt acgatgccta tttggacatg gttgacggag cttcatgctg cttagacact    6600
gccagttttt gccctgcaaa gctgcgcagc tttccaaaga aacactccta tttggaaccc    6660
acaatacgat cggcagtgcc ttcagcgatc cagaacacgc tccagaacgt cctggcagct    6720 gcccacaaaaa gaaattgcaa tgtcacgcaa atgagagaat gcccgtatt ggattcggcg    6780 gcctttaatg tggaatgctt caagaaatat gcgtgtaata atgaatattg ggaaacgttt    6840
aaagaaaacc ccatcaggct tactgaagaa aacgtggtaa attacattac caaattaaaa    6900
ggaccaaaag ctgctgctct ttttgcgaag acacataatt tgaatatgtt gcaggacata    6960
ccaatggaca ggtttgtaat ggacttaaag agagacgtga aagtgactcc aggaacaaaa    7020
catactgaag aacggcccaa ggtacaggtg atccaggctg ccgatccgct agcaacagcg    7080
tatctgtgcg gaatccaccg agagctggtt aggagattaa atgcggtcct gcttccgaac    7140
attcatacac tgtttgatat gtcggctgaa gactttgacg ctattatagc cgagcacttc    7200
cagcctgggg attgtgttct ggaaactgac atcgcgtcgt tgataaaag tgaggacgac    7260 gccatggctc tgaccgcgtt aatgattctg gaagacttag gtgtggacgc agagctgttg    7320
acgctgattg aggcggcttt cggcgaaatt tcatcaatac atttgcccac taaaactaaa    7380
tttaaattcg gagccatgat gaaatctgga atgttcctca cactgtttgt gaacacagtc    7440
```

```
attaacattg taatcgcaag cagagtgttg agagaacggc taaccggatc accatgtgca   7500
gcattcattg gagatgacaa tatcgtgaaa ggagtcaaat cggacaaatt aatggcagac   7560
aggtgcgcca cctggttgaa tatggaagtc aagattatag atgctgtggt gggcgagaaa   7620
gcgccttatt tctgtggagg gtttattttg tgtgactccg tgaccggcac agcgtgccgt   7680
gtggcagacc ccctaaaaag gctgtttaag cttggcaaac ctctggcagc agacgatgaa   7740
catgatgatg acaggagaag ggcattgcat gaagagtcaa cacgctggaa ccgagtgggt   7800
attctttcag agctgtgcaa ggcagtagaa tcaaggtatg aaaccgtagg aacttccatc   7860
atagttatgg ccatgactac tctagctagc agtgttaaat cattcagcta cctgagaggg   7920
gccccctataa ctctctacgg ctaacctgaa tggactacga catagtctag tccgccaaga   7980
tatcggcgcg ccgtttaaac ggccggcctt aattaagtaa cgatacagca gcaattggca   8040
agctgcttac atagaactcg cggcgattgg catgccgctt taaaattttt attttatttt   8100
tcttttcttt tccgaatcgg attttgtttt taatatttca aaaaaaaaaa aaaaaaaaa    8160
aaaaaaaaaa aaaaaaaacc cctctctaaa cggaggggtt ttttcagcg taactggact    8220
ggccacagtt aggcggccgc gcatgttcat catcagtaac ccgtatcgtg agcatcctct   8280
ctcgtttcat cggtatcatt acctccatga acagaaatcc cccttacacg gaggcatcag   8340
tgaccaaaca ggaaaaaacc gcccttaaca tggcccgctt tatcagaagc cagacattaa   8400
cgcttctgga gaaactcaac gagctggacg cggatgaaca ggcagacatc tgtgaatcgc   8460
ttcacgacca cgctgatgag ctttaccgca gctgcctcgc gcgtttcggt gatgacggtg   8520
aaaacctctg acacatgcag ctcccggaga cggtcacagc ttgtctgtaa gcggatgccg   8580
ggagcagaca gcccgtcag ggcgcgtcag cgggtgttgg cgggtgtcgg ggcgcagcca   8640
tgacccagtc acgtagcgat agcggagtgt atactggctt aactatgcgg catcagagca   8700
gattgtactg agagtgcacc atatgcggtg tgaaataccg cacagatgcg taaggagaaa   8760
ataccgcatc aggcgctcgc ttcctcgctc actgactcgc tgcgctcggt cgttcggctg   8820
cggcgagcgg tatcagctca ctcaaaggcg gtaatacggt tatccacaga atcaggggat   8880
aacgcaggaa agaacatgtg agcaaaaggc cagcaaaagg ccaggaaccg taaaaaggcc   8940
gcgttgctgg cgtttttcca taggctccgc cccccctgacg agcatcacaa aaatcgacgc   9000
tcaagtcaga ggtggcgaaa cccgacagga ctataaagat accaggcgtt ccccctgga    9060
agctccctcg tgcgctctcc tgttccgacc ctgccgctta ccggatacct gtccgccttt   9120
ctcccttcgg gaagcgtggc gctttctcat agctcacgct gtaggtatct cagttcggtg   9180
taggtcgttc gctccaagct gggctgtgtg cacgaacccc ccgttcagcc cgaccgctgc   9240
gccttatccg gtaactatcg tcttgagtcc aacccggtaa gacacgactt atcgccactg   9300
gcagcagcca ctggtaacag gattagcaga gcgaggtatg taggcggtgc tacagagttc   9360
ttgaagtggt ggcctaacta cggctacact agaaggacag tatttggtat ctgcgctctg   9420
ctgaagccag ttaccttcgg aaaaagagtt ggtagctctt gatccggcaa acaaaccacc   9480
gctggtagcg gtggtttttt tgtttgcaag cagcagatta cgcgcagaaa aaaaggatct   9540
caagaagatc ctttgatctt ttctacgggg tctgacgctc agtggaacga aaactcacgt   9600
taagggattt tggtcatgag attatcaaaa aggatcttca cctagatcct tttaaattaa   9660
aaatgaagtt ttaaatcaat ctaaagtata tatgagtaaa cttggtctga cagttattag   9720
aaaaattcat ccagcagacg ataaaacgca atacgctggc tatccggtgc cgcaatgcca   9780
tacagcacca gaaaacgatc cgcccattcg ccgcccagtt cttccgcaat atcacgggtg   9840
```

-continued

```
gccagcgcaa tatcctgata acgatccgcc acgcccagac ggccgcaatc aataaagccg    9900
ctaaaacggc cattttccac cataatgttc ggcaggcacg catcaccatg ggtcaccacc    9960
agatcttcgc catccggcat gctcgctttc agacgcgcaa acagctctgc cggtgccagg    10020
ccctgatgtt cttcatccag atcatcctga tccaccaggc ccgcttccat acgggtacgc    10080
gcacgttcaa tacgatgttt cgcctgatga tcaaacggac aggtcgccgg gtccagggta    10140
tgcagacgac gcatggcatc cgccataatg ctcactttt ctgccggcgc cagatggcta    10200
gacagcagat cctgacccgg cacttcgccc agcagcagcc aatcacggcc cgcttcggtc    10260 accatccca gcaccgccgc acacggaaca ccggtggtgg ccagccagct cagacgcgcc    10320
gcttcatcct gcagctcgtt cagcgcaccg ctcagatcgg ttttcacaaa cagcaccgga    10380
cgaccctgcg cgctcagacg aaacaccgcc gcatcagagc agccaatggt ctgctgcgcc    10440
caatcatagc caaacagacg ttccacccac gctgccgggc tacccgcatg caggccatcc    10500
tgttcaatca tactcttcct ttttcaatat tattgaagca tttatcaggg ttattgtctc    10560
atgagcggat acatatttga atgtatttag aaaaataaac aaatagggt tccgcgcaca    10620 tttccccgaa aagtgccacc tgacgtctaa gaaaccatta ttatcatgac attaagcatc    10680
cgcctttcgt tttatttgac catgttggta tg                                  10712
```

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34

```
aaccctctc taaacggagg ggtttttt                                        29
```

<210> SEQ ID NO 35
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35

```
cgcggaaccc ctatttgttt attttttctaa atacattcaa atatgtatcc gctcatgaga    60
caataaccct gataaatgct tcaataatat tgaaaaagga agagt                     105
```

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36

```
ctctctacgg ctaacctgaa tgga                                            24
```

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
taatacgact cactatag                                                 18

<210> SEQ ID NO 38
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aaaaaaaaaa aaaaaaaaaa aaaaaaaaaa aaaaaaaaa                          39

<210> SEQ ID NO 39
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
taggagaaag ttcacgttga catcgaggaa gacagcccat tcctcagagc tttgcagcgg    60
agcttcccgc agtttgaggt agaagccaag caggtcactg ataatgacca tgctaatgcc   120
agagcgtttt cgcatctggc ttcaaaactg atcgaaacgg aggtggaccc atccgacacg   180
atccttgaca ttgga                                                   195

<210> SEQ ID NO 40
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atagtcagca tagtacattt catctgacta atactacaac accaccacca tgaatagagg    60
attctttaac atgctcggcc gccgcccctt cccggccccc actgccatgt ggaggccgcg   120
gagaaggagg caggcggccc cg                                           142

<210> SEQ ID NO 41
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaagcggag ctactaactt cagcctgctg aagcaggctg agacgtgga ggagaaccct    60 ggacct                                                              66

<210> SEQ ID NO 42
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| cgcagccatg | acccagtcac | gtagcgatag | cggagtgtat | actggcttaa | ctatgcggca | 60 |
| tcagagcaga | ttgtactgag | agtgcaccat | atgcggtgtg | aaataccgca | cagatgcgta | 120 |
| aggagaaaat | accgcatcag | g | | | | 141 |

<210> SEQ ID NO 43
<211> LENGTH: 5796
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

| atgaatagag | gattctttaa | catgctcggc | cgccgcccct | tcccggcccc | cactgccatg | 60 |
| tggaggccgc | ggagaaggag | gcaggcggcc | ccgggaagcg | gagctactaa | cttcagcctg | 120 |
| ctgaagcagg | ctggagacgt | ggaggagaac | cctggacctg | agaaagttca | cgttgacatc | 180 |
| gaggaagaca | gcccattcct | cagagctttg | cagcggagct | tcccgcagtt | tgaggtagaa | 240 |
| gccaagcagg | tcactgataa | tgaccatgct | aatgccagag | cgttttcgca | tctggcttca | 300 |
| aaactgatcg | aaacggaggt | ggacccatcc | gacacgatcc | ttgacattgg | aagtgcgccc | 360 |
| gcccgcagaa | tgtattctaa | gcacaagtat | cattgtatct | gtccgatgag | atgtgcggaa | 420 |
| gatccggaca | gattgtataa | gtatgcaact | aagctgaaga | aaaactgtaa | ggaataact | 480 |
| gataaggaat | tggacaagaa | aatgaaggag | ctcgccgccg | tcatgagcga | ccctgacctg | 540 |
| gaaactgaga | ctatgtgcct | ccacgacgac | gagtcgtgtc | gctacgaagg | gcaagtcgct | 600 |
| gtttaccagg | atgtatacgc | ggttgacgga | ccgacaagtc | tctatcacca | agccaataag | 660 |
| ggagttagag | tcgcctactg | gataggcttt | gacaccaccc | cttttatgtt | taagaacttg | 720 |
| gctggagcat | atccatcata | ctctaccaac | tgggccgacg | aaaccgtgtt | aacggctcgt | 780 |
| aacataggcc | tatgcagctc | tgacgttatg | gagcggtcac | gtagagggat | gtccattctt | 840 |
| agaaagaagt | atttgaaacc | atccaacaat | gttctattct | ctgttggctc | gaccatctac | 900 |
| cacgagaaga | gggacttact | gaggagctgg | cacctgccgt | ctgtatttca | cttacgtggc | 960 |
| aagcaaaatt | acacatgtcg | gtgtgagact | atagttagtt | gcgacgggta | cgtcgttaaa | 1020 |
| agaatagcta | tcagtccagg | cctgtatggg | aagccttcag | gctatgctgc | tacgatgcac | 1080 |
| cgcgagggat | tcttgtgctg | caaagtgaca | gacacattga | acggggagag | ggtctctttt | 1140 |
| cccgtgtgca | cgtatgtgcc | agctacattg | tgtgaccaaa | tgactggcat | actggcaaca | 1200 |
| gatgtcagtg | cggacgacgc | gcaaaaactg | ctggttgggc | tcaaccagcg | tatagtcgtc | 1260 |
| aacggtcgca | cccagagaaa | caccaatacc | atgaaaaatt | accttttgcc | cgtagtggcc | 1320 |
| caggcatttg | ctaggtgggc | aaaggaatat | aaggaagatc | aagaagatga | aaggccacta | 1380 |
| ggactacgag | atagacagtt | agtcatgggg | tgttgttggg | cttttagaag | gcacaagata | 1440 |
| acatctattt | ataagcgccc | ggatacccaa | accatcatca | agtgaacag | cgatttccac | 1500 |
| tcattcgtgc | tgcccaggat | aggcagtaac | acattggaga | tcgggctgag | aacaagaatc | 1560 |
| aggaaaatgt | tagaggagca | caaggagccg | tcacctctca | ttaccgccga | ggacgtacaa | 1620 |
| gaagctaagt | gcgcagccga | tgaggctaag | gaggtgcgtg | aagccgagga | gttgcgcgca | 1680 |
| gctctaccac | ctttggcagc | tgatgttgag | gagcccactc | tggaagccga | tgtcgacttg | 1740 |
| atgttacaag | aggctgggc | cggctcagtg | gagacacctc | gtggcttgat | aaaggttacc | 1800 |

```
agctacgatg gcgaggacaa gatcggctct tacgctgtgc tttctccgca ggctgtactc    1860
aagagtgaaa aattatcttg catccaccct ctcgctgaac aagtcatagt gataacacac    1920
tctggccgaa aagggcgtta tgccgtggaa ccataccatg gtaaagtagt ggtgccagag    1980
ggacatgcaa tacccgtcca ggactttcaa gctctgagtg aaagtgccac cattgtgtac    2040
aacgaacgtg agttcgtaaa caggtacctg caccatattg ccacacatgg aggagcgctg    2100
aacactgatg aagaatatta caaaactgtc aagcccagcg agcacgacgg cgaatacctg    2160
tacgacatcg acaggaaaca gtgcgtcaag aaagaactag tcactgggct agggctcaca    2220
ggcgagctgg tggatcctcc cttccatgaa ttcgcctacg agagtctgag aacacgacca    2280
gccgctcctt accaagtacc aaccatanggg gtgtatggcg tgccaggatc aggcaagtct    2340
ggcatcatta aaagcgcagt caccaaaaaa gatctagtgg tgagcgccaa gaaagaaaac    2400
tgtgcagaaa ttataaggga cgtcaagaaa atgaaagggc tggacgtcaa tgccagaact    2460
gtggactcag tgctcttgaa tggatgcaaa caccccgtag agaccctgta tattgacgaa    2520
gcttttgctt gtcatgcagg tactctcaga gcgctcatag ccattataag acctaaaaag    2580
gcagtgctct gcggggatcc caaacagtgc ggttttttta acatgatgtg cctgaaagtg    2640
cattttaacc acgagatttg cacacaagtc ttccacaaaa gcatctctcg ccgttgcact    2700
aaatctgtga cttcggtcgt ctcaaccttg ttttacgaca aaaaaatgag aacgacgaat    2760
ccgaaagaga ctaagattgt gattgacact accggcagta ccaaacctaa gcaggacgat    2820
ctcattctca cttgtttcag agggtgggtg aagcagttgc aaatagatta caaaggcaac    2880
gaaataatga cggcagctgc ctctcaaggg ctgacccgta aagtgtgta tgccgttcgg    2940
tacaaggtga atgaaaatcc tctgtacgca cccacctctg aacatgtgaa cgtcctactg    3000
acccgcacgg aggaccgcat cgtgtggaaa acactagccg gcgacccatg gataaaaaca    3060
ctgactgcca agtaccctgg gaatttcact gccacgatag aggagtggca agcagagcat    3120
gatgccatca tgaggcacat cttggagaga ccggacccta ccgacgtctt ccagaataag    3180
gcaaacgtgt gttgggccaa ggcttagtg ccggtgctga agaccgctgg catagacatg    3240
accactgaac aatggaacac tgtggattat tttgaaacgg acaaagctca ctcagcagag    3300
atagtattga ccaactatg cgtgaggttc tttggactcg atctggactc cggtctatt    3360
tctgcaccca ctgttccgtt atccattagg aataatcact gggataactc cccgtcgcct    3420
aacatgtacg ggctgaataa agaagtggtc cgtcagctct ctcgcaggta cccacaactg    3480
cctcgggcag ttgccactgg aagagtctat gacatgaaca ctggtacact gcgcaattat    3540
gatccgcgca taaacctagt acctgtaaac agaagactgc ctcatgcttt agtcctccac    3600
cataatgaac acccacagag tgacttttct tcattcgtca gcaaattgaa gggcagaact    3660
gtcctggtgg tcggggaaaa gttgtccgtc ccaggcaaaa tggttgactg gttgtcagac    3720
cggcctgagg ctaccttcag agctcggctg gatttaggca tcccaggtga tgtgcccaaa    3780
tatgacataa tatttgttaa tgtgaggacc ccatataaat accatcacta tcagcagtgt    3840
gaagaccatg ccattaagct tagcatgttg accaagaaag cttgtctgca tctgaatccc    3900
ggcggaacct gtgtcagcat aggttatggt tacgctgaca gggccagcga aagcatcatt    3960
ggtgctatag cgcggcagtt caagttttcc cgggtatgca aaccgaaatc ctcacttgaa    4020
gagacggaag ttctgtttgt attcattggg tacgatcgca aggcccgtac gcacaatcct    4080
tacaagcttt catcaacctt gaccaacatt tatacaggtt ccagactcca cgaagccgga    4140
tgtgcaccct catatcatgt ggtgcgaggg gatattgcca cggccaccga aggagtgatt    4200
```

```
ataaatgctg ctaacagcaa aggacaacct ggcggagggg tgtgcggagc gctgtataag    4260
aaattcccgg aaagcttcga tttacagccg atcgaagtag gaaaagcgcg actggtcaaa    4320
ggtgcagcta acatatcat tcatgccgta ggaccaaact tcaacaaagt ttcggaggtt     4380
gaaggtgaca acagttggc agaggcttat gagtccatcg ctaagattgt caacgataac    4440
aattacaagt cagtagcgat tccactgttg tccaccggca tcttttccgg gaacaaagat    4500
cgactaaccc aatcattgaa ccatttgctg acagctttag acaccactga tgcagatgta    4560
gccatatact gcagggacaa gaaatgggaa atgactctca aggaagcagt ggctaggaga    4620
gaagcagtgg aggagatatg catatccgac gactcttcag tgcagaaacc tgatgcagag    4680
ctggtgaggg tgcatccgaa gagttctttg gctggaagga agggctacag cacaagcgat    4740
ggcaaaactt tctcatattt ggaagggacc aagtttcacc aggcggccaa ggatatagca    4800
gaaattaatg ccatgtggcc cgttgcaacg gaggccaatg agcaggtatg catgtatatc    4860
ctcggagaaa gcatgagcag tattaggtcg aaatgccccg tcgaagagtc ggaagcctcc    4920
acaccaccta gcacgctgcc ttgcttgtgc atccatgcca tgactccaga aagagtacag    4980
cgcctaaaag cctcacgtcc agaacaaatt actgtgtgct catcctttcc attgccgaag    5040
tatagaatca ctggtgtgca agatccaa tgctcccagc ctatattgtt ctcaccgaaa    5100
gtgcctgcgt atattcatcc aaggaagtat ctcgtgaaaa caccaccggt agacgagact    5160
ccggagccat cggcagagaa ccaatccaca gaggggacac ctgaacaacc accacttata    5220
accgaggatg agaccaggac tagaacgcct gagccgatca tcatcgaaga ggaagaagag    5280
gatagcataa gtttgctgtc agatggcccg acccaccagg tgctgcaagt cgaggcagac    5340
attcacgggc cgcccctctgt atctagctca tcctggtcca ttcctcatgc atccgacttt    5400
gatgtggaca gtttatccat acttgacacc ctggaggag ctagcgtgac cagcggggca    5460
acgtcagccg agactaactc ttacttcgca aagagtatgg agtttctggc gcgaccggtg    5520
cctgcgcctc gaacagtatt caggaaccct ccacatcccg ctccgcgcac aagaacaccg    5580
tcacttgcac ccagcagggc ctgctcgaga accagcctag tttccacccc gccaggcgtg    5640
aatagggtga tcactagaga ggagctcgag gcgcttaccc cgtcacgcac tcctagcagg    5700
tcggtctcga gaaccagcct ggtctccaac ccgccaggcg taaatagggt gattacaaga    5760
gaggagtttg aggcgttcgt agcacaacaa caatga                             5796
```

<210> SEQ ID NO 44
<211> LENGTH: 2382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
ggctcagtgg agacacctcg tggcttgata aaggttacca gctacgatgg cgaggacaag     60
atcggctctt acgctgtgct ttctccgcag gctgtactca agagtgaaaa attatcttgc    120
atccaccctc tcgctgaaca agtcatagtg ataacacact ctggccgaaa agggcgttat    180
gccgtggaac cataccatgg taaagtagtg gtgccagagg gacatgcaat acccgtccag    240
gactttcaag ctctgagtga agtgccacc attgtgtaca acgaacgtga gttcgtaaac    300
aggtacctgc accatattgc cacacatgga ggagcgctga caactgatga agaatattac    360
aaaactgtca agcccagcga gcacgacggc gaatacctgt acgacatcga caggaaacag    420
```

```
tgcgtcaaga aagaactagt cactgggcta gggctcacag gcgagctggt ggatcctccc    480
ttccatgaat tcgcctacga gagtctgaga acacgaccag ccgctcctta ccaagtacca    540
accatagggg tgtatggcgt gccaggatca ggcaagtctg gcatcattaa aagcgcagtc    600
accaaaaaag atctagtggt gagcgccaag aaagaaaact gtgcagaaat tataagggac    660
gtcaagaaaa tgaaagggct ggacgtcaat gccagaactg tggactcagt gctcttgaat    720
ggatgcaaac accccgtaga gaccctgtat attgacgaag cttttgcttg tcatgcaggt    780
actctcagag cgctcatagc cattataaga cctaaaaagg cagtgctctg cggggatccc    840
aaacagtgcg gttttttttaa catgatgtgc ctgaaagtgc attttaacca cgagatttgc    900
acacaagtct tccacaaaag catctctcgc cgttgcacta aatctgtgac ttcggtcgtc    960
tcaaccttgt tttacgacaa aaaaatgaga acgacgaatc cgaaagagac taagattgtg   1020
attgacacta ccggcagtac caaacctaag caggacgatc tcattctcac ttgtttcaga   1080
gggtgggtga agcagttgca aatagattac aaaggcaacg aaataatgac ggcagctgcc   1140
tctcaagggc tgacccgtaa aggtgtgtat gccgttcggt acaaggtgaa tgaaaatcct   1200
ctgtacgcac ccacctctga acatgtgaac gtcctactga cccgcacgga ggaccgcatc   1260
gtgtggaaaa cactagccgg cgacccatgg ataaaaacac tgactgccaa gtaccctggg   1320
aatttcactg ccacgataga ggagtggcaa gcagagcatg atgccatcat gaggcacatc   1380
ttggagagac cggaccctac cgacgtcttc cagaataagg caaacgtgtg ttgggccaag   1440
gctttagtgc cggtgctgaa gaccgctggc atagacatga ccactgaaca atggaacact   1500
gtggattatt ttgaaacgga caaagctcac tcagcagaga tagtattgaa ccaactatgc   1560
gtgaggttct ttggactcga tctggactcc ggtctatttt ctgcacccac tgttccgtta   1620
tccattagga ataatcactg ggataactcc ccgtcgccta acatgtacgg gctgaataaa   1680
gaagtggtcc gtcagctctc tcgcaggtac ccacaactgc ctcgggcagt tgccactgga   1740
agagtctatg acatgaacac tggtacactg cgcaattatg atccgcgcat aaacctagta   1800
cctgtaaaca gaagactgcc tcatgcttta gtcctccacc ataatgaaca cccacagagt   1860 gactttctt cattcgtcag caaattgaag gcagaactg tcctggtggt cggggaaaag    1920
ttgtccgtcc caggcaaaat ggttgactgg ttgtcagacc ggcctgaggc taccttcaga   1980
gctcggctgg atttaggcat cccaggtgat gtgcccaaat atgacataat atttgttaat   2040
gtgaggaccc catataaata ccatcactat cagcagtgtg aagaccatgc cattaagctt   2100
agcatgttga ccaagaaagc ttgtctgcat ctgaatcccg gcggaacctg tgtcagcata   2160
ggttatggtt acgctgacag ggccagcgaa agcatcattg gtgctatagc gcggcagttc   2220
aagttttccc gggtatgcaa accgaaatcc tcacttgaag agacggaagt tctgtttgta   2280
ttcattgggt acgatcgcaa ggcccgtacg cacaatcctt acaagctttc atcaaccttg   2340
accaacattt atacaggttc cagactccac gaagccggat gt                      2382

<210> SEQ ID NO 45
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
tacatctttt cctccgacac cggtcaaggg catttacaac aaaaatcagt aaggcaaacg     60
```

```
gtgctatccg aagtggtgtt ggagaggacc gaattggaga tttcgtatgc cccgcgcctc      120
gaccaagaaa aagaagaatt actacgcaag aaattacagt taaatcccac acctgctaac      180
agaagcagat accagtccag gaaggtggag aacatgaaag ccataacagc tagacgtatt      240
ctgcaaggcc tagggcatta tttgaaggca gaaggaaaag tggagtgcta ccgaaccctg      300
catcctgttc ctttgtattc atctagtgtg aaccgtgcct tttcaagccc caaggtcgca      360
gtggaagcct gtaacgccat gttgaaagag aactttccga ctgtggcttc ttactgtatt      420
attccagagt acgatgccta tttggacatg gttgacggag cttcatgctg cttagacact      480
gccagttttt gccctgcaaa gctgcgcagc tttccaaaga aacactccta tttggaaccc      540
acaatacgat cggcagtgcc ttcagcgatc cagaacacgc tccagaacgt cctggcagct      600
gccacaaaaa gaaattgcaa tgtcacgcaa atgagagaat tgcccgtatt ggattcggcg      660
gcctttaatg tggaatgctt caagaaatat gcgtgtaata atgaatattg ggaaacgttt      720
aaagaaaacc ccatcaggct tactgaagaa aacgtggtaa attacattac caaattaaaa      780
ggaccaaaag ctgctgctct ttttgcgaag acacataatt tgaatatgtt gcaggacata      840
ccaatggaca ggtttgtaat ggacttaaag agagacgtga agtgactcc aggaacaaaa      900 catactgaag aacggcccaa ggtacaggtg atccaggctg ccgatccgct agcaacagcg      960
tatctgtgcg aatccaccg agagctggtt aggagattaa atgcggtcct gcttccgaac     1020
attcatacac tgtttgatat gtcggctgaa gactttgacg ctattatagc cgagcacttc     1080
cagcctgggg attgtgttct ggaaactgac atcgcgtcgt ttgataaaag tgaggacgac     1140
gccatggctc tgaccgcgtt aatgattctg gaagactag gtgtggacgc agagctgttg     1200
acgctgattg aggcggcttt cggcgaaatt tcatcaatac atttgcccac taaaactaaa     1260
tttaaattcg gagccatgat gaaatctgga atgttcctca cactgtttgt gaacacagtc     1320
attaacattg taatcgcaag cagagtgttg agagaacggc taaccggatc accatgtgca     1380
gcattcattg gagatgacaa tatcgtgaaa ggagtcaaat cggacaaatt aatggcagac     1440
aggtgcgcca cctggttgaa tatggaagtc aagattatag atgctgtggt gggcgagaaa     1500
gcgccttatt tctgtggagg gtttatttg tgtgactccg tgaccggcac agcgtgccgt     1560
gtggcagacc ccctaaaaag gctgtttaag cttggcaaac ctctggcagc agacgatgaa     1620
catgatgatg acaggagaag ggcattgcat gaagagtcaa cacgctggaa ccgagtgggt     1680
attctttcag agctgtgcaa ggcagtagaa tcaaggtatg aaaccgtagg aacttccatc     1740
atagttatgg ccatgactac tctagctagc agtgttaaat cattcagcta cctgagaggg     1800 gccccctataa ctctctacgg c                                              1821

<210> SEQ ID NO 46
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gcaccctcat atcatgtggt gcgaggggat attgccacgg ccaccgaagg agtgattata       60
aatgctgcta acagcaaagg acaacctggc ggaggggtgt gcggagcgct gtataagaaa      120
ttcccggaaa gcttcgattt acagccgatc gaagtaggaa aagcgcgact ggtcaaaggt      180
gcagctaaac atatcattca tgccgtagga ccaaacttca caaagtttc ggaggttgaa      240
```

```
ggtgacaaac agttggcaga ggcttatgag tccatcgcta agattgtcaa cgataacaat    300
tacaagtcag tagcgattcc actgttgtcc accggcatct tttccgggaa caaagatcga    360
ctaacccaat cattgaacca tttgctgaca gctttagaca ccactgatgc agatgtagcc    420
atatactgca gggacaagaa atgggaaatg actctcaagg aagcagtggc taggagagaa    480
gcagtggagg agatatgcat atccgacgac tcttcagtga cagaacctga tgcagagctg    540
gtgagggtgc atccgaagag ttctttggct ggaaggaagg gctacagcac aagcgatggc    600
aaaactttct catatttgga agggaccaag tttcaccagg cggccaagga tatagcagaa    660
attaatgcca tgtggcccgt tgcaacggag gccaatgagc aggtatgcat gtatatcctc    720
ggagaaagca tgagcagtat taggtcgaaa tgccccgtcg aagagtcgga agcctccaca    780
ccacctagca cgctgccttg cttgtgcatc catgccatga ctccagaaag agtacagcgc    840
ctaaaagcct cacgtccaga acaaattact gtgtgctcat cctttccatt gccgaagtat    900
agaatcactg gtgtgcagaa gatccaatgc tcccagccta tattgttctc accgaaagtg    960
cctgcgtata ttcatccaag gaagtatctc gtggaaacac caccggtaga cgagactccg   1020
gagccatcgg cagagaacca atccacagag gggacacctg aacaaccacc acttataacc   1080
gaggatgaga ccaggactag aacgcctgag ccgatcatca tcgaagagga agaagaggat   1140
agcataagtt tgctgtcaga tggcccgacc caccaggtgc tgcaagtcga ggcagacatt   1200
cacgggccgc cctctgtatc tagctcatcc tggtccattc ctcatgcatc cgactttgat   1260
gtggacagtt atccatact tgacaccctg gagggagcta gcgtgaccag cggggcaacg   1320
tcagccgaga ctaactctta cttcgcaaag agtatggagt ttctggcgcg accggtgcct   1380
gcgcctcgaa cagtattcag gaaccctcca catcccgctc cgcgcacaag aacaccgtca   1440
cttgcaccca gcagggcctg ctcgagaacc agcctagttt ccaccccgcc aggcgtgaat   1500
agggtgatca ctagagagga gctcgaggcg cttaccccgt cacgcactcc tagcaggtcg   1560
gtctcgagaa ccagcctggt ctccaacccg ccaggcgtaa atagggtgat tacaagagag   1620
gagtttgagg cgttcgtagc acaacaacaa tgacggtttg atgcgggtgc a            1671
```

<210> SEQ ID NO 47
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
gagaaagttc acgttgacat cgaggaagac agcccattcc tcagagcttt gcagcggagc     60
ttcccgcagt ttgaggtaga agccaagcag gtcactgata atgaccatgc taatgccaga    120
gcgttttcgc atctggcttc aaaactgatc gaaacggagg tggacccatc cgacacgatc    180
cttgacattg gaagtgcgcc cgcccgcaga atgtattcta agcacaagta tcattgtatc    240
tgtccgatga gatgtgcgga agatccggac agattgtata gtatgcaac taagctgaag    300
aaaaactgta aggaaataac tgataaggaa ttggacaaga aaatgaagga gctcgccgcc    360
gtcatgagcg accctgacct ggaaactgag actatgtgcc tccacgacga cgagtcgtgt    420
cgctacgaag gcaagtcgc tgtttaccag gatgtatacg cggttgacgg accgacaagt    480
ctctatcacc aagccaataa gggagttaga gtcgcctact ggataggctt tgacaccacc    540
cctttttatgt ttaagaactt ggctggagca tatccatcat actctaccaa ctgggccgac    600
```

```
gaaaccgtgt taacggctcg taacataggc ctatgcagct ctgacgttat ggagcggtca      660
cgtagaggga tgtccattct tagaaagaag tatttgaaac catccaacaa tgttctattc      720
tctgttggct cgaccatcta ccacgagaag agggacttac tgaggagctg cacctgccg       780 tctgtatttc acttacgtgg caagcaaaat tacacatgtc ggtgtgagac tatagttagt      840
tgcgacgggt acgtcgttaa agaatagct  atcagtccag gcctgtatgg aagccttca       900 ggctatgctg ctacgatgca ccgcgaggga ttcttgtgct gcaaagtgac agacacattg      960
aacggggaga gggtctcttt tcccgtgtgc acgtatgtgc cagctacatt gtgtgaccaa     1020
atgactggca tactggcaac agatgtcagt gcggacgacg cgcaaaaact gctggttggg     1080
ctcaaccagc gtatagtcgt caacggtcgc acccagagaa acaccaatac catgaaaaat     1140 tacctttgc  ccgtagtggc ccaggcattt gctaggtggg caaaggaata taaggaagat     1200
caagaagatg aaaggccact aggactacga gatagacagt tagtcatggg gtgttgttgg     1260
gcttttagaa ggcacaagat aacatctatt tataagcgcc cggataccca aaccatcatc     1320
aaagtgaaca gcgatttcca ctcattcgtg ctgcccagga taggcagtaa cacattggag     1380
atcgggctga gaacaagaat caggaaaatg ttagaggagc acaaggagcc gtcacctctc     1440
attaccgccg aggacgtaca agaagctaag tgcgcagccg atgaggctaa ggaggtgcgt     1500
gaagccgagg agttgcgcgc agctctacca cctttggcag ctgatgttga ggagcccact     1560
ctggaagccg atgtcgactt gatgttacaa gaggctgggg cc                       1602

<210> SEQ ID NO 48
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atgattgaac aggatggcct gcatgcgggt agcccggcag cgtgggtgga acgtctgttt       60
ggctatgatt gggcgcagca gaccattggc tgctctgatg cggcggtgtt tcgtctgagc      120
gcgcagggtc gtccggtgct gtttgtgaaa accgatctga gcggtgcgct gaacgagctg      180
caggatgaag cggcgcgtct gagctggctg gccaccaccg tgttccgtg  tgcggcggtg      240 ctggatgtgg tgaccgaagc gggccgtgat tggctgctgc tgggcgaagt gccgggtcag      300
gatctgctgt ctagccatct ggcgccggca gaaaaagtga gcattatggc ggatgccatg      360
cgtcgtctgc ataccctgga cccggcgacc tgtccgtttg atcatcaggc gaaacatcgt      420
attgaacgtg cgcgtacccg tatggaagcg gcctggtgg  atcaggatga tctggatgaa      480
gaacatcagg gcctggcacc ggcagagctg tttgcgcgtc tgaaagcgag catgccggat      540
ggcgaagatc tggtggtgac ccatggtgat gcgtgcctgc cgaacattat ggtgaaaaat      600 ggccgttta  gcggctttat tgattgcggc cgtctgggcg tggcggatcg ttatcaggat      660
attgcgctgg ccacccgtga tattgcggaa gaactgggcg gcgaatgggc ggatcgtttt      720
ctggtgctgt atggcattgc ggcaccggat agccagcgta ttgcgttta  tcgtctgctg      780 gatgaatttt tctaataa                                                    798

<210> SEQ ID NO 49
<211> LENGTH: 192
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 49

```
gtgaccaaac aggaaaaaac cgcccttaac atggcccgct ttatcagaag ccagacatta    60
acgcttctgg agaaactcaa cgagctggac gcggatgaac aggcagacat ctgtgaatcg   120
cttcacgacc acgctgatga gctttaccgc agctgcctcg cgcgtttcgg tgatgacggt   180
gaaaacctct ga                                                       192
```

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
ataggcggcg catgagagaa gcccagacca attacctacc caaa                     44
```

<210> SEQ ID NO 51
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
atacagcagc aattggcaag ctgcttacat agaactcgcg gcgattggca tgccgcttta    60 aaattttat tttatttttc ttttcttttc cgaatcggat tttgttttta atatttc       117
```

<210> SEQ ID NO 52
<211> LENGTH: 845
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
ccattgcata cgttgtatcc atatcataat atgtacattt atattggctc atgtccaaca    60
ttaccgccat gttgacattg attattgact agttattaat agtaatcaat tacggggtca   120
ttagttcata gcccatatat ggagttccgc gttacataac ttacggtaaa tggcccgcct   180
ggctgaccgc ccaacgaccc ccgcccattg acgtcaataa tgacgtatgt tcccatagta   240
acgccaatag ggactttcca ttgacgtcaa tgggtggagt atttacggta aactgcccac   300
ttggcagtac atcaagtgta tcatatgcca agtacgcccc ctattgacgt caatgacggt   360
aaatggcccg cctggcatta tgcccagtac atgaccttat gggactttcc tacttggcag   420
tacatctacg tattagtcat cgctattacc atggtgatgc ggttttggca gtacatcaat   480
gggcgtggat agcggtttga ctcacgggga tttccaagtc tccacccat tgacgtcaat   540 gggagtttgt tttggcacca aaatcaacgg gactttccaa aatgtcgtaa caactccgcc   600
ccattgacgc aaatgggcgg taggcgtgta cggtgggagg tctatataag cagagctctc   660
cctatcagtg atagagatct ccctatcagt gatagagatc gtcgacgagc tcgtttagtg   720
aaccgtcaga tcgcctggag acgccatcca cgctgttttg acctccatag aagacaccgg   780
```

```
gaccgatcca gcctccgcgg ccgggaacgg tgcattggaa cgcggattcc ccgtgccaag      840
agtga                                                                  845
```

<210> SEQ ID NO 53
<211> LENGTH: 227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
ctgtgccttc tagttgccag ccatctgttg tttgcccctc ccccgtgcct tccttgaccc       60
tggaaggtgc cactcccact gtcctttcct aataaaatga ggaaattgca tcgcattgtc      120
tgagtaggtg tcattctatt ctggggggtg gggtggggca ggacagcaag ggggaggatt      180
gggaagacaa tagcaggcat gctggggatg cggtgggctc tatggcc                   227
```

<210> SEQ ID NO 54
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Val
65                  70                  75
```

<210> SEQ ID NO 55
<211> LENGTH: 4
<212> TYPE: PRT
<213> ORGANISM: Unknown
<220> FEATURE:
<223> OTHER INFORMATION: Description of Unknown:
      "KDEL" motif peptide

<400> SEQUENCE: 55

```
Lys Asp Glu Leu
1
```

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 56

His His Ala Ala
1

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Lys Ser Tyr Leu
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Lys Ser Tyr
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Glu Lys Arg
1
```

VACCINES BASED ON MUTANT CALR AND JAK2 AND THEIR USES

CROSS-REFERENCE TO RELATED APPLICATIONS

This application claims priority to U.S. Provisional Application No. 62/936,841, filed Nov. 18, 2019, and U.S. Provisional Application No. 62/936,846, filed Nov. 18, 2019, the disclosure of each of which are hereby incorporated by reference in its entirety.

SEQUENCE LISTING

The instant application contains a Sequence Listing which has been submitted electronically in ASCII format and is hereby incorporated by reference in its entirety. The ASCII copy, created on Apr. 9, 2024, is named 103693.002008_SL.txt and is 66,689 bytes in size.

FIELD

Provided are vaccines, polypeptides and polynucleotides based on mutant calreticulin (CALR) and Janus Kinase 2 (JAK2) sequences, vectors, host cells, viruses, and methods of making and using them.

BACKGROUND

The classical myeloproliferative neoplasms (MPNs), also called BCR-ABL-MPNs, are the most frequent diseases among the myeloproliferative disorders. MPNs are characterized by excessive production of terminally differentiated blood cells that are fully functional. Classical MPNs have been classified into three entities: polycythemia vera (PV), essential thrombocythemia (ET), and primary myelofibrosis (PMF), which have frequent disease-related complications, such as venous and arterial thrombosis, hemorrhages, and transformation to acute myeloid leukemia (AML). All MPN entities arise from a single somatically mutated hematopoietic stem cell (HSC) that clonally expands and gives rise to virtually all myeloid cells, and B and NK cells. The clonal expansion of the MPN HSC is accompanied by single- or multi-lineage hyperplasia.

PV is characterized not only by an excess of erythrocytes and predominant erythroid lineage involvement but is also associated with a variable hyperplasia of the megakaryocytic/granulocytic lineages. ET is characterized by an increased platelet count with a megakaryocytic hyperplasia, whereas PMF is a more heterogeneous disorder, defined by the presence of bone marrow fibrosis (specifically excess of collagen fibers) and megakaryocytic hyperplasia. Myeloproliferation in PMF initially predominates in the bone marrow and later expands to extramedullary sites, such as the spleen. Diagnosis at disease onset is often challenging, but a 2016 revision of the World Health Organization (WHO) diagnostic criteria for MPN is helping to define both the molecular, clinical, and symptomatic presentation of MPN. However, in many patients, progression of ET and PV to secondary myelofibrosis (MF) is observed. Furthermore, boundaries between these three disorders cannot be well established, especially between ET and PMF. Thus, transitional entities may emerge describing disease states such as prefibrotic PMF (or early PMF) that displays an ET phenotype at diagnosis with typical bone marrow histology, but with a high probability of progression to MF and worse prognosis than true ET.

More than 50% of patients with MPNs harbor the JAK2V617F mutation. In addition, mutations in exon 9 of the calreticulin (CALR) gene are found in approximately 60% of patients with JAK2 wild type essential thrombocytemia (ET) or primary myelofibrosis (PMF).

In 2005, a G to T somatic mutation at Nucleotide 1849, in Exon 14 of JAK2 was discovered. This mutation, results in the substitution of valine to phenylalanine at Codon 617 (V617F) in the pseudokinase domain of JAK2. This mutation can be found in around 70% of myeloproliferative neoplasms (MPNs): 95% of polycythemia vera (PV) and 50% to 60% of ET and PMF. JAK2V617F often undergoes a transition from heterozygosity to homozygosity due to occurrence of mitotic recombination resulting in copy-neutral loss of heterozygosity along a variable size region on the short arm of Chromosome 9 (9pLOH). JAK2V617F arises in a multipotent hematopoietic progenitor, is present in all myeloid lineages, and can be also detected in lymphoid cells, mainly B and natural killer (NK) cells and more rarely and later in disease in T cells. J AK2V617F is mainly restricted to classical MPNs with the exception of refractory anemia with ring sideroblasts and thrombocytosis (RARS T). However, JAK2V617F has been detected at very low level (lower than 1%) in the normal population, including in a neonate. It is one of the most frequent mutations found in the clonal hematopoiesis associated with aging (clonal hematopoiesis of indeterminate potential). Presence of JAK2V71F mutations leads to constitutive activation of signal transducer and activator of transcription (STAT) signaling leading to increased cell proliferation, activation, and autocrine/paracrine release. JAK2V617F mutation has also been identified in patients with cardiovascular indications.

In 2013, frameshift mutations in Exon 9 of the CALR gene were identified in essential thrombocythemia (ET) and primary myelofibrosis (PMF) patients that were negative for the V617F mutation in the JAK2 gene (JAK2V617F) and for mutations in the thrombopoietin receptor (MPL) gene. Over 50 frameshift mutations were identified, with >85% leading to an identical 44-amino-acid-mutant C terminal tail. Mutation of the C terminal tail removes a KDEL motif (SEQ ID NO: 55) leading to loss of endoplasmic reticulum (ER) retention and translocation to the cell surface membrane. Additionally, the mutant version of CALR has a positively charged C terminal tail that disrupts Ca2+ binding and that limits canonical function. The two most frequent CALR mutations correspond to a 52 bp deletion (p.L367fs*46), also called Type 1, and a 5 bp insertion (p.K385fs*47), also called Type 2. There are great differences in the frequency between Type 1 and Type 2 mutations in ET and PMF: in ET, Type 1 and Type 2 mutations are closely distributed (55% versus 35%), whereas in PMF, Type 1 are largely predominant (75% versus 15%) Altogether, these results indicate that mutant CALR is an oncogenic driver and that CALRmut induces transformation through the MPL-JAK2-STAT signaling pathway.

MPN patients have high symptom burden, life-threatening complications, and risk of progression to acute leukemia while also having limited treatment options. MPN patient treatments are best divided into the categories of observation, medical therapies, and allogeneic stem cell transplantation (allo-SCT). Medical therapies themselves fall into the categories of cytoreductive agents, single-agent JAK inhibitors, and the immunomodulatory agent interferon (IFN)-α. The current standard of care, and only approved therapeutic, specifically for patients with MPN, is the small-molecule JAK1/2 inhibitor JAKAFI© (ruxolitinib). JAKAFI© (ruxolitinib) was the first targeted US food and drug administration (FDA)-approved medication for intermediate to high risk PMF and post-polycythemia vera myelofibrosis (PPV-MF) and post-essential thrombocythemia myelofibrosis (PET-MF) but has also gained approval in both the PV and graft-versus-host disease (GVHD) patient population more recently. Efficacy was established in the COMFORT-I and COMFORT-II studies and showed significant reduction in spleen size as the primary endpoint. However, discontinuation due to loss of response, disease progression and treatment-related adverse events involved about 50% of the patients at 3 years and 75% at 5 years. JAKAFI© (ruxolitinib) therapy has also been associated with increased risk for aggressive B-cell lymphoma in MF patients. Indeed, in a study of 107 MF patients that discontinued JAKAFI© (ruxolitinib) treatment, the medium overall survival was just 14 months. Although there is a subset of patients that may derive a survival benefit with JAKAFI© (ruxolitinib) use, the majority of MPN patients continue to progress in their disease.

SUMMARY

The disclosure provides a polypeptide comprising at least two or more epitope sequences of the following: Janus kinase 2 (JAK2) epitope of SEQ ID NO: 6 (FCGDENILV), JAK2 epitope of SEQ ID NO: 5. (VLNYGVCFC), JAK2 epitope of SEQ ID NO: 4 (KLSHKH LVLNYGVCFCGDENILVQEFVKFG), calreticulin (CALR) epitope of SEQ ID NO: 1 (MKDKQDEEQRTRRMMRTKMRMRRMRRTRRKMRRKMSPARPRTSCREACLQGWTE) and CALR epitope of SEQ ID NO: 2 (EEAEDNCRRMMRTK).

The disclosure also provides a polypeptide comprising two or more repeats of SEQ ID NO: 6. In some embodiments, the polypeptide comprises 2, 3, 4, 5, or more than 5 repeats of SEQ ID NO: 6 separated by a linker sequence such as AAY, RR or DPP, HHAA (SEQ ID NO: 56), HHA, HHL, RKSYL (SEQ ID NO: 57), RKSY (SEQ ID NO: 58), SSL, or REKR (SEQ ID NO: 59).

The disclosure also provides a polypeptide of SEQ ID NO:28 (FCGDENILVAA YFCGDENILV) comprising two polypeptides of SEQ ID NO: 6 linked by the non-natural linker sequence AAY.

The disclosure also provides polynucleotides encoding for the polypeptides disclosed herein and vectors comprising the polynucleotides encoding for the polypeptides disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, comprising administering to a subject in need thereof any of the polynucleotides, polypeptides or vectors disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises a plurality of administrations of any of the compositions comprising polynucleotides, polypeptides or vectors disclosed herein.

The disclosure also provides administering an anti-CTLA-4 antibody, an anti-PD-1 or an anti-PD-L1 antibody in combination with any of the compositions comprising polynucleotides, polypeptides or vectors disclosed herein.

The disclosure also provides methods of inducing an immune response and methods of treating, preventing, reducing a risk of onset or delaying the onset of a clinical condition characterized by an expression of JAK2V617F or CALR exon 9 mutant, or both JAK2V617F and CALR exon 9 mutant, wherein the method comprises administering two or more times to a subject in need thereof a vector comprising a polynucleotide encoding JAK2 epitope of SEQ ID NO: 6 (FCGDENILV), JAK2 epitope of SEQ ID NO: 5 (VLNYGVCFC), CALR epitope of SEQ ID NO: 1 (MKDKQDEEQRTRRMMRTKMRMRRMRRTRRKMRRKMSPARPRTSCRE ACLQGWTE) and CALR epitope of SEQ ID NO: 2 (EEAEDNCRRMMRTK); wherein the vector is Ad26, GAd20, MVA or a self-replicating RNA.

In some embodiments, the method of inducing an immune response and the methods of treating, preventing, reducing a risk of onset or delaying the onset of a clinical condition characterized by an expression of JAK2V617F or CALR exon 9 mutant, or both JAK2V617F and CALR exon 9 mutant, comprises administering two or more times to a subject in need thereof a vector comprising a polynucleotide encoding a polypeptide comprising two or more repeats of SEQ ID NO: 6; wherein the vector is Ad26, GAd20, MVA or a self-replicating RNA.

The disclosure also provides methods for treating or preventing a myeloproliferative disease in a subject, wherein the method comprises administering two or more times to a subject in need thereof a vector comprising a polynucleotide encoding JAK2 epitope of SEQ ID NO: 6 (FCGDENTLV), JAK2 epitope of SEQ ID NO: 5 (VLNYGVCFC), CALR epitope of SEQ ID NO: 1 (MKDKQDEEQRTRRMMRTKMRMRRMRRTRRKMRRKMSPARPRTSCREAC LQGWTE) and CALR epitope of SEQ ID NO: 2 (EEAEDNCRRMMRTK); wherein the vector is Ad26, GAd20, MVA or a self-replicating RNA.

BRIEF DESCRIPTION OF THE DRAWINGS

FIG. 21B shows self-replicating RNA LS.CALR-JAK2-2×9mer primes anti-CALR CD4 T cell responses. The data shows IFNγ, TNFα and IL-2 production of splenocytes restimulated with overlapping CALR peptides measured by flow cytometry. Symbols represent individual mice (n=5), bars represent mean with SD. **p<0.01, Mann-Whitney test.

FIG. 22B shows lipid nanoparticle formulated self-replicating RNALS.CALR-JAK2-2×9mer priming anti-CALR CD4 T cell responses. The data shows IFNγ, TNFα and IL-2 production of splenocytes restimulated with overlapping CALR peptides measured by flow cytometry. Symbols represent individual mice (n=5), bars represent mean with SD.*p<0.05, **p<0.01, Mann-Whitney test.

DETAILED DESCRIPTION

Definitions

Figure 1:
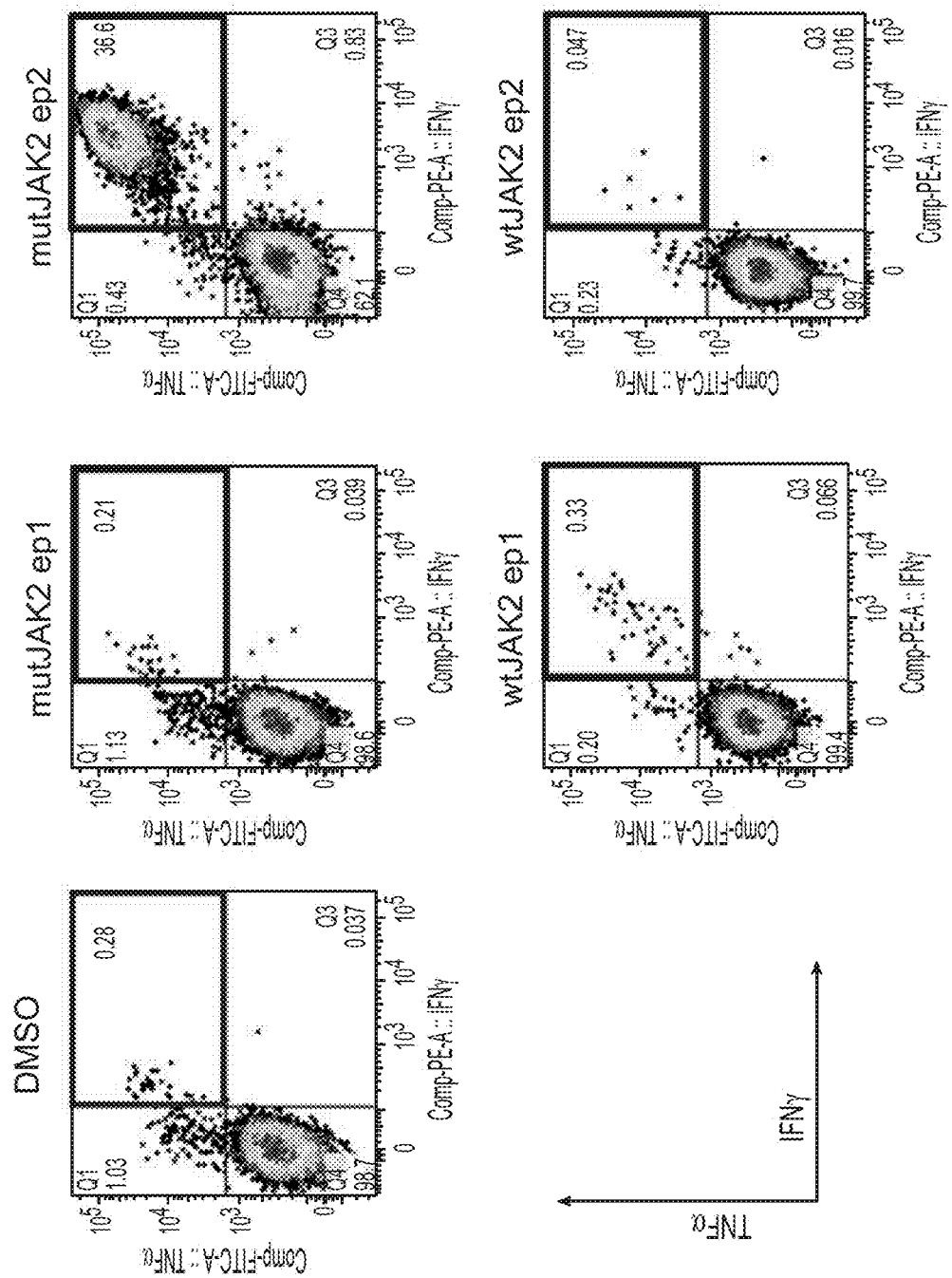
FIG. 1 shows JAK2 V617F+ HLA A02:01+ MPN donor T-cell response to mutJAK2 class I epitopes 1 and 2.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Adjuvant" and "immune stimulant" are used interchangeably herein and are defined as one or more substances that cause stimulation of the immune system. In this context, an adjuvant is used to enhance an immune response to the vaccines of the disclosure.

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Antigen presenting cell" (APC) refers to any cell that presents on its surface an antigen in association with a major histocompatibility complex molecule, either MHC class I or MHC class II molecule, or both.

"Antibody" refers to an immunoglobulin molecule including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649, Int. Pat. Publ. No. WO1994/13804 or Int. Pat. Publ. No. WO1992/01047.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"CALR" refers to human calreticulin. Human CALR protein comprises an amino acid sequence as shown for example in UniProt accession number P27797.

"Downstream loop" or "DLP motif" refers to a polynucleotide sequence comprising at least one RNA stem-loop, which when placed downstream of a start codon of an open reading frame (ORF) provides increased translation the ORF compared to an otherwise identical construct without the DLP motif.

"Enhance" or "induce" when in reference to an immune response refers to increasing the scale and/or efficiency of an immune response or extending the duration of the immune response. The terms are used interchangeably with "augment".

"Epitope sequence" as used herein, refers to a part of a polypeptide or an amino acid sequence, for example a part of the primary, secondary, tertiary, or quaternary structure of the polypeptide or an amino acid sequence, that is recognized by the immune system, for example antibodies, B cells (e.g., B lymphocytes) and/or T cells.

"Expression vector" refers to a vector that can be utilized in a biological system or in a reconstituted biological system to direct the translation of a polypeptide encoded by a polynucleotide sequence present in the expression vector.

"Facilitator element" refers to any polynucleotide or polypeptide element that is operably linked to a polynucleotide or a polypeptide, and include promoters, enhancers, polyadenylation signals, stop codons, protein tags, such as histidine tag, and the like.

"Heterologous" refers to two or more polynucleotides or two or more polypeptides that are not found in the same relationship to each other in nature.

"Immunogenic fragment" refers to a polypeptide that is recognized by cytotoxic T lymphocytes, helper T lymphocytes or B cells when the fragment is in complex with MHC class I or MHC class II molecules.

"In-frame" refers to the reading frame of codons in a first polynucleotide being the same as the reading frame of codons in a second polynucleotide which are joined together to form a polynucleotide. In-frame polynucleotide encodes a polypeptide encoded by both the first polynucleotide and the second polynucleotide.

"Immunogenic" refers to a polypeptide that comprises one or more immunogenic fragments.

"Immune response" refers to any response to an immunogenic polypeptide or polynucleotide or fragment by the immune system of a vertebrate subject. Exemplary immune responses include local and systemic cellular as well as humoral immunity, such as cytotoxic T lymphocyte (CTL) responses, including antigen-specific induction of CD8+ CTLs, helper T-cell responses including T-cell proliferative responses and cytokine release, and B-cell responses including antibody response.

"In combination with" means that two or more therapeutic agents are be administered to a subject together in a mixture, concurrently as single agents or sequentially as single agents in any order.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"JAK2" refers to human Janus kinase 2. Human JAK2 protein comprises an amino acid sequence as shown for example in UniPort accession number 0060674.

"Mutant CALR" refers to CALR harboring one or more exon 9 mutations.

"Mutant JAK2" refers to JAK2 harboring V617F mutation.

"Non-naturally occurring" refers to a molecule that does not exist in nature.

"Operatively linked" sequences refers to both expression control sequences that are contiguous with the nucleic acid sequences that they regulate and regulatory sequences that act in trans, or at a distance to control the regulated nucleic acid sequence.

"Philadelphia chromosome" or "Ph" refers to a well-known chromosomal translocation between chromosomes 9 and 22, resulting in the oncogenic BCR-ABL gene fusion with constitutively active tyrosine kinase activity. The translocation results in a portion of the BCR gene from chromosome 22q11 becoming fused with a portion of the ABL gene from chromosome 9q34, and is designated as t(9;22)(q34;q1 1) under the International System for Human Cytogenetic Nomenclature (ISCN). Depending on the precise location of the fusion, the molecular weight of the resulting fusion protein can range from 185 to 210 kDa. "Philadelphia chromosome" refers to all BCR-ABL fusion proteins formed due the (9;22)(q34;q1 1) translocation.

"Polynucleotide" refers to a molecule comprising a chain of nucleotides covalently linked by a sugar-phosphate backbone or other equivalent covalent chemistry. Examples of polynucleotides include RNA and DNA.

"Polypeptide" or "protein" refers to a molecule that comprises at least two amino acid residues linked by a peptide bond to form a polypeptide.

"Prevent", "preventing", "prevention", or "prophylaxis" of a disease or disorder means preventing that a disorder occurs in subject.

"Prime-boost" or "prime-boost regimen" refers to a method of treating a subject involving priming a T-cell response with a first vaccine followed by boosting the immune response with a second vaccine. The first vaccine and the second vaccine are typically distinct. These prime-boost immunizations elicit immune responses of greater height and breadth than can be achieved by priming and boosting with the same vaccine. The priming step initiates memory cells and the boost step expands the memory response. Boosting can occur once or multiple times.

"Recombinant" refers to polynucleotides, polypeptides, vectors, viruses and other macromolecules that are prepared, expressed, created or isolated by recombinant means.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Replicon" refers to a viral nucleic acid that is capable of directing the generation of copies of itself and includes RNA as well as DNA. For example, double-stranded DNA versions of arterivirus genomes can be used to generate a single-stranded RNA transcript that constitutes an arterivirus replicon. Generally, a viral replicon contains the complete genome of the virus.

"RNA replicon" (or "self-replicating RNA", or "self-replicating RNA molecule" or "srRNA") refer to RNA molecule which contains all of the genetic information required for directing its own amplification or self-replicating within a permissive cell. To direct its own replication, the RNA molecule: 1) encodes polymerase, replicase, or other proteins which may interact with viral or host cell-derived proteins, nucleic acids or ribonucleoproteins to catalyze the RNA amplification process; and 2) contains cis-acting RNA sequences required for replication and transcription of the replicon-encoded RNA. Self-replicating RNA molecule is typically derived from the genomes of positive strand RNA viruses and can be used as a basis of introducing foreign sequences to host cells by replacing viral sequences encoding structural or non-structural genes or inserting the foreign sequences 5' or 3' of the sequences encoding the structural or non-structural genes. Foreign sequences may be introduced into the subgenomic regions of alphaviruses. Self-replicating RNA molecule may be packaged into recombinant virus particles, such as recombinant alphavirus particles or alternatively delivered to the host using lipid nanoparticles (LNP). Self-replicating RNA may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. Self-replicating RNAs are described, for example, in WO2017/180770, WO2018/075235, and WO2019143949A2.

"Specifically binds", "specific binding", "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant (KD) of about 1×10-7 M or less, for example about 5×10-8 M or less, about 1×10-8 M or less, about 1×10-9 M or less, about 1×10-10 M or less, about 1×10-11 M or less, or about 1×10-12 M or less, typically with the KD that is at least one hundred fold less than its KD for binding to a non-specific antigen (e.g., BSA, casein). In the context of the molecules described herein, "specific binding" refers to binding of the proteinaceous molecule to the CALR/JAK2 mutant polypeptides, CALR mutant polypeptides or JAK2 mutant polypeptides alone or in complex with HLA without detectable binding to a wild-type CALR or JAK2 alone or in complex with HLA.

"Subgenomic RNA" refers to an RNA molecule of a length or size which is smaller than the genomic RNA from which it was derived. The viral subgenomic RNA can be transcribed from an internal promoter, whose sequences reside within the genomic RNA or its complement. Transcription of a subgenomic RNA can be mediated by viral-encoded polymerase(s) associated with host cell-encoded proteins, ribonucleoprotein(s), or a combination thereof. Numerous RNA viruses generate subgenomic mRNAs (sgRNAs) for expression of their 3'-proximal genes. The viral subgenomic RNA can be transcribed from an internal promoter, whose sequences reside within the genomic RNA or its complement. Transcription of a subgenomic RNA can be mediated by viral-encoded polymerase(s) associated with host cell-encoded proteins, ribonucleoprotein(s), or a combination thereof.

"Subgenomic replicon" refers to a viral nucleic acid that contains something less than the full complement of genes and other features of the viral genome, yet is still capable of directing the generation of copies of itself. For example, the sub-genomic replicons of arterivirus may contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subject have previously had the disorder, or limiting or preventing recurrence of symptoms in subjects that were previously symptomatic for the disorder.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the subject.

"Vaccine" refers to a composition that comprises one or more immunogenic polypeptides, polynucleotides encoding immunogenic polypeptides or fragments, vectors comprising polynucleotides encoding immunogenic polypeptides, or any combination thereof intentionally administered to induce acquired immunity in the recipient (e.g. subject).

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Viral vector" refers to a vector construct that includes at least one polynucleotide element of viral origin and has the capacity to be packaged into a viral vector particle.

"Variant", "mutant" or "altered" refers to a polypeptide or a polynucleotide that differs from a reference polypeptide or a reference polynucleotide by one or more modifications, for example one or more substitutions, insertions or deletions.

Polypeptides

Disclosed herein are polypeptides comprising epitope sequences of mutant CALR and mutant JAK2 that may elicit an immune response in a subject. In some embodiments, the polypeptide may comprise at least two or more epitope sequences selected from the group consisting of:

CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;

CALR epitope of SEQ ID NO: 2 (EEAEDN-CRRMMRTK) or having at least 90% sequence identity to SEQ ID NO: 2;

JAK2 epitope of SEQ ID NO: 4 (KLSHKHLVLNYGVCFCGDENILVQEFVKFG) or having at least 90% sequence identity to SEQ ID NO: 4;

JAK2 epitope of SEQ ID NO: 5 (VLNYGVCFC) or at least 90% sequence identity to SEQ ID NO: 5;

JAK2 epitope of SEQ ID NO: 6 (FCGDENILV) or having at least 90% sequence identity to SEQ ID NO: 6; and combinations thereof.

In some embodiments, the disclosure provides a polypeptide comprising epitope sequences of CALR epitope of SEQ ID NO: 1 or having at least 90% sequence identity to SEQ ID NO: 1; CALR epitope of SEQ ID NO: 2 or having at least 90% sequence identity to SEQ ID NO: 2; and JAK2 epitope of SEQ ID NO: 4 or having at least 90% sequence identity to SEQ ID NO: 4. The epitope sequences of SEQ ID NO: 1, 2, and 4 may be present in any order and can be separated by a linker. Exemplary linker sequences include AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the disclosure provides a polypeptide comprising epitope sequences of Janus kinase 2 (JAK2) epitope of SEQ ID NO: 6 or having at least 90% sequence identity to SEQ ID NO: 6, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 1, and 2 may be present in any order and can be separated by a linker. Exemplary linker sequences include AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the disclosure also provides a polypeptide comprising epitope sequences of Janus kinase 2 (JAK2) epitope of SEQ ID NO: 6 or having at least 90% sequence identity to SEQ ID NO: 6, JAK2 epitope of SEQ ID NO: 5 or having at least 90% sequence identity to SEQ ID NO: 5, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 5, 1, and 2 may be present in any order and can be separated by a linker, such as AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

The disclosure also provides a polypeptide comprising amino acid sequences of one or more of the following: SEQ ID NO: 12, SEQ ID NO: 10, SEQ ID NO: 13, SEQ ID NO: 11, SEQ ID NO: 3, SEQ ID NO: 4, SEQ ID NO: 6, SEQ ID NO: 7, SEQ ID NO: 28, SEQ ID NO: 31, or an immunogenic fragment thereof.

In some embodiments, the disclosure provides a polypeptide comprising an amino acid sequence of SEQ ID NO: 3 or having at least 90% sequence identity, or at least 95% sequence identity, or at least 99% sequence identity to SEQ ID NO: 3.

In some embodiments, the disclosure provides a polypeptide comprising an amino acid sequence of SEQ ID NO: 4 or having at least 90% sequence identity, or at least 95% sequence identity, or at least 99% sequence identity to SEQ ID NO: 4.

In some embodiments, the disclosure provides a polypeptide comprising an amino acid sequence of SEQ ID NO: 7 or having at least 90% sequence identity, or at least 95% sequence identity, or at least 99% sequence identity to SEQ ID NO: 7.

In some embodiments, the disclosure provides a polypeptide comprising an amino acid sequence of SEQ ID NO: 9 or having at least 90% sequence identity, or at least 95% sequence identity, or at least 99% sequence identity to SEQ ID NO: 9.

In some embodiments, the disclosure provides a polypeptide comprising an amino acid sequence of SEQ ID NO: 10 or having at least 90% sequence identity, or at least 95% sequence identity, or at least 99% sequence identity to SEQ ID NO: 10.

In some embodiments, the disclosure provides a polypeptide comprising an amino acid sequence of SEQ ID NO: 11 or having at least 90% sequence identity, or at least 95% sequence identity, or at least 99% sequence identity to SEQ ID NO: 11.

In some embodiments, the disclosure provides a polypeptide comprising an amino acid sequence of SEQ ID NO: 12 or having at least 90% sequence identity, or at least 95% sequence identity, or at least 99% sequence identity to SEQ ID NO: 12.

In some embodiments, the disclosure provides a polypeptide comprising an amino acid sequence of SEQ ID NO: 13 or having at least 90% sequence identity, or at least 95% sequence identity, or at least 99% sequence identity to SEQ ID NO: 13.

In some embodiments, the disclosure provides a polypeptide comprising an amino acid sequence of SEQ ID NO: 14 or having at least 90% sequence identity, or at least 95% sequence identity, or at least 99% sequence identity to SEQ ID NO: 14.

In some embodiments, the disclosure provides a polypeptide comprising an amino acid sequence of SEQ ID NO: 15 or having at least 90% sequence identity, or at least 95% sequence identity, or at least 99% sequence identity to SEQ ID NO: 15.

In some embodiments, the disclosure provides a polypeptide comprising an amino acid sequence of SEQ ID NO: 28 or having at least 90% sequence identity, or at least 95% sequence identity, or at least 99% sequence identity to SEQ ID NO: 28.

In some embodiments, the disclosure provides a polypeptide comprising an amino acid sequence of SEQ ID NO: 31 or having at least 90% sequence identity, or at least 95% sequence identity, or at least 99% sequence identity to SEQ ID NO: 31.

In some embodiments, the polypeptide comprises a polypeptide comprising an amino acid sequence of SEQ ID NO: 6 or having at least 90% sequence identity, or at least 95% sequence identity, or at least 99% sequence identity to SEQ ID NO: 6. The disclosure also provides a polypeptide comprising two or more repeats of SEQ ID NO: 6. In some embodiments, the polypeptide comprises 2, 3, 4, 5, or more than 5 repeats of SEQ ID NO: 6. In some embodiments, the repeats of SEQ ID NO: 6 can be separated by a linker. Exemplary linker sequences include AAY, RR or DPP, HHAA (SEQ ID NO: 56), HHA, HHL, RKSYL (SEQ ID NO: 57), RKSY (SEQ ID NO: 58), SSL, or REKR (SEQ ID NO: 59).

In some embodiments, the linkers disclosed herein may comprise a protease cleavage site such that the polypeptides may be cleaved in vivo in a subject into peptide fragments comprising epitope sequences, resulting in improved immune response.

In some embodiments, the polypeptides of the disclosure may further comprise a leader sequence or T-cell enhancer sequence (TCE) at the N-terminus. Leader sequences can increase the expression and/or increase immunological response. Exemplary leader sequences include the α chain of the TCR receptor of T$^2$ lymphocytes (HAVT20) (MACPGFLWALVISTC LEFSMA; SEQ ID NO: 8), a ubiquitin signal sequence (Ubiq) (MQIFVKTLTGKTITLEVEPSDTIENVKAKIQDKEGIPPDQQRLIF-AGKQLEDGRTLSDYNIQKESTLHLVLRLRGV; SEQ ID NO: 54), or a T cell enhancer (TCE) sequence, such as a peptide fragment of length of 28aa from the mandarin fish invariant chain (MGQKEQIHTLQKNSERMSKQL-TRSSQAV; SEQ ID NO: 29). It is believed that the leader sequences may help in increasing an immune response to the epitopes disclosed herein.

Polynucleotides

The disclosure also provides polynucleotides that encode any of the polypeptides disclosed herein.

In some embodiments, the polynucleotide encodes a polypeptide that comprises at least two or more epitope sequences selected from the group consisting of:
  CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;
  CALR epitope of SEQ ID NO: 2 (EEAEDN-CRRMMRTK) or having at least 90% sequence identity to SEQ ID NO: 2;
  JAK2 epitope of SEQ ID NO: 4 (KLSHKHLVLNYGVCFCGDENILVQEFVKFG) or having at least 90% sequence identity to SEQ ID NO: 4;
  JAK2 epitope of SEQ ID NO: 5 (VLNYGVCFC) or at least 90% sequence identity to SEQ ID NO: 5;
  JAK2 epitope of SEQ ID NO: 6 (FCGDENILV) or having at least 90% sequence identity to SEQ ID NO: 6; and combinations thereof.

In some embodiments, the disclosure provides a polynucleotide encoding a polypeptide comprising epitope sequences of CALR epitope of SEQ ID NO: 1 or having at least 90% sequence identity to SEQ ID NO: 1; CALR epitope of SEQ ID NO: 2 or having at least 90% sequence identity to SEQ ID NO: 2; and JAK2 epitope of SEQ ID NO: 4 or having at least 90% sequence identity to SEQ ID NO: 4. The epitope sequences of SEQ ID NO: 1, 2, and 4 may be present in any order and can be separated by a linker.

In some embodiments, the disclosure provides a polynucleotide encoding a polypeptide comprising epitope sequences of Janus kinase 2 (JAK2) epitope of SEQ ID NO: 6 (FCGDENILV) or having at least 90% sequence identity to SEQ ID NO: 6, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 1, and 2 may be present in any order and can be separated by a linker.

In some embodiments, the disclosure provides a polynucleotide encoding a polypeptide comprising epitope sequences of Janus kinase 2 (JAK2) epitope of SEQ ID NO: 6 or having at least 90% sequence identity to SEQ ID NO: 6, JAK2 epitope of SEQ ID NO: 5 or having at least 90% sequence identity to SEQ ID NO: 5, calreticulin (CALR) epitope of SEQ ID NO: 1 or having at least 90% sequence identity to SEQ ID NO: 1, and CALR epitope of SEQ ID NO: 2 or having at least 90% sequence identity to SEQ ID NO: 2. The epitope sequences of SEQ ID NO: 6, 5, 1, and 2 may be present in any order and can be separated by a linker.

In some embodiments, the isolated polynucleotide encodes a polypeptide comprising an amino acid sequence of SEQ ID NO: 3 or having at least 90% sequence identity, or at least 95% sequence identity, or at least 99% sequence identity to SEQ ID NO: 3.

In some embodiments, the isolated polynucleotide encodes a polypeptide comprising an amino acid sequence of SEQ ID NO: 4 or having at least 90% sequence identity, or at least 95% sequence identity, or at least 99% sequence identity to SEQ ID NO: 4.

In some embodiments, the isolated polynucleotide encodes a polypeptide comprising an amino acid sequence of SEQ ID NO: 7 or having at least 90% sequence identity, or at least 95% sequence identity, or at least 99% sequence identity to SEQ ID NO: 7.

In some embodiments, the isolated polynucleotide encodes a polypeptide comprising an amino acid sequence of SEQ ID NO: 12 or having at least 90% sequence identity, or at least 95% sequence identity, or at least 99% sequence identity to SEQ ID NO: 12.

In some embodiments, the isolated polynucleotide encodes a polypeptide comprising an amino acid sequence of SEQ ID NO: 13 or having at least 90% sequence identity, or at least 95% sequence identity, or at least 99% sequence identity to SEQ ID NO: 13.

In some embodiments, the isolated polynucleotide encodes a polypeptide comprising an amino acid sequence of SEQ ID NO: 6 or having at least 90% sequence identity, or at least 95% sequence identity, or at least 99% sequence identity to SEQ ID NO: 6.

The disclosure also provides an isolated polynucleotide encoding a polypeptide comprising two or more repeats of SEQ ID NO: 6. In some embodiments, the polynucleotide encodes for a polypeptide comprising 2, 3, 4, 5, or more than 5 repeats of SEQ ID NO: 6. In some embodiments, the repeats of SEQ ID NO: 6 can be separated by a linker.

In some embodiments, the polynucleotide is selected from the group consisting of: a nucleic acid sequence of SEQ ID NO: 16 or having at least 90% sequence identity, or at least 95% sequence identity, or at least 99% sequence identity to SEQ ID NO: 16; a nucleic acid sequence of SEQ ID NO: 17 or having at least 90% sequence identity, or at least 95% sequence identity, or at least 99% sequence identity to SEQ ID NO: 17; a nucleic acid sequence of SEQ ID NO: 18 or having at least 90% sequence identity, or at least 95% sequence identity, or at least 99% sequence identity to SEQ ID NO: 18; a nucleic acid sequence of SEQ ID NO: 19 or having at least 90% sequence identity, or at least 95% sequence identity, or at least 99% sequence identity to SEQ ID NO: 19; a nucleic acid sequence of SEQ ID NO: 20 or having at least 90% sequence identity, or at least 95% sequence identity, or at least 99% sequence identity to SEQ ID NO: 20; a nucleic acid sequence of SEQ ID NO: 21 or having at least 90% sequence identity, or at least 95% sequence identity, or at least 99% sequence identity to SEQ ID NO: 21; a nucleic acid sequence of SEQ ID NO: 22 or having at least 90% sequence identity, or at least 95% sequence identity, or at least 99% sequence identity to SEQ ID NO: 22; a nucleic acid sequence of SEQ ID NO: 26 or having at least 90% sequence identity, or at least 95% sequence identity, or at least 99% sequence identity to SEQ ID NO: 26; and a nucleic acid sequence of SEQ ID NO: 27 or having at least 90% sequence identity, or at least 95% sequence identity, or at least 99% sequence identity to SEQ ID NO: 27.

In some embodiments, the polynucleotide comprises DNA.

In some embodiments, the polynucleotide comprises RNA.

In some embodiments, RNA is mRNA or self-replicating RNA.

In some embodiments, the polynucleotide comprises a promoter, an enhancer, a polyadenylation site, a Kozak sequence, a stop codon, or any combination thereof.

Methods of generating polynucleotides of the disclosure are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Vectors

The disclosure also provides vectors comprising any of the polynucleotides disclosed herein. The disclosure also provides vectors comprising a polynucleotide encoding for any of the polypeptides disclosed herein.

In some embodiments, the vector comprises a polynucleotide encoding a polypeptide that comprises at least two or more epitope sequences selected from the group consisting of:

CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;

CALR epitope of SEQ ID NO: 2 (EEAEDN-CRRMMRTK) or having at least 90% sequence identity to SEQ ID NO: 2;

JAK2 epitope of SEQ ID NO: 4 (KLSHKHLVLNYGVCFCGDENILVQEFVKFG) or having at least 90% sequence identity to SEQ ID NO: 4;

JAK2 epitope of SEQ ID NO: 5 (VLNYGVCFC) or at least 90% sequence identity to SEQ ID NO: 5;

JAK2 epitope of SEQ ID NO: 6 (FCGDENILV) or having at least 90% sequence identity to SEQ ID NO: 6; and combinations thereof.

The vector may be a vector intended for expression of the polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors or artificial chromosomes.

Suitable vectors that may be used are—Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWL-neo, pSV2cat, pOG44, PXR1, pSG (Stratagene), pSVK3, pBPV, pMSG and pSVL (Pharmacia).

The disclosure provides an expression vector comprising the polynucleotide of the disclosure. The disclosure also provides an expression vector comprising the polynucleotide encoding for the polypeptide of the disclosure.

The disclosure also provides a viral vector comprising any of the polynucleotides of the disclosure.

The disclosure also provides a viral vector comprising a polynucleotide encoding any of the polypeptides of the disclosure.

Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), Great ape adenovirus vectors (GAd), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, and bacterial spores.

In some embodiments, the viral vector is derived from adenovirus, poxvirus, alphavirus, adeno-associated virus, retrovirus or a self-replicating RNA molecule.

Adenoviral Vectors

In some embodiments, the viral vector is derived from an adenovirus.

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (Pan), Gorilla (Gorilla), Orangutan (Pongo), Bonobo (Panpaniscus) and common chimpanzee (Pan troglodytes). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus (GAd) vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Figure 6:
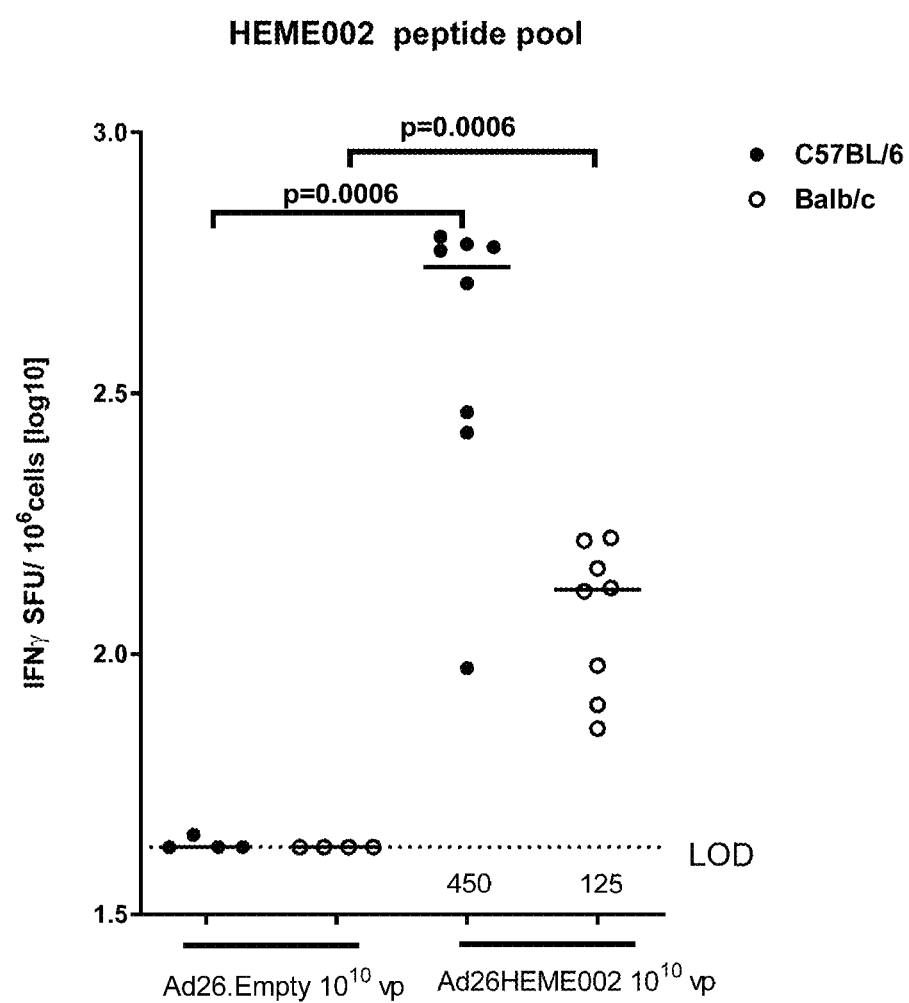
FIG. 6 shows IFN-γ ELISpot responses in splenocytes from C57BL/6 or Balb/c mice immunized IM with Ad26HEME002 (LS_CALR_JAK2-2×9mer, SEQ ID NO: 10) (n=8/group) or Ad26.Empty (n=4) at a dose of $10^{10}$ VP, at 2 weeks post immunization. Splenocytes were stimulated overnight with a 15-mer peptide pool spanning the HEME002 sequence. The number of IFN-γ SFU per $10^6$ splenocytes was determined by ELISpot. The mean response per group is indicated with a horizontal line. The dotted lines indicate the background of the assay defined as the 95% percentile of SFU observed in non-stimulated splenocytes (43 SFU/$10^6$ cells). Statistical analysis was done using Wilcoxon Rank Sum test, values below 43 SFU/$10^6$ cells were set to this cut-off. VP, virus particle; LOD, limit of detection.

Adenovirus vectors are known in the art. The sequences of most of the human and non-human adenoviruses are known, and for others can be obtained using routine procedures. An exemplary genome sequence of Ad26 is found in GenBank Accession number EF153474 and in SEQ ID NO: 1 of Int. Pat. Publ. No. WO2007/104792. An exemplary genome sequence of Ad35 is found in FIG. 6 of Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

Adenovirus vectors are engineered to comprise at least one functional deletion or a complete removal of a gene product that is essential for viral replication, such as one or more of the adenoviral regions E1, E2 and E4, therefore rendering the adenovirus to be incapable of replication. The deletion of the E1 region may comprise deletion of EIA, EIB 55K or EIB 21K, or any combination thereof. Replication deficient adenoviruses are propagated by providing the proteins encoded by the deleted region(s) in trans by the producer cell by utilizing helper plasmids or engineering the produce cell to express the required proteins. Adenovirus vectors may also have a deletion in the E3 region, which is dispensable for replication, and hence such a deletion does not have to be complemented. The adenovirus vector of the disclosure may comprise a functional deletion or a complete removal of the E1 region and at least part of the E3 region. The adenovirus vector of the disclosure may further comprise a functional deletion or a complete removal of the E4 region and/or the E2 region. Suitable producer cells that can be utilized are human retina cells immortalized by E1, e.g. 911 or PER.C6 cells (see, e.g., U.S. Pat. No. 5,994,128), E1-transformed amniocytes (See, e.g., EP 1230354), E 1-transformed A549 cells (see e.g. Int. Pat. Publ. No. WO1998/39411, U.S. Pat. No. 5,891,690). Exemplary vectors that may be used are Ad26 comprising a functional E1 coding region that is sufficient for viral replication, a deletion in the E3 coding region and a deletion in the E4 coding region, provided that E4 open reading frame 6/7 is not deleted (see e.g. U.S. Pat. No. 9,750,801)

In some embodiments, the adenovirus vector is a human adenovirus (Ad) vector. In some embodiments, the Ad vector is derived from Ad5. In some embodiments, the Ad vector is derived from Ad11. In some embodiments, the Ad vector is derived from Ad7. In some embodiments, the Ad vector is derived from Ad26. In some embodiments, the Ad vector is derived from Ad34. In some embodiments, the Ad vector is derived from Ad35. In some embodiments, the Ad vector is derived from Ad48. In some embodiments, the Ad vector is derived from Ad49. In some embodiments, the Ad vector is derived from Ad50.

In some embodiments, the adenovirus vector is a great ape adenovirus (GAd) vector. In some embodiments, the GAd vector is derived from GAd20. In some embodiments, the GAd vector is derived from GAd19. In some embodiments, the GAd vector is derived from GAd21. In some embodiments, the GAd vector is derived from GAd25. In some embodiments, the GAd vector is derived from GAd26. In some embodiments, the GAd vector is derived from GAd27. In some embodiments, the GAd vector is derived from GAd28. In some embodiments, the GAd vector is derived from GAd29. In some embodiments, the GAd vector is derived from GAd30. In some embodiments, the GAd vector is derived from GAd31. In some embodiments, the GAd vector is derived from ChAd3. In some embodiments, the GAd vector is derived from ChAd4. In some embodiments, the GAd vector is derived from ChAd5. In some embodiments, the GAd vector is derived from ChAd6. In some embodiments, the GAd vector is derived from ChAd7. In some embodiments, the GAd vector is derived from ChAd8. In some embodiments, the GAd vector is derived from ChAd9. In some embodiments, the GAd vector is derived from ChAd9. In some embodiments, the GAd vector is derived from ChAd10. In some embodiments, the GAd vector is derived from ChAd11. In some embodiments, the GAd vector is derived from ChAd16. In some embodiments, the GAd vector is derived from ChAd17. In some embodiments, the GAd vector is derived from ChAd19. In some embodiments, the GAd vector is derived from ChAd20. In some embodiments, the GAd vector is derived from ChAd22. In some embodiments, the GAd vector is derived from ChAd24. In some embodiments, the GAd vector is derived from ChAd26. In some embodiments, the GAd vector is derived from ChAd30. In some embodiments, the GAd vector is derived from ChAd31. In some embodiments, the GAd vector is derived from ChAd32. In some embodiments, the GAd vector is derived from ChAd31. In some embodiments, the GAd vector is derived from ChAd33. In some embodiments, the GAd vector is derived from ChAd37. In some embodiments, the GAd vector is derived from ChAd38. In some embodiments, the GAd vector is derived from ChAd44. In some embodiments, the GAd vector is derived from ChAd55. In some embodiments, the GAd vector is derived from ChAd63. In some embodiments, the GAd vector is derived from ChAd68. In some embodiments, the GAd vector is derived from ChAd73. In some embodiments, the GAd vector is derived from ChAd82. In some embodiments, the GAd vector is derived from ChAd83. GAd19-21 and GAd25-31 are described in Int. Pat. Publ. No. WO2019/008111 and represents strains with high immunogenicity and no pre-existing immunity in the general human population. The polynucleotide sequence of GAd20 genome is disclosed in Int. Pat. Publ. No. WO2019/008111.

The polynucleotides of the disclosure may be inserted into a site or region (insertion region) in the vector that does not affect virus viability of the resultant recombinant virus. The polynucleotides of the disclosure may be inserted into the deleted E1 region in parallel (transcribed 5' to 3') or anti-parallel (transcribed in a 3' to 5' direction relative to the vector backbone) orientation. In addition, appropriate transcriptional regulatory elements that are capable of directing expression of the polypeptide or the polypeptide of the disclosure in the mammalian host cells that the vector is being prepared for use may be operatively linked to the polypeptide or the polypeptide of the disclosure.

Recombinant adenoviral particles may be prepared and propagated according to any conventional technique in the field of the art (e.g., Int. Pat. Publ. No. WO1996/17070) using a complementation cell line or a helper virus, which supplies in trans the missing viral genes necessary for viral replication. The cell lines 293, PER.C6, E1 A549 and 911 are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and Int. Pat. Publ. No. WO1997/04119). The adenoviral particles may be recovered from the culture supernatant but also from the cells after lysis and optionally further purified according to standard techniques (e.g., chromatography, ultracentrifugation, as described in Int. Pat. Publ. No. WO1996/27677, Int. Pat.

Publ. No. WO1998/00524, Int. Pat. Publ. No. WO1998/26048 and Int. Pat. Publ. No. WO2000/50573). The construction and methods for propagating adenoviral vectors are also described in for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

Provided herein is a viral vector comprising any of the polynucleotides of the disclosure, wherein the vector is derived from hAd26 (also referred to has Ad26).

In some embodiments, the Ad26 vector comprises a polynucleotide of SEQ ID NO: 16 or having at least 90% sequence identity, or at least 95% sequence identity, or at least 99% sequence identity to SEQ ID NO: 16.

In some embodiments, the Ad26 vector comprises a polynucleotide of SEQ ID NO: 17 or having at least 90% sequence identity, or at least 95% sequence identity, or at least 99% sequence identity to SEQ ID NO: 17.

In some embodiments, the Ad26 vector comprises a polynucleotide of SEQ ID NO: 18 or having at least 90% sequence identity, or at least 95% sequence identity, or at least 99% sequence identity to SEQ ID NO: 18.

In some embodiments, the Ad26 vector comprises a polynucleotide of SEQ ID NO: 19 or having at least 90% sequence identity, or at least 95% sequence identity, or at least 99% sequence identity to SEQ ID NO: 19.

In some embodiments, the Ad26 vector comprises a polynucleotide of SEQ ID NO: 20 or having at least 90% sequence identity, or at least 95% sequence identity, or at least 99% sequence identity to SEQ ID NO: 20.

In some embodiments, the Ad26 vector comprises a polynucleotide of SEQ ID NO: 21 or having at least 90% sequence identity, or at least 95% sequence identity, or at least 99% sequence identity to SEQ ID NO: 21.

In some embodiments, the Ad26 vector comprises a polynucleotide of SEQ ID NO: 22 or having at least 90% sequence identity, or at least 95% sequence identity, or at least 99% sequence identity to SEQ ID NO: 22.

In some embodiments, the Ad26 vector comprises a polynucleotide of SEQ ID NO: 23 or having at least 90% sequence identity, or at least 95% sequence identity, or at least 99% sequence identity to SEQ ID NO: 23.

In some embodiments, the Ad26 vector comprises a polynucleotide of SEQ ID NO: 24 or having at least 90% sequence identity, or at least 95% sequence identity, or at least 99% sequence identity to SEQ ID NO: 24.

In some embodiments, the Ad26 vector comprises a polynucleotide of SEQ ID NO: 25 or having at least 90% sequence identity to SEQ ID NO: 25.

In some embodiments, the Ad26 vector comprises a polynucleotide of SEQ ID NO: 26 or having at least 90% sequence identity, or at least 95% sequence identity, or at least 99% sequence identity to SEQ ID NO: 26.

In some embodiments, the Ad26 vector comprises a polynucleotide of SEQ ID NO: 27 or having at least 90% sequence identity, or at least 95% sequence identity, or at least 99% sequence identity to SEQ ID NO: 27.

In some embodiments, the Ad26 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the Ad26 vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the Ad26 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the Ad26 vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the Ad26 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the Ad26 vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the Ad26 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the Ad26 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the Ad26 vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the Ad26 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the Ad26 vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the Ad26 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the Ad26 vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the Ad26 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the Ad26 vector comprises a polynucleotide encoding an amino acid sequence of SEQ ID NO: 31 or having at least 90% sequence identity, or at least 95% sequence identity, or at least 99% sequence identity to SEQ ID NO: 31.

Provided herein is a viral vector comprising any of the polynucleotides of the disclosure, wherein the vector is derived from GAd20.

In some embodiments, the GAd20 vector comprises a polynucleotide of SEQ ID NO: 16 or having at least 90% sequence identity, or at least 95% sequence identity, or at least 99% sequence identity to SEQ ID NO: 16.

In some embodiments, the GAd20 vector comprises a polynucleotide of SEQ ID NO: 17 or having at least 90% sequence identity, or at least 95% sequence identity, or at least 99% sequence identity to SEQ ID NO: 17.

In some embodiments, the GAd20 vector comprises a polynucleotide of SEQ ID NO: 18 or having at least 90% sequence identity, or at least 95% sequence identity, or at least 99% sequence identity to SEQ ID NO: 18.

In some embodiments, the GAd20 vector comprises a polynucleotide of SEQ ID NO: 19 or having at least 90% sequence identity, or at least 95% sequence identity, or at least 99% sequence identity to SEQ ID NO: 19.

In some embodiments, the GAd20 vector comprises a polynucleotide of SEQ ID NO: 20 or having at least 90% sequence identity, or at least 95% sequence identity, or at least 99% sequence identity to SEQ ID NO: 20.

In some embodiments, the GAd20 vector comprises a polynucleotide of SEQ ID NO: 21 or having at least 90% sequence identity, or at least 95% sequence identity, or at least 99% sequence identity to SEQ ID NO: 21.

In some embodiments, the GAd20 vector comprises a polynucleotide of SEQ ID NO: 22 or having at least 90% sequence identity, or at least 95% sequence identity, or at least 99% sequence identity to SEQ ID NO: 22.

In some embodiments, the GAd20 vector comprises a polynucleotide of SEQ ID NO: 23 or having at least 90% sequence identity, or at least 95% sequence identity, or at least 99% sequence identity to SEQ ID NO: 23.

In some embodiments, the GAd20 vector comprises a polynucleotide of SEQ ID NO: 24 or having at least 90% sequence identity, or at least 95% sequence identity, or at least 99% sequence identity to SEQ ID NO: 24.

In some embodiments, the GAd20 vector comprises a polynucleotide of SEQ ID NO: 25 or having at least 90% sequence identity, or at least 95% sequence identity, or at least 99% sequence identity to SEQ ID NO: 25.

In some embodiments, the GAd20 vector comprises a polynucleotide of SEQ ID NO: 26 or having at least 90% sequence identity, or at least 95% sequence identity, or at least 99% sequence identity to SEQ ID NO: 26.

In some embodiments, the GAd20 vector comprises a polynucleotide of SEQ ID NO: 27 or having at least 90% sequence identity, or at least 95% sequence identity, or at least 99% sequence identity to SEQ ID NO: 27.

In some embodiments, the GAd20 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the GAd20 vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the GAd20 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the GAd20 vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the GAd20 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the GAd20 vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the GAd20 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the GAd20 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the GAd20 vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the GAd20 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the GAd20 vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the GAd20 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the GAd20 vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the GAd20 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the GAd20 vector comprises a polynucleotide encoding an amino acid sequence of SEQ ID NO: 31 or having at least 90% sequence identity, or at least 95% sequence identity, or at least 99% sequence identity to SEQ ID NO: 31.

Poxvirus Vectors

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC or Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (Meyer et al., J. Gen. Virol., 72: 1031-1038 (1991) and U.S. Pat. No. 10,035,832). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007.) Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). It was shown in a variety of animal models that the resulting MVA was significantly avirulent (Mayr, A. & Danner, K. Vaccination against pox diseases under immunosuppressive conditions, Dev. Biol. Stand. 41: 225-34, 1978). Being that many passages were used to attenuate MVA, there are a number of different strains or isolates, depending on the passage number in CEF cells, such as MVA 476 MG/14/78, MVA-571, MVA-572, MVA-574, MVA-575 and MVA-BN. MVA 476 MG/14/78 is described for example in Int. Pat. Publ. No. WO2019/115816A1. MVA-572 strain was deposited at the European Collection of Animal Cell Cultures ("ECACC"), Health Protection Agency, Microbiology Services, Porton Down, Salisbury SP4 OJG, United Kingdom ("UK"), under the deposit number ECACC 94012707 on Jan. 27, 1994. MVA-575 strain was deposited at the ECACC under deposit number ECACC 00120707 on Dec. 7, 2000; MVA-Bavarian Nordic ("MVA-BN") strain was deposited at the ECACC under deposit number V00080038 on Aug. 30, 2000. The genome sequences of MVA-BN and MVA-572 are available at GenBank (Accession numbers DQ983238 and DQ983237, respectively). The genome sequences of other MVA strains can be obtained using standard sequencing methods.

Vectors and viruses of the disclosure may be derived from any MVA strain or further derivatives of the MVA strain. A further exemplary MVA strain is deposit VR-1508, deposited at the American Type Culture collection (ATCC), Manassas, Va. 20108, USA.

Derivatives of MVA refer to viruses exhibiting essentially the same characteristics as the parent MVA but exhibiting differences in one or more parts of their genomes.

In some embodiments, the MVA vector is derived from MVA 476 MG/14/78. In some embodiments, the MVA vector is derived from MVA-571. In some embodiments, the MVA vector is derived from MVA-572. In some embodiments, the MVA vector is derived from MVA-574. In some embodiments, the MVA vector is derived from MVA-575. In some embodiments, the MVA vector is derived from MVA-BN.

The polynucleotide of the disclosure may be inserted into a site or region (insertion region) in the MVA vector that does not affect virus viability of the resultant recombinant virus. Such regions can be readily identified by testing segments of virus DNA for regions that allow recombinant formation without seriously affecting virus viability of the recombinant virus. The thymidine kinase (TK) gene is an insertion region that may be used and is present in many viruses, such as in all examined poxvirus genomes. Additionally, MVA contains 6 natural deletion sites, each of which may be used as insertion sites (e.g. deletion I, II, III, IV, V, and VI; see e.g. U.S. Pat. Nos. 5,185,146 and 6,440,442). One or more intergenic regions (IGR) of the MVA may also be used as an insertion site, such as IGRs IGR07/08, IGR 44/45, IGR 64/65, IGR 88/89, IGR 136/137, and IGR 148/149 (see e.g. U.S. Pat. Publ. No. 2018/0064803). Additional suitable insertion sites are described in Int. Pat. Publ. No. WO2005/048957.

Recombinant poxviral particles such as rMVA are prepared as described in the art (Piccini, et al., 1987, Methods of Enzymology 153: 545-563; U.S. Pat. Nos. 4,769,330; 4,772,848; 4,603,112; 5,100,587 and 5,179,993). In an exemplary method, the DNA sequence to be inserted into the virus can be placed into an E. coli plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within E. coli bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences. rMVA particles may be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

Provided herein is a viral vector comprising any of the polynucleotides of the disclosure, wherein the vector is derived from MVA.

In some embodiments, the MVA vector comprises a polynucleotide of SEQ ID NO: 16 or having at least 90% sequence identity, or at least 95% sequence identity, or at least 99% sequence identity to SEQ ID NO: 16.

In some embodiments, the MVA vector comprises a polynucleotide of SEQ ID NO: 17 or having at least 90% sequence identity, or at least 95% sequence identity, or at least 99% sequence identity to SEQ ID NO: 17.

In some embodiments, the MVA vector comprises a polynucleotide of SEQ ID NO: 18 or having at least 90% sequence identity, or at least 95% sequence identity, or at least 99% sequence identity to SEQ ID NO: 18.

In some embodiments, the MVA vector comprises a polynucleotide of SEQ ID NO: 19 or having at least 90% sequence identity, or at least 95% sequence identity, or at least 99% sequence identity to SEQ ID NO: 19.

In some embodiments, the MVA vector comprises a polynucleotide of SEQ ID NO: 20 or having at least 90% sequence identity, or at least 95% sequence identity, or at least 99% sequence identity to SEQ ID NO: 20.

In some embodiments, the MVA vector comprises a polynucleotide of SEQ ID NO: 21 or having at least 90% sequence identity, or at least 95% sequence identity, or at least 99% sequence identity to SEQ ID NO: 21.

In some embodiments, the MVA vector comprises a polynucleotide of SEQ ID NO: 22 or having at least 90% sequence identity, or at least 95% sequence identity, or at least 99% sequence identity to SEQ ID NO: 22.

In some embodiments, the MVA vector comprises a polynucleotide of SEQ ID NO: 23 or having at least 90% sequence identity, or at least 95% sequence identity, or at least 99% sequence identity to SEQ ID NO: 23.

In some embodiments, the MVA vector comprises a polynucleotide of SEQ ID NO: 24 or having at least 90% sequence identity, or at least 95% sequence identity, or at least 99% sequence identity to SEQ ID NO: 24.

In some embodiments, the MVA vector comprises a polynucleotide of SEQ ID NO: 25 or having at least 90% sequence identity, or at least 95% sequence identity, or at least 99% sequence identity to SEQ ID NO: 25.

In some embodiments, the MVA vector comprises a polynucleotide of SEQ ID NO: 26 or having at least 90% sequence identity, or at least 95% sequence identity, or at least 99% sequence identity to SEQ ID NO: 26.

In some embodiments, the MVA vector comprises a polynucleotide of SEQ ID NO: 27 or having at least 90% sequence identity, or at least 95% sequence identity, or at least 99% sequence identity to SEQ ID NO: 27.

In some embodiments, the MVA vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the MVA vector comprises a polynucleotide encoding an amino acid sequence of SEQ ID NO: 2 or having at least 90% sequence identity, or at least 95% sequence identity, or at least 99% sequence identity to SEQ ID NO: 2.

In some embodiments, the MVA vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the MVA vector comprises a polynucleotide encoding an amino acid sequence of SEQ ID NO: 4 or having at least 90% sequence identity, or at least 95% sequence identity, or at least 99% sequence identity to SEQ ID NO: 4.

In some embodiments, the MVA vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the MVA vector comprises a polynucleotide encoding an amino acid sequence of SEQ ID NO: 6 or having at least 90% sequence identity, or at least 95% sequence identity, or at least 99% sequence identity to SEQ ID NO: 6.

In some embodiments, the MVA vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the MVA vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the MVA vector comprises a polynucleotide encoding an amino acid sequence of SEQ ID NO: 10 or having at least 90% sequence identity, or at least 95% sequence identity, or at least 99% sequence identity to SEQ ID NO: 10.

In some embodiments, the MVA vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the MVA vector comprises a polynucleotide encoding an amino acid sequence of SEQ ID NO: 12 or having at least 90% sequence identity, or at least 95% sequence identity, or at least 99% sequence identity to SEQ ID NO: 12.

In some embodiments, the MVA vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the MVA vector comprises a polynucleotide encoding an amino acid sequence of SEQ ID NO: 14 or having at least 90% sequence identity, or at least 95% sequence identity, or at least 99% sequence identity to SEQ ID NO: 14.

In some embodiments, the MVA vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the MVA vector comprises a polynucleotide encoding an amino acid sequence of SEQ ID NO: 31 or having at least 90% sequence identity, or at least 95% sequence identity, or at least 99% sequence identity to SEQ ID NO: 31.

Self-replicating RNA Molecules

Self-replicating RNA may be derived from alphavirus. Alphaviruses may belong to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

The self-replicating RNA molecules can be derived from alphavirus genomes, meaning that they have some of the structural characteristics of alphavirus genomes, or similar to them. The self-replicating RNA molecules can be derived from modified alphavirus genomes.

Self-replicating RNA molecules may be derived from Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV).

In some embodiments, the alphavirus-derived self-replicating RNA molecule is a Venezuelan equine encephalitis virus (VEEV).

The self-replicating RNA molecules can contain RNA sequences from (or amino acid sequences encoded by) a wild-type New World or Old World alphavirus genome. Any of the self-replicating RNA molecules disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome.

Self-replicating RNA molecules contain all of the genetic information required for directing their own amplification or self-replication within a permissive cell. To direct their own replication, self-replicating RNA molecules encode polymerase, replicase, or other proteins which may interact with viral or host cell-derived proteins, nucleic acids or ribonucleoproteins to catalyze the RNA amplification process; and contain cis-acting RNA sequences required for replication and transcription of the replicon-encoded RNA. Thus, RNA replication leads to the production of multiple daughter RNAs. These daughter RNAs, as well as collinear subgenomic transcripts, can be translated to provide in situ expression of a gene of interest, or can be transcribed to provide further transcripts with the same sense as the delivered RNA which are translated to provide in situ expression of the gene of interest. The overall results of this sequence of transcriptions is a huge amplification in the number of the introduced replicon RNAs and so the encoded gene of interest becomes a major polypeptide product of the cells.

Figure 18A:
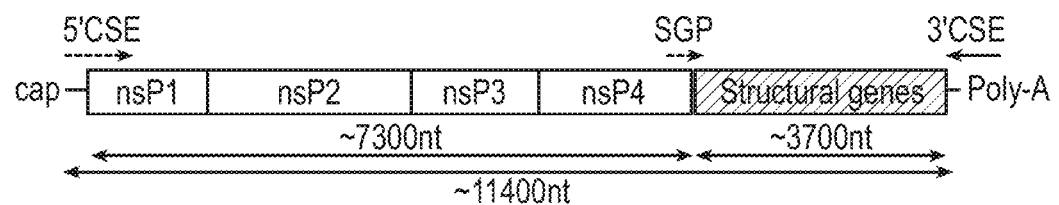
FIG. 18A shows the schematic representation of the alphavirus genome of the Semliki Forest virus, a positive-sensed, single-stranded RNA that encodes the non-structural polyproteins (nsP1-nsP4; replicase) at the 5'-end and the structural genes (capsid and glycoproteins) at the 3'-end.

There are two open reading frames (ORF's) in the genome of alphaviruses, non-structural (ns) and structural genes. The ns ORF encodes proteins (nsP1-nsP4) necessary for transcription and replication of viral RNA and are produced as a polyprotein and are the virus replication machinery. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome. An exemplary depiction of an alphavirus genome is shown in FIG. 18A.

Figure 18B:
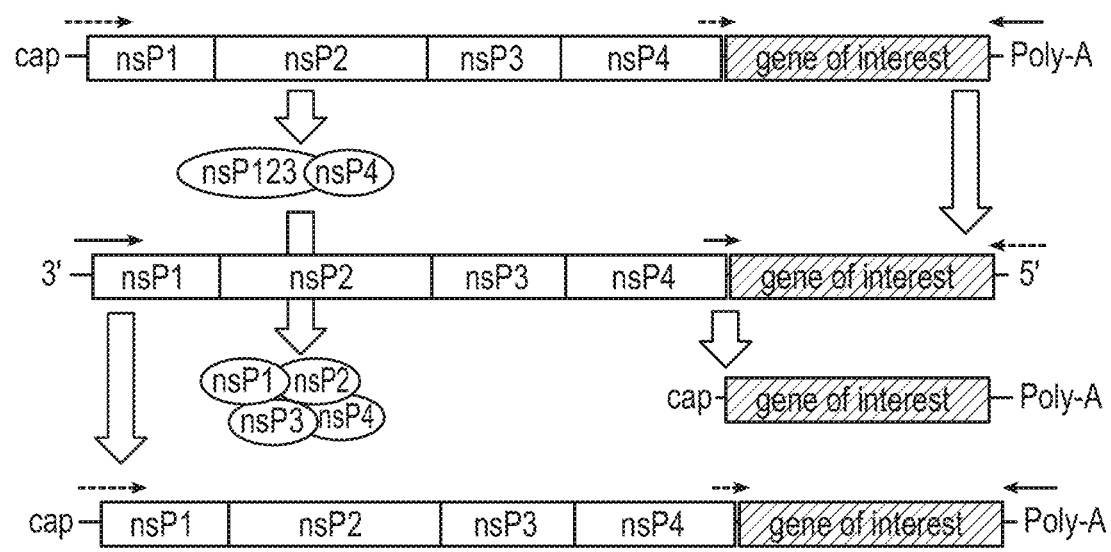
FIG. 18B shows the schematic representation of an exemplary self-replicating RNA molecule (replicon) derived from alphavirus replicons, where viral structural genes are replaced by gene of interest under the transcriptional control of a subgenomic promoter (SGP). Conserved sequence elements (CSE) at the 5' and 3'-end act as promoters for minus-strand and positive-strand RNA transcription. After the replicon is delivered into a cell, the non-structural polyprotein precursor (nsP1234) is translated from in vitro transcribed replicon. nsP1234 is at early stages auto-proteolytically processed to the fragments nsP123 and nsP4, which transcribes negative-stranded copies of the replicon. Later, nsP123 is completely processed to single proteins, which assemble to the (+) strand replicase to transcribe new positive-stranded genomic copies, as well as (+) stranded subgenomic transcripts that code for the gene of interest. Subgenomic RNA as well as new genomic RNA is capped and poly-adenylated. Inactive promoters are dotted arrows; active promoters are lined arrows.

Self-replicating RNA molecules can be used as basis of introducing foreign sequences to host cells by replacing viral sequences encoding structural genes or inserting the foreign sequences 5' or 3' of the sequences encoding the structural genes. They can be engineered to replace the viral structural genes downstream of the replicase, which are under control of a subgenomic promoter, by genes of interest (GOI), e.g. the polynucleotide encoding for the polypeptide of the disclosure. Upon transfection, the replicase which is translated immediately, interacts with the 5' and 3' termini of the genomic RNA, and synthesizes complementary genomic RNA copies. Those act as templates for the synthesis of novel positive-stranded, capped, and poly-adenylated genomic copies, and subgenomic transcripts (FIG. 18B). Amplification eventually leads to very high RNA copy numbers of up to $2 \times 10^5$ copies per cell. The result is a uniform and/or enhanced expression of a GOI (e.g. the polynucleotide encoding for the polypeptide of the disclosure) that can affect vaccine efficacy or therapeutic impact of a treatment. Vaccines based on self-replicating RNA molecules can therefore be dosed at very low levels due to the very high copies of RNA generated compared to conventional viral vector. One of the significant values of the compositions and methods disclosed herein is that vaccine efficacy can be increased in individuals that are in a chronic or acute state of immune activation.

The self-replicating RNA molecules of the disclosure comprising the RNA encoding for the CALR/JAK2 or JAK2 epitope 2 polypeptides of the disclosure may be utilized as therapeutics by delivering them to a subject having a myeloproliferative neoplasms using various technologies, including viral vectors as described herein or other delivery technologies as also described herein.

The disclosure provides a self-replicating RNA molecule containing all of the genetic information required for directing its own amplification or self-replication within a permissive cell.

The disclosure also provides a self-replicating RNA molecule that can be used as the basis of introducing foreign sequences to host cells (e.g. the CALR/JAK2 or the JAK2 epitope 2 polypeptides of the disclosure) by replacing viral sequences encoding structural genes.

Provided herein is a viral vector comprising any of the polynucleotides of the disclosure, wherein the vector is a self-replicating RNA molecule.

In some embodiments, the self-replicating RNA molecule comprises an RNA sequence derived from a polynucleotide of SEQ ID NO: 16 or having at least 90% sequence identity, or at least 95% sequence identity, or at least 99% sequence identity to SEQ ID NO: 16.

In some embodiments, the self-replicating RNA molecule comprises an RNA sequence derived from a polynucleotide of SEQ ID NO: 17 or having at least 90% sequence identity, or at least 95% sequence identity, or at least 99% sequence identity to SEQ ID NO: 17.

In some embodiments, the self-replicating RNA molecule comprises an RNA sequence derived from a polynucleotide of SEQ ID NO: 18 or having at least 90% sequence identity, or at least 95% sequence identity, or at least 99% sequence identity to SEQ ID NO: 18.

In some embodiments, the self-replicating RNA molecule comprises an RNA sequence derived from a polynucleotide of SEQ ID NO: 19 or having at least 90% sequence identity, or at least 95% sequence identity, or at least 99% sequence identity to SEQ ID NO: 19.

In some embodiments, the self-replicating RNA molecule comprises an RNA sequence derived from a polynucleotide of SEQ ID NO: 20 or having at least 90% sequence identity, or at least 95% sequence identity, or at least 99% sequence identity to SEQ ID NO: 20.

In some embodiments, the self-replicating RNA molecule comprises an RNA sequence derived from a polynucleotide of SEQ ID NO: 21 or having at least 90% sequence identity, or at least 95% sequence identity, or at least 99% sequence identity to SEQ ID NO: 21.

In some embodiments, the self-replicating RNA molecule comprises an RNA sequence derived from a polynucleotide of SEQ ID NO: 22 or having at least 90% sequence identity, or at least 95% sequence identity, or at least 99% sequence identity to SEQ ID NO: 22.

In some embodiments, the self-replicating RNA molecule comprises an RNA sequence derived from a polynucleotide of SEQ ID NO: 23 or having at least 90% sequence identity, or at least 95% sequence identity, or at least 99% sequence identity to SEQ ID NO: 23.

In some embodiments, the self-replicating RNA molecule comprises an RNA sequence derived from a polynucleotide of SEQ ID NO: 24 or having at least 90% sequence identity, or at least 95% sequence identity, or at least 99% sequence identity to SEQ ID NO: 24.

In some embodiments, the self-replicating RNA molecule comprises an RNA sequence derived from a polynucleotide of SEQ ID NO: 25 or having at least 90% sequence identity, or at least 95% sequence identity, or at least 99% sequence identity to SEQ ID NO: 25.

In some embodiments, the self-replicating RNA molecule comprises an RNA sequence derived from a polynucleotide of SEQ ID NO: 26 or having at least 90% sequence identity, or at least 95% sequence identity, or at least 99% sequence identity to SEQ ID NO: 26.

In some embodiments, the self-replicating RNA molecule comprises an RNA sequence derived from a polynucleotide of SEQ ID NO: 27 or having at least 90% sequence identity, or at least 95% sequence identity, or at least 99% sequence identity to SEQ ID NO: 27.

In some embodiments, the self-replicating RNA molecule comprises an RNA sequence encoding an amino acid sequence of SEQ ID NO: 1 or having at least 90% sequence identity, or at least 95% sequence identity, or at least 99% sequence identity to SEQ ID NO: 1.

In some embodiments, the self-replicating RNA molecule comprises an RNA sequence encoding an amino acid sequence of SEQ ID NO: 2 or having at least 90% sequence identity, or at least 95% sequence identity, or at least 99% sequence identity to SEQ ID NO: 2.

In some embodiments, the self-replicating RNA molecule comprises an RNA sequence encoding an amino acid sequence of SEQ ID NO: 3 or having at least 90% sequence identity, or at least 95% sequence identity, or at least 99% sequence identity to SEQ ID NO: 3.

In some embodiments, the self-replicating RNA molecule comprises an RNA sequence encoding an amino acid sequence of SEQ ID NO: 4 or having at least 90% sequence identity, or at least 95% sequence identity, or at least 99% sequence identity to SEQ ID NO: 4.

In some embodiments, the self-replicating RNA molecule comprises an RNA sequence encoding an amino acid sequence of SEQ ID NO: 5 or having at least 90% sequence identity, or at least 95% sequence identity, or at least 99% sequence identity to SEQ ID NO: 5.

In some embodiments, the self-replicating RNA molecule comprises an RNA sequence encoding an amino acid sequence of SEQ ID NO: 6 or having at least 90% sequence identity, or at least 95% sequence identity, or at least 99% sequence identity to SEQ ID NO: 6.

In some embodiments, the self-replicating RNA molecule comprises an RNA sequence encoding an amino acid sequence of SEQ ID NO: 7 or having at least 90% sequence identity, or at least 95% sequence identity, or at least 99% sequence identity to SEQ ID NO: 7.

In some embodiments, the self-replicating RNA molecule comprises an RNA sequence encoding an amino acid sequence of SEQ ID NO: 9 or having at least 90% sequence identity, or at least 95% sequence identity, or at least 99% sequence identity to SEQ ID NO: 9.

In some embodiments, the self-replicating RNA molecule comprises an RNA sequence encoding an amino acid sequence of SEQ ID NO: 10 or having at least 90% sequence identity, or at least 95% sequence identity, or at least 99% sequence identity to SEQ ID NO: 10.

In some embodiments, the self-replicating RNA molecule comprises an RNA sequence encoding an amino acid sequence of SEQ ID NO: 11 or having at least 90% sequence identity, or at least 95% sequence identity, or at least 99% sequence identity to SEQ ID NO: 11.

In some embodiments, the self-replicating RNA molecule comprises an RNA sequence encoding an amino acid sequence of SEQ ID NO: 12 or having at least 90% sequence identity, or at least 95% sequence identity, or at least 99% sequence identity to SEQ ID NO: 12.

In some embodiments, the self-replicating RNA molecule comprises an RNA sequence encoding an amino acid sequence of SEQ ID NO: 13 or having at least 90% sequence identity, or at least 95% sequence identity, or at least 99% sequence identity to SEQ ID NO: 13.

In some embodiments, the self-replicating RNA molecule comprises an RNA sequence encoding an amino acid sequence of SEQ ID NO: 14 or having at least 90% sequence identity, or at least 95% sequence identity, or at least 99% sequence identity to SEQ ID NO: 14.

In some embodiments, the self-replicating RNA molecule comprises an RNA sequence encoding an amino acid sequence of SEQ ID NO: 15 or having at least 90% sequence identity, or at least 95% sequence identity, or at least 99% sequence identity to SEQ ID NO: 15.

In some embodiments, the self-replicating RNA molecule comprises an RNA sequence encoding an amino acid sequence of SEQ ID NO: 31 or having at least 90% sequence identity, or at least 95% sequence identity, or at least 99% sequence identity to SEQ ID NO: 31.

Any of the above self-replicating RNA molecules can further comprise one or more of the following:
  one or more nonstructural genes nsP1, nsP2, nsP3 and nsP4;
  at least one of a DLP motif, a 5' UTR, a 3'UTR and a Poly A; and
  a subgenomic promoter.

In some embodiments, for example, the self-replicating RNA molecule can comprise one or more of the following:
  one or more nonstructural genes nsP1, nsP2, nsP3 and nsP4;
  at least one of a DLP motif, a 5' UTR, a 3'UTR and a Poly A; and
  a subgenomic promoter; and an RNA encoding for amino acids of SEQ ID NOs: 3, 4, 5, 6, 7, 9, 10, 11, 12, 13, 14, 15, or 31, and operably linked to the subgenomic promoter.

In some embodiments, the self-replicating RNA molecule comprises an RNA sequence encoding a protein or peptide; 5' and 3' alphavirus untranslated regions; RNA sequences encoding amino acid sequences derived from New World alphavirus VEEV nonstructural proteins nsP1, nsP2, nsP3 and nsP4; a sub-genomic promoter that is operably linked to and regulates translation of the RNA sequence encoding the protein; a 5' cap and a 3' poly-A tail; positive sense, single-stranded RNA; a DLP from Sindbis virus upstream of the non-structural protein 1(nsP1); a 2A ribosome skipping element; and a nsp1 nucleotide repeat downstream of the 5'-UTR and upstream of the DLP.

In some embodiments, the self-replicating RNA molecules may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size.

Any of the above-disclosed self-replicating RNA molecules can further include a coding sequence for an autoprotease peptide (e.g., autocatalytic self-cleaving peptide), where the coding sequence for the autoprotease is optionally operably linked upstream to the second nucleic acid sequence.

Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro and in vivo eukaryotic systems. As such, the concept of autoproteases is available to one of skill in the art as many naturally occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequence for the autoprotease peptide is operably linked downstream of the DLP motif and upstream to the first and second polynucleotides.

In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

In some embodiments, the autoprotease peptide is selected from the group consisting of porcine teschovirus-1 2A (P2A), foot-and-mouth disease virus (FMDV) 2A (F2A), Equine Rhinitis A Virus (ERAV) 2A (E2A), Thosea asigna virus 2A (T2A), cytoplasmic polyhedrosis virus 2A (BmCPV2A), Flacherie Virus 2A (BmIFV2A), and a combination thereof.

In some embodiments, the autoprotease peptide is porcine teschovirus-1 2A (P2A).

The incorporation of the P2A peptide in the modified viral RNA replicons of the present disclosure allows release of protein encoded by GOI (e.g.CALR-JAK2 or JAK2 epitope 2 polypeptide of the disclosure) from the capsid-GOI fusion.

In some embodiments disclosed herein, the porcine teschovirus-1 2A (P2A) peptide sequence is engineered in-frame immediately after the DLP sequence and in-frame immediately upstream of all GOI.

Any of the above-disclosed self-replicating RNA molecules can further include a coding sequence downstream Loop (DLP) motif.

Some viruses have sequences capable of forming one or more stem-loop structures which regulate, for example increase, capsid gene expression. Viral capsid enhancer as used herein refers to a regulatory element comprising sequences capable of forming such stem-loop structures. In some examples, the stem-loop structures are formed by sequences within the coding sequence of a capsid protein and named Downstream Loop (DLP) sequence. As disclosed herein, these stem-loop structures or variants thereof can be used to regulate, for example increase, expression level of genes of interest. For example, these stem-loop structures or variants thereof can be used in a recombinant vector (e.g., in a heterologous viral genome) for enhancing transcription and/or translation of coding sequence operably linked downstream thereto.

Alphavirus replication in host cells is known to induce the double-stranded RNA-dependent protein kinase (PKR). PKR phosphorylates the eukaryotic translation initiation factor 2a (eIF2a). Phosphorylation of eIF2a blocks translation initiation of mRNA and in doing so keeps viruses from a completing a productive replication cycle. Infection of cells with Sindbis virus induces PKR that results in phosphorylation of eIF2a, yet the viral subgenomic mRNA is efficiently translated while translation of all other cellular mRNAs is restricted. The efficient translation of the viral subgenomic mRNA in Sindbis virus is made possible by the presence of a stable RNA hairpin loop (or DLP motif) located downstream of the wild type AUG initiator codon for the virus capsid protein (e.g., capsid enhancer). It has been reported that the DLP structure can stall a ribosome on the wild type AUG and this supports translation of the subgenomic mRNA without the requirement for functional eIF2a. Thus, subgenomic mRNAs of Sindbis virus (SINV) as well as of other alphaviruses are efficiently translated even in cells that have highly active PKR resulting in complete phosphorylation of eIF2a.

The DLP structure was first characterized in Sindbis virus (SINV) 26S mRNA and also detected in Semliki Forest virus (SFV). Similar DLP structures have been reported to be present in at least 14 other members of the Alphavirus genus including New World (for example, MAYV, UNAV, EEEV (NA), EEEV (SA), AURAV and Old World (SV, SFV, BEBV, RRV, SAG, GETV, MIDV, CHIKV, and ONNV) members. The predicted structures of these Alphavirus 26S mRNAs were constructed based on SHAPE (selective 2'-hydroxyl acylation and primer extension) data (Toribio et al., Nucleic Acids Res. May 19; 44(9):4368-80, 2016), the content of which is hereby incorporated by reference). Stable stem-loop structures were detected in all cases except for CHIKV and ONNV, whereas MAYV and EEEV showed DLPs of lower stability (Toribio et al., 2016 supra). The highest DLP activities were reported for those Alphaviruses that contained the most stable DLP structures.

As an example, members of the Alphavirus genus can resist the activation of antiviral RNA-activated protein kinase (PKR) by means of the dowsntream loop (DLP) present within in viral 26S transcripts, which allows an eIF2-independent translation initiation of these mRNAs. The downstream loop (DLP), is located downstream from the AUG in SINV 26S mRNA and in other members of the Alphavirus genus.

In some embodiments, the nucleic acid molecules of the disclosure can include a coding sequence for a gene of interest (GOI) operably linked to DLP motif(s) and/or the coding sequence for the DLP motifs.

In some embodiments, the self-replicating RNA molecule of the disclosure comprises a downstream loop (DLP).

In some embodiments, the downstream loop (DLP) comprises at least one RNA-stem-loop.

In some instances, DLP activity depends on the distance between the DLP motif and the initiation codon AUG (AUGi). The AUG-DLP spacing in Alphavirus 26S mRNAs is tuned to the topology of the ES6S region of the ribosomal 18S rRNA in a way that allows the placement of the AUGi in the P site of the 40S subunit stalled by the DLP, allowing the incorporation of Met-tRNA without the participation of eIF2. In the case of Sindbis virus, the DLP motif is found in the first ~150 nt of the Sindbis subgenomic RNA. The hairpin is located downstream of the Sindbis capsid AUG initiation codon (AUG at nt 50 of the Sindbis subgenomic RNA) and results in stalling a ribosome such that the correct capsid gene AUG is used to initiate translation. Previous studies of sequence comparisons and structural RNA analysis revealed the evolutionary conservation of DLP in SINV and predicted the existence of equivalent DLP structures in many members of the Alphavirus genus (see e.g., Ventoso, J. Virol. 9484-9494, Vol. 86, September 2012).

Without being bound by any particular theory, it is believed that placing the DLP motif upstream of a coding sequence for any GOI typically results in a fusion-protein of N-terminal capsid amino acids that are encoded in the hairpin region to the GOI encoded protein because initiation occurs on the capsid AUG not the GOI AUG.

In some embodiments, the self-replicating RNA molecule comprises a downstream loop placed upstream of the non-structural protein 1(nsP1).

In some embodiments, the downstream loop is placed upstream of the non-structural protein 1 (nsP1) and is joined to the nsP1 by a porcine teschovirus-1 2A (P2A) ribosome skipping element.

The DLP-containing self-replicating RNA of the disclosure can be useful in conferring a resistance to the innate immune system in a subject. Unmodified RNA replicons are sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform and/or enhanced expression of a GOI that can impact vaccine efficacy or therapeutic impact of a treatment.

The DLP motif of the self-replicating RNA of the disclosure can confer efficient mRNA translation in cellular environments where cellular mRNA translation is inhibited. When a DLP is linked with translation of a replicon vector's non-structural protein genes the replicase and transcriptase proteins are capable of initiating functional replication in PKR activated cellular environments. When a DLP is linked with translation of subgenomic mRNAs robust GOI expression is possible even when cellular mRNA is restricted due to innate immune activation. Accordingly, engineering self-replicating RNA that contain DLP structures to help drive translation of both non-structural protein genes and subgenomic mRNAs provides a powerful way to overcome innate immune activation.

Examples of a self-replicating RNA vector comprising a DLP motif are described in US Patent Application Publication US2018/0171340 and the International Patent Application Publication WO2018106615, the content of which is incorporated herein by reference in its entirety.

Any of the above-disclosed self-replicating RNA molecules can further comprise nonstructural genes nsP1, nsP2, nsP3 and/or nsP4. In some embodiments, the self-replicating RNA molecule does not encode a functional viral structural protein.

Alphavirus genomes encode non-structural proteins nsP1, nsP2, nsP3, and nsP4, which are produced as a single polyprotein precursor, sometimes designated P1234 (or nsP1-4 or nsP1234), and which is cleaved into the mature proteins through proteolytic processing (FIG. 18B). nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD). nsP4 is about 70 kDa in size and contains the core RNA-dependent RNA polymerase (RdRp) catalytic domain. After infection the alphavirus genomic RNA is translated to yield a P1234 polyprotein, which is cleaved into the individual proteins.

Alphavirus genomes also encode three structural proteins: the core nucleocapsid protein C, and the envelope proteins P62, and E1 that associate as a heterodimer. Structural proteins are under the control of a subgenomic promoter and can be replaced by gene of interests (GIO).

In some embodiments of the present disclosure, the self-replicating RNA can lack (or not contain) the sequence(s) of at least one (or all) of the structural viral proteins (e.g. nucleocapsid protein C, and envelope proteins P62, 6K, and E1). In these embodiments, the sequences encoding one or more structural genes can be substituted with one or more sequences such as, for example, a coding sequence for at least one protein or peptide (or other gene of interest (GOI)) e.g. the CALR/JAK2 polypeptides or JAK2 epitope 2 polypeptides of the disclosure.

In some embodiments, the self-replicating RNA lack sequences encoding alphavirus structural proteins; or do not encode alphavirus (or, optionally, any other) structural proteins. In some embodiments, the self-replicating RNA molecules are further devoided of a part or the entire coding region for one or more viral structural proteins. For example, the alphavirus expression system may be devoid of a portion of or the entire coding sequence for one or more of the viral capsid protein C, E1 glycoprotein, E2 glycoprotein, E3 protein and 6K protein.

In some embodiments, the self-replicating RNA molecule does not contain coding sequences for at least one of the structural viral proteins. In these instances, the sequences encoding structural genes can be substituted with one or more sequences such as, for example, a coding sequence for a GOI e.g., CALR/JAK2 or JAK2 epitope 2 polynucleotides of the disclosure FIG. 18.

The disclosure also provides a self-replicating RNA molecule comprising nonstructural genes nsP1, nsP2, nsP3 and nsP4, and wherein the self-replicating RNA molecule does not encode a functional viral structural protein.

In some embodiments, the disclosure provides a self-replicating RNA molecule comprising the coding sequence for at least one, at least two, at least three, or at least four nonstructural viral proteins (e.g. nsP1, nsP2, nsP3, nsP4). The nsP1, nsP2, nsP3, and nsP4 proteins encoded by the replicon are functional or biologically active proteins.

In some embodiments, the self-replicating RNA molecule includes the coding sequence for a portion of the at least one nonstructural viral protein. For example, the self-replicating RNA molecules can include about 10%, 20%, 30%, 40%, 50%, 60%, 70%, 80%, 90%, 95%, 100%, or a range between any two of these values, of the encoding sequence for the at least one nonstructural viral protein. In some embodiments, the self-replicating RNA molecule can include the coding sequence for a substantial portion of the at least one nonstructural viral protein. As used herein, a "substantial portion" of a nucleic acid sequence encoding a nonstructural viral protein comprises enough of the nucleic acid sequence encoding the nonstructural viral protein to afford putative identification of that protein, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993).

In some embodiments, the self-replicating RNA molecule can include the entire coding sequence for the at least one nonstructural protein. In some embodiments, the self-replicating RNA molecule comprises substantially all the coding sequence for the native viral nonstructural proteins. In certain embodiments, the one or more nonstructural viral proteins are derived from the same virus.

In some embodiments, the downstream loop DLP of the self-replicating RNA molecule placed upstream of the nonstructural protein 1(nsP1) is derived from Sindbis virus.

In some embodiments, the self-replicating RNA molecule comprises nsP1, nsP2, nsP3 and nsP4 sequences derived from the Venezuelan equine encephalitis virus (VEEV) and a DLP motif derived from the Sindbis virus (SIN).

In some embodiments, the self-replicating RNA molecules also have an RNA sub-sequence encoding an amino acid sequence derived from an alphavirus nsP3 macro domain, and an RNA sub-sequence encoding an amino acid sequence derived from an alphavirus nsP3 central domain. The self-replicating RNA molecules can also have an RNA sub-sequence encoding an amino acid sequence derived entirely from an Old World alphavirus nsP3 hypervariable domain; or can have an amino acid sequence having a portion derived from a New World alphavirus nsP3 hypervariable domain, and a portion derived from an Old World alphavirus nsP3 hypervariable domain. i.e. the hyper variable domain (HVD) can be a hybrid or chimeric New World/Old World sequence.

In some embodiments, the self-replicating RNA molecules can have an RNA sequence encoding amino acid sequences derived from a wild type New World alphavirus nsP1, nsP2, nsP3 and nsP4 protein sequences. In other embodiments, the one or more nonstructural proteins are derived from different viruses.

In some embodiments, the self-replicating RNA molecule may have an RNA sequence encoding an nsP3 macro domain derived from a wild type alphavirus nsP3, and an nsP3 central domain derived from a wild type alphavirus nsP3. In various embodiments the macro and central domain (s) can both be derived from a New World wild type alphavirus nsP3 or can both be derived from an Old World wild type alphavirus nsP3 protein. In other embodiments, the macro domain can be derived from a New World wild type alphavirus macro domain and the central domain can be derived from an Old World wild type alphavirus central domain, or vice versa. The various domains can be of any sequence described herein.

In some embodiments, the self-replicating RNA molecule contains non VEEV nonstructural proteins nsP1, nsP2, nsP3 and nsP4.

The accumulated experimental evidence has demonstrated that replication/amplification of VEEV and other alphavirus genomes and their defective interfering (DI) RNAs is determined by three promoter elements: (i) the conserved 3'-terminal sequence element (3' CSE) and the following poly(A) tail; (ii) the 5' UTR, which functions as a key promoter element for both negative- and positive-strand RNA synthesis; and (iii) the 51-nt conserved sequence element (51-nt CSE), which is located in the nsP1-coding sequence and functions as an enhancer of alphavirus genome replication (Kim et al., PNAS, 2014, 111: 10708-10713, and references therein).

Any of the above-disclosed self-replicating RNA molecules can further include an unmodified 5' untranslated region (5'UTR).

Previous studies have demonstrated that during VEEV and Sindbis virus infections only a small portion of viral nonstructural proteins (nsPs) is colocalized with dsRNA replication intermediates. Thus, it appears that a large fraction of nsPs are not involved in RNA replication (Gorchakov R, et al. (2008) A new role for ns polyprotein cleavage in Sindbis virus replication. J Virol 82(13):6218-6231). This has provided an opportunity to exploit the under used ns proteins for amplification of the subgenomic RNAs encoding proteins of interest, which is normally transcribed from the subgenomic promoter and is not further amplified In some embodiments, a fragment of the nsP1 of the self-replicating RNA molecule of the disclosure is duplicated downstream of the 5'-UTR and upstream of the DLP.

In some embodiments the first 193 nucleotides of nsP1 are duplicated downstream of the 5' UTR and upstream of the DLP In some embodiment, a self-replicating RNA molecule comprises a modified 5' untranslated region (5'-UTR). For example, the modified 5'-UTR can comprise one or more nucleotide substitutions at position 1, 2, 4, or a combination thereof. Preferably, the modified 5'-UTR comprises a nucleotide substitution at position 2, more preferably, the modified 5'-UTR has a U->G substitution at position 2. Examples of such self-replicating RNA molecules are described in US Patent Application Publication US2018/0104359 and the International Patent Application Publication WO2018075235, the content of which is incorporated herein by reference in its entirety.

In some embodiments, the UTRs can be wild type New World or Old World alphavirus UTR sequences, or a sequence derived from any of them. The 5' UTR can be of any suitable length, such as about 60 nt or 50-70 nt or 40-80 nt. In some embodiments the 5' UTR can also have conserved primary or secondary structures (e.g. one or more stem-loop(s)) and can participate in the replication of alphavirus or of replicon RNA. The 3' UTR can be up to several hundred nucleotides, for example it can be 50-900 or 100-900 or 50-800 or 100-700 or 200 nt –700 nt. The '3 UTR also can have secondary structures, e.g. a step loop, and can be followed by a polyadenylate tract or poly-A tail.

The 5' and 3' untranslated regions can be operably linked to any of the other sequences encoded by the replicon. The UTRs can be operably linked to a promoter and/or sequence encoding a protein or peptide by providing sequences and spacing necessary for recognition and transcription of the other encoded sequences.

The GOI, e.g the CALR/JAK2 or the JAK2 epitope 2 polynucleotides of the disclosure can be expressed under the control of a subgenomic promoter. In certain embodiments, instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses. Subgenomic promoters range from 24 nucleotide (Sindbis virus) to over 100 nucleotides (Beet necrotic yellow vein virus) and are usually found upstream of the transcription start.

The self-replicating RNA molecules can have a 3' poly-A tail. It can also include a poly-A polymerase recognition sequence (e.g. AAUAAA) near its 3' end.

In those instances where the self-replicating RNA molecule is to be packaged into a recombinant alphavirus particle, it can contain one or more sequences, so-called packaging signals, which serve to initiate interactions with alphavirus structural proteins that lead to particle formation. In some embodiments, the alphavirus particles comprise RNA derived from one or more alphaviruses; and structural proteins wherein at least one of said structural proteins is derived from two or more alphaviruses.

In some embodiments, the self-replicating RNA molecule comprises a VEEV derived vector wherein the structural viral proteins (e.g. nucleocapsid protein C, and envelope proteins P62, 6K, and E1) are removed and replaced by the coding sequence of the CARL.JAK2 or the JAK2 epitope 2 polypeptides of the disclosure.

Other Viral Vectors and Recombinant Viruses

The viral vector comprising the polynucleotide of the disclosure may be derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{n}$ particles or copies of DNA in contrast to naked DNA doses of 50 μg or about $10^{15}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

The viral vector comprising the polynucleotide of the disclosure also include Retroviral vectors. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323).

The polynucleotides encoding the polypeptide of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, Bio-Techniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Regulatory Elements

The polynucleotides encoding the polypeptides of the disclosure may be operably linked to one or more regulatory elements in the vector. The regulatory elements may comprise promoters, enhancers, polyadenylation signals, repressors and the like. As used herein, the term "operably linked" is to be taken in its broadest reasonable context and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499. Polyadenylation signals may be derived from SV40 or bovine growth hormone (BGH).

The self-replicating RNA vectors comprising the polynucleotide encoding the polypeptide of the disclosure can further comprise any regulatory elements to establish conventional function(s) of the vector, including but not limited to replication and expression of the polypeptide of the disclosure encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., the polypeptides of the disclosure) from a start codon to a stop codon. Regulatory elements of the expression cassette can be operably linked to a polynucleotide sequence encoding the polypeptides of interest. Any components suitable for use in an expression cassette described herein can be used in any combination and in any order to prepare vectors of the application.

The vector can comprise a promoter sequence, preferably within an expression cassette, to control expression of the polypeptides of the disclosure. The term "promoter" is used in its conventional sense and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including viral, bacterial, fungal, plants, insects, and animals. A promoter can be a homologous promoter (i.e., derived from the same genetic source as the vector) or a heterologous promoter (i.e., derived from a different vector or genetic source). Preferably, the promoter is located upstream of the polynucleotide encoding the polypeptides of the disclosure within an expression cassette. For example, in a self-replicating RNA, the promoter can be a subgenomic promoter for the alphavirus.

In a self-replicating RNA, the vector can further comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., the polypeptides of the disclosure) within an expression cassette of the vector. Enhancer sequences are regulatory DNA sequences that, when bound by transcription factors, enhance the transcription of an associated gene. An enhancer sequence is preferably located upstream of the polynucleotide sequence encoding the polypeptides of the disclosure, but downstream of a promoter sequence within an expression cassette of the vector.

Any enhancer sequence known to those skilled in the art in view of the present disclosure can be used.

Any of the components or sequences of the self-replicating RNA vector of the disclosure can be functionally or operably linked to any other of the components or sequences. The components or sequences of the self-replicating RNA molecule can be operably linked for the expression of the at least one protein or peptide (or biotherapeutic) in a host cell or treated organism and/or for the ability of the replicon to self-replicate.

A promoter or UTR operably linked to a coding sequence is capable of effecting the transcription and expression of the coding sequence when the proper enzymes are present. The promoter need not be contiguous with the coding sequence, so long as it functions to direct the expression thereof. Thus, an operable linkage between an RNA sequence encoding a protein or peptide and a regulatory sequence (for example, a promoter or UTR) is a functional link that allows for expression of the polynucleotide of interest. Operably linked can also refer to sequences such as the sequences encoding the RdRp (e.g. nsP4), nsP1-4, the UTRs, promoters, and other sequences encoding in the RNA replicon, are linked so that they enable transcription and translation of the biotherapeutic molecule and/or replication of the replicon. The UTRs can be operably linked by providing sequences and spacing necessary for recognition and translation by a ribosome of other encoded sequences.

A molecule is functional or biologically active if it performs at least 50% of the same activity as its natural (or wild type), corresponding molecule, but a functional molecule can also perform at least 60% or at least 70% or at least 90% or at least 95% or 100% of the same activity as its natural (or wild type) corresponding molecule. The self-replicating RNA molecules can also encode an amino acid sequence derived from or based on a wild type alphavirus amino acid sequence, meaning that they have at least 60% or at least 65% or at least 68% or at least 70% or at least 80% or at least 70% or at least 80% or at least 90% or at least 95% or at least 97% or at least 98% or at least 99% or 100% or 80-99% or 90-100% or 95-99% or 95-100% or 97-99% or 98-99% sequence identity with an amino acid sequence (which can be a corresponding sequence) encoded by a wild type RNA alphavirus genome, which can be a New World or Old World alphavirus genome. Sequences derived from other sequences can be up to 5% or up to 10% or up to 20% or up to 30% longer or shorter than the original sequence. In any of the embodiments the sequence identity can be at least 95% or at least 97% or at least 98% or at least 99% or 100% for any nucleotide sequence encoding (or amino acid sequence having) a G3BP or FXR binding site thereon. These sequences can also be up to 5% or up to 10% or up to 20% or up to 30% longer or shorter than the original sequence.

Host Cells

The disclosure also provides a host cell comprising any of the above vectors of the disclosure. In some embodiments, the host cell is prokaryotic or eukaryotic host cell. In some embodiments, the host cell is PER.C6, PER.C6 TetO, a chicken embryo fibroblast (CEF), CHO, HEK293, HT-1080, HKB-11, CAP, HuH-7, or Age1 cell line.

Compositions

The disclosure also provides compositions comprising any of the polynucleotides, any of the polypeptides, and any of the vectors disclosed herein. In some embodiments, the compositions may comprise a vector comprising any of the nucleotides disclosed herein, wherein the vector is selected from Ad26, GAd20, MVA, or a self-replicating RNA molecule.

Any of the compositions described above may comprise or may be formulated into a pharmaceutical composition comprising the composition and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

The composition may comprise one or more adjuvants. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine). Other non-limiting examples of adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be used include lectins, growth factors, cytokines, and lymphokines such as alpha-interferon, gamma interferon, platelet derived growth factor (PDGF), granulocyte-colony stimulating factor (GCSF), granulocyte macrophage colony stimulating factor (GMCSF), tumor necrosis factor (TNF), epidermal growth factor (EGF), IL-1, IL-2, IL-4, IL-6, IL-8, IL-10, IL-12 or TLR agonists, and particulate adjuvants (e g immunostimulatory complexes (ISCOMS).

Nanoparticles

In some embodiments, the compositions may comprise nanoparticles. Any of the polynucleotides of the disclosure may be attached to or in contact with nanoparticles for delivery to a subject. Delivery of any of the polynucleotides or polypeptides of the disclosure using nanoparticles may eliminate the need to include a virus or an adjuvant in the vaccine composition. The polynucleotides of the disclosure may be DNA or RNA. The nanoparticles may contain immune danger signals that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells.

The nanoparticles are typically from about 1 nm to about 100 nm in diameter, such as about 20 nm to about 40 nm. Nanoparticles with a mean diameter of 20 to 40 nm may facilitate uptake of the nanoparticle to the cytosol (see. e.g. WO2019/135086). Exemplary nanoparticles are polymeric nanoparticles, inorganic nanoparticles, liposomes, lipid nanoparticles (LNP), an immune stimulating complex (ISCOM), a virus-like particle (VLP), or a self-assembling protein. The nanoparticles may be calcium phosphate nanoparticles, silicon nanoparticles or gold nanoparticles. The polymeric nanoparticles may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene or one or more natural polymers such as a polysaccharide, for example pullulan, alginate, inulin, and chitosan. The use of a polymeric nanoparticles may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may also form hydrogel nanoparticles, hydrophilic three-dimensional polymer networks with favorable properties including flexible mesh size, large surface area for multivalent conjugation, high water content, and high loading capacity for antigens. Polymers such as Poly (L-lactic acid) (PLA), PLGA, PEG, and polysaccharides are suitable for forming hydrogel nanoparticles. Inorganic nanoparticles typically have a rigid structure and comprise a shell in which an antigen is encapsulated or a core to which the antigen may be covalently attached. The core may comprise one or more atoms such as gold (Au), silver (Ag), copper (Cu) atoms, Au/Ag, Au/Cu, Au/Ag/Cu, Au/Pt, Au/Pd or Au/Ag/Cu/Pd or calcium phosphate (CaP).

In some embodiments, the nanoparticles may be liposomes. Liposomes are typically formed from biodegradable, non-toxic phospholipids and comprise a self-assembling phospholipid bilayer shell with an aqueous core. Liposomes may be an unilamellar vesicle comprising a single phospholipid bilayer, or a multilamellar vesicle that comprises several concentric phospholipid shells separated by layers of water. As a consequence, liposomes may be tailored to incorporate either hydrophilic molecules into the aqueous core or hydrophobic molecules within the phospholipid bilayers. Liposomes may encapsulate polynucleotides or the polypeptides or fragments thereof of the disclosure within the core for delivery. Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. The liposomes may comprise a targeting molecule for targeting liposome complexes to a particular cell type. Targeting molecule may comprise a binding partner (e.g., a ligand or receptor) for a biomolecule (e.g., a receptor or ligand) on the surface of a blood vessel or a cell found in a target tissue. Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028). Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The self-replicating RNA molecules and/or compositions comprising the same can also be formulated as a nanoparticle using a combination of polymers, lipids, and/or other biodegradable agents, such as, but not limited to, calcium phosphate, polymers. Components can be combined in a core-shell, hybrid, and/or layer-by-layer architecture, to allow for fine-tuning of the nanoparticle so that delivery of the molecules and/or compositions of the disclosure can be enhanced.

In some embodiments, the nanoparticles can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powder like form. This film is covered with an aqueous solution of the polypeptide or polynucleotide and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium may comprise the nucleic acid at a concentration which is desired in the interior volume of the liposomes in the final liposome suspension. Suitable lipids that may be used to form multilamellar vesicles include DOTMA (Feigner, et al., 1987, Proc. Natl. Acad. Sci. USA 84: 7413-7417), DOGS or Transfectain™ (Behr, et al., 1989, Proc. Natl. Acad. Sci. USA 86: 6982-6986), DNERIE or DORIE (Feigner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

In some embodiments, the nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*).

In some embodiments, the nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

Other molecules suitable for complexing with the polynucleotides of the disclosure include cationic molecules, such as, polyamidoamine (Haensler and Szoka, 1993, Bioconjugate Chem. 4: 372-379), dendritic polylysine (Int. Pat. Publ. No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744,166), DNA-gelatin coacervates (see, e.g., U.S. Pat. Nos. 6,207,195; 6,025,337; 5,972,707) or DEAE dextran (Lopata, et al., 1984, Nucleic Acid Res. 12: 5707-5717).

In some embodiments, the self-replicating RNA molecule can be packaged or encapsulated in cationic molecules, such as, polyamidoamine (Haensler and Szoka, 1993, Bioconjugate Chem. 4: 372-379), dendritic polylysine (Int. Pat. Publ. No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744, 166), DNA-gelatin coacervates (see, e.g., U.S. Pat. Nos. 6,207,195; 6,025,337; 5,972,707) or DEAE dextran (Lopata, et al., 1984, Nucleic Acid Res. 12: 5707-5717), dendrimers (see, e.g., WO1996/19240), or polyethylenimine (PEI) (see, e.g., Sun et al., 2014, Mol Med Rep. 10(5):2657-2662).

The disclosed self-replicating RNA molecules and/or compositions comprising the self-replicating RNA molecules encoding any of the polypeptides of the disclosure can be encapsulated using one or more liposomes, lipoplexes, and/or lipid nanoparticles. Liposomes are artificially prepared vesicles which can primarily be composed of a lipid bilayer and can be used as a delivery vehicle for the administration of polynucleotides and self-replicating RNA molecules. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the polynucleotides and self-replicating RNA molecules disclosed herein.

The formation of liposomes can depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, the self-replicating RNA molecule is encapsulated in, bound to or adsorbed on a liposome, a lipoplex, a lipid nanoparticle, or combinations thereof, preferably the self-replicating RNA molecule is encapsulated in a lipid nanoparticle.

In some embodiments, the self-replicating RNA molecule encoding the any of the polypeptides of the disclosure can be fully encapsulated within the lipid portion of the particle, thereby protecting the RNA from nuclease degradation. "Fully encapsulated" means that the RNA is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In some embodiments, the self-replicating RNA molecules and/or compositions of the disclosure comprising the same can be formulated in a lipid vesicle which can have crosslinks between functionalized lipid bilayers. In some embodiments, the self-replicating RNA molecules and/or compositions of the disclosure can be formulated in a lipid-polycation complex. The formation of the lipid-polycation complex can be accomplished by methods known in the art. As a non-limiting example, the polycation can include a cationic peptide or a polypeptide such as, but not limited to, polylysine, polyornithine and/or polyarginine and the cationic peptides. In some embodiments, the self-replicating RNA molecules and/or compositions disclosed herein can be formulated in a lipid-polycation complex which can further include a neutral lipid such as, but not limited to, cholesterol or dioleoyl phosphatidylethanolamine (DOPE). The lipid nanoparticle formulation can be influenced by, but not limited to, the selection of the cationic lipid component, the degree of cationic lipid saturation, the nature of the PEGylation, ratio of all components and biophysical parameters such as size.

Figure 20:
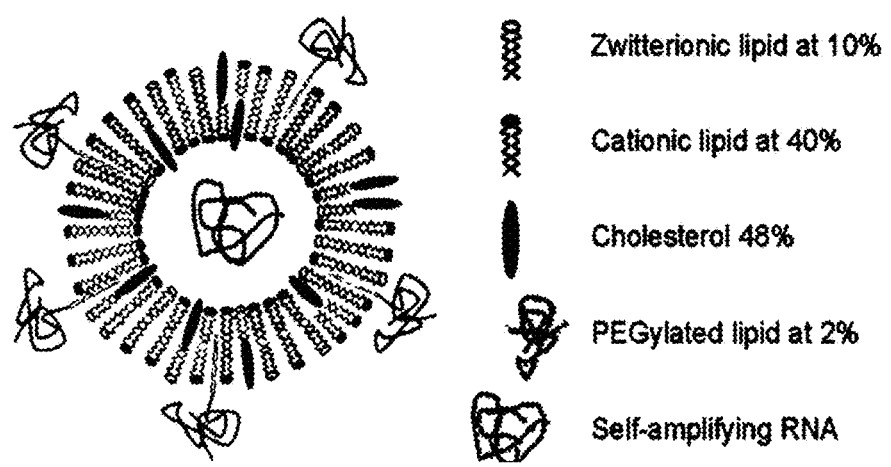
FIG. 20 is a schematic illustration of an exemplary lipid nanoparticle (LNP) encapsulating self-amplifying RNA, with the percent molar ratios of lipid components as indicated (Geall et al., PNAS, 2012, 109:14604-14609).

In some embodiments, the self-replicating RNA molecule disclosed herein is encapsulated in a lipid nanoparticle (LNP) as shown in FIG. 20. Lipid nanoparticles typically comprise four different lipids—an ionizable lipid, a neutral helper lipid, cholesterol, and a diffusible polyethylene glycol (PEG) lipid. LNPs are similar to liposomes but have slightly different function and composition. LNPs are designed toward encapsulating polynucleotides, such as DNA, mRNA, siRNA and sRNA. Traditional liposomes contain an aqueous core surrounded by one or more lipid bilayers. LNPs may assume a micelle-like structure, encapsulating polynucleotides in a non-aqueous core. LNPs typically contain a cationic lipid, a non-cationic lipid, and a lipid that prevents aggregation of the particle (e.g., a PEG-lipid conjugate). LNPs are useful for systemic applications, as they exhibit extended circulation lifetimes following intravenous (i.e.) injection and accumulate at distal sites (e.g., sites physically separated from the administration site). The LNPs may have a mean diameter of about 50 nm to about 150 nm, such as about 60 nm to about 130 nm, or about 70 nm to about 110 nm, or about 70 nm to about 90 nm, and are substantially nontoxic. Preparation of polynucleotide loaded LNPs are disclosed in, e.g., U.S. Pat. Nos. 5,976,567; 5,981,501; 6,534,484; 6,586,410; 6,815,432; and PCT Publication No. WO 96/40964. Polynucleotide containing LNPs are described for example in WO2019/191780.

In some embodiments, the lipid nanoparticles comprise a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may encapsulate at least 1, 2, 3, 4, 5, 6, 7, 8, 9, 10, or more self-replicating RNA molecules that encode for one or more polypeptides.

In some embodiments, the LNP formulations comprising a polycationic composition can be used for the delivery of the self-replicating RNA molecules described herein in vivo and/or ex vitro. The disclosure further provides a LNP formulations comprising a cationic lipid.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the pKa of the cationic lipid and is substantially neutral at a pH above the pKa. The cationic lipids may also be termed titratable cationic lipids. In some embodiments, the cationic lipids comprise: a protonatable tertiary amine (e.g., pH-titratable) head group; C18 alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, 7-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-B11).

The disclosure also provides an encapsulated self-replicating RNA molecule, wherein the cationic lipid comprises a protonatable tertiary amine. In some embodiments, the cationic lipid is di((Z)-non-2-en-1-yl) 8,8'-((((2-(dimethylamino)ethyl)thio)carbonyl)azanediyl) dioctanoate.

In some embodiments, the cationic lipid compounds are relatively non-cytotoxic. The cationic lipid compounds may be biocompatible and biodegradable. The cationic lipid may have a pKa in the range of approximately 5.5 to approximately 7.5, more preferably between approximately 6.0 and approximately 7.0.

The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the self-replicating RNA molecule to be delivered, they can be synthesized from commercially available starting materials; and/or they are pH responsive and can be engineered with a desired pKa.

Lipid nanoparticle formulations can be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and can be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain. The lipid particles may comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g, HO-PEG-S, HO-PEG-S—NHS, HO-PEG-NH2).

The PEG moiety of the PEG-lipid conjugates described herein may comprise an average molecular weight ranging from 550 daltons to 10,000 daltons. Examples of PEG-lipids include, but are not limited to, PEG coupled to dialkyloxy-propyls (PEG-DAA), PEG coupled to diacylglycerol (PEG-DAG), PEG coupled to phospholipids such as phosphatidyl-ethanolamine (PEG-PE), PEG conjugated to ceramides, PEG conjugated to cholesterol or a derivative thereof, and mixtures thereof. In some embodiments, the PEG conjugated lipid is a DMG-PEG-2000.

The self-replicating RNA molecules can also be formulated in a particle comprising non-cationic lipids. Suitable non-cationic lipids include, for example, neutral uncharged, zwitterionic, or anionic lipids capable of producing a stable complex. Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoyl-phosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal),phosphatidylethanolamine phosphatidylethanolamine phosphatidylethanolamine phosphatidylethanolamine, phosphatidylethanolamine, phosphatidylethanolaminedipalmitoyl-dimyristoyl-distearoyl-monomethyl-dimethyl-dielaidoyl-stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5a-cholestanol, 5a-coprostanol, cholesteryl-(2'-hydroxy)-ethyl ether, cholesteryl-(4'-hydroxy)-butyl ether, and 6-ketocholestanol; non-polar analogues such as 5a-cholestane, cholestenone, 5a-cholestanone, 5a-cholestanone, and cholesteryl decanoate; and mixtures thereof. In preferred embodiments, the cholesterol derivative is a polar analogue such as cholesteryl-(4'-hydroxy)-butyl ether. In some embodiments, the phospholipid is DSPC. In some embodiments, the non-cationic lipid present in lipid particles comprises or consists of a mixture of one or more phospholipids and cholesterol or a derivative thereof. In some embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, LNPs may comprise 30-70% cationic lipid compound, 0-60% cholesterol, 0-30% phospholipid, and 1-10% polyethylene glycol (PEG).

In some embodiments, the cationic lipid, zwitterion lipid, cholesterol and conjugated lipid are combined in a molar ratio of 50:7:40:3, respectively in the lipid nanoparticle In some embodiments, the LNP formulations described herein can additionally comprise a permeability enhancer molecule.

In some embodiments, the nanoparticle formulations can be a carbohydrate nanoparticle comprising a carbohydrate carrier and self-replicating RNA molecule. As a non-limiting example, the carbohydrate carrier can include, but is not limited to, an anhydride-modified phytoglycogen or glycogen-type material, phtoglycogen octenyl succinate, phytoglycogen beta-dextrin, and anhydride-modified phytoglycogen beta-dextrin.

Kits

The disclosure also provides a kit comprising one or more compositions, one or more polynucleotides, one or more polypeptides or one or more vectors of the disclosure. The disclosure also provides a kit comprising one or more recombinant viruses of the disclosure. The kits may be used to facilitate performing the methods described herein. In some embodiments, the kit further comprises reagents to facilitate entry of the vaccines of the disclosure into a cell, such as lipid-based formulations or viral packaging materials.

In some embodiments, the kit comprises one or more Ad26 vectors comprising any of the polynucleotides of the disclosure. In some embodiments, the kit comprises one or more MVA vectors comprising any of the polynucleotides of the disclosure. In some embodiments, the kit comprises one or more GAd20 vectors comprising any of the polynucleotides of the disclosure. In some embodiments, the kit comprises one or more self-replicating RNA molecules comprising any of the polynucleotides of the disclosure.

In some embodiments, the kit comprises an Ad26 vector of the disclosure and a MVA vector of the disclosure. In some embodiments, the kit comprises a GAd20 vector of the disclosure and a MVA vector of the disclosure. In some embodiments, the kit comprises an Ad26 vector of the disclosure and a Gad20 vector of the disclosure. In some embodiments, the kit comprises a self-replicating RNA molecule of the disclosure and a Gad20 vector of the disclosure. In some embodiments, the kit comprises a self-replicating RNA molecule of the disclosure and a MVA vector of the disclosure. In some embodiments, the kit comprises a self-replicating RNA molecule of the disclosure and an Ad26 vector of the disclosure. In some embodiments, the kit comprises one or more polynucleotides of the disclosure. In some embodiments, the kit comprises one or more polypeptides of the disclosure. In some embodiment, the kit comprises one or more cells of the disclosure.

Other Molecules
Peptide-HLA Complex

The disclosure also provides a protein complex comprising human leukocyte antigen (HLA) and a polypeptide comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 9, SEQ ID NO: 10, SEQ ID NO:11, SEQ ID NO:11, SEQ ID NO:12, SEQ ID NO:13, SEQ ID NO:14, SEQ ID NO:15, SEQ ID NO:28, SEQ ID NO: 31, or a fragment thereof.

In some embodiments, the fragment is an immunogenic fragment of any of the polypeptides disclosed herein. In some embodiments, the fragment is between about 6 and 25 amino acids long. In some embodiments, the fragment is about 6 amino acids long. In some embodiments, the fragment is about 7 amino acids long. In some embodiments, the fragment is about 8 amino acids long. In some embodiments, the fragment is about 9 amino acids long. In some embodiments, the fragment is about 10 amino acids long. In some embodiments, the fragment is about 11 amino acids long. In some embodiments, the fragment is about 12 amino acids long. In some embodiments, the fragment is about 13 amino acids long. In some embodiments, the fragment is about 14 amino acids long. In some embodiments, the fragment is about 15 amino acids long. In some embodiments, the fragment is about 16 amino acids long. In some embodiments, the fragment is about 17 amino acids long. In some embodiments, the fragment is about 18 amino acids long. In some embodiments, the fragment is about 19 amino acids long. In some embodiments, the fragment is about 20 amino acids long. In some embodiments, the fragment is about 21 amino acids long. In some embodiments, the fragment is about 22 amino acids long. In some embodiments, the fragment is about 23 amino acids long. In some embodiments, the fragment is about 24 amino acids long. In some embodiments, the fragment is about 25 amino acids long.

In some embodiments, HLA is class I HLA or class II HLA.

In some embodiments, HLA is HLA-A*02:01, HLA-A*03:01, HLA-B*07:02 and HLA-C*07:02, or any combination thereof.

In some embodiments, the protein complex is conjugated to a detection agent or a cytotoxic agent.

The disclosure also provides an isolated proteinaceous molecule that specifically binds the polypeptide of the disclosure or the complex of the HLA and the polypeptide.

Proteinaceous Molecules

In some embodiments, the proteinaceous molecule is an antibody, an alternative scaffold, a chimeric antigen receptor (CAR) or a T cell receptor (TCR).

In some embodiments, the proteinaceous molecule is an antibody.

In some embodiments, the proteinaceous molecule is an alternative scaffold.

In some embodiments, the proteinaceous molecule is a chimeric antigen receptor (CAR).

In some embodiments, the proteinaceous molecule is a T cell receptor (TCR).

Binding of the proteinaceous molecule to the polypeptide or the peptide-HLA complex of the disclosure may be determined experimentally using any suitable method. Such methods may utilize ProteOn XPR36, Biacore 3000 or KinExA instrumentation, ELISA or competitive binding assays known to those skilled in the art. The measured binding may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. "Insubstantial" refers to binding that is 100-fold less when compared to the measured binding of the proteinaceous molecule to the polypeptides or HLA/peptide the disclosure.

Antibodies

Antibodies binding the polypeptides or HLA/peptide complexes may be generated using known methods. For example, the hybridoma method of Kohler and Milstein, Nature 256:495, 1975 may be used to generate monoclonal antibodies. In the hybridoma method, a mouse or other host animal, such as a hamster, rat or monkey, is immunized with one or more polypeptides or fragments thereof, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding and affinity.

Various host animals may be used to produce the antibodies. For example, Balb/c mice, rats or chickens may be used to generate antibodies containing the VH/VL pair, and llama and alpaca may be used to generated heavy chain only (VHH) antibodies using standard immunization protocols. The antibodies made in non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) and superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or any combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www.trianni_com) and Ablexis (www_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions. The antibodies of the disclosure may be isolated for example from phage display library expressing antibody heavy and light chain variable regions as polypeptides with bacteriophage pIX coat protein. The libraries may be screened for phage binding to the desired antigen and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580, 717, 5,969,108, 6,172,197, 5,885,793; 6,521,404; 6,544, 731; 6,555,313; 6,582,915 and 6,593,081.

Preparation of immunogenic antigens and monoclonal antibody production may be performed using any suitable technique, such as recombinant protein production or by chemical synthesis of peptides. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Alternative Scaffolds

Alternative scaffolds (also referred to as antibody mimetics) that bind the polypeptides or HLA/peptide complexes may be generated using various scaffolds known in the art and described herein. Alternative scaffolds may be monobodies, designed to incorporate the fibronectin type III domain (Fn3) of fibronectin or tenascin as a protein scaffold (U.S. Pat. Nos. 6,673,901; 6,348,584) or synthetic FN3 domains such as tencon as described in U.S. Pat. Publ. No. 2010/0216708 and U.S. Pat. Pub. No. 2010/0255056. Additional alternative scaffolds comprise Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. Alternative scaffolds are single chain polypeptidic frameworks that contains a highly structured core associated with variable domains of high conformational tolerance allowing insertions, deletions, or other substitutions within the variable domains. Libraries introducing diversity to one or more variable domains, and in some instances to the structured core, may be generated using known protocols and the resulting libraries may be screened for binding to the neoantigen of the disclosure, and the identified binders may be further characterized for their specificity using known methods. Alternative scaffold may be derived from Protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, A., "Alternative Non-Antibody Scaffolds for Molecular Recognition," *Curr. Opin. Biotechnol.* 18:295-304 (2005); Hosse et al., "A New Generation of Protein Display Scaffolds for Molecular Recognition," *Protein Sci.* 15:14-27 (2006); Nicaise et al., "Affinity Transfer by CDR Grafting on a Nonimmunoglobulin Scaffold," *Protein Sci.* 13:1882-1891 (2004); Nygren and Uhlen, "Scaffolds for Engineering Novel Binding Sites in Proteins," *Curr. Opin. Struc. Biol.* 7:463-469 (1997).

Chimeric Antigen Receptors (CAR)

CARs may be generated that bind the polypeptides or HLA/peptide complexes. Chimeric antigen receptors (CARs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

The CAR typically comprises an extracellular domain that binds the antigen, an optional linker, a transmembrane domain, and a cytosolic domain comprising a costimulatory domain and/or a signaling domain.

The extracellular domain of the CAR may contain any polypeptide that binds the desired antigen. The extracellular domain may comprise a scFv, a portion of an antibody or an alternative scaffold. The CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of the CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD1 9, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI 1a, LFA-1, ITGAM, CDI 1b, ITGAX, CDI 1c, ITGB1, CD29, ITGB2, CD18, LFA-1, ITGB7, TNFR2, DNAM1 (CD226), SLAMF4

(CD244, 2B4), CD84, CD96 (Tactile), CEACAMI, CRTAM, Ly9 (CD229), CD160 (BY55), PSGL1, CD100 (SEMA4D), SLAMF6 (NTB-A, Lyl08), SLAM (SLAMFI, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMFI), CD152 (CTLA4), CD223 (LAG3), CD270 (HVEM), CD278 (ICOS), DAP10, LAT, NKD2C SLP76, TRIM, and ZAP70.

The intracellular signaling domain of the CAR may be derived from the signaling domains of for example CD3ζ, CD3ε, CD22, CD79a, CD66d or CD39. "Intracellular signaling domain," refers to the part of the CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of the CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin.

Exemplary CARs that may be used are for example CAR that contains an extracellular domain that binds HLA in complex with a fragment of the CALR/JAK2 polypeptides of the disclosure, CD8 transmembrane domain and CD3ζ signaling domain. Other exemplary CARs contain CD8 or CD28 transmembrane domain, CD28, 41BB or OX40 costimulatory domain and CD3ζ signaling domain.

The CARs are generated by standard molecular biology techniques. The extracellular domain that binds the desired antigen may be derived from antibodies or their antigen binding fragments generated using the technologies described herein.

T-cell Receptor (TCR)

TCRs may be generated that bind the HLA/peptide complexes of the disclosure. The TCRs may be identified based on T-cell binding to the HLA/peptide complex, followed by sequencing of the TCR. The identified TCR may be identified from
αβ T cells. The identified TCRs may be further engineered to improve their affinity, stability, solubility or the like. For example, TCRs may be cysteine stabilized, expressed as soluble TCRs, as single chain TCRs, as fusion with N-terminal or C-terminal epitope tags, engineered to improve stability with mutations in hydrophobic core, such as positions 11, 13, 19, 21, 53, 76, 89, 91 or 94 of the α chain, domain swapped with α and β chain variable and/or constant domains swapped as described in U.S. Pat. Nos. 7,329,731, 7,569,664, 9,133,264, 9,624,292, US2016/0130319 and U.S. Pat. No. 9,884,075.

Methods of Using any of the Compositions Herein

Provided herein are methods for treating a subject with the compositions disclosed herein. The methods provided herein comprise administering any of the polynucleotides, polypeptides, vectors, and compositions of the disclosure. The polynucleotides, polypeptides, vectors, compositions and administration regimens of the disclosure may be used to treat, prevent or reduce the risk of a clinical condition.

In some embodiments, the clinical condition is a cancer, a myeloproliferative disease, or a cardiovascular disease.

In some embodiments, the clinical condition is a cancer selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

In some embodiments, the clinical condition is a myeloproliferative disease selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

In some embodiments, the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis or a clonal hematopoiesis.

In some embodiments, the subject is Philadelphia chromosome negative. In some embodiments, the subject is treatment naïve. In some embodiments, the subject has become or is suspected to become resistant or refractory to one or more anti-cancer therapeutic. In some embodiments, the subject is not eligible for stem cell transplantation. In some embodiments, the subject has been treated with stem cell transplantation.

In some embodiments, a method of treating, preventing, reducing a risk of onset or delaying the onset of a clinical condition characterized by an expression of JAK2V617F and/or CALR exon 9 mutant in a subject comprises administering to the subject in need thereof any of the compositions disclosed herein, and wherein the administration comprises one or more administrations of the composition. In some embodiments, the clinical condition is a cancer, a myeloproliferative disease, or a cardiovascular disease.

In some embodiments, a method of inducing an immune response in a subject carrying JAK2V617F and/or CALR exon 9 mutation comprises administering to the subject in need thereof any of the compositions disclosed herein, and wherein the administration comprises one or more administrations of the composition.

In some embodiments, a method of treating or preventing a myeloproliferative disease in a subject comprises administering to the subject in need thereof any of the compositions disclosed herein, and wherein the administration comprises one or more administrations of the composition. In some embodiments, the myeloproliferative disease is selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

In some embodiments, a method of treating cancer in a subject comprises administering to the subject in need thereof any of the compositions disclosed herein, and wherein the administration comprises one or more administrations of the composition. In some embodiments, the cancer is selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

In some embodiments, a method of treating a cardiovascular disease in a subject comprises administering to the subject in need thereof a composition comprising any of the compositions disclosed herein, and wherein the administration comprises one or more administrations of the composition. In some embodiments, the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis, and a clonal hematopoiesis.

In some embodiments, the methods disclosed herein comprise administering to the subject in need thereof a composition comprising a polypeptide that comprises at least two or more epitope sequences or a polynucleotide encoding a polypeptide that comprises at least two or more epitope sequences or a vector comprising a polynucleotide encoding for a polypeptide that comprises at least two or more epitope sequences, wherein the epitope sequences are selected from:
  CALR epitope of SEQ ID NO: 1 (MKDKQDEEQR-TRRMMRTKMRMRRMRR TRRKMRRKMSPAR-PRTSCREACLQGWTE) or having at least 90% sequence identity to SEQ ID NO: 1;
  CALR epitope of SEQ ID NO: 2 (EEAEDN-CRRMMRTK) or having at least 90% sequence identity to SEQ ID NO: 2;
  JAK2 epitope of SEQ ID NO: 4 (KLSHKHLVLNY-GVCFCGDENILVQEFVKFG) or having at least 90% sequence identity to SEQ ID NO: 4;
  JAK2 epitope of SEQ ID NO: 5 (VLNYGVCFC) or at least 90% sequence identity to SEQ ID NO: 5;
  JAK2 epitope of SEQ ID NO: 6 (FCGDENILV) or having at least 90% sequence identity to SEQ ID NO: 6; and combinations thereof.

In any of the methods disclosed herein, the composition that is administered to a subject may comprise a vector selected from an adenovirus vector, an alphaviral vector, a poxvirus vector, an adeno-associated virus vector, a retrovirus vector, a self-replicating RNA molecule, and a combination thereof. In some embodiments, the vector is selected from Ad26 vector, MVA vector, GAd20 vector, a self-replicating RNA molecule, and combinations thereof.

In some embodiments, the methods disclosed herein comprise one or more administrations of the compositions provided in the disclosure. For example, the method comprises a first administration followed by a second administration, with a time period between the two administrations.

In some embodiments, the first administration and the second administration may comprise the same or different compositions. For example, the first administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the second administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration and the second administration are administered once in a lifetime of the subject. In some embodiments, first administration and the second administration are administered two or more times in the lifetime of the subject.

In some embodiments, the time period between the first administration and the second administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the first administration and the second administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the first administration and the second administration is about 2 weeks.

In some embodiments, the time period between the first administration and the second administration is about 4 weeks.

In some embodiments, the first administration and the second administration constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following examples are provided to further describe some of the embodiments disclosed herein. The examples are intended to illustrate, not to limit, the disclosed embodiments. In some embodiments, the first administration and second administration can comprise any combination of vectors provided in Table 1 or any combination of epitopes provided in Table 2 below.

TABLE 1

Vector composition in first and second administration

| First administration | Second administration |
|---|---|
| Ad26 | MVA |
| Ad26 | GAd20 |
| Ad26 | Self-replicating RNA molecule |
| Ad26 | Ad26 |
| MVA | Ad26 |
| MVA | GAd20 |
| MVA | Self-replicating RNA molecule |
| MVA | MVA |
| GAd20 | Ad26 |
| GAd20 | MVA |
| GAd20 | Self-replicating RNA molecule |
| GAd20 | GAd20 |
| Self-replicating RNA molecule | Ad26 |
| Self-replicating RNA molecule | MVA |
| Self-replicating RNA molecule | GAd20 |
| Self-replicating RNA molecule | Self-replicating RNA molecule |

TABLE 2

Epitopes present in the vector composition of the first and second administration.

| Vaccine cohort | First administration | SEQ ID NO: | Second administration | SEQ ID NO: |
|---|---|---|---|---|
| 1 | CALR1 epitope 1 and 2 + JAK2 epitope 2 | 1, 2, 6 | CALR1 epitope 1 and 2 + JAK2 epitope 2 | 1, 2, 6 |
| 2 | CALR1 epitope 1 and 2 + JAK2 epitope 2 | 1, 2, 6 | CALR1 epitope 1 and 2 + JAK2 epitope 2 + JAK2 epitope 1 | 1, 2, 6, 5 |
| 3 | CALR-JAK2-2x9mer | 12 | CALR-JAK2-2x9mer | 12 |
| 4 | CALR-JAK2-30mer | 13 | CALR-JAK2-30mer | 13 |
| 5 | LS_CALR-JAK2-2x9mer | 10 | LS_CALR-JAK2-2x9mer | 10 |
| 6 | LS_CALR-JAK2-2x9mer | 10 | TCE_CALR-JAK2-2x9mer | 31 |
| 7 | LS_CALR-JAK2-30mer | 11 | LS_CALR-JAK2-30mer | 11 |
| 8 | TCE_CALR-JAK2-2x9mer | 31 | TCE_CALR-JAK2-2x9mer | 31 |
| 9 | JAK2 epitope 2 | 6 | JAK2 epitope 2 | 6 |
| 10 | CALR-JAK2-2x9mer | 12 | JAK2 epitope 2 | 6 |
| 11 | CALR-JAK2-30mer | 13 | JAK2 epitope 2 | 6 |
| 9 | JAK2epitope2.AAY.JAK2epitope2 | 28 | JAK2epitope2.AAY.JAK2epitope2 | 28 |
| 10 | CALR-JAK2-2x9mer | 12 | JAK2epitope2.AAY.JAK2epitope2 | 28 |
| 11 | CALR-JAK2-30mer | 13 | JAK2epitope2.AAY.JAK2epitope2 | 28 |

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, and JAK2 epitope of SEQ ID NO: 6, wherein the vector is selected from Ad26 vector, MVA vector, GAd20 vector, or a self-replicating RNA molecule; and
  a second administration comprising a second composition comprising a vector comprising a polynucleotide encoding CALR epitope of SEQ ID NO: 1, CALR epitope of SEQ ID NO: 2, and JAK2 epitope of SEQ ID NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26 vector; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26 vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
  a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;
  a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Third Administration

In some embodiments, any of the methods disclosed herein may further comprise a third administration. For example, the method may comprise a first administration, a second administration, followed by a third administration, with a time period between each administration.

In some embodiments, the first administration, second administration, and third administration may comprise the same or different compositions. For example, the first administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the second administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6. In some embodiments, the third administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration, the second administration, and the third administration are administered once in a lifetime of the subject. In some embodiments, the first, second, and third administration are administered two or more times in the lifetime of the subject.

In some embodiments, the time period between the second administration and the third administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the second administration and the third administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the second administration and the third administration is about 6 weeks.

In some embodiments, the time period between the second administration and the third administration is about 8 weeks.

In some embodiments, the first administration, second administration, and third administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following examples are provided to further describe some of the embodiments disclosed herein. The first, second, and third administrations used in the methods disclosed herein can comprise any combination of the epitopes and compositions provided in Table 3 and Table 4 below.

TABLE 3

Epitopes present in the vector composition of first, second, and third administration

| Vaccine cohort | First administration | SEQ ID NO: | Second administration | SEQ IDs NO: | Third administration | SEQ ID NO: |
|---|---|---|---|---|---|---|
| 1 | CALR1 epitope 1 and 2 + JAK2 epitope 2 | 1, 2, 6 | CALR1 epitope 1 and 2 + JAK2 epitope 2 | 1, 2, 6 | CALR1 epitope 1 and 2 + JAK2 epitope 2 | 1, 2, 6 |
| 2 | CALR1 epitope 1 and 2 + JAK2 epitope 2 | 1, 2, 6 | CALR1 epitope 1 and 2 + JAK2 epitope 2 + JAK2 epitope 1 | 1, 2, 6, 5 | CALR1 epitope 1 and 2 + JAK2 epitope 2 + JAK2 epitope 1 | 1, 2, 6, 5 |
| 3 | CALR-JAK2-2x9mer | 12 | CALR-JAK2-2x9mer | 12 | CALR-JAK2-2x9mer | 12 |
| 4 | CALR-JAK2-30mer | 13 | CALR-JAK2-30mer | 13 | CALR-JAK2-30mer | 13 |
| 5 | LS_CALR-JAK2-2x9mer | 10 | LS_CALR-JAK2-2x9mer | 10 | LS_CALR-JAK2-2x9mer | 10 |
| 6 | LS_CALR-JAK2-2x9mer | 10 | TCE_CALR-JAK2-2x9mer | 31 | TCE_CALR-JAK2-2x9mer | 31 |
| 7 | LS_CALR-JAK2-30mer | 11 | LS_CALR-JAK2-30mer | 11 | LS_CALR-JAK2-30mer | 11 |
| 8 | TCE_CALR-JAK2-2x9mer | 31 | TCE_CALR-JAK2-2x9mer | 31 | TCE_CALR-JAK2-2x9mer | 31 |
| 9 | JAK2 epitope 2 | 6 | JAK2 epitope 2 | 6 | JAK2 epitope 2 | 6 |

TABLE 4

Vector composition in first, second and third administration

| First administration | Second administration | Thrid administration |
|---|---|---|
| Ad26 | Ad26 | Ad26 |
| Ad26 | Ad26 | MVA |
| Ad26 | Ad26 | GAd20 |
| Ad26 | Ad26 | Self-replicating RNA molecule |
| Ad26 | MVA | Ad26 |
| Ad26 | MVA | MVA |
| Ad26 | MVA | GAd20 |
| Ad26 | MVA | Self-replicating RNA molecule |
| Ad26 | GAd20 | Ad26 |
| Ad26 | GAd20 | MVA |
| Ad26 | GAd20 | GAd20 |
| Ad26 | GAd20 | Self-replicating RNA molecule |
| Ad26 | Self-replicating RNA molecule | Ad26 |
| Ad26 | Self-replicating RNA molecule | MVA |
| Ad26 | Self-replicating RNA molecule | GAd20 |
| Ad26 | Self-replicating RNA molecule | Self-replicating RNA molecule |
| MVA | Ad26 | Ad26 |
| MVA | Ad26 | MVA |
| MVA | Ad26 | GAd20 |
| MVA | Ad26 | Self-replicating RNA molecule |
| MVA | MVA | Ad26 |
| MVA | MVA | MVA |
| MVA | MVA | GAd20 |
| MVA | MVA | Self-replicating RNA molecule |
| MVA | GAd20 | Ad26 |
| MVA | GAd20 | MVA |
| MVA | GAd20 | GAd20 |
| MVA | GAd20 | Self-replicating RNA molecule |
| MVA | Self-replicating RNA molecule | Ad26 |
| MVA | Self-replicating RNA molecule | MVA |
| MVA | Self-replicating RNA molecule | GAd20 |
| MVA | Self-replicating RNA molecule | Self-replicating RNA molecule |
| GAd20 | Ad26 | Ad26 |
| GAd20 | Ad26 | MVA |
| GAd20 | Ad26 | GAd20 |
| GAd20 | Ad26 | Self-replicating RNA molecule |
| GAd20 | MVA | Ad26 |
| GAd20 | MVA | MVA |
| GAd20 | MVA | GAd20 |
| GAd20 | MVA | Self-replicating RNA molecule |
| GAd20 | GAd20 | Ad26 |
| GAd20 | GAd20 | MVA |
| GAd20 | GAd20 | GAd20 |
| GAd20 | GAd20 | Self-replicating RNA molecule |
| GAd20 | Self-replicating RNA molecule | Ad26 |
| GAd20 | Self-replicating RNA molecule | MVA |
| GAd20 | Self-replicating RNA molecule | GAd20 |
| GAd20 | Self-replicating RNA molecule | Self-replicating RNA molecule |
| Self-replicating RNA molecule | Ad26 | Ad26 |
| Self-replicating RNA molecule | Ad26 | MVA |
| Self-replicating RNA molecule | Ad26 | GAd20 |
| Self-replicating RNA molecule | Ad26 | Self-replicating RNA molecule |
| Self-replicating RNA molecule | MVA | Ad26 |
| Self-replicating RNA molecule | MVA | MVA |
| Self-replicating RNA molecule | MVA | GAd20 |
| Self-replicating RNA molecule | MVA | Self-replicating RNA molecule |

TABLE 4-continued

Vector composition in first, second and third administration

| First administration | Second administration | Thrid administration |
|---|---|---|
| Self-replicating RNA molecule | GAd20 | Ad26 |
| Self-replicating RNA molecule | GAd20 | MVA |
| Self-replicating RNA molecule | GAd20 | GAd20 |
| Self-replicating RNA molecule | GAd20 | Self-replicating RNA molecule |
| Self-replicating RNA molecule | Self-replicating RNA molecule | Ad26 |
| Self-replicating RNA molecule | Self-replicating RNA molecule | MVA |
| Self-replicating RNA molecule | Self-replicating RNA molecule | GAd20 |
| Self-replicating RNA molecule | Self-replicating RNA molecule | Self-replicating RNA molecule |

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
 a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
 a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
 a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule;

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
 a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26;
 a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26; and
 a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
 a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is Ad26;
 a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA; and
 a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
 a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd;
 a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd; and
 a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:
 a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20;
 a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule; and a third administration comprising a third composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Fourth Administration

In some embodiments, any of the methods disclosed herein may further comprise a fourth administration. For example, the method may comprise a first administration, a second administration, a third administration, and a fourth administration, with a time period between each administration. In some embodiments, the first administration, second administration, third administration, and fourth administration may comprise same or different compositions.

For example, the fourth administration may comprise a composition comprising a vector selected from Ad26 vector, GAd20 vector, MVA vector or self-replicating RNA molecule encoding for epitope sequences represented by SEQ NO: 1, SEQ NO: 2, SEQ NO: 4, SEQ NO: 5, and SEQ NO: 6.

In some embodiments, the first administration, the second administration, the third administration, and the fourth administration are administered once in a lifetime of the subject. In some embodiments, the first, second, third, and the fourth administration are administered two or more times in the lifetime of the subject.

In some embodiments, the time period between the third administration and the fourth administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the third administration and the fourth administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the third administration and the fourth administration is about 4 weeks.

In some embodiments, the time period between the third administration and the fourth administration is about 8 weeks.

In some embodiments, the first administration, second administration, third administration, and the fourth administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

In some embodiments, a method of inducing an immune response or a method of treating, preventing, reducing a risk of onset or delaying the onset of a clinical condition characterized by an expression of JAK2V617F and/or CALR exon 9 mutant in a subject comprises a treatment cycle, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Maintenance Administration

In some embodiments, the method further comprises administering to the subject a composition at regular intervals during the treatment cycles, and may continue even after the treatment cycles have ended. For example, the composition may be administered to a subject every month during the treatment regimen, and may continue for additional 6 months. In some embodiments, the composition may be administered between two treatment cycles. In some embodiments, the composition may be any of the compositions disclosed herein, such as a composition comprising a vector selected from Ad26 vector, GAd20 vector, MVA vector or self-replicating RNA molecule encoding the epitope sequences Dose and Route of Administration In some embodiments, the compositions comprising adenovirus vectors is administered at a dose from about $1\times10^4$ IFU (Infectious Unit) to about $1\times10^{12}$ IFU per dose, about $1\times10^4$ IFU to about $1\times10^{11}$ IFU per dose, about $1\times10^4$ IFU to about $1\times10^{10}$ IFU per dose, about $1\times10^4$ IFU to about $1\times10^9$ IFU per dose, about $1\times10^4$ IFU to about $1\times10^8$ IFU per dose, or about $1\times10^4$ IFU to about $1\times10^6$ IFU per dose.

In some embodiments, the compositions comprising adenovirus vectors is administered at a dose from about $1\times10^6$ VP (viral particles) to about $1\times10^{14}$ VP per dose, about $1\times10^6$ VP to about $1\times10^{12}$ VP per dose, about $1\times10^6$ VP to about $1\times10^{10}$ VP per dose, about $1\times10^6$ VP to about $1\times10^8$ VP per dose, or about $1\times10^6$ VP to about $1\times10^7$ VP per dose.

In some embodiments, a composition comprising Ad26 vector is administered at about $1\times10^{10}$ IFU per dose. In some embodiments, a composition comprising Ad26 vector is administered at about $1\times10^{11}$ IFU per dose. In some embodiments, a composition comprising Ad26 vector is administered at about $1\times10^{10}$ VP per dose. In some embodiments, a composition comprising Ad26 vector is administered at about $1\times10^{11}$ VP per dose.

In some embodiments, a composition comprising GAd20 vector is administered at about $1\times10^8$ IFU per dose. In some embodiments, a composition comprising GAd20 vector is administered at about $1\times10^{10}$ IFU per dose. In some embodiments, a composition comprising GAd20 vector is administered at about $1\times10^{10}$ VP per dose. In some embodiments, a composition comprising GAd20 vector is administered at about $1\times10^{11}$ VP per dose.

In some embodiments, the compositions comprising poxvirus vectors is administered at dose from about $1\times10^4$ IFU (Infectious Unit) to about $1\times10^{12}$ IFU per dose, about $1\times10^4$ IFU to about $1\times10^{11}$ IFU per dose, about $1\times10^4$ IFU to about $1\times10^{10}$ IFU per dose, about $1\times10^4$ IFU to about $1\times10^9$ IFU per dose, about $1\times10^4$ IFU to about $1\times10^8$ IFU per dose, or about $1\times10^4$ IFU to about $1\times10^6$ IFU per dose.

In some embodiments, a composition comprising MVA vector is administered from about $1\times10^8$ IFU per dose. In some embodiments, a composition comprising MVA vector is administered from about $1\times10^{10}$ IFU per dose.

In some embodiments, the compositions comprising self-replicating RNA molecule is administered at a dose from about 1 microgram to about 100 microgram, about 1 microgram to about 90 micrograms, about 1 microgram to about 80 microgram to about 70 micrograms, about 1 microgram to about 60 micrograms, about 1 microgram to about 50 micrograms, about 1 microgram to about 40 micrograms, about 1 microgram to about 30 micrograms, about 1 microgram to about 20 micrograms, about 1 microgram to about 10 micrograms, or about 1 microgram to about 5 micrograms of the self-replicating RNA molecule.

In some embodiments, the compositions disclosed herein may be administered to a subject by a variety of routes such as subcutaneous, topical, oral and intramuscular. Administration of the compositions may be accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present disclosure also has the objective of providing suitable topical, oral, systemic and parenteral formulations for use in the methods of prophylaxis and treatment.

In some embodiments, intramuscular administration of the vaccine composition can be achieved by using a needle. An alternative is the use of a needleless injection device to administer the composition (using, e.g., Biojector™) or a freeze-dried powder containing the vaccine composition. For intravenous, cutaneous or subcutaneous injection, or injection at the site of affliction, the composition may be the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against the mutant CALR and/or mutant JAK2 before development of clinical symptoms. The compositions of the disclosure are administered to a subject, giving rise to an immune response in the subject. The amount of the composition able to in induce a detectable immune response is defined to be an "immunologically effective dose." The compositions of the disclosure may induce a humoral as well as a cell-mediated immune response. In a typical embodiment, the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In one exemplary regimen, the composition comprising adenovirus vector is administered (e.g., intramuscularly) in a volume ranging between about 100 µL to about 10 ml containing concentrations of about $10^4$ to $10^{12}$ virus particles/ml. The adenovirus vector composition may be administered in a volume ranging between 0.25 and 1.0 ml, such as in a volume of 0.5 ml.

In one exemplary regimen, the composition comprising MVA vector is administered (e.g., intramuscularly) in a volume ranging between about 100 µl to about 10 ml of saline solution containing a dose of about $1 \times 10^7$ TCID$_{50}$ to $1 \times 10^9$ TCID$_{50}$ (50% Tissue Culture Infective Dose) or InfU. (Infectious Unit). The MVA vector composition may be administered in a volume ranging between 0.25 and 1.0 ml.

Second Therapeutic Agent

In some embodiments, the methods disclosed herein further comprise administering a second therapeutic agent. In some embodiments, the second therapeutic is an immunostimulating agent, a chemotherapeutic agent, an antibiotic, a checkpoint inhibitor, or a cellular therapy.

In some embodiments, the second therapeutic is selected from CTLA-4 antibody, CTLA4 ligand, a PD-1 axis inhibitor, PD-L1 axis inhibitor, a TLR agonist, a CD40 agonist, an OX40 agonist, hydroxyurea, ruxolitinib, fedratinib, a 41BB agonist, aa CD28 agonist, a STING antagonist, a RIG-1 antagonist, TCR-T therapy, CAR-T therapy, FLT3 ligand, aluminum sulfate, BTK inhibitor, a JAK inhibitor, CD38 antibody, CDK inhibitor, CD33 antibody, CD37 antibody, CD25 antibody, GM-CSF inhibitor, IL-2, IL-15, IL-7, CD3 redirection molecules, pomalimib, IFNγ, IFNα, TNFα, VEGF antibody, CD70 antibody, CD27 antibody, BCMA antibody or a GPRC5D antibody, and combinations thereof.

In some embodiments, the second therapeutic is a checkpoint inhibitor selected from pilimumab, cetrelimab, pembrolizumab, nivolumab, sintilimab, cemiplimab, toripalimab, camrelizumab, tislelizumab, dostralimab, spartalizumab, prolgolimab, balstilimab, budigalimab, sasanlimab, avelumab, atezolizumab, durvalumab, envafolimab, or iodapolimab, or any combination thereof.

In some embodiments, the second therapeutic is the JAK inhibitor.

In some embodiments, the second therapeutic agent may be administered in combination with a first composition of the first administration or a second composition of the second administration or a third composition of the third administration, or a fourth composition of the fourth administration.

In some embodiments, the anti-CTLA-4 antibody is combined with any of the first, or the second, or the third, or the fourth administration of the composition of the disclosure.

In some embodiments, the anti-PD-1 or anti-PD-L1 antibody is combined with any of the first, or the second, or the third, or the fourth administration of the composition of the disclosure.

In some embodiments, the checkpoint inhibitors are administered at as dose of about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, or about 250 to about 300 mg/kg.

EXAMPLES

Example 1: Identification of JAK2 V617F Epitope 2 and In-Silico Immunogenicity Assessment of JAK2 V617F epitopes A 17mer sequence of the JAK2 protein with the V617F mutation as the central residue, and all 9-mers of contiguous amino acids that are contained in this 17mer sequence, were generated. In-silico predictions of the binding affinity of these 9-mers to common HLA-A and HLA-B alleles was predicted using netMHCpan4.0. Binding predictions were categorized into three categories of weak binding (predicted affinity >500 nM); moderate binding (predicted affinity between 50 nM to 500 nM), and strong binding (predicted affinity <50 nM) to commonly occurring HLA-A alleles. 9-mer JAK2 epitope 1 of SEQ ID NO: 5 (VLNYGVCFC) and a novel 9-mer JAK2 epitope 2 of SEQ ID NO: 6 (FCGDENILV) were selected from this analysis for further experimental follow-up. The peptide of SEQ ID NO: 6 has not been previously described as being an immunogenic JAK2 fragment. The predicted binding affinity of JAK2 epitope 2 shown in Table 5 is lower than the binding of JAK2 epitope 1.

TABLE 5

Affinity of JAK2 epitope 2.

| Allele | Binding affinity nM | Binding Rank |
|---|---|---|
| HLA-A01:01 | 22680 | 11 |
| HLA-A02:01 | 2878 | 7 |
| HLA-A03:01 | 42208 | 84 |
| HLA-A24:02 | 41245 | 52 |
| HLA-B07:02 | 40322 | 66 |
| HLA-B08:01 | 35548 | 69 |
| HLA-B15:01 | 38417 | 76 |

TABLE 5-continued

Affinity of JAK2 epitope 2.

| Allele | Binding affinity nM | Binding Rank |
|---|---|---|
| HLA-B27:05 | 40573 | 84 |
| HLA-B40:01 | 39076 | 44 |

Binding categories are non-binders = rank > 2.0; moderate binders = rank between 0.5 to 2.0; strong binders = Rank < 0.5.

Example 2: Mutant JAK2 Versus Wild-Type JAK2 Epitope Immunogenicity in Disease Patient Samples PBMCs were isolated from Essential thrombocythemia (ET) or Primary Myelofibrosis (PMF) patients with a confirmed JAK617F mutation. Individual Class-I-associated mutJAK2 or wild-type JAK2 peptides were exogenously administered at 5 µg/ml concentration to 250,000 PBMCs on day 0. Cells were cultured for 10 days in the presence on 10 IU/ml of human IL-2 and 10 ng/ml of human IL-15, and subsequently evaluated for frequency of mutant or wild-type JAK2 antigen-specific T cells by peptide-pulse recall and intracellular staining flow cytometry analysis for IFNγ and TNFα producing CD8+ T cells. An antigen specific response was considered positive if the frequency of JIFNγ/TNFα~+ CD8+ T cells was three-fold greater compared to cells treated cells with DMSO only on Day 0 and greater than 0.1%. Results are summarized in Table 6.

TABLE 6

| Disease | Donor Number | Control viral antigens CEF response | Mutant JAK2 epitope 2 | Mutant JAK2 epitope 1 | Wild Type JAK2 epitope 2 | Wild Type JAK2 epitope 1 |
|---|---|---|---|---|---|---|
| PMF | 120174174 | Yes | Yes (30%) | No | No | No |
| PMF | 120250311 | Yes | No | No | No | No |
| PMF | 120800910 | No | No | No | No | No |
| PMF | 120800936 | Yes | Yes (0.63%) | Yes (0.62%) | No | No |
| PMF | 120817869 | Yes | No | No | No | No |
| ET | 120708928 | Yes | No | No | No | No |
| ET | 120815833 | Yes | Yes (30.6%) | No | No | Yes (1.3%) |
| ET | 120824685 | Yes | No | No | No | No |

YES indicates a 3-fold increase in frequency of IFNγ/TNFα + CD8+ T cells compared to DMSO only stimulated cells for each donor. The parentheses indicate the actual frequency of IFNγ/TNFα + CD8+ T cells.

FIG. 1 shows the immunogenicity of JAK2 epitope 1 and JAK2 epitope 2 in disease patient samples compared to the wild-type sequences of the same epitope regions. The corresponding wild-type peptide sequences for mutJAK2 Epitopes I and II were also evaluated and shown to have similar responses as DMSO control.

Example 3: Design and Generation of the CALR.JAK2 Polynucleotides and Polypeptides for Ad26 and MVA Expression To select a vaccine composition that resulted in good antigen expression and T-cell activation, a series of CALR.JAK2 polynucleotides and polypeptides were designed and tested.

CALR Type 1 and Type 2 mutations were included into the polynucleotide. Based on in silico T cell epitope prediction and HLA binding studies, a 54-mer peptide (SEQ ID NO: 1) of the CALR mutant Type 1 and a truncated 14-mer peptide (SEQ ID NO: 2) of the CALR mutant Type 2 protein was included into the polynucleotide. The CARL portion of the polynucleotide encodes the amino acid sequence shown in SEQ ID NO: 3. To ensure good intracellular processing of all proteins, the individual peptides were connected by AAY (ala-ala-tyr) linkers that promote proteasomal cleavage.

Also based on in silico T cell epitope prediction and HLA binding studies, two distinct JAK2 peptides, a 30-mer peptide (SEQ ID NO: 4) or two 9-mer peptides (SEQ ID NO: 5 or SEQ ID NO: 6) were included, each of which containing the V617F mutation. The peptide of SEQ ID NO: 6 has not been described earlier as being an immunogenic JAK2 fragment.

To ensure good intracellular processing of all proteins, the individual peptides were also connected by AAY (ala-ala-tyr) linkers that promote proteasomal cleavage. SEQ ID NO: 7 represents the amino acid sequence of the JAK2 two 9-mers separated by the AAY linker.

Two different constructs were designed in which the CALR portions were identical, but the JAK2 portion was either the 30-mer peptide or the two 9-mer peptides. These two different transgenes were designed with either no leader sequence (LS), a HAVT20 LS (MACPGFLWALVIST-CLEFSMA; SEQ ID NO: 8), or a ubiquitin signal (Ubiq) (MQIFVKTLTGKTITLEVEPSDTIENVKAKIQDKEG-IPPDQQRLIFAGKQLEDGRTLSDYNI QKESTLHLVLRLRGV; SEQ ID NO: 54) at the N-terminus. The constructs are listed in Table 3. The HAVT20 LS should direct the transgene into the ER, whereas the ubiquitin sequence targets the proteasome. This could result in different levels of expression of the TG between the constructs. In addition, a construct encoding only the sequence from two mutant CALR proteins was generated, which was used as a control for the expression of the CALR protein. The protein and polynucleotide sequence of the transgenes are shown in Table 7. The polynucleotide sequences shown were optimized for adenovirus expression.

TABLE 7

Constructs for adenovirus expression

| Construct name | Mutant CALR sequences | JAK2 mutant sequences |
|---|---|---|
| LS_CALR | CALR mutant Type 1, truncated CALR mutant Type 2 | none |
| LS_CALR_JAK2-2x9mer | CALR mutant Type 1, truncated CALR mutant Type 2 | 2x9-mer |
| LS_CALR_JAK2-30mer | CALR mutant Type 1, truncated CALR mutant Type 2 | 30-mer |

TABLE 7-continued

Constructs for adenovirus expression

| Construct name | Mutant CALR sequences | JAK2 mutant sequences |
|---|---|---|
| CALR_JAK2-2x9mer | CALR mutant Type 1, truncated CALR mutant Type 2 | 2x9-mer |
| CALR_JAK2-30mer | CALR mutant Type 1, truncated CALR mutant Type 2 | 30-mer |
| Ubiq_CALR_JAK2-2x9mer | CALR mutant Type 1, truncated CALR mutant Type 2 | 2x9-mer |
| Ubiq_CALR_JAK2-30mer | CALR mutant Type 1, truncated CALR mutant Type 2 | 30-mer |

LS: leader sequence; Ubiq: ubiquitin

TABLE 8

CALR.JAK2 polypeptide SEQ ID and polynucleotide SEQ ID NOs

| construct name | Protein SEQ ID NO: | Polynucleotide SEQ ID NO: |
|---|---|---|
| LS_CALR | 9 | 16 |
| LS_CALR_JAK2-2x9mer | 10 | 17 |
| LS_CALR_JAK2-30mer | 11 | 18 |
| CALR_JAK2-2x9mer | 12 | 19 |
| CALR_JAK2-30mer | 13 | 20 |
| Ubiq_CALR_JAK2-2x9mer | 14 | 21 |
| Ubiq_CALR_JAK2-30mer | 15 | 22 |

The CALR.JAK2 constructs were cloned into pUC57 shuttle plasmid using standard methods for adenovirus expression. The expression cassette consisted of a tetracycline operator (TetO)-containing cytomegalovirus (CMV) promoter, to allow use in combination with the PER.C6 TetR cell line, a Kozak sequence, the CALR.JAK2 polynucleotide and the simian virus 40 (SV40) polyadenylation signal flanked by Ad26-specific sequences outside the expression cassette. These flanking Ad26-specific sequences were homologous to the Ad26 backbone plasmid sequence to ensure plasmid generation by homologous recombination. The sequence was human-gene optimized for enhanced transgene expression.

To test CALR.JAK2 expression by these different constructs, HTEK293 cells were transfected with the respective DNA plasmids and expression in cell lysates was examined by Western blot 72 hours post transfection. In addition, proteasome activity was inhibited by adding proteasome inhibitor MG132 4 hours before collecting the samples to examine the effect on the transgene expression. All constructs expressed the CALR.JAK2 epitopes and the highest expression was observed for the constructs with the HAVT20 LS. Proteasome inhibition modestly enhanced transgene expression by the constructs with a ubiquitin signal, but this difference could not be quantified by Western blot. Based on the CALR.JAK2 expression data, the two constructs with the HATV20 leader sequence (LS) were selected for production of adenovirus, i.e., Ad26.LS_CALR_JAK2-3Omer (Ad26HEME001) and Ad26.LS_CALR_JAK2-2x9mer (Ad26HEME002). In addition, Ad26-LS-CALR (AD26HEME003) was produced to serve as a possible control. The polynucleotide sequence of Ad26HEME001 containing the tetracycline operator (TetO)-containing cytomegalovirus (CMV) promoter, a Kozak sequence, CALR.JAK2 and the simian virus 40 (SV40) polyadenylation signal is shown in SEQ ID NO: 23. The polynucleotide sequence of the Ad26HEME002 containing the tetracycline operator (TetO)-containing cytomegalovirus (CMV) promoter, a Kozak sequence, CALR.JAK2 and the simian virus 40 (SV40) polyadenylation signal is shown in SEQ ID NO: 24.

To select the cell line for Ad26HEME001 and Ad26HEME002 production, virus rescue-ability was measured by transfection of viral genome DNA in PER.C6® compared to PER.C6 TetR cells. Cytopathic effect (CPE) and plaque formation (together showing rescue-ability) were comparable between the Ad26HEME001 and Ad26HEME002 constructs (Table 9). In summary, both constructs showed full CPE within 8 days on PER.C6 TetR, but not on PER.C6® cells. Ad26HEME001 and Ad26HEME002 showed about 13 and about 11 plaques respectively on PER.C6® cells and >100 plaques on PER.C6 TetR cells for co-easy transfections at Day 8. This indicated that the rescue-ability was inhibited on PER.C6® cells. Adenoviral vectors that are difficult to rescue have limited productivity characteristics and have a high risk on deletions and mutations in the transgene expression cassette. Based on these results, PER.C6 TetR was selected as cell line for virus production of Ad26HEME001 and Ad26HEME002. Ad26HEME003 was also produced on PER.C6 TetR cells.

TABLE 9

| | Full CPE PER.C6 ®/ PER.C6 TetR | # plaques PER.C6 ®/ PER.C6 TetR |
|---|---|---|
| Ad26HEME001 | No CPE/<8 days | 13/>100 |
| Ad26HEME002 | No CPE/<8 days | 11/>100 |

Example 4: Generation of Ad26HEME001 and Ad26HEME002

Research batches were generated from cells transfected with single-genome pAd26HEME001 (pAd26.LS_CALR_JAK2-3Omer), pAd26HEME002 (pAd26.LS_CALR_JAK2-2×9mer), and pAd26HEME003 (pAd26.LS_CALR) plasmids.

The pUC57 plasmid DNA, was used to clone the Ad26 Early Region 1 (E1) TG expression cassette into the pAd26 backbone to generate the pAd26HEME001, pAd26HEME002, and pAd26HEME003 plasmids. The E1 region in the pAd26 backbone was deleted to render the vector replication-incompetent in non-complementing cells such as human cells. In addition, a part of the Ad26 Early Region 3 (E3) region was removed (ΔE3) to create sufficient space in the viral genome for insertion of foreign antigens, and the Ad26 Early Region 4 (E4) open reading frame (orf) 6 was exchanged by the adenovirus Type 5 (Ad5) homologue to enable production of replication-incompetent Ad26 vectors in Ad5-E1-complementing cell lines like HEK293, PER.C6®, and HER96 cells. The pAd26 backbone was linearized by using a unique restriction site (AsiSI) in the region in which the TG cassette was later introduced. Both ends of this linearized plasmid contained overlapping sequences homologous to the Ad26-specific sequences present at the outsides of the E1 transgene expression cassette. This enabled plasmid generation by cloning the transgene cassette into the pAd26 backbone using homologous recombination techniques. The complete plasmid sequences were verified.

To generate the Ad26HEME001, Ad26HEME002, and Ad26HEME003 vectors, the plasmids were transfected into PER.C6 TetR cells. Virus was amplified on PER.C6 TetR cells, purified, and tested for integrity and identity of the adenovirus genome and correct expression of the TG.

Batch generation and characterization

One Ad26HEME001, two Ad26HEME002, and one Ad26HEME003 research batches were generated and characterized for assessment of infectivity, transgene expression, batch genetic stability, and relative productivity in suspension PER.C6 (sPER.C6) TetR cells. All research batches were generated on adherent PER.C6 TetR cells. Batch quality was characterized by expression of the encoded antigen under non-replicating conditions, the number of virus particles (VP) and infectious units (IU).

All produced research batches showed expression of the encoded antigen as shown by Western blot and all batches had low VP/IU ratios. The research batch of Ad26HEME001 showed a VP/IU ratio of 29. The two research batches of Ad26HEME002 showed a VP/IU ratio of 5, and Ad26HEME003 showed a VP/IU ratio of 8. Both genetic stability and productivity are important for the feasibility to scale-up production of adenoviral vectors to clinical trial material (CTM) or commercial scale. The risk for genetic instability as defined by changes in the vector genome and outgrowth of a population with undesired properties during propagation in the production cell line can be assessed by propagation of several virus populations at small scale. For all research batches, genetic stability was assessed on the final batch material, by identity polymerase chain reaction (ID PCR) for the transgene region, E3 gene region, and E4 gene region. In addition, the polymerase chain reaction (PCR) product of the transgene region was sequenced. All research batches were found to be genetically stable.

Productivity (as defined by titers of VP/mL) was assessed in small-scale experiments by comparing the vaccine candidate vector to respective benchmark controls, of which performance in the 1OL process intensified (PIN)-bioreactor is known. In brief, sPER.C6 TetR cells were transduced with 70, 300, and 900 VP/cell of purified research batch material and two Ad26 benchmark controls. Ad26HEME001, Ad26HEME002, and Ad26HEME003 showed comparable productivity to the standard control at 70, 300, and 900 VP/cell, indicating that all three vectors are good producers (controls showed expected outcome) with $\sim 10^{11}$ VP/ml produced after 2-3 days in culture.

The polynucleotide sequence of Ad26HEME002 vector including the various elements is shown in SEQ ID NO: 24 and the amino acid sequences encoded by them is shown is SEQ ID NO: 10.

Example 5: Generation of MVA.CALR.JAK2 and GAd20.CALR.JAK2 Construct

Amino acid sequence for CALR.JAK2 transgene was converted into nucleotide sequence based on the human codon usage. Termination motifs for the MVA vector (TTTTTnT) were avoided. BamH1 restriction site and a KOZAK sequence were then added upstream the nucleotide sequence. Two STOP codons followed by Asc1 restriction site were added downstream the nucleotide sequence. A T cell enhancer (TCE) polynucleotide encoding a small peptide fragment with length of 28aa from the mandarin fish invariant chain (SEQ ID NO: 29) was placed at the N-terminus of the transgene. Preclinical data has shown this sequence to increase the immunological response of the viral vector. The synthesis of the transgene was performed using known methods.

The MVA transgene cloned under the control of the vaccinia P7.5 early/late promoter (SEQ ID NO: 32) was inserted by homologous recombination into the deletion III locus of MVA (FlankIII-1 and −2 regions) and the recombinant virus particles were produced using known methods.

The GAd20 transgene was subcloned into a shuttle plasmid between CMV promoter with two TetO repeats and a BGH polyA via EcoRI-Not1 restriction sites. The resulting expression cassette was transferred into the GAd20 genome by homologous recombination in suitable *E. coli* strains, transformed with the CMV-transgene-BGH DNA fragment and with a construct carrying the GAd20 genome. Recombination involved CMV and BGH as homology arms, that were already present in the GAd20 construct in place of the E1 deletion (insertion site of the transgene). Recombinant GAd20 vectors were then rescued by transfection of the E1 complementing, TetR expressing M9 cells and amplified by subsequent re-infection of fresh M9 cells.

MVA and GAd20 vectors expressing the polypeptide TCE_CALR_JAK2-2×9mer (SEQ ID NO: 31) (HCalJ-9.9) were generated using know methods.

Example 6: Ad26.CALR.JAK2 Vectors Express, Process and Present Antigen to Autologous T Cells The purpose of this study was to test human antigen-presenting cells (APCs) capacity to process and present the vaccine's neoantigens and mount T-cell responses.

Frozen vials of autologous $CD1c^+$ DCs and autologous $CD4^+/CD8^+$ T cells were isolated via magnetic bead negative selection. $CD1c^+$ DCs were infected at a multiplicity of infection (MOI) of 50,000 VP overnight with Ad26HEME002 or Ad5HEME002 (Ad5 vector engineered to express the LS_CALR_JAK2-2×9mer transgene). At 18 to 24 hours post infection, identical donor autologous T cells were mixed with $CD1c^+$ DCs at a 10:1 ratio. Human IL-15 at 10 ng/mL was added to culture on Day 0 and half media changes with 2×IL-15 and IL-2 (10 IU/mL) were performed every 2 to 3 days until Day 11. On Day 11, peptides corresponding to CALRmut, JAK2V617F, or Adeno Hexon protein (positive control) were added to DC/T-cell culture overnight together with protein transport inhibitors. The resulting cultures were stained for T-cell markers (CD4, CD8, CD3) and markers of activated T cells (IFN-γ, TNF-α) and analyzed by flow cytometry. Increased IFN-γ and TNF-α staining after overnight stimulation of peptides on Day 11 indicated expansion of CALRmutant, and/or JAK2V617F antigen specific T cells specifically due to Ad26/Ad5-HEME002-driven transgene expression. A 3-fold increase in IFN-γ and TNF-α double-positive CD8 T cells over Ad26/Ad5 empty vector was considered a positive response. Exclusion criteria were (i) Adeno Hexon responses below 0.5% IFN-γ and TNF-α double-positive T cells, or (ii)<1% viral antigen (adeno CEF construct) IFN-γ and TNF-α double-positive T cells; in which case the experiment was considered suboptimal and the negative response was likely a technical failure of the donor or the experimental set up.

Figure 2:
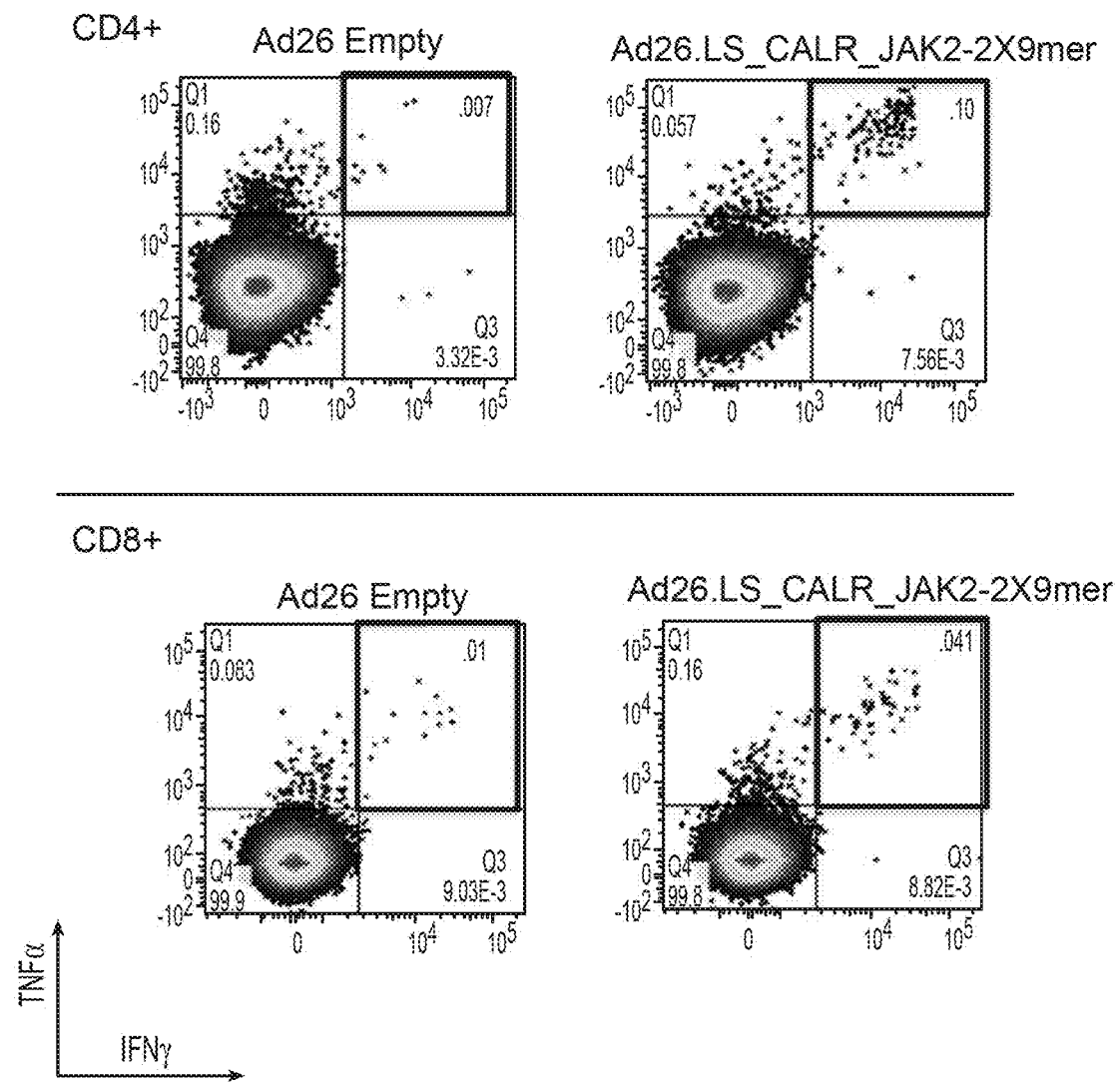
FIG. 2 shows flow cytometry intracellular cytokine staining for IFN-γ/TNF-α response from both CD4+ and CD8+ T cells. Normal donor dendritic cells were infected with adenovirus 26 vectors containing either an empty vector or a polynucleotide encoding for LS_CALR.JAK2 2X9mer of SEQ ID NO: 10. Autologous CD4/CD8 T cells were added to dendritic cells 24 hours post infection. Dendritic and T cell s were co-cultured for 11 days and restimulated with a pool of peptides specific mutCALR.
Figure 3:
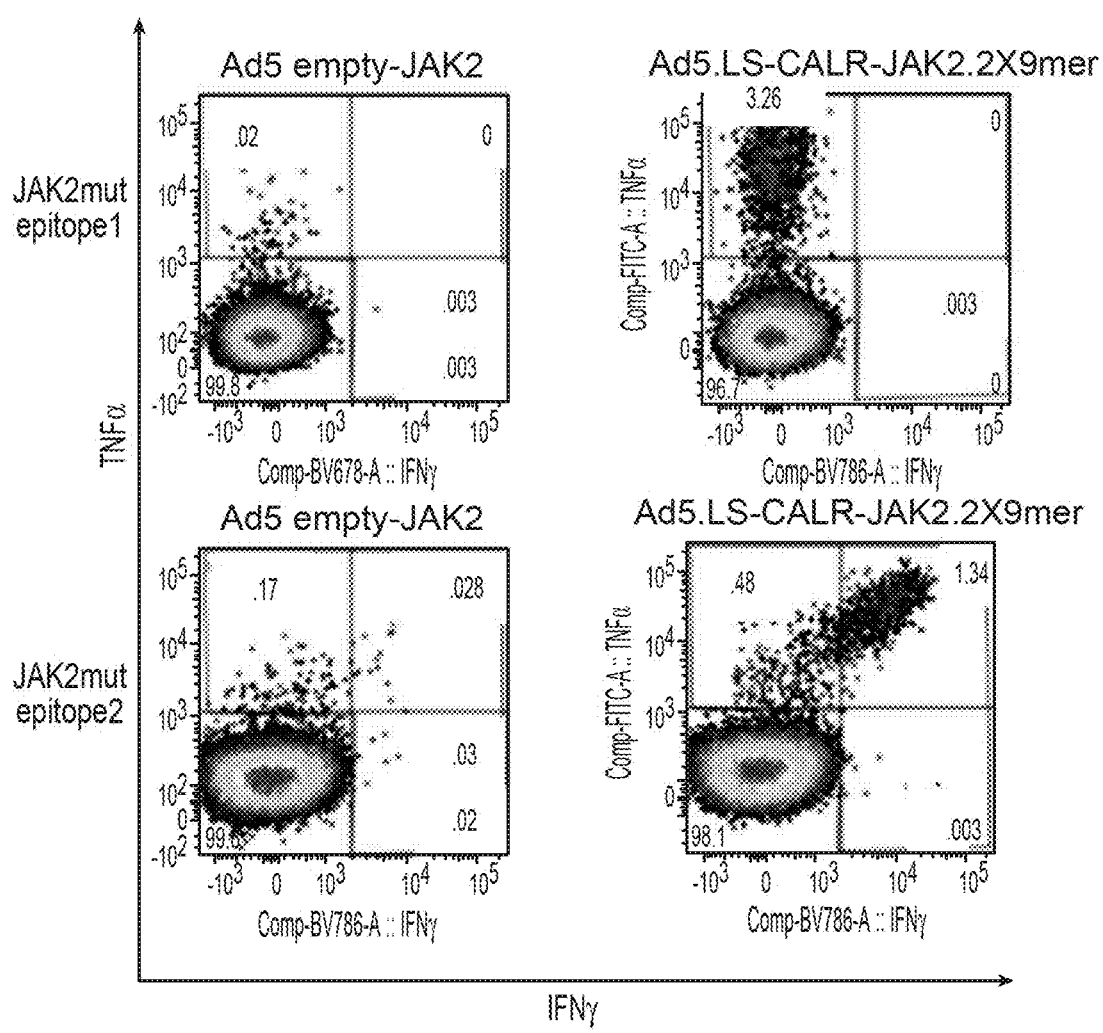
FIG. 3 shows flow cytometry intracellular cytokine staining for IFN-γ/TNF-α response from CD8+ T cells. Normal donor dendritic cells were infected with adenovirus 5 vectors containing either an empty vector or a polynucleotide encoding for LS_CALR/JAK2 2X9mer of SEQ ID NO: 10. Autologous CD8 T cells were added to dendritic cells 24 hours post infection. Dendritic and T cell s were co-cultured for 11 days and restimulated with 9mer peptides specific to either muJAK2 epitope 1 (SEQ ID NO: 5) or epitope 2 (SEQ ID NO: 6).
Figure 4:
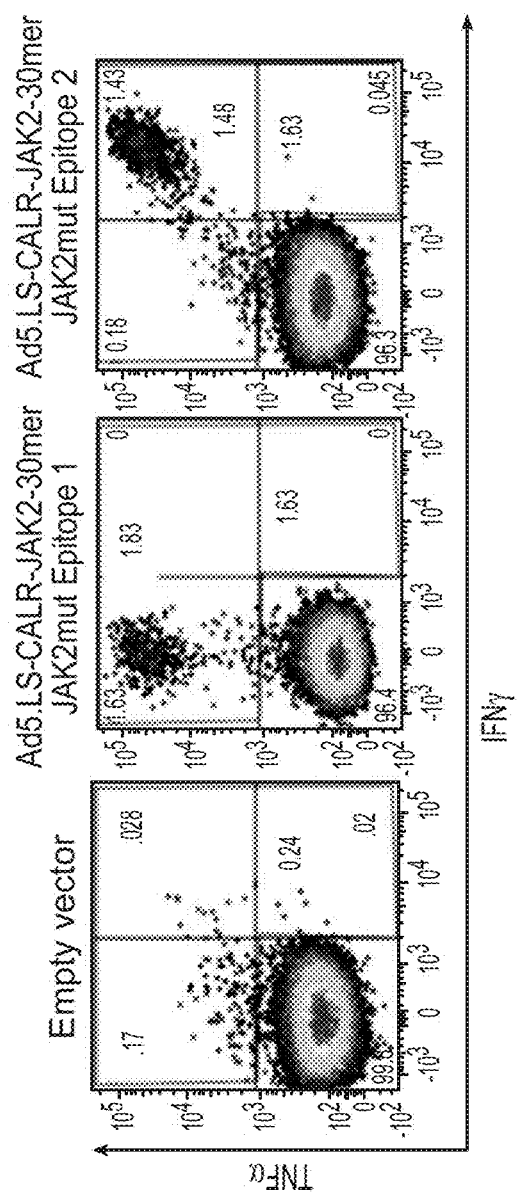
FIG. 4 shows flow cytometry intracellular cytokine staining for IFN-γ/TNF-α response from CD8+ T cells. Normal donor dendritic cells were infected with adenovirus 5 vectors containing either an empty vector or a polynucleotide encoding for LS_CALR.JAK2-30mer (SEQ ID NO: 11). Autologous CD8 T cells were added to dendritic cells 24 hours post infection. Dendritic and T cell s were co-cultured for 11 days and restimulated with a 9mer peptide specific to either mutJAK2 epitope 1 (SEQ ID NO: 5) or epitope 2 (SEQ ID NO:6).

A total of 24 unique healthy donor cells were screened. FIG. 2 shows a representative result of screening on one donor for CALRmutant specific T cell responses. In the experiment, the cells were gated on live/CD3+/CD8+ cells and IFN-γ and TNF-α staining assessed. Both CD8 (class I) and CD4 (class II) responses were observed after infection. The experiments were conducted across 3 independent analyses and the frequency of response was similar across the experiments, about 35% regardless wheatear Ad26 or Ad5 was used. FIG. 3 shows that both JAK2 epitopes included into the vaccine (SEQ ID NO: 5 (VLNYGVCFC); epitope 1 in FIG. 3 and SEQ ID NO: 6; FCGDENILV epitope 2 in FIG. 3) are immunogenic. FIG. 4 shows a representative result of screening one donor for JAK2 mutant specific T cell responses. The data demonstrated that both JAK2 mutant neoepitopes were processed from the vaccine transgene sequence indicating that these epitopes can be presented by cancer cells. The HLA types of all tested donors are shown in Table 10.

TABLE 10

| Donor | HLA A1 | HLA B1 | HLA C1 | HLA A2 | HLA B2 | HLA C2 |
|---|---|---|---|---|---|---|
| 2480 | 03:01 | 15:03 | 2:10 | 23:01 | 44:02 | 05:01 |
| 013B | 01:01 | 07:02 | 07:01 | 03:01 | 08:01 | 07:02 |
| 4384 | 24:02 | 35:01 | 04:01 | 30:01 | 42:01 | 07:01 |
| 118 | 02:01 | 14:02 | 1:01 | 68:02:00 | 27:05 | 8:02 |
| 676 | 1:01 | 08:01 | 3:04 | 32:01:00 | 15:01 | 7:01 |
| 274 | 03:01 | | | | | |
| 3942 | 02:02 | 08:01 | 03:04 | 03:01 | | 07:02 |
| 240 | 03:01 | 15:03 | 02:10 | 23:01 | 44:02:00 | 5:01 |
| 644 | 03:01 | 07:02 | 06:02 | 66:01:00 | 13:02 | 7:02 |
| 359 | 1:01 | 07:02 | 7:01 | 03:01 | 08:01 | 7:01 |
| 538 | 02:01 | 27:05 | 1:02 | 03:01 | 38:01:00 | 12:03 |

Example 7: Ad26.CALR.JAK2 Vectors Express Induced Cellular Responses in Mice

The purpose of the study was to test if the T-cell responses induced by Ad26-containing Ad26HEME001 or A26HEME002 were higher than that induced by the empty Ad26 vector using IFN-γ enzyme-linked immunospot assay (ELISpot), and to select the optimal mouse strain for further immunogenicity studies.

The C57BL/6 and Balb/c mouse strains were tested for this immunogenicity study as epitope prediction analysis showed that potential CD8 T-cell epitopes were present in these mice strains. Mice were injected with a dose of $10^{10}$ VP/mouse of Ad26HEME001 or Ad26HEME002, or an Ad26 not encoding a transgene (Ad26.Empty). 15-mer overlapping peptide pools spanning the Ad26HEME001 or Ad26HEME002 insert were used to assess the cellular immune response 14 days after a prime vaccination (IFN-γ ELISpot). The experimental groups are shown in Table 11.

TABLE 11

| Group | Animal nr | Description of groups | Mouse strain |
|---|---|---|---|
| 1a | 4 | Ad26.Empty dose $10^{10}$ VP | C57BL/6 |
| 1b | 4 | Ad26.Empty dose $10^{10}$ VP | Balb/c |
| 2 | 8 | Ad26HEME001 dose $10^{10}$ VP | C57BL/6 |
| 3 | 8 | Ad26HEME002 dose $10^{10}$ VP | C57BL/6 |
| 4 | 8 | Ad26HEME001 dose $10^{10}$ VP | Balb/c |
| 5 | 8 | Ad26HEME002 dose $10^{10}$ VP | Balb/c |

Figure 5:
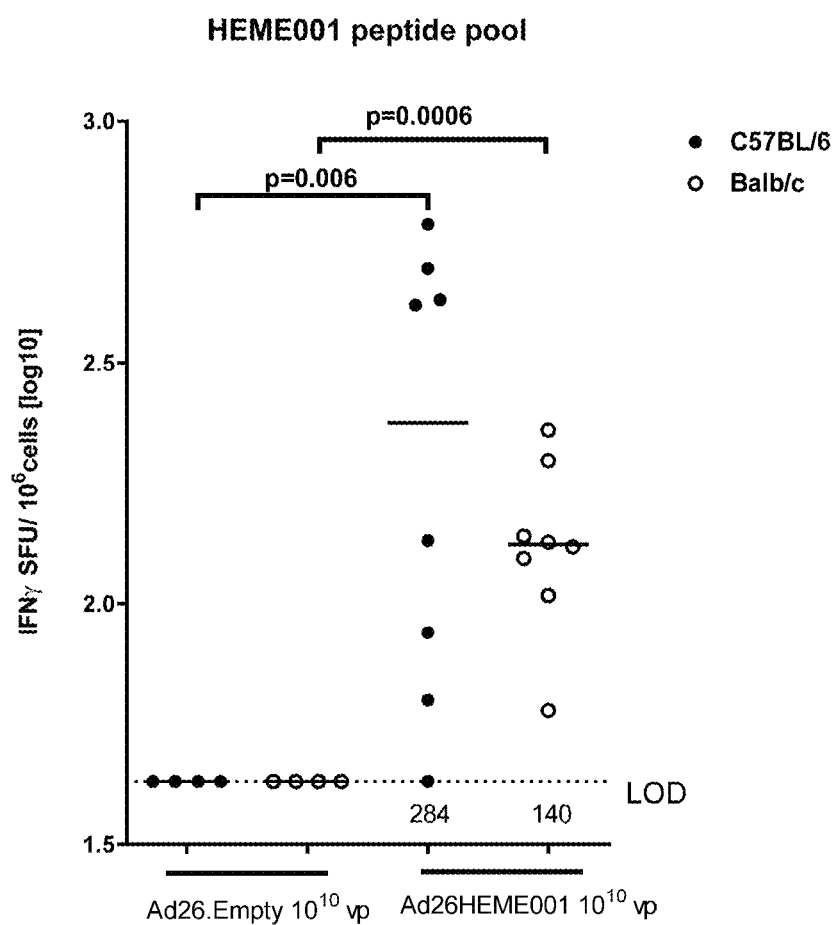
FIG. 5 shows IFN-γ ELISpot responses in splenocytes from C57BL/6 or Balb/c mice immunized IM with Ad26HEME001 (LS_CALR_JAK2-30mer, SEQ ID NO: 11) (n=8/group) or Ad26.Empty (n=4) at a dose of $10^{10}$ VP, at 2 weeks post immunization. Splenocytes were stimulated overnight with a 15-mer peptide pool spanning the HEME001 sequence. The number of IFN-γ SFU per $10^6$ splenocytes was determined by ELISpot. The mean response per group is indicated with a horizontal line. The dotted lines indicate the background of the assay defined as the 95% percentile of SFU observed in non-stimulated splenocytes (43 SFU/$10^6$ cells). Statistical analysis was done using Wilcoxon Rank Sum test, values below 43 SFU/$10^6$ cells were set to this cut-off. VP, virus particle; LOD, limit of detection.

An insert-specific T-cell response was elicited 14 days after the prime, in C57BL/6 and Balb/c mice as measured by IFN-γ ELISpot, and there was a significantly higher immune-response induced in animals immunized with Ad26HEME001 (FIG. 5) or Ad26HEME002 (FIG. 6) over that induced by Ad26.Empty-immunized animals. No cellular immune response was detected against the LS peptide (data not shown). There was no significant difference between the immune response induced by the two vectors when looking across mouse strain. Similarly, there was no significant difference between the immune response towards the HEME001 peptide pool induced by Balb/c and C57BL/6 when looking across the vaccine candidates. There was a significant difference between the immune response towards the HEME002 peptide pool induced by Balb/c and C57BL/6 when looking across the vaccine candidates.

Example 8: Ad26.CALR.JAK2 and MVA.CALR.JAK2 Vectors Induce Cellular Responses in Mice The purpose of these studies was to determine if a modified vaccinia Ankara (MVA) vector encoding HCalJ-9.9 (i.e., MVA-HCalJ-9.9, MVAHEME002) could boost the immune response induced by a prime immunization with Ad26HEME002 in Balb/c mice. The Balb/c mouse strain was selected based on the data described in Example 7 where less variation was seen with the Balb/c mouse strain compared to the C57BL/6 mouse strain.

In the first study, Ad26HEME002 was dosed $10^{10}$ VP and MVA-HCalJ-9.9 was dosed $10^7$ IU. At Week 0, mice were immunized by IM injection with Ad26HEME002; half of the animals did not receive a boost immunization (Group 2) and half of the animals were boosted at Week 3 with MVA-HCalJ-9.9 (Group 3). Another group of mice were immunized (prime) with MVA-HCalJ-9.9 at Week 3 (Group 1). Control mice were primed at Week 0 with Ad26.Empty (Group 4). At Week 4, all animals were sacrificed and splenocytes were stimulated with 15-mer overlapping peptide pools spanning the Ad26HEME002 insert, or a peptide pool covering the CALR sequence in the insert, or 9-mers covering the two JAK2 9-mer sequences. The induction of IFN-γ-producing cells was measured by IFN-γ ELISpot. Table 12 shows the various experimental groups.

TABLE 12

| Group | Animal nr | Description of groups |
|---|---|---|
| 1 (#5) | 5 | MVA-HCalJ-9.9 dose $10^7$ IU |
| 2 (#7) | 10 | Ad26HEME002 dose $10^{10}$ VP |
| 3 (#8) | 10 | Ad26HEME002 dose $10^{10}$ VP/ MVA-HCalJ-9.9 dose $10^7$ IU |
| 4 (#9) | 3 | Ad26.Empty dose $10^{10}$ VP |

Figure 7:
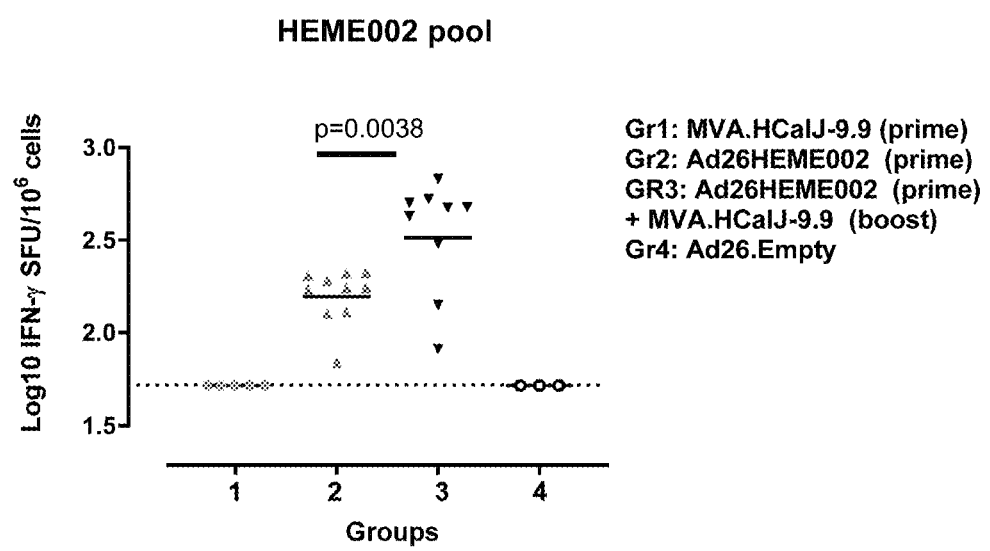
FIG. 7 shows IFN-γ ELISpot responses in splenocytes from C57BL/6 mice immunized IM with Ad26HEME002 (LS_CALR_JAK2-2×9mer, SEQ ID NO: 10), MVA-HCalJ-9.9 (TCE_CALR_JAK2-2×9mer, SEQ ID NO: 26), or Ad26.Empty (n=10/group, except for Group 1 [MVA-HCalJ-9.9] which had 5 animals and Group 10 [Ad26.Empty] which had 3 animals). At Week 4, splenocytes were stimulated overnight with a peptide pool spanning the sequence of Ad26HEME002. The number of IFN-γ SFU per $10^6$ splenocytes was determined by ELISpot. The geometric mean response per group is indicated with a horizontal line. The dotted lines in the graphs indicate the background of the assay defined as the 95% percentile of SFU observed in non-stimulated splenocytes. For difference testing comparing Ad26HEME002 prime-only with Ad26HEME002 prime immunization and boost with MVA-HCalJ-9.9, an ANOVA was performed on $log_{10}$-transformed ELISpot data. Values below 52 SFU/$10^6$ cells were set as cut-off. The horizontal bars correspond to the mean of each group. Gr: group.
Figure 8:
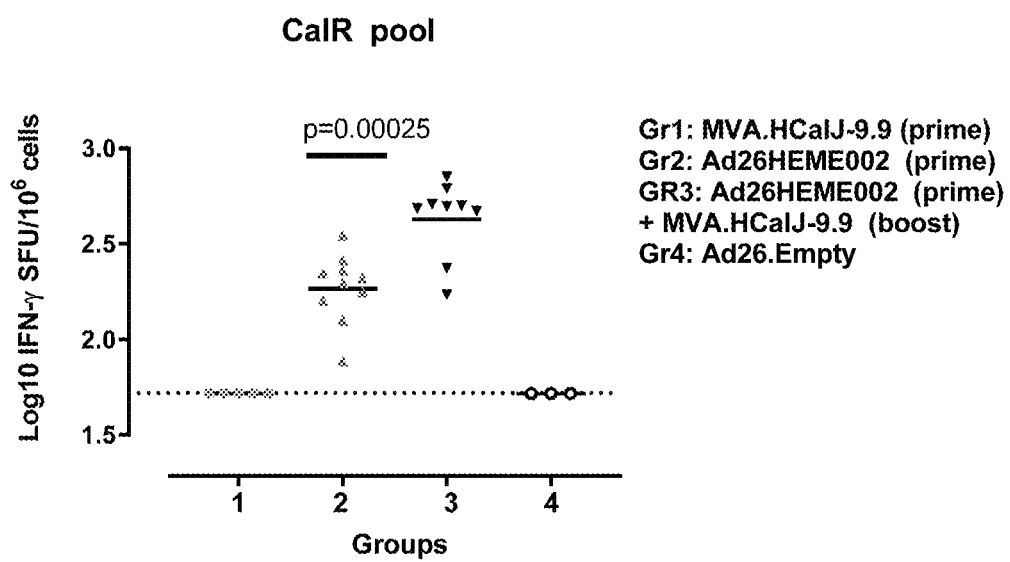
FIG. 8 shows IFN-γ ELISpot responses in splenocytes from C57BL/6 mice immunized IM with Ad26HEME002 (LS_CALR_JAK2-2×9mer; SEQ ID NO: 10), MVA-HCalJ-9.9 (TCE_CALR_JAK2-2×9mer; SEQ ID NO: 26), or Ad26.Empty (n=10/group, except for Group 1 [MVA-HCalJ-9.9] which had 5 animals and Group 4 [Ad26.Empty] which had 3 animals). At Week 4, splenocytes were stimulated overnight with a peptide pool spanning CALRmut sequence. The number of IFN-γ SFU per $10^6$ splenocytes was determined by ELISpot. The geometric mean response per group is indicated with a horizontal line. The dotted lines in the graphs indicate the background of the assay defined as the 95% percentile of SFU observed in non-stimulated splenocytes. For difference testing comparing Ad26HEME002 prime-only with Ad26HEME002 prime immunization and boost with MVA-HCalJ-9.9, an ANOVA was performed on $log_{10}$-transformed ELISpot data. Values below 52 SFU/$10^6$ cells were set as cut-off. The horizontal bars correspond to the mean of each group. Gr: group.

All animals immunized with either Ad26HEME002 alone or in combination with MVA-HCalJ-9.9 boost developed IFN-γ-producing cells upon stimulation with a peptide pool made up of 15mer peptides overlapping by 11 amino acids and covering the entire HEME002 (LS_CALR.JAK2.2× 9mer) (FIG. 7) or a mutCALR peptide pool consisting of 15mer peptides overlapping by 11 amino acids and covering only the mutCALR portion of HEME002 (FIG. 8). In contrast no induction of cytokine-producing cells was detected upon stimulation with the two 9-mer JAK2 peptides (data not shown). Importantly, a boost with MVA-HCalJ-9.9 after prime immunization with Ad26HEME002 (Group 3) induced a significantly higher response than animals only primed at Week 0 with Ad26HEME002 (Group 2) (HEME002 peptide pool: p=0.038; CALRmut peptide pool: p=0.00025; ANOVA). In conclusion, ELISpot data showed that MVA was able to boost the insert-specific cellular immune response induced by a prime immunization with Ad26HEME002.

Figure 9:
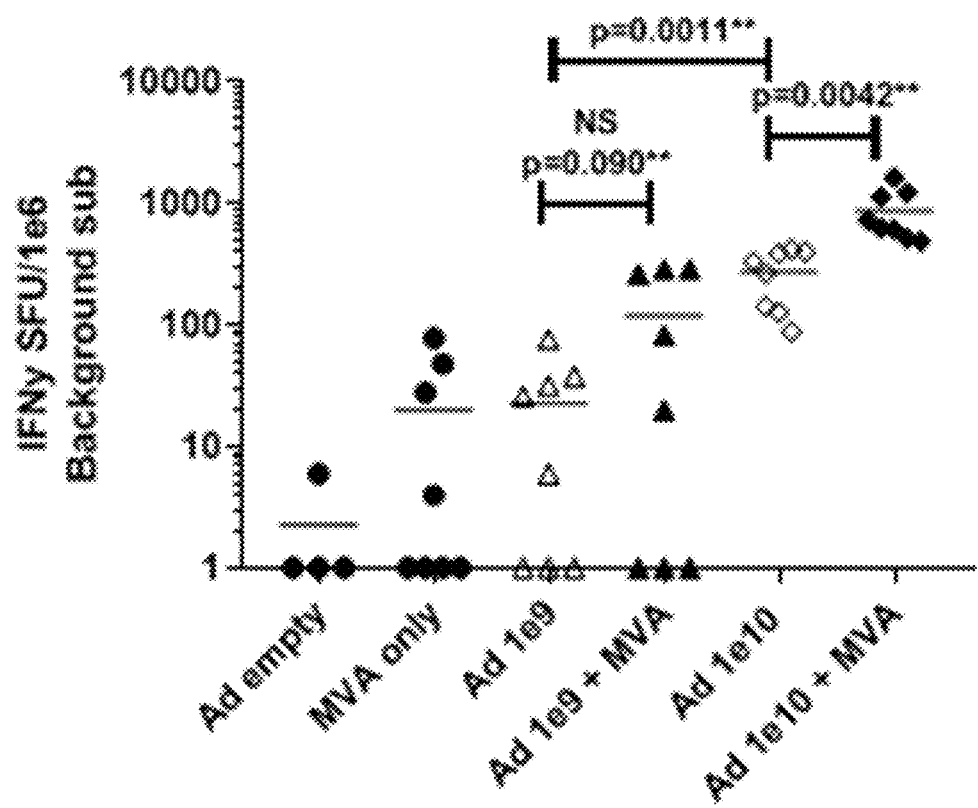
FIG. 9 shows IFN-γ ELISpot responses in splenocytes from Balb/c mice immunized IM with Ad26HEME002 (LS_CALR_JAK2-2×9mer; SEQ ID NO: 10), MVA-HCalJ-9.9 (TCE_CALR_JAK2-2×9mer; SEQ ID NO: 26), or Ad26.Empty (n=8/group). At Week 4, splenocytes were isolated and stimulated overnight with a peptide pool spanning the sequence of HEME002. The number of IFN-γ SFU per $10^6$ splenocytes was determined by ELISpot. The mean response per group is indicated with a horizontal line. Each individual data point is background subtracted using splenocytes not stimulated overnight with peptide to assess background SFU/$10^6$ splenocytes. For difference testing comparing Ad26HEME002 prime-only with Ad26HEME002 prime immunization and boost with MVA-HCalJ-9.9, an unpaired t-test with Welches correct (unequal SD) was run to assess statistical significance. SFU: spot-forming unit; Ad empty: Ad26.Empty; MVA only: MVA-HCalJ-9.9 (TCE_CALR_JAK2-2×9mer; SEQ ID NO: 26); Ad: Ad26HEME002 (LS_CALR_JAK2-2×9mer; SEQ ID NO: 10).

In the second study, Ad26HEME002 was dosed $10^9$ VP or $10^{10}$ VP and MVA-HCalJ-9.9 was dosed $10^7$ IU. At Week 0, mice were immunized by IM injection with Ad26HEME002 followed by boost at Week 3 with MVA-HCalJ-9.9. At Week 4, all animals were sacrificed and splenocytes were stimulated with 15-mer overlapping peptide pools spanning the Ad26HEME002 insert, or a peptide pool covering the CALR sequence in the insert, or 9-mers covering the two JAK2 9-mer sequences. The induction of IFN-γ-producing cells was measured by IFN-γ ELISpot. Ad26HEME002 prime at $1\times10^{10}$ VP followed by MVA-HCalJ-9.9 boost at $1\times10^7$ plaque-forming units (pfu) resulted in a statistically significant increase in IFN-γ when compared to Ad26.Empty vector at $1\times10^{10}$ VP alone (3.2-fold increase, p=0.0042). In contrast, no significant change in IFN-γ was observed at a lower dose of Ad26HEME002 prime at $1\times10^9$ VP followed by MVA-HCalJ-9.9 boost at $1\times10^7$ pfu (p=0.090). Increased IFN-γ-producing splenocytes were observed with $1\times10^{10}$ VP Ad26HEME002 compared to $1\times10^9$ VP dosing. FIG. 9 shows the results of the experiment.

Example 9: Immunogenicity of Ad26HEME002 and MVA-HCalJ 9.9 in Non-Human Primates (NHP)

The primary aim of the study was to determine whether vaccination with Ad26HEME002 and MVA-HCalJ-9.9 induces CALR- and/or JAK2-specific T-cell responses that were higher in magnitude and duration than vaccination with Ad26HEME002 alone in NHP. The secondary aim was to evaluate if an anti-CTLA-4 monoclonal antibody i.e., YERVOY© (ipilimumab) ([Ipi]) in combination with Ad26HEME002 and MVA-HCalJ-9.9 is capable of enhancing the immune responses. In addition, an explorative objective was to evaluate if anti-CTLA-4 antibodies in combination with homologues two-regimen dosing of Ad26HEME002 was able to enhance the insert-specific T-cell responses compared to Ad26HEME002 one-regimen dosing.

Cynomolgus macaques were immunized IM with Ad26HEME002 and/or MVA-HCalJ-9.9 alone or in combination with Ipi (10 mg/kg intravenously [IV]) according to schedule shown in Table 13. Briefly, NHPs were immunized with Ad26HEME002 ($5\times10^{10}$ VP, IM) alone (Group 1 and Group 2) or in combination with Ipi 10 mg/kg IV (Group 3 and Group 4). Animals were boosted at Week 4 and 8 with MVA-HCalJ-9.9 alone ($10^8$ IU, IM, Group 2) or MVA-HCalJ-9.9 in combination with Ipi 10 mg/kg IV (Group 3), or animals were boosted with Ad26HEME002 in combination with Ipi at Week 4 followed by a dosing at Week 14 with MVA-HCalJ-9.9 in combination with Ipi 10 mg/kg IV (Group 4), or animals did not receive any boost (Group 1). Animals were bled at various time points and PBMCs and serum were isolated for immunological assays. The induction of immune responses to CALRmut or JAK2 was evaluated in PBMCs at various time points during the study by IFN-γ ELISpot using peptide pools spanning either CALRmut or JAK2 2×9-mer insert sequence, the leader sequence, or the whole insert (HEME002; CALR_JAK2-2×9mer).

TABLE 13

| Group | Animal nr | Immunization (Week 0) | (Week 4) | (Week 8) | (Week 14) | Ipi mg/kg IV |
|---|---|---|---|---|---|---|
| 1 | 5 | Ad26HEME002 ($5 \times 10^{10}$ VP) | NA | NA | NA | NA |
| 2 | 7 | Ad26HEME002 ($5 \times 10^{10}$ VP) | MVA-HCalJ-9.9 ($10^8$ IU) | MVA-HCalJ-9.9 ($10^8$ IU) | NA | NA |
| 3 | 7a | Ad26HEME002 ($5 \times 10^{10}$ VP) | MVA-HCalJ-9.9 ($10^8$ IU) | MVA-HCalJ-9.9 ($10^8$ IU) | NA | 10 |
| 4 | 5 | Ad26HEME002 ($5 \times 10^{10}$ VP) | Ad26HEME002 ($5 \times 10^{10}$ VP) | NA | MVA-HCalJ-9.9 ($10^8$ IU) | 10 |

Ipi, ipilimumab; nr, number; VP, viral particles; IU, infectious units; IV, intravenously; PBMC, peripheral blood mononuclear cell.

High non-specific background responses were seen in a few of the animals at various time points across the study, which may obscure the interpretation of particularly low responses. All animals were included in the data set.

Figure 10:
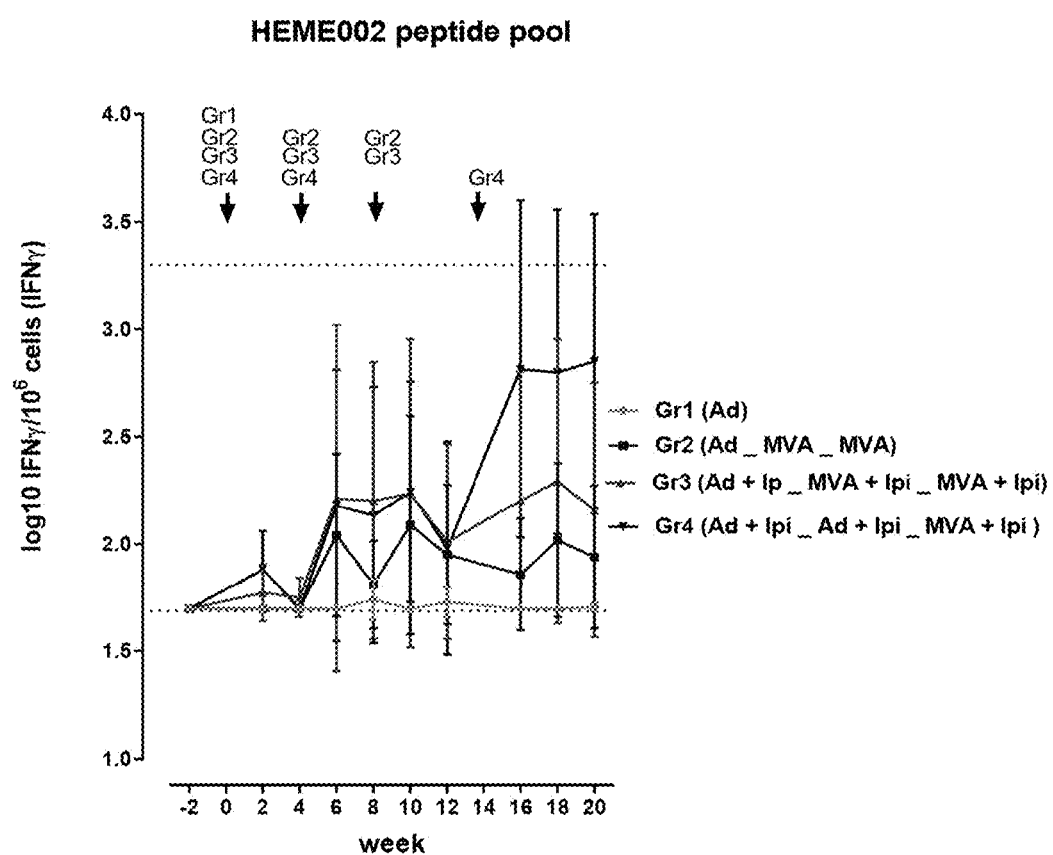
FIG. 10 shows the kinetic of induction of IFN-γ-producing human HEME002-specific T-cells in non-human primates immunized with Ad26HEME002,LS_CALR_JAK2-2×9mer; SEQ ID NO: 10 (Ad) and/or MVA-HCalJ-9.9 TCE_CALR_JAK2-2×9mer; SEQ ID NO: 26 (MVA) alone or in combination with YERVOY© (ipilimumab) (Ipi) over time measured by ELISpot. Human HEME002-specific T-cell responses per $10^6$ PBMC were measured over time. Assay positivity was defined as SFU/$10^6$ cells of background subtracted response >50 SFU/$10^6$ cells and SFU/$10^6$ cells of background subtracted response >2×medium response. Values failing the assay positivity criteria were adjusted to 50 SFU/$10^6$ cells. Shown are the $log_{10}$-transformed data. The lower dotted line was set at 50 SFU/$10^6$ cells and corresponds to the LOD, whereas the upper dotted line was set at 2,000 SFU/$10^6$ cells and corresponds to the ULOQ. The arrows points refer to the time of immunization per group. The arrow bars are standard deviations. LOD: lower limit of detection; ULOQ: upper limit of quantitation. Gr: Group. Groups from the top of the graph: Top line: Gr4; second line from the top: Gr3, third line from the top: Gr2, fourth line from the top: Gr1.

There was no detectable immune response to the JAK2 or the leader sequence peptide pools at any of the measured time point (data not shown). The magnitude and responder rate measured to CALR and CALR_JAK2-2×9mer (HEME002) peptide pools was very similar and therefore only the CALR_JAK2-2×9mer (HEME002) data set is shown. FIG. 10 shows the kinetic of induction of IFN-γ-producing human HEME002-specific T-cells across the four groups. A single Ad26HEME002 immunization did not elicit detectable IFN-γ-producing cells to the HEME002 peptide pool in any of the animals (FIG. 10). In contrast, low, but detectable HEME002-specific IFN-γ-producing cells were detected in 5 out of 12 animals immunized with Ad26HEME002 in combination with Ipi (Group 3 and Group 4 combined) at Week 2 (FIG. 12) and 4 (data not shown) and this immune response was significantly higher than that detected in animals dosed with Ad26HEME002 only (p<0.001).

Figure 11:
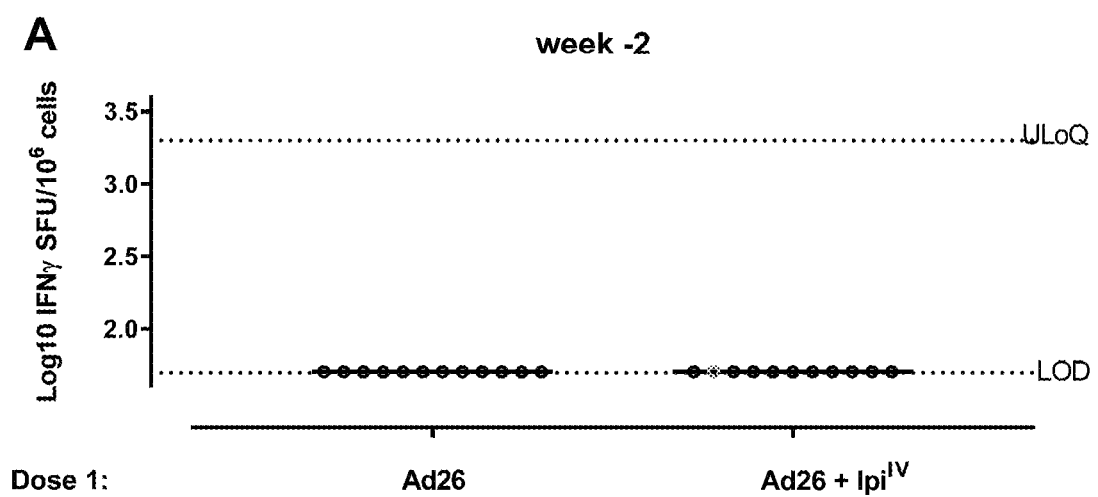
FIG. 11 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2× 9mer; SEQ ID NO: 26 (MVA) alone or in combination with YERVOY© (ipilimumab) (Ipi) per group at Week −2 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have p<0.05. The lower dotted line was set at 50 SFU/$10^6$ cells and corresponded to the LOD, whereas the upper dotted line was set at 2,000 SFU/$10^6$ cells and corresponded to the ULOQ. Shown are the $log_{10}$-transformed data.
Figure 12:
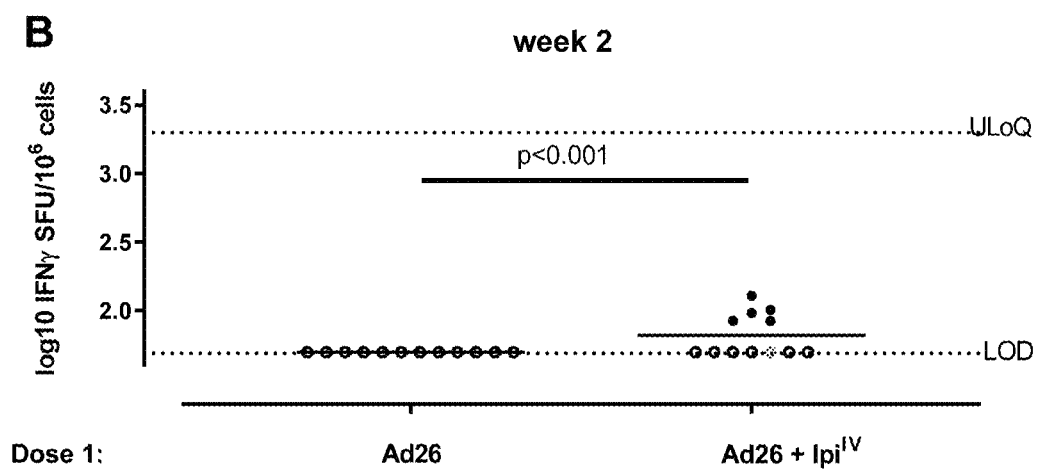
FIG. 12 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY© (ipilimumab) (Ipi) per group at Week 2 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have p<0.05. The lower dotted line was set at 50 SFU/$10^6$ cells and corresponded to the LOD, whereas the upper dotted line was set at 2,000 SFU/$10^6$ cells and corresponded to the ULOQ. Shown are the $\log_{10}$-transformed data.
Figure 13:
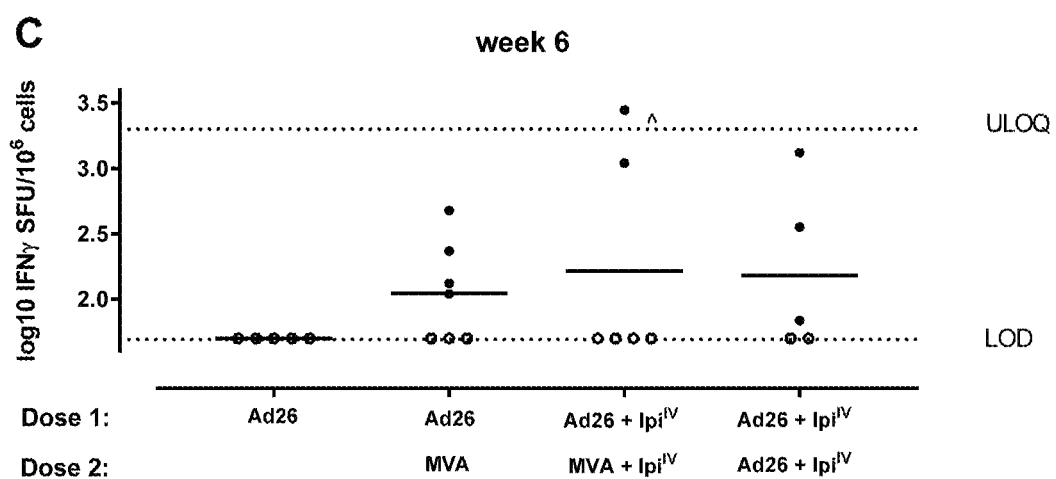
FIG. 13 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY© (ipilimumab) (Ipi) per group at Week 6 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have p<0.05. The lower dotted line was set at 50 SFU/$10^6$ cells and corresponded to the LOD, whereas the upper dotted line was set at 2,000 SFU/$10^6$ cells and corresponded to the ULOQ. Shown are the $\log_{10}$-transformed data.
Figure 14:
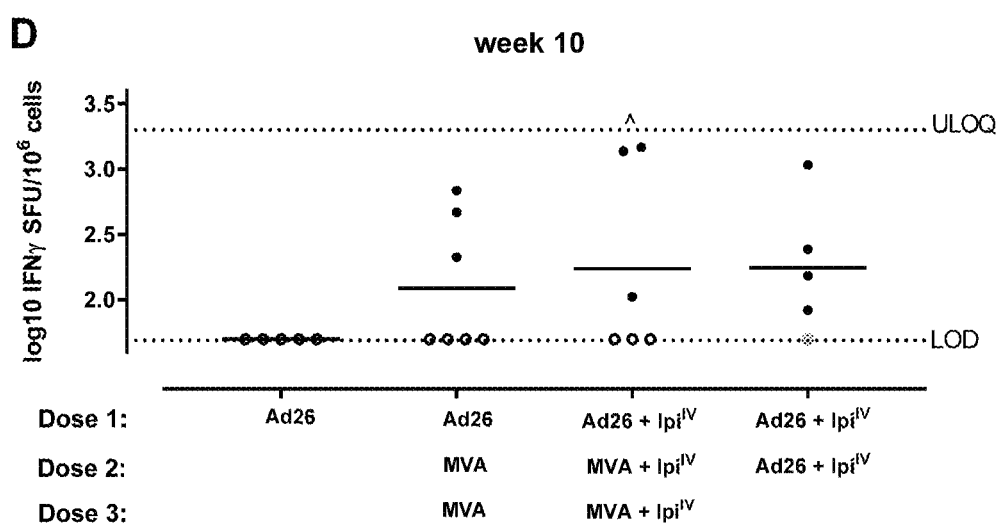
FIG. 14 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY© (ipilimumab) (Ipi) per group at Week 10 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have p<0.05. The lower dotted line was set at 50 SFU/$10^6$ cells and corresponded to the LOD, whereas the upper dotted line was set at 2,000 SFU/$10^6$ cells and corresponded to the ULOQ. Shown are the $\log_{10}$-transformed data.
Figure 15:
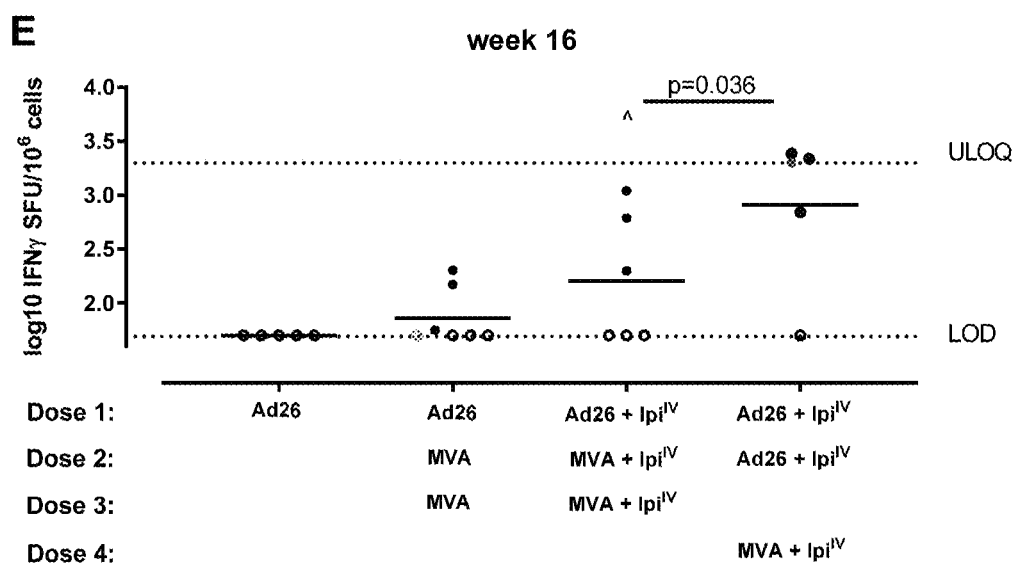
FIG. 15 shows induction of IFN-γ producing HEME002-specific T-cells in non-human primates immunized with Ad26HEME002, LS_CALR_JAK2-2×9mer, SEQ ID NO: 10 (Ad) and/or MVA-HCalJ-9.9, TCE_CALR_JAK2-2×9mer; SEQ ID NO: 26 (MVA) alone or in combination with YERVOY© (ipilimumab) (Ipi) per group at Week 16 of the study. IFN-γ production was assessed by ELISpot. Values shown were background subtracted and a value below 50 SFU/$10^6$ cells was set to that value (indicated in open black symbols). Animals with high background response >150 SFU/$10^6$ cells are indicated in grey symbols. The bar indicates the group mean. Statistical analysis was performed on the complete data set using a Tobit model with Likelihood ratio tests and applying a Bonferroni adjustment, significant responses have p<0.05. The lower dotted line was set at 50 SFU/$10^6$ cells and corresponded to the LOD, whereas the upper dotted line was set at 2,000 SFU/$10^6$ cells and corresponded to the ULOQ. Shown are the $\log_{10}$-transformed data.
Figure 16:
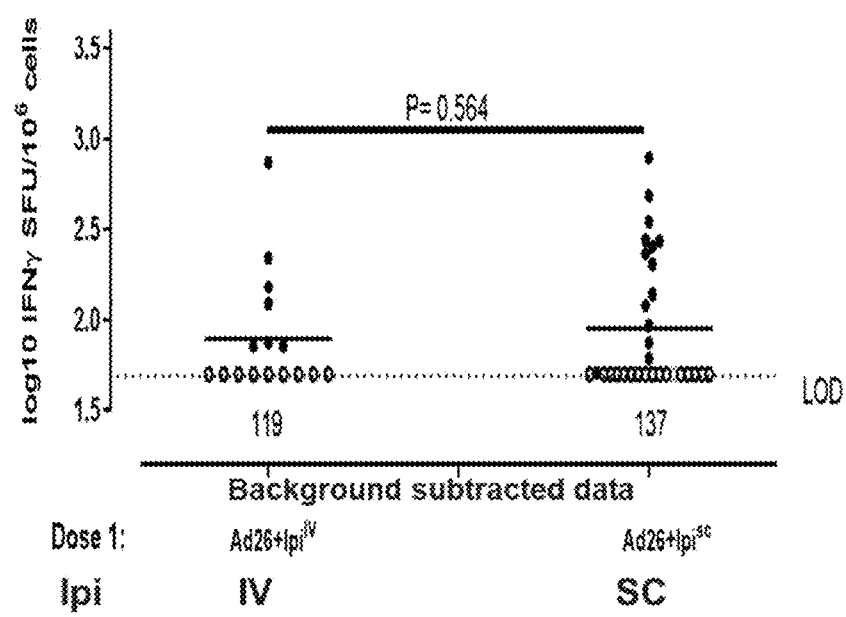
FIG. 16 shows that anti-CTLA4 antibody Ipilimumab administered SC is equal to IV at priming antigen specific T cell responses in NHP. Ipilimumab was dosed at 3 mg/kg IV or SC at time of vector immunization. IFNγ producing cells from 250K cynomolgus PBMCs were stimulated overnight with mutCALR specific peptides and analyzed by Elipot. mutCALR peptide response was calculated based on mutCALR specific response background. The bar indicates the group mean. Statistical analysis was performed on the complete data set, using a Tobit model with Likelihood ratio tests and applying a Bonferroni adjustment, Significant responses have p<0.05.

An immune response to CALR_JAK2-2×9mer (HEME002) was seen from Week 6 onward in animals dosed with Ad26HEME002 and MVA-HCalJ-9.9. There was only minor change in the responder rate (3-4 out of 7 animals) whether the animals had received one dose (FIG. 13) or two doses (FIG. 14) of MVA-HCalJ-9.9. Of the responding animals, the mean magnitude of HEME002 immune response ranged from 129 to 453 SFU/$10^6$ cells (FIG. 13-15). FIG. 11 shows the immune response at -2 weeks of the study (i.e. 2 weeks prior to first dose). FIG. 12 shows the immune response at 2 weeks. FIG. 13 shows the immune response at week 6. FIG. 14 shows the immune response at week 10. FIG. 15 shows the immune response at week 16. Animals dosed with MVA-HCalJ-9.9 in combination with Ipi at Week 4 and at Week 8 (Group 3) had an increase in the magnitude of the HEME002-specific immune response compared to after the Ad26HEME002 immunization (average mean response of responding animals: 93 SFU/$10^6$ cells at Week 2, 1,945 SFU/$10^6$ cells at Week 6, and 983 SFU/$10^6$ cells at Week 10), while there was no increase in the overall responder rate comparing before and after MVA dosing.

There was an increase in the magnitude of IFN-γ-producing cells following two doses with Ad26HEME002 in combination with Ipi compared to a single dosing with Ad26HEME002 in combination with Ipi (Group 4): average mean HEME002 response of responding animals of 93 SFU/10$^6$ cells at Week 2 (post first dosing) and 580 SFU/10$^6$ cells at Week 6 (post second dosing). At Week 14, Group 4 received a dosing with MVA-HCalJ-9.9 in combination with Ipi, which resulted in a 4.6-fold increase in the average mean response of responding animals (400 SFU/10$^6$ cells at Week 12 and 1,827 SFU/10$^6$ cells at Week 16; Tobit on change score p<0.001), whereas no change in the responder rate was seen. Of the responding animals, only minor contraction of the immune response was seen, with an average response of 1,698 SFU/10$^6$ cells for HEME002 at Week 20 (6 weeks post dosing with MVA-HCalJ-9.9+Ipi) (Group 4).

An analysis of area under the curve (AUC; Tobit with Bonferroni correction) for the HEME002 immune response was done for the following time windows: (i) Week 2 to Week 20, (ii) Week 2 to Week 12, and (iii) Week 16 to Week 20. Due to the high variation and high amount of censored values, there was no statistically significant difference found when comparing the AUC for Group 1 and Group 2, or AUC for Group 2 and Group 3 (FIG. 10). In contrast, there was a significant difference in the AUC for the HEME002 response when comparing Group 3 and Group 4 for the time window Week 16 to 20 (p=0.029). Animal #3002 (sample #14) was euthanized on Day 43. Animal #4003 (sample #22) Week 16 showed wells which were too numerous to count, and this sample was set at 2,000 SFU/10$^6$ cells and was also used for statistical analysis.

The nonclinical studies demonstrate that the produced Ad26 and MVA vectors expressing CALRmut and JAK2 2×9-mer fusion protein was able to give rise to T-cell activation in vitro and induce a cellular immune response in mice and NHP.

Example 10: MutCALR/MutJAK2 Construct Study, Dosing, and Scheduling

The primary aim of the study was to compare subcutaneous (SC) versus IV administration of antiCTLA4 antibody in combination with an Ad/Ad/MVA vaccine. The aim was also to evaluate multi dosing of anti-CTLA4 antibody versus single dose in combination with an Ad/Ad/MVA vaccine. The secondary aim was to evaluate if the combination of the anti-CTLA-4 monoclonal antibody i.e., YERVOY© (ipilimumab) ([Ipi]) with an anti PD-1 antibody (Nivolumab) is able to further enhance a specific T cell response.

The anti-CLTA4 antibody was administered SC at the same time as Ad26 vaccination localized to the Ad26 injection. Alternatively, anti-CTLA4 antibody was IV infused over time immediately after Ad26 administration. SC administration of anti-CTLA4 antibody was compared to IV administration at 3 mg/kg per animal. At week 2 analysis 16 animals received anti CTLA4 IV (3 mg/kg) and 31 animals had received anti CTLA4 (3 mg/kg) via SC

TABLE 14

| | | | IO Agent | | | |
|---|---|---|---|---|---|---|
| Group | Prime/Boost Day 0 and Day 28 | Boost' Day 84 | Day 0 | Day 28 | Day 84 | Day 29 start every 28 days |
| 1 | Ad26/Ad26 | MVA | aCTLA4 3mpk iv | aCTLA4 3mpk iv | aCTLA4 3mpk iv | — |
| 2 | Ad26/Ad26 | MVA | aCTLA4 3mpk iv | | | — |
| 3 | Ad26/Ad26 | MVA | aCTLA4 3mpk sc | aCTLA4 3mpk sc | aCTLA4 3mpk sc | — |
| 4 | Ad26/Ad26 | MVA | aCTLA4 3mpk sc | | | — |
| 5 | Ad26/Ad26 | MVA | aCTLA4 3mpk sc | aCTLA4 3mpk sc | aCTLA4 3mpk sc | aPD1 10mpk IV |
| 6 | Ad26/Ad26 | MVA | aCTLA4 3mpk sc | | | aPD1 10mpk IV |

IV, intravenously; sc, sub cutaneous.

Figure 17:
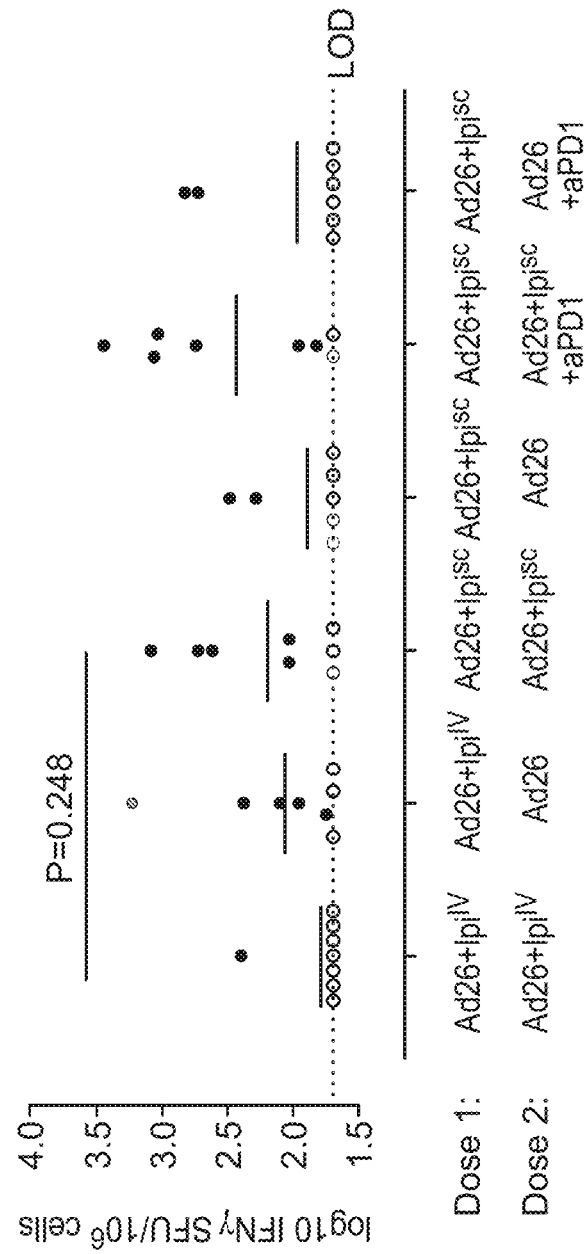
FIG. 17 shows that the inclusion of anti-PD-1 antibody (Nivolumab 10 mg/kg IV) starting at week 4 to Ad/Ad/MVA+ either 1 dose (Group 6) or 2 doses (group 5) of ipilimumab (SC) improves magnitude of mutCALR specific T cell response compared to animals dosed with Ad/Ad/MVA+ ipilimumab (SC) alone. Ad26: Ad26HEME002, LS_CALR_JAK2-2×9mer, SEQ ID NO: 10; Ipi; ipilimumab; aPD1: Nivolumab.

Inclusion of anti aPD-1 antibody (Nivolumab 10 mg/kg IV) starting at week 4 to Ad/Ad/MVA+ipilimumab improves the magnitude of mutCALR specific T cell response (FIG. 17). The mutCALR peptide response was calculated based on mutCALR specific response-background. Week 6 Preliminary ELISpot analysis also indicate that multiple doses with anti aCTLA4 antibody and Ad/Ad/MVA dosing regimen is superior than a single dose (FIG. 17).

Example 11: Generation of Self-Replicating RNA CALR_JAK2-2×9 Construct

The LS_CALR.JAK2-2×9mer polynucleotide was cloned into a self-replicating RNA.

Figure 19:
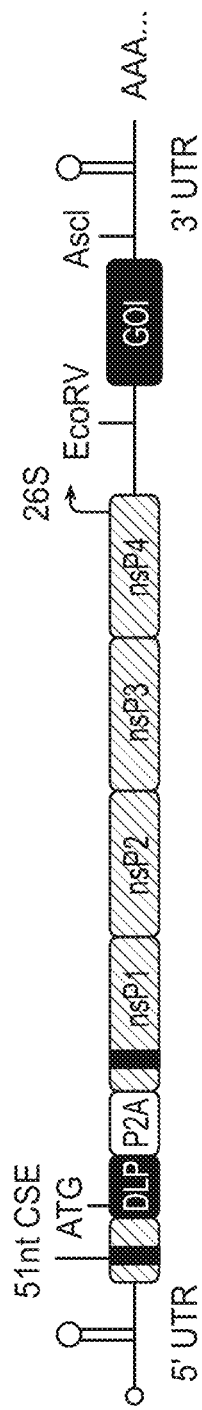
FIG. 19 is a schematic illustration of an exemplary self-amplifying RNA derived from an alphavirus that contains a 5'-cap, nonstructural genes (NSP1-4), 26S subgenomic promoter (grey arrow), the gene of interest (GOI), and a 3'-polyadenylated tail. The illustration also shows the 2A ribosome skipping element (P2A) and the duplicated first 193 nucleotides of nsP1 downstream of the 5'-UTR and upstream of the DLP except for the start codon.

The TC-83 strain of Venezuelan Equine Encephalitis Virus (VEEV) genome sequence served as the base sequence used to construct the replicon of the invention. This sequence was modified by placing the Downstream LooP (DLP) from Sindbis virus upstream of the non-structural protein 1 (nsP1) with the two joined by a 2A ribosome skipping element from porcine teschovirus-1. The first 193 nucleotides of nsP1 were duplicated downstream of the 5' UTR and upstream of the DLP except for the start codon, which was mutated to TAG. This insured all regulatory and secondary structures necessary for replication were maintained but prevented translation of this partial nsp1 sequence. The structural genes were removed and EcoR V and Asc I restriction sites were placed downstream of the subgenomic promoter as a multiple cloning site (MCS) to facilitate insertion of any gene of interest (FIG. 19). The LS_CALR_JAK2-2×9mer was inserted in the cloning site. The transgene was synthesized as a dsDNA fragment by IDT with 40 bp of homology to the MCS at their 5' and 3' ends and cloned into the VEEV derived self-replicating RNA vector digested with EcoRV and AscI using NEB HiFi DNA assembly master mix (cat #E2621S).

The polynucleotide sequence of the full self-replicating RNA plasmid is shown in SEQ ID NO: 33. The polynucleotide sequence of the T7 terminator is shown in SEQ ID NO: 34. The polynucleotide sequence of the AmpR promoter is shown in SEQ ID NO: 35. The polynucleotide sequence of the minimal 26S promoter is shown in SEQ ID NO: 36. The polynucleotide sequence of the T7 promoter is shown in SEQ ID NO: 37. The polynucleotide sequence of the Poly A site is shown in SEQ ID NO: 38. The polynucleotide sequence of the Alpha 5' replication sequence from nsP1 is shown SEQ ID NO: 39. The polynucleotide sequence of the DLP SEQ is shown in ID NO: 40. The polynucleotide sequence of P2A is shown in SEQ ID NO: 41. The polynucleotide sequence of Bom is shown in SEQ ID NO:42. The polynucleotide sequence of the DLP nsp ORF is shown in SEQ ID NO: 43. The polynucleotide sequence of nsP2 is shown in SEQ ID NO: 44. The polynucleotide sequence of nsP4 is shown is SEQ ID NO: 45. The polynucleotide sequence of nsP3 is shown in SEQ ID NO: 46. The polynucleotide sequence of the nsP1 is shown in SEQ ID NO: 47. The polynucleotide sequence of KanR is shown is SEQ ID NO: 48. The polynucleotide sequence of Rop is shown in SEQ ID NO: 49. The polynucleotide sequence of the 5'UTR is shown in SEQ ID NO: 50. The polynucleotide sequence of the 3'UTR is shown in SEQ ID NO: 51.

Example 12: srRNA.CALR/JAK2 Replicon RNA Platform Induces Cellular Responses in Mice The purpose of these studies was to determine if a self-replicating RNA molecule encoding CALR_JAK2-2×9mer could prime immune responses in Balb/c mice. The Balb/c mouse strain was selected based on the data described in Example 7 where less variation was seen with the Balb/c mouse strain compared to the C57BL/6 mouse strain.

In the first study, a self-replication RNA encoding LS_CALR_JAK2-2×9mer (srRNA.CALR/JAK2))was dosed at 3, 10 and 30 µg. At Week 0, Balb/c mice were immunized by IM injection with srRNA.CALR/JAK2 at the indicated doses (3, 10 and 30 µg) and a control group was injected with saline. At Week 2, all animals were sacrificed and splenocytes were stimulated with 15-mer overlapping peptide (SEQ ID NO: 3) pools covering the CALR sequence in the insert, or 9-mers covering the two JAK2 9-mer sequences (SEQ ID NO:7). The induction of IFN-γ-producing cells was measured by IFN-γ ELISpot. CD8 and CD4 polyfunctional T cell responses were determined by measuring the production of IFN-γ, TNFα and IL-2 by flow cytometry. Table 15 shows the various experimental groups.

TABLE 15

| Group | Animal nr | Description of groups |
|---|---|---|
| 1 | 5 | Saline |
| 2 | 5 | srRNA.CALR/JAK2 3 µg |
| 3 | 5 | srRNA.CALR/JAK2 10 µg |
| 4 | 5 | srRNA.CALR/JAK2 30 µg |

Figure 21A:
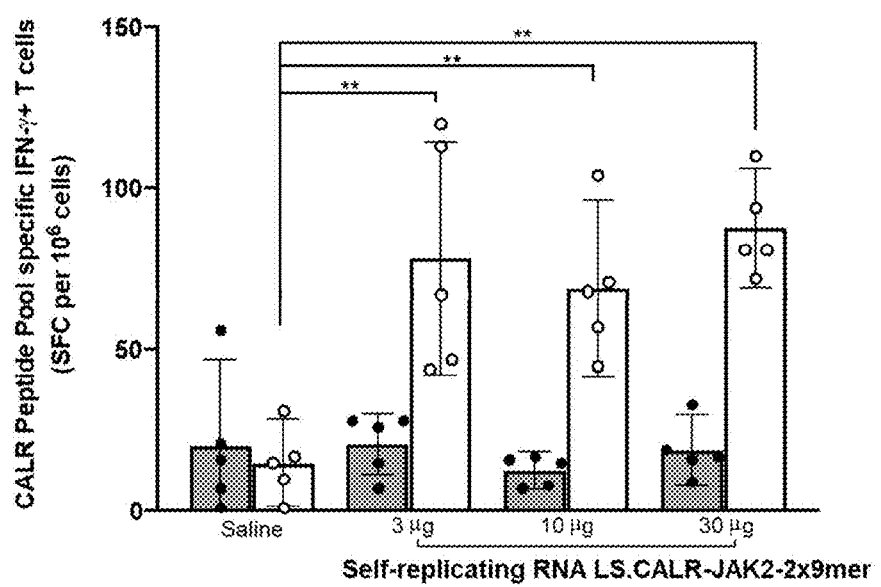
FIG. 21A shows self-replicating RNA LS.CALR-JAK2-2×9mer primes anti-CALR CD4 T cell responses. The data shows IFNγ production by splenocytes restimulated with an overlapping CALR peptide library (unfilled bars) or DMSO (grey bars) as measured by ELISpot.

All animals immunized with srRNA.CALR/JAK2 developed IFNγ-producing cells upon stimulation with peptides covering CALRmut sequence (FIG. 21A), in contrast no induction of cytokine-producing cells was detected upon stimulation with the two 9-mer JAK2 peptides (SEQ ID NO: 5 and 6) (data not shown). Intracellular flow cytometry showed that the anti-CALR response is CD4 driven and is polyfunctional at all doses tested (FIG. 21).

Figure 22A:
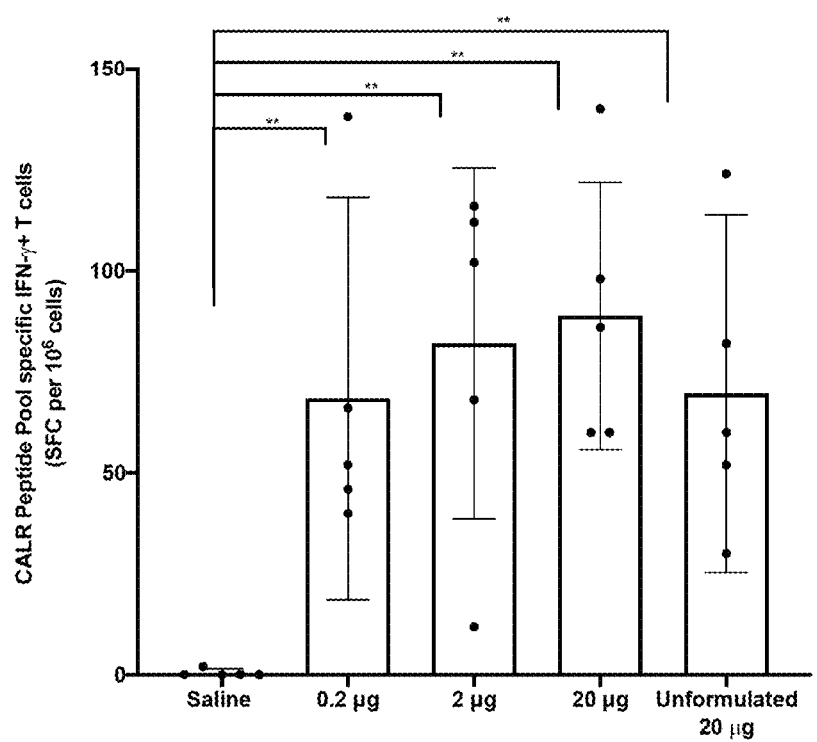
FIG. 22A shows lipid nanoparticle formulated self-replicating RNA LS.CALR-JAK2-2×9mer priming anti-CALR CD4 T cell responses. Balb/c mice were immunized with the indicated doses of LNP formulated self-replicating RNA LS.CALR-JAK2-2×9mer, as well as the unformulated version at 20 g, and 14 days later spleens were analyzed. The figure shows IFNγ production by splenocytes restimulated with an overlapping CALR peptide library (DMSLO background subtracted) as measured by ELISpot.

Self-replicating RNA molecules in the first study were injected naked into the animals. For the second study we formulated the self-replication RNA molecule in a lipid nanoparticle (LNP) and performed a similar study outlined in Table 16. Similar to the first study, all animals immunized with srRNA.CALR/JAK2 developed IFNγ-producing cells upon stimulation with peptides covering CALRmut sequence (FIG. 22A), in contrast no induction of cytokine-producing cells was detected upon stimulation with the two 9-mer JAK2 peptides (SEQ ID NO: 5 and 6) (data not shown). Intracellular flow cytometry showed that the anti-CALR response is CD4 driven and is polyfunctional at all doses tested in both unformulated and LNP-formulated versions (FIG. 22B).

TABLE 16

| Group | Animal nr | Description of groups |
|---|---|---|
| 1 | 5 | Saline |
| 2 | 5 | srRNA.CALR/JAK2 0.2 µg LNP formulated |
| 3 | 5 | srRNA.CALR/JAK2 2 µg LNP formulated |
| 4 | 5 | srRNA.CALR/JAK2 20 µg LNP formulated |
| 5 | 5 | srRNA.CALR/JAK2 20 µg unformulated |

In the third study we tested srRNA.CALR/JAK2 in combination with two other vaccine platforms, Ad26 and MVA to determine whether heterologous prime/boost regimens increase anti-CALR T cell function. All platforms encoded the CALR_JAK2-2×9mer construct. On week 0, Balb/c mice were injected with saline, Ad26HEME002 (1010PFU) or srRNA/CALR.JAK2 (20 µg). On week 4 mice were injected with either Ad26HEME002, MVA-HCalJ-9.9 ($10^7$ PFU) or srRNA.CALR/JAK2 and spleens were analyzed one week post boost (see experimental design below, Table 17). A control group was added to bridge to historical data using Ad26/MVA with a 3 week prime/boost interval and spleen analysis 2 weeks post boost. Spleens were analyzed by ELISpot and ICS as described above using overlapping CALR peptides.

TABLE 17

| Group | Animal nr | Description of groups |
|---|---|---|
| 1 | 5 | Saline |
| 2 | 8 | srRNA prime only |
| 3 | 8 | Ad26 prime only |
| 4 | 8 | srRNA/srRNA |
| 5 | 8 | Ad26/Ad26 |
| 6 | 8 | srRNA/Ad26 |
| 7 | 8 | Ad26/srRNA |
| 8 | 8 | srRNA/MVA |
| 9 | 8 | Ad26/MVA |
| 10 | 6 | Ad26/MVA 3 week interval |

Figure 23A:
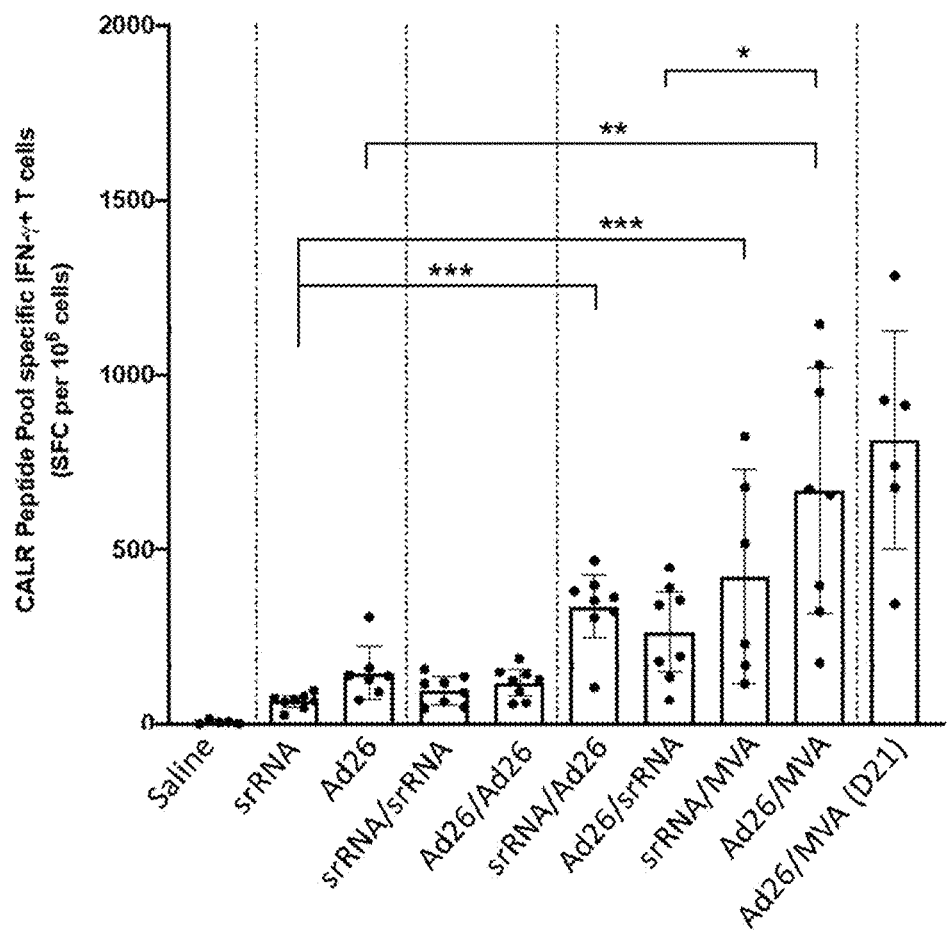
FIG. 23A shows vaccine regimens boosting anti-CALR CD4 T cell responses. Balb/c mice were primed then boosted with various combinations of Ad26, self-replicating RNA molecule (replicon) or MVA as indicated in the figure then spleens were analyzed. The figure shows IFNγ production by splenocytes restimulated with an overlapping CALR peptide library (DMSO background subtracted) as measured by ELISpot.
Figure 23B:
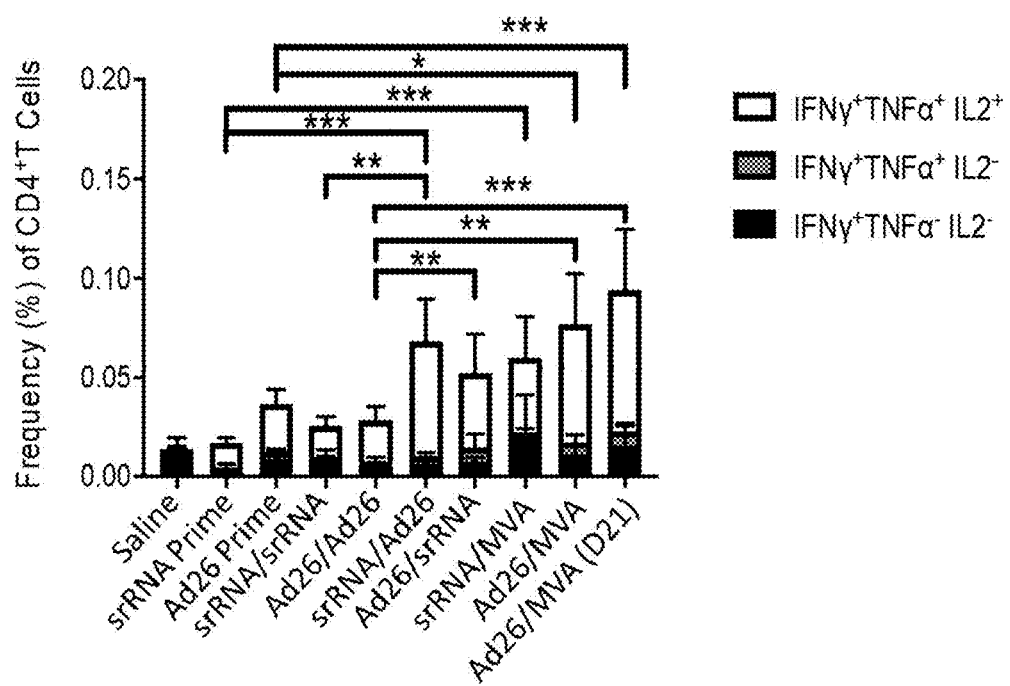
FIG. 23B shows vaccine regimens boosting anti-CALR CD4 T cell responses. The data shows IFNγ, TNFα and IL-2 production of splenocytes restimulated with overlapping CALR peptides measured by flow cytometry. Symbols represent individual mice, bars represent mean with SD. *p<0.05, p<0.01, *p<0.001 Mann-Whitney test.

The addition of Ad26 or MVA boost to the self-replicating RNA prime resulted in statistically significant boosts according to IFNγ ELISpot (p<0.001, 5.1 and 6.5 fold increase respectively). The addition of self-replicating RNA as a boosting agent following Ad26 prime resulted in a 1.7 fold increase over Ad26 prime alone (not statistically significant) (FIG. 23A). Intracellular cytokine staining shows that following self-replication RNA prime, the addition of Ad26 and/or MVA as a boost results in statistically significant increases in polyfunctional IFNγ+ TNFα+IL-2+CD4 T cells (p<0.001, 4.9 and 3.6 fold increase respectively). Boosting with self-replicating RNA following Ad26 prime leads to a 2-fold increase in polyfunctional triple cytokine positive T cells over Ad26 prime alone (not statistically significant) (FIG. 23B).

Example 13. Immunogenicity of srRNA.CALR/JAK2 and MVA-HCalJ-9.9 in Non-Human Primates (NHP)

The primary aim of this study will be to determine whether vaccination with srRNA.CALR/JAK2 and MVA-HCalJ-9.9 induces antigen specific T-cell responses that are higher in magnitude and duration than vaccination with srRNA.CALR/JAK2 alone in NHP. The secondary aim is to evaluate if an anti-CTLA-4 monoclonal antibody i.e., YER-VOY® (ipilimumab) ([Ipi]) in combination with srRNA.CALR/JAK2 and MVA-HCalJ-9.9 can enhance the vaccine induced immune response. In addition, an explorative objective is to evaluate if anti-PD-1 monoclonal antibodies OPDIVO© (nivolumab) in combination with vaccine regimen and anti-CTLA-4 antibody is comparable or increases insert-specific T-cell responses compared to animals dosed without anti-PD-1. Cynomolgus macaques are immunized IM with srRNA.CALR/JAK2, and/or MVA-HCalJ-9.9 alone or in combination with Ipi (3 mg/kg sub cutaneous [SC]) or in combination with Nivolumab (10 mg/kg intravenous [IV] according to schedule shown in Table 18. Briefly, NHPs will be immunized with srRNA.CALR/JAK2 and MVA-HCalJ-9.9 in combination with Ipi 3 mg/kg SC (Group 2) or in combination with Ipi 3 mg/kg SC and Nivolumab IV 10 mg/kg IV (Group 4). Animals are bled at various time points and PBMCs and serum are isolated for immunological assays. The induction of immune responses specific to CALR antigens are evaluated in PBMCs at various time points during the study by IFNγ ELISpot using peptide pools comprised of 15mer overlapping peptides corresponding to the entire CALR insert sequence.

The srRNA.CALR/JAK2 vaccine is expected to elicit an antigen specific T cell response that can be further increased when administered as a regimen in combination with MVA-HCalJ-9.9. Use of immune checkpoint blockade monoclonal antibodies anti-CTLA-4 and/or anti PD-1 antibodies in combination with srRNA.CALR/JAK2 and MVA-HCalJ-9.9 will lead to higher magnitude, quality, and more durable antigen specific T cell response.

TABLE 18

| Group | Day 0/28 | Day 70 | Anti-CTLA-4 mAb | Anti-PD-1 mAb |
|---|---|---|---|---|
| 1 | srRNA/srRNA | MVA | — | — |
| 2 | srRNA/srRNA | MVA | 0, 28, 70 | — |
| 3 | srRNA/srRNA | MVA | 0, 28, 70 | 29, 57, 84, 113 |

Example 14. Immunogenicity of GAd.CALR.JAK2 and Continuous Presentation of srRNA.CALR/JAK2 in Non-Human Primates (NHP)

The primary aim of this study is to confirm that vaccination with GAd20.CALR.JAK2 induces antigen specific T-cell responses in combination with anti-CTL-4 antibody and MVA or sRNA. The study is also designed to determine whether vaccination with srRNA.CALR/JAK2 increases T-cell when combined with GAd20 or GAD20/MVA and whether srRNA can be used in place of MVA. The objective of this study is also to evaluated whether GAD20/MVA/srRNA in combination with antiCTLA4 antibody can induce antigen specific T cell responses greater than GAD20/MVA/srRNA alone. Addition of a srRNA.CALR/JAK2 vector to an GAd20/MVA vaccine as a triple combination is expected to drive greater and more durable antigen specific T cell responses in cancer patients.

The second aim of this study is to assess srRNA-.CALR.JAK2 multi-dose regimen capacity to eliminate the need of anti CTL-4 antibody, completely or after administration of MVA. In addition, the study is constructed to determine if srRNA can be administered multiple times (monthly) to continually increase or maintain antigen specific T cell responses. The highest and most durable levels of anti-mutCALR/mutJAK2 targeted T cells generated will require continuous neo-antigen presentation by a vector not susceptible to Ab-mediated neutralization resulting in malignant clone clearance and clinical benefit for MPN patients.

One potential advantage of a self-replicating RNA based vaccine is the lack of vector specific immunity developed. Absence of vector specific immune response can allow for repeated administration of the self-replicating RNA without diminishment of antigen presentation due to an inability of the self-replicating RNA based vaccine to generate neutralizing antibodies specific to the vector. Multi-dose regimens are tested to evaluate if srRNA.CALR/JAK2 can maintain an antigen specific T cell response by administration on a monthly intramuscular dosing schedule.

For this study, cynomolgus macaques are immunized according to schedule shown in Table 19. Animals are bled at various time points and PBMCs and serum are isolated for immunological assays. The induction of immune responses specific to CALR antigens are evaluated in PBMCs at various time points during the study by IFNγ ELISpot using peptide pools comprised of 15mer overlapping peptides corresponding to the entire CALR insert sequence Administration of srRNA.CALR/JAK2 after GAd20/MVA immunization will allow for continued boosting to prolonge antigen specific T cell response independent or in combination with CPI administration. Multi dose srRNA-.CALR/JAK2 self-replication RNA based regimens are expected to elicit higher magnitude of T cell responses with a longer duration.

TABLE 19

| Group | Description of Groups |
|---|---|
| 1 | GAd20/MVA/srRNA |
| 2 | GAd20/MVA/srRNA/srRNA |
| 3 | GAd20/srRNA/srRNA/srRNA |
| 4 | GAD20/GAD20/MVA + anti CTLA4 antibody 3 mg/kg IV |
| 5 | GAD20/GAD20 /MVA/srRNA/srRNA/srRNA + anti CTLA4 antibody 3 mg/kg IV |
| 6 | GAD20/GAD20/srRNA/srRNA/srRNA/srRNA + anti CTLA4 antibody 3 mg/kg IV |
| 4 | GAD20/GAD20/srRNA/srRNA/srRNA/srRNA |

Embodiments

The following list of embodiments is intended to complement, rather than displace or supersede, the previous descriptions.

Embodiment 1. A polypeptide comprising at least two or more epitope sequences selected from the group consisting of:
MKDKQDEEQRTRRMMRTKMRMRRMRRTRRKM-RRKMSPARPRTSCREACLQG WTE (SEQ ID NO: 1) or at least 90% sequence identity to SEQ ID NO: 1;
EEAEDNCRRMMRTK (SEQ ID NO: 2) or at least 90% sequence identity to SEQ ID NO: 2;
KLSHKHLVLNYGVCFCGDENILVQEFVKFG (SEQ ID NO: 4) or at least 90% sequence identity to SEQ ID NO: 4;
VLNYGVCFC (SEQ ID NO: 5) or at least 90% sequence identity to SEQ ID NO: 5;
FCGDENILV (SEQ ID NO: 6) or at least 90% sequence identity to SEQ ID NO: 6; and combinations thereof.

Embodiment 2. The polypeptide of embodiment 1, wherein the polypeptide comprises the epitope sequences:
MKDKQDEEQRTRRMMRTKMRMRRMRRTRRK-MRRKMSPARPRTSCREACLQG WTE (SEQ ID NO: 1) or at least 90% sequence identity to SEQ ID NO: 1;
EEAEDNCRRMMRTK (SEQ ID NO: 2) or at least 90% sequence identity to SEQ ID NO: 2;

VLNYGVCFC (SEQ ID NO: 5) or at least 90% sequence identity to SEQ ID NO: 5; and

FCGDENILV (SEQ ID NO: 6) or at least 90% sequence identity to SEQ ID NO: 6.

Embodiment 3. The polypeptide of embodiment 1, wherein the polypeptide comprises the epitope sequences:

MKDKQDEEQRTRRMMRTKMRMRRMRR-TRRKMRRKMSPARPRTSCREACLQG WTE (SEQ ID NO: 1) or at least 90% sequence identity to SEQ ID NO: 1;

EEAEDNCRRMMRTK (SEQ ID NO: 2) or at least 90% sequence identity to SEQ ID NO: 2; and KLSHKHLVLNYGVCFCGDENILVQEFVKFG (SEQ ID NO: 4) or at least 90% sequence identity to SEQ ID NO: 4.

Embodiment 4. The polypeptide of embodiment 1, wherein the polypeptide comprises the epitope sequences:

MKDKQDEEQRTRRMMRTKMRMRRMRR-TRRKMRRKMSPARPRTSCREACLQG WTE (SEQ ID NO: 1) or at least 90% sequence identity to SEQ ID NO: 1; and EEAEDNCRRMMRTK (SEQ ID NO: 2) or at least 90% sequence identity to SEQ ID NO: 2.

Embodiment 5. The polypeptide of any one of embodiments 1-4, further comprising a leader sequence at N terminus selected from:

```
                                    (SEQ ID NO: 8)
MACPGFLWALVISTCLEFSMA;

(SEQ ID NO: 54)
MQIFVKTLTGKTITLEVEPSDTIENVKAKIQDKEGIPPDQQRLIFAGKQL

EDGRTLSDYNIQKESTLHLVLRLRGV;
and (SEQ ID NO: 29)
MGQKEQIHTLQKNSERMSKQLTRSSQAV.
```

Embodiment 6. The polypeptide of any of embodiments 1-5, wherein the epitope sequences are connected to each other by a linker sequence.

Embodiment 7. The polypeptide of embodiment 6, wherein the linker sequence is selected from AAY, RR, DPP, HHAA (SEQ ID NO: 56), HHA, HHL, RKSYL (SEQ ID NO: 57), RKSY (SEQ ID NO: 58), SSL, or REKR (SEQ ID NO: 59).

Embodiment 8. The polypeptide of embodiment 6, wherein the linker sequence comprises a protease cleavage site.

Embodiment 9. The polypeptide of embodiment 1, wherein the polypeptide is selected from:
an amino acid sequence of SEQ ID NO: 3 or having at least 90% sequence identity to SEQ ID NO: 3;
an amino acid sequence of SEQ ID NO: 7 or having at least 90% sequence identity to SEQ ID NO: 7;
an amino acid sequence of SEQ ID NO: 9 or having at least 90% sequence identity to SEQ ID NO: 9;
an amino acid sequence of SEQ ID NO: 10 or having at least 90% sequence identity to SEQ ID NO: 10;
an amino acid sequence of SEQ ID NO: 11 or having at least 90% sequence identity to SEQ ID NO: 11;
an amino acid sequence of SEQ ID NO: 12 or having at least 90% sequence identity to SEQ ID NO: 12;
an amino acid sequence of SEQ ID NO: 13 or having at least 90% sequence identity to SEQ ID NO: 13;
an amino acid sequence of SEQ ID NO:14 or having at least 90% sequence identity to SEQ ID NO: 14;
an amino acid sequence of SEQ ID NO: 15 or having at least 90% sequence identity to SEQ ID NO: 15; and
an amino acid sequence of SEQ ID NO: 31 or having at least 90% sequence identity to SEQ ID NO: 31.

Embodiment 10. A polynucleotide encoding a polypeptide of any one of embodiments 1-9.

Embodiment 11. The polynucleotide of embodiment 10, wherein the polynucleotide is selected from the group consisting of:
a nucleic acid sequence of SEQ ID NO: 16 or having at least 90% sequence identity to SEQ ID NO: 16;
a nucleic acid sequence of SEQ ID NO: 17 or having at least 90% sequence identity to SEQ ID NO: 17;
a nucleic acid sequence of SEQ ID NO: 18 or having at least 90% sequence identity to SEQ ID NO: 18;
a nucleic acid sequence of SEQ ID NO: 19 or having at least 90% sequence identity to SEQ ID NO: 19;
a nucleic acid sequence of SEQ ID NO: 20 or having at least 90% sequence identity to SEQ ID NO: 20;
a nucleic acid sequence of SEQ ID NO: 21 or having at least 90% sequence identity to SEQ ID NO: 21;
a nucleic acid sequence of SEQ ID NO: 22 or having at least 90% sequence identity to SEQ ID NO: 22;
a nucleic acid sequence of SEQ ID NO: 26 or having at least 90% sequence identity to SEQ ID NO: 26; and
a nucleic acid sequence of SEQ ID NO: 27 or having at least 90% sequence identity to SEQ ID NO: 27.

Embodiment 12. A vector comprising a polynucleotide of embodiment 10 or embodiment 11.

Embodiment 13. The vector of embodiment 12, wherein the vector is selected from an adenovirus vector, an alphaviral vector, a poxvirus vector, an adeno-associated virus vector, a retrovirus vector, a self-replicating RNA molecule, and a combination thereof.

Embodiment 14. The vector of embodiment 13, wherein the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Embodiment 15. The vector of embodiment 13, wherein the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Embodiment 16. The vector of embodiment 12, wherein the vector is the adenovirus vector comprising a polynucleotide encoding any one of the polypeptides of one of embodiments 1-9.

Embodiment 17. The vector of embodiment 12, wherein the vector is the self-replicating RNA molecule comprising a polynucleotide encoding any one of the polypeptides of any one of embodiments 1-9.

Embodiment 18. The vector of embodiment 12, wherein the vector is Ad26 comprising a polynucleotide encoding a polypeptide of SEQ ID NO: 10 or having at least 90% sequence identity to SEQ ID NO: 10.

Embodiment 19. The vector of embodiment 12, wherein the vector is MVA vector comprising a polynucleotide encoding a polypeptide of SEQ ID NO: 31 or having at least 90% sequence identity to SEQ ID NO: 31.

Embodiment 20. The vector of embodiment 12, wherein the vector is GAd20 comprising a polynucleotide encoding a polypeptide of SEQ ID NO: 31 or having at least 90% sequence identity to SEQ ID NO: 31.

Embodiment 21. The vector of embodiment 12, wherein the vector is a self-replicating RNA molecule comprising a polynucleotide encoding a polypeptide of SEQ ID NO: 12 or having at least 90% sequence identity to SEQ ID NO: 12.

Embodiment 22. A pharmaceutical composition comprising a polypeptide of any one of embodiments 1-9.

Embodiment 23. A pharmaceutical composition comprising a polynucleotide any one of embodiments 10 and 11.

Embodiment 24. A pharmaceutical composition comprising a vector of any one of embodiments 12-21.

Embodiment 25. The pharmaceutical composition of embodiment 24, wherein the vector is selected from an Ad26 vector, a MVA vector, a GAd20 vector, a self-replicating RNA molecule, and combinations thereof.

Embodiment 26. A method of treating, preventing, reducing a risk of onset or delaying the onset of a clinical condition characterized by an expression of JAK2V617F and/or CALR exon 9 mutant in a subject comprising administering to the subject in need thereof a pharmaceutical composition of any one of embodiments 22-25.

Embodiment 27. A method of inducing an immune response in a subject carrying JAK2V617F and/or CALR exon 9 mutation comprising administering to the subject in need thereof a pharmaceutical composition of any one of embodiments 22-25.

Embodiment 28. A method of treating or preventing a myeloproliferative disease in a subject comprising administering to the subject in need thereof a pharmaceutical composition of any one of embodiments 22-25.

Embodiment 29. A method of treating cancer in a subject comprising administering to the subject in need thereof a pharmaceutical composition of any one of embodiments 22-25.

Embodiment 30. A method of treating a cardiovascular disease in a subject comprising administering to the subject in need thereof a pharmaceutical composition of any one of embodiments 22-25.

Embodiment 31. A method of treating, preventing, reducing a risk of onset or delaying the onset of a clinical condition characterized by an expression of JAK2V617F and/or CALR exon 9 mutant in a subject comprising administering to the subject in need thereof a composition comprising a vector comprising a polynucleotide encoding at least two or more epitope sequences selected from the group consisting of:
  CALR epitope of SEQ ID NO: 1 or having at least 90% sequence identity to SEQ ID NO: 1;
  CALR epitope of SEQ ID NO: 2 or having at least 90% sequence identity to SEQ ID NO: 2;
  JAK2 epitope of SEQ ID NO: 4 or having at least 90% sequence identity to SEQ ID NO: 4;
  JAK2 epitope of SEQ ID NO: 5 or at least 90% sequence identity to SEQ ID NO: 5;
  JAK2 epitope of SEQ ID NO: 6 or having at least 90% sequence identity to SEQ ID NO: 6; and combinations thereof, and wherein the administration comprises one or more administrations of the composition.

Embodiment 32. A method of inducing an immune response in a subject carrying JAK2V617F and/or CALR exon 9 mutation comprising administering to the subject in need thereof a composition comprising a vector comprising a polynucleotide encoding at least two or more epitope sequences selected from the group consisting of:
  CALR epitope of SEQ ID NO: 1 or having at least 90% sequence identity to SEQ ID NO: 1;
  CALR epitope of SEQ ID NO: 2 or having at least 90% sequence identity to SEQ ID NO: 2;
  JAK2 epitope of SEQ ID NO: 4 or having at least 90% sequence identity to SEQ ID NO: 4;
  JAK2 epitope of SEQ ID NO: 5 or at least 90% sequence identity to SEQ ID NO: 5;
  JAK2 epitope of SEQ ID NO: 6 or having at least 90% sequence identity to SEQ ID NO: 6; and combinations thereof, and
wherein the administration comprises one or more administrations of the composition.

Embodiment 33. A method of treating or preventing a myeloproliferative disease in a subject comprising administering to the subject in need thereof a composition comprising a vector comprising a polynucleotide encoding at least two or more epitope sequences selected from the group consisting of:
  CALR epitope of SEQ ID NO: 1 or having at least 90% sequence identity to SEQ ID NO: 1;
  CALR epitope of SEQ ID NO: 2 or having at least 90% sequence identity to SEQ ID NO: 2;
  JAK2 epitope of SEQ ID NO: 4 or having at least 90% sequence identity to SEQ ID NO: 4;
  JAK2 epitope of SEQ ID NO: 5 or at least 90% sequence identity to SEQ ID NO: 5;
  JAK2 epitope of SEQ ID NO: 6 or having at least 90% sequence identity to SEQ ID NO: 6; and combinations thereof, and wherein the administration comprises one or more administrations of the composition.

Embodiment 34. The method of embodiment 33, wherein the myeloproliferative disease is selected from primary myelofibrosis (MPN), polycythemia vera (PV), essential thrombocythemia (ET), primary myelofibrosis (PFM), secondary myelofibrosis, acute myeloid leukemia (AML), secondary AML, chronic myelogenous leukemia (CML), clonal hematopoiesis of indeterminate potential (CHIP), and chronic myelomonocytic leukemia (CMML).

Embodiment 35. A method of treating cancer in a subject comprising administering to the subject in need thereof a composition comprising a vector comprising a polynucleotide encoding at least two or more epitope sequences selected from the group consisting of:
  CALR epitope of SEQ ID NO: 1 or having at least 90% sequence identity to SEQ ID NO: 1;
  CALR epitope of SEQ ID NO: 2 or having at least 90% sequence identity to SEQ ID NO: 2;
  JAK2 epitope of SEQ ID NO: 4 or having at least 90% sequence identity to SEQ ID NO: 4;
  JAK2 epitope of SEQ ID NO: 5 or at least 90% sequence identity to SEQ ID NO: 5;
  JAK2 epitope of SEQ ID NO: 6 or having at least 90% sequence identity to SEQ ID NO: 6; and combinations thereof, and
wherein the administration comprises one or more administrations of the composition.

Embodiment 36. The method of embodiment 35, wherein the cancer is selected from lung cancer, lymphoid cancer, acute lymphoid leukemia, acute myeloid leukemia, chronic myelogenous leukemia, Burkitt's lymphoma, Hodgkin's lymphoma, plasma cell myeloma, biliary tract cancer, bladder cancer, liver cancer, pancreatic cancer, prostate cancer, skin cancer, thyroid cancer, stomach cancer, large intestine cancer, colon cancer, urinary tract cancer, central nervous system cancer, neuroblastoma, kidney cancer, breast cancer, cervical cancer, testicular cancer, and soft tissue cancer.

Embodiment 37. A method of treating a cardiovascular disease in a subject comprising administering to the subject in need thereof a composition comprising a vector comprising a polynucleotide encoding at least two or more epitope sequences selected from the group consisting of:
  CALR epitope of SEQ ID NO: 1 or having at least 90% sequence identity to SEQ ID NO: 1;
  CALR epitope of SEQ ID NO: 2 or having at least 90% sequence identity to SEQ ID NO: 2;
  JAK2 epitope of SEQ ID NO: 4 or having at least 90% sequence identity to SEQ ID NO: 4;
  JAK2 epitope of SEQ ID NO: 5 or at least 90% sequence identity to SEQ ID NO: 5;
  JAK2 epitope of SEQ ID NO: 6 or having at least 90% sequence identity to SEQ ID NO: 6; and combinations thereof, and
wherein the administration comprises one or more administrations of the composition.

Embodiment 38. The method of embodiment 37, wherein the cardiovascular disease is selected from an acute coronary syndrome, an ischemic cerebrovascular disease, an ischemic heart disease, a thrombosis, a venous thromboembolism, a deep vein thrombosis, a pulmonary embolism, a catastrophic intra-abdominal thromboses, a peripheral arterial disease, a hypertension, a heart failure, an atrial fibrillation, a coronary heart disease, an atherosclerosis, and a clonal hematopoiesis.

Embodiment 39. The method of any one of embodiments 31-38, wherein the vector is selected from an adenovirus vector, an alphaviral vector, a poxvirus vector, an adeno-associated virus vector, a retrovirus vector, a self-replicating RNA molecule, and a combination thereof.

Embodiment 40. The method of any one of embodiments 31-39, wherein the vector is selected from Ad26 vector, MVA vector, GAd20 vector, a self-replicating RNA molecule, and combinations thereof.

Embodiment 41. The method of any one of embodiments 31-39, wherein the vector is an Ad26 vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 42. The method of any one of embodiments 31-39, wherein the vector is a GAd20 vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 43. The method of any one of embodiments 31-39, wherein the vector is a MVA vector comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and JAK2 epitope of SEQ ID NO: 6.

Embodiment 44. The method of any one of embodiments 31-39, wherein the vector is a self-replicating RNA molecule comprising a polynucleotide encoding a polypeptide comprising epitope sequences of calreticulin (CALR) epitope of SEQ ID NO: 1, CALR epitope of SEQ ID NO: 2, JAK2 epitope of SEQ ID NO: 5, and Janus kinase 2 (JAK2) epitope of SEQ ID NO: 6.

Embodiment 45. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

Embodiment 46. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule; and
  a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is selected from Ad26 vector, MVA vector, GAd20 vector, or a self-replicating RNA molecule.

Embodiment 47. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and
  a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector.

Embodiment 48. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector.

Embodiment 49. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 50. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 51. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 52. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule.

Embodiment 53. The method of any one of embodiments 31-52, further comprising administering a second therapeutic agent selected from a CTLA-4 antibody, a PD-1 antibody, a PD-L1 antibody, a TLR agonist, a CD40 agonist, an OX40 agonist, hydroxyurea, ruxolitinib, fedratinib, a 41BB agonist, a CD28 agonist, FLT3 ligand, aluminum sulfate, a BTK inhibitor, a JAK inhibitor, a CD38 antibody, a CDK inhibitor, a CD33 antibody, a CD37 antibody, a CD25 antibody, a GM-CSF inhibitor, IL-2, IL-15, IL-7, IFNγ, IFNα, TNFα, a VEGF antibody, a CD70 antibody, a CD27 antibody, a BCMA antibody, a GPRCSD antibody, and combinations thereof.

Embodiment 54. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is GAd20 vector; and
  a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a MVA vector; and
  wherein the treatment cycle further comprising administering a checkpoint inhibitor selected from an anti CTLA-4 antibody, a PD-1 antibody, and a PD-L1 antibody, in combination with the first, second, and/or third composition.

Embodiment 55. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector;
  a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;
  a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and
  a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and
  wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 56. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating;
  a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;
  a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and
  a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and
  wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 57. The method of any one of embodiments 31-44, comprising one or more treatment cycles, wherein each cycle comprises:
  a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;
  a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is MVA vector;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 58. The method of any one of embodiments 31-44, comprising one or more treatment cycles, wherein each cycle comprises:

a first administration comprising a first composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector; and a second administration comprising a second composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a GAd20 vector;

a third administration comprising a third composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating;

a fourth administration comprising a fourth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule;

a fifth administration comprising a fifth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and a sixth administration comprising a sixth composition comprising a vector comprising a polynucleotide encoding CALR epitope of SEQ ID NO: 1, CALR epitope of SEQ ID NO: 2, JAK2 epitope of SEQ ID NO: 5, and JAK2 epitope of SEQ ID NO: 6, wherein the vector is a self-replicating RNA molecule; and wherein the treatment cycle further comprising administering a checkpoint inhibitor selected from an anti CTLA-4 antibody, a PD-1 antibody, and a PD-L1 antibody, in combination with the first, second, third, fourth, fifth, and/or sixth composition.

Embodiment 58. The method of any one of embodiments 31-44, comprising one or more treatment cycles, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule.

Embodiment 59. The method of any one of embodiments 31-44, comprising one or more treatment cycles, wherein each cycle comprises:

a first administration comprising a first composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a second administration comprising a second composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule;

a third administration comprising a third composition comprising a vector comprising a polynucleotide encoding 2 or more tandem repeats of JAK2 epitope of SEQ ID NO: 6, wherein the vector is selected from Ad26 vector, MVA vector, GAd20 vector, or a self-replicating RNA molecule; and wherein the treatment cycle further comprising administering a checkpoint inhibitor selected from an anti CTLA-4 antibody, a PD-1 antibody, and a PD-L1 antibody, in combination with the first, second, and/or third composition.

SEQUENCE LISTING

| SEQ ID NO: | Epitope | Sequence |
|---|---|---|
| 1 | CALR epitope I | MKDKQDEEQRTRRMMRTKMRMRRMRRTRRKMRRKMSPARPRTSCREACLQGWTE |
| 2 | CALR epitope II | EEAEDNCRRMMRTK |
| 3 | CALR epitope I-AAY-CALR epitope II | MKDKQDEEQRTRRMMRTKMRMRRMRRTRRKMRRKMSPARPRTSCREACLQGWTEAAYEEAEDNCRRMMRTK |
| 4 | JAK2 30mer epitope | KLSHKHLVLNYGVCFCGDENILVQEFVKFG |
| 5 | JAK2 epitope 1 | VLNYGVCFC |
| 6 | JAK2 epitope 2 | FCGDENILV |
| 7 | 2X9mer JAK2 | VLNYGVCFCAAYFCGDENILV |
| 8 | HAVt20 Leader sequence (LS) | MACPGFLWALVISTCLEFSMA |
| 9 | LS_CALR (HEME003) | MACPGFLWALVISTCLEFSMAMKDKQDEEQRTRRMMRTKMRMRRMRRTRRKMRRKMSPARPRTSCREACLQGWTEAAYEEAEDNCRRMMRTK |
| 10 | LS_CALR_JAK2-2x9mer (HEME002) | MACPGFLWALVISTCLEFSMAMKDKQDEEQRTRRMMRTKMRMRRMRRTRRKMRRKMSPARPRTSCREACLQGWTEAAYEEAEDNCRRMMRTKAAYVLNYGVCFCAAYFCGDENILV |
| 11 | LS_CALR_JAK2-30mer (HEME001) | MACPGFLWALVISTCLEFSMAMKDKQDEEQRTRRMMRTKMRMRRMRRTRRKMRRKMSPARPRTSCREACLQGWTEAAYEEAEDNCRRMMRTKAAYKLSHKHLVLNYGVCFCGDENILVQEFVKFG |
| 12 | CALR_JAK2-2x9mer | MKDKQDEEQRTRRMMRTKMRMRRMRRTRRKMRRKMSPARPRTSCREACLQGWTEAAYEEAEDNCRRMMRTKAAYVLNYGVCFCAAYFCGDENILV |
| 13 | CALR_JAK2-30mer | MKDKQDEEQRTRRMMRTKMRMRRMRRTRRKMRRKMSPARPRTSCREACLQGWTEAAYEEAEDNCRRMMRTKAAYKLSHKHLVLNYGVCFCGDENILVQEFVKFG |
| 14 | Ubiq_CALR_JAK2-2x9mer | MQIFVKTLTGKTITLEVEPSDTIENVKAKIQDKEGIPPDQQRLIFAGKQLEDGRTLSDYNIQKESTLHLVLRLRGVRKDKQDEEQRTRRMMRTKMRMRRMRRTRRKMRRKMSPARPRTSCREACLQGWTEAAYEEAEDNCRRMMRTKAAYVLNYGVCFCAAYFCGDENILV |
| 15 | Ubiq_CALR_JAK2-30mer | MQIFVKTLTGKTITLEVEPSDTIENVKAKIQDKEGIPPDQQRLIFAGKQLEDGRTLSDYNIQKESTLHLVLRLRGVRKDKQDEEQRTRRMMRTKMRMRRMRRTRRKMRRKMSPARPRTSCREACLQGWTEAAYEEAEDNCRRMMRTKAAYKLSHKHLVLNYGVCFCGDENILVQEFVKFG |
| 16 | LS_CALR | ATGGCATGCCCAGGCTTCCTGTGGGCCCTGGTCATCAGCACCTGTCTGGAGTTTTCCATGGCCATGAAGGACAAGCAGGATGAGGAGCAGCGGACCCGGAGAATGATGAGGACAAAGATGCGCATGAGGCGCATGCGGAGAACAAGGCGCAAGATGCGGAGAAAGATGTCTCCAGCAAGGCCTAGAACCAGCTGCAGGGAGGCATGTCTGCAGGGATGGACAGAGGCAGCATACGAGGAGGCAGAGGACAACTGCAGGCGCATGATGAGGACCAAG |
| 17 | LS_CALR_JAK2-2x9mer | ATGGCATGCCCAGGCTTCCTGTGGGCCCTGGTCATCAGCACCTGTCTGGAGTTTTCCATGGCCATGAAGGACAAGCAGGATGAGGAGCAGCGGACCCGGAGAATGATGAGGACAAAGATGCGCATGAGGCGCATGCGGAGAACAAGGCGCAAGATGCGGAGAAAGATGTCTCCAGCAAGGCCTAGAACCAGCTGCAGGGAGGCATGTCTGCAGGGATGGACAGAGGCAGCATACGAGGAGGCAGAGGACAACTGCAGGCGCATGATGAGGACCAAGGCCGCCTACGTGCTGAATTATGGCGTGTGCTTCTGTGCCGCCTATTTTTGTGGCGATGAGAACATCCTGGTG |
| 18 | LS_CALR_JAK2-30mer | ATGGCATGCCCAGGCTTCCTGTGGGCCCTGGTCATCAGCACCTGTCTGGAGTTTTCCATGGCCATGAAGGACAAGCAGGATGAGGAGCAGCGGACCCGGAGAATGATGAGGACAAAGATGCGCATGAGGCGCATGCGGAGAACAAGGCGCAAGATGCGGAGAAAGATGTCTCCAGCAAGGCCTAGAACCAGCTGCAGGGAGGCATGTCTGCAGGGATGGACAGAGGCAGCATACGAGGAGGCAGAGGACAACTGCAGGCGCATGATGAGGACCAAGGCCGCCTACAAGCTGAGCCACAAGCACCTGGTGCTGAACTATGGCGTGTGCTTCTGTGGCGATGAGAATATCCTGGTGCAGGAGTTCGTGAAGTTTGGC |
| 19 | CALR_JAK2-2x9mer for Ad26 | ATGAAGGACAAGCAGGATGAGGAGCAGCGGACCCGGAGAATGATGAGGACAAAGATGCGCATGAGGCGCATGCGGAGAACAAGGCGCAAGATGCGGAGAAAGATGTCTCAGCAAGGCCTAGAACCAGCTGCAGGGAGGCATGTCTGCAGGGATGGACAGAGGCAGCATACGAGGAGGCAGAGGACAACTGCAGGCGCATGATGAGGACCAAGGCCGCCTACGTGCTGAATTATGGCGTGTGCTTCTGTGCCGCCTATTTTTGTGGCGATGAGAACATCCTGGTG |

SEQUENCE LISTING

| SEQ ID NO: | Epitope | Sequence |
|---|---|---|
| 20 | CALR_JAK2-30mer | ATGAAGGACAAGCAGGATGAGGAGCAGCGGACCCGGAGAATGATGAGGACAAAG<br>ATGCGCATGAGGCGCATGCGGAGAACAAGGCGCAAGATGCGGAGAAAGATGTCTC<br>CAGCAAGGCCTAGAACCAGCTGCAGGGAGGCATGTCTGCAGGGATGGACAGAGGC<br>AGCATACGAGGAGGCAGAGGACAACTGCAGGCGCATGATGAGGACCAAGGCCGCC<br>TACAAGCTGAGCCACAAGCACCTGGTGCTGAACTATGGCGTGTGCTTCTGTGGCGA<br>TGAGAATATCCTGGTGCAGGAGTTCGTGAAGTTTGGC |
| 21 | Ubiq_CALR_JAK2-2x9mer | ATGCAGATCTTCGTGAAGACCCTGACAGGCAAGACCATCACACTGGAGGTGGAGC<br>CCTCCGACACCATCGAGAACGTGAAGGCCAAGATCCAGGACAAGGAGGGCATCCC<br>CCCTGATCAGCAGCGGCTGATCTTTGCCGGCAAGCAGCTGGAGGACGGCAGAACCC<br>TGTCTGATTACAATATCCAGAAGGAGAGCACACTGCACCTGGTGCTGCGGCTGAGA<br>GGCGTGAGGAAGGACAAGCAGGATGAGGAGCAGCGCACCCGGAGAATGATGCGG<br>ACAAAGATGAGAATGAGGCGCATGCGGAGAACCAGGCGCAAGATGCGGAGAAAG<br>ATGAGCCCAGCAAGGCCACGCACCTCCTGCAGGGAGGCATGTCTGCAGGGATGGA<br>CAGAGGCAGCCTATGAGGAGGCCGAGGACAACTGCAGGCGCATGATGCGGACAAA<br>GGCCGCCTACGTGCTGAATTATGCGTGTGCTTCTGTGCCGCCTATTTTTGTGGCGA<br>TGAGAACATCCTGGTG |
| 22 | Ubiq_CALR_JAK2-30mer | ATGCAGATCTTCGTGAAGACCCTGACAGGCAAGACCATCACACTGGAGGTGGAGC<br>CCTCCGACACCATCGAGAACGTGAAGGCCAAGATCCAGGACAAGGAGGGCATCCC<br>CCCTGATCAGCAGCGGCTGATCTTTGCCGGCAAGCAGCTGGAGGACGGCAGAACCC<br>TGTCTGATTACAATATCCAGAAGGAGAGCACACTGCACCTGGTGCTGCGGCTGAGA<br>GGCGTGAGGAAGGACAAGCAGGATGAGGAGCAGCGCACCCGGAGAATGATGCGG<br>ACAAAGATGAGAATGAGGCGCATGCGGAGAACCAGGCGCAAGATGCGGAGAAAG<br>ATGAGCCCAGCAAGGCCACGCACCTCCTGCAGGGAGGCATGTCTGCAGGGATGGA<br>CAGAGGCAGCCTATGAGGAGGCCGAGGACAACTGCAGGCGCATGATGCGGACAAA<br>GGCCGCCTACAAGCTGTCTCACAAGCACCTGGTGCTGAACTATGGCGTGTGCTTCT<br>GTGGCGATGAGAATATCCTGGTGCAGGAGTTCGTGAAGTTTGGCTGATAA |
| 23 | polynucleotide sequence of the Ad26HEME001 transgene containing the tetracycline operator (TetO)-containing cytomegalovirus (CMV) promoter, a Kozak sequence and the transgene and the simian virus 40 (SV40) polyadenylation signal | TCAATATTGGCCATTAGCCATATTATTCATTGGTTATATAGCATAAATCAATATTGG<br>CTATTGGCCATTGCATACGTTGTATCCATATCATAATATGTACATTTATATTGGCTC<br>ATGTCCAACATTACCGCCATGTTGACATTGATTATTGACTAGTTATTAATAGTAATC<br>AATTACGGGGTCATTAGTTCATAGCCCATATATGGAGTTCCGCGTTACATAACTTAC<br>GGTAAATGGCCCGCCTGGCTGACCGCCCAACGACCCCCGCCCATTGACGTCAATAA<br>TGACGTATGTTCCCATAGTAACGCCAATAGGGACTTTCCATTGACGTCAATGGGTG<br>GAGTATTTACGGTAAACTGCCCACTTGGCAGTACATCAAGTGTATCATATGCCAAG<br>TACGCCCCCTATTGACGTCAATGACGGTAAATGGCCCGCCTGGCATTATGCCCAGT<br>ACATGACCTTATGGGACTTTCCTACTTGGCAGTACATCTACGTATTAGTCATCGCTA<br>TTACCATGGTGATGCGGTTTTGGCAGTACATCAATGGGCGTGGATAGCGGTTTGAC<br>TCACGGGGATTTCCAAGTCTCCACCCCATTGACGTCAATGGGAGTTTGTTTTGGCAC<br>CAAAATCAACGGGACTTTCCAAAATGTCGTAACAACTCCGCCCCATTGACGCAAAT<br>GGGCGGTAGGCGTGTACGGTGGGAGGTCTATATAAGCAGAGCTCTCCCTATCAGTG<br>ATAGAGATCTCCCTATCAGTGATAGAGATCGTCGACGAGCTCGTTTAGTGAACCGT<br>CAGATCGCCTGGAGACGCCATCCACGCTGTTTTGACCTCCATAGAAGACACCGGGA<br>CCGATCCAGCCTCCGCGGCCGGGAACGGTGCATTGGATCTAGAGCCACCATGGCAT<br>GCCCAGGCTTCCTGTGGGCCCTGGTCATCAGCACCTGTCTGGAGTTTTCCATGGCCA<br>TGAAGGACAAGCAGGATGAGGAGCAGCGGACCCGGAGAATGATGAGGACAAAGA<br>TGCGCATGAGGCGCATGCGGAGAACAAGGCGCAAGATGCGGAGAAAGATGTCTCC<br>AGCAAGGCCTAGAACCAGCTGCAGGGAGGCATGTCTGCAGGGATGGACAGAGGCA<br>GCATACGAGGAGGCAGAGGACAACTGCAGGCGCATGATGAGGACCAAGGCCGCCT<br>ACAAGCTGAGCCACAAGCACCTGGTGCTGAACTATGGCGTGTGCTTCTGTGGCGAT<br>GAGAATATCCTGGTGCAGGAGTTCGTGAAGTTTGGCTGATAAGGTACCATCCGAAC<br>TTGTTTATTGCAGCTTATAATGGTTACAAATAAAGCAATAGCATCACAAATTTCACA<br>AATAAAGCATTTTTTTCACTGCATTCTAGTTGTGGTTTGTCCAAACTCATCAATGTA<br>TCTTATCATGTCT |
| 24 | polynucleotide sequence of the Ad26HEME002 transgene containing the tetracycline operator (TetO)-containing cytomegalovirus (CMV) promoter, a Kozak sequence and the transgene and the simian virus 40 (SV40) polyadenylation signal | TCAATATTGGCCATTAGCCATATTATTCATTGGTTATATAGCATAAATCAATATTGG<br>CTATTGGCCATTGCATACGTTGTATCCATATCATAATATGTACATTTATATTGGCTC<br>ATGTCCAACATTACCGCCATGTTGACATTGATTATTGACTAGTTATTAATAGTAATC<br>AATTACGGGGTCATTAGTTCATAGCCCATATATGGAGTTCCGCGTTACATAACTTAC<br>GGTAAATGGCCCGCCTGGCTGACCGCCCAACGACCCCCGCCCATTGACGTCAATAA<br>TGACGTATGTTCCCATAGTAACGCCAATAGGGACTTTCCATTGACGTCAATGGGTG<br>GAGTATTTACGGTAAACTGCCCACTTGGCAGTACATCAAGTGTATCATATGCCAAG<br>TACGCCCCCTATTGACGTCAATGACGGTAAATGGCCCGCCTGGCATTATGCCCAGT<br>ACATGACCTTATGGGACTTTCCTACTTGGCAGTACATCTACGTATTAGTCATCGCTA<br>TTACCATGGTGATGCGGTTTTGGCAGTACATCAATGGGCGTGGATAGCGGTTTGAC<br>TCACGGGGATTTCCAAGTCTCCACCCCATTGACGTCAATGGGAGTTTGTTTTGGCAC<br>CAAAATCAACGGGACTTTCCAAAATGTCGTAACAACTCCGCCCCATTGACGCAAAT<br>GGGCGGTAGGCGTGTACGGTGGGAGGTCTATATAAGCAGAGCTCTCCCTATCAGTG<br>ATAGAGATCTCCCTATCAGTGATAGAGATCGTCGACGAGCTCGTTTAGTGAACCGT<br>CAGATCGCCTGGAGACGCCATCCACGCTGTTTTGACCTCCATAGAAGACACCGGGA<br>CCGATCCAGCCTCCGCGGCCGGGAACGGTGCATTGGATCTAGAGCCACCATGGCAT<br>GCCCAGGCTTCCTGTGGGCCCTGGTCATCAGCACCTGTCTGGAGTTTTCCATGGCCA<br>TGAAGGACAAGCAGGATGAGGAGCAGCGGACCCGGAGAATGATGAGGACAAAGA |

| SEQ ID NO: | Epitope | Sequence |
|---|---|---|
| | | TGCGCATGAGGCGCATGCGGAGAACAAGGCGCAAGATGCGGAGAAAGATGTCTCC<br>AGCAAGGCCTAGAACCAGCTGCAGGGAGGCATGTCTGCAGGGATGGACAGAGGCA<br>GCATACGAGGAGGCAGAGGACAACTGCAGGCGCATGATGAGGACCAAGGCCGCCT<br>ACGTGCTGAATTATGGCGTGTGCTTCTGTGCCGCCTATTTTTGTGGCGATGAGAACA<br>TCCTGGTGTGATAAGGTACCATCCGAACTTGTTTATTGCAGCTTATAATGGTTACAA<br>ATAAAGCAATAGCATCACAAATTTCACAAATAAAGCATTTTTTTCACTGCATTCTAG<br>TTGTGGTTTGTCCAAACTCATCAATGTATCTTATCATGTCT |
| 25 | HCalJ-9.9<br>(TCE_CALR JAK<br>2-2x9mer) Full<br>insert DNA for<br>expression in<br>MVA and Gad20 | GATCACTAATTCCAAACCCACCCGCTTTTTATAGTAAGTTTTTCACCCATAAATAAT<br>AAATACAATAATTAATTTCTCGTAAAAGTAGAAAATATATTCTAATTTATTGCACG<br>GTAAGGAAGTAGAATCATAAAGAACAGTGACGGATCCCGCGACTTCGCCGCCATG<br>GGCCAGAAGGAACAGATTCATACGCTTCAGAAAAATTCTGAACGAATGTCAAAGC<br>AATTGACACGAAGTTCTCAGGCAGTAATGAAGGACAAACAAGACGAAGAACAACG<br>AACTAGGCGGATGATGAGGACTAAGATGAGGATGCGGAGGATGAGACGGACGCGA<br>CGCAAGATGCGCCGGAAAATGTCTCCCGCCCGGCCAAGGACGTCTTGTCGGGAAGC<br>CTGTTTGCAGGGCTGGACCGAAGCAGCTTACGAAGAAGCAGAAGACAATTGTCGG<br>CGAATGATGAGAACGAAGGCTGCTTACGTGCTTAACTATGGAGTGTGCTTCTGCGC<br>TGCCTATTTCTGCGGAGATGAGAACATTCTGGTGTAGTAAAGGCGCGCC |
| 26 | HCalJ-9.9<br>(TCE_CALR JAK<br>2-2x9mer)<br>Transgene only<br>with leader<br>sequence for<br>expression in<br>MVA and Gad20 | ATGGGCCAGAAGGAACAGATTCATACGCTTCAGAAAAATTCTGAACGAATGTCAA<br>AGCAATTGACACGAAGTTCTCAGGCAGTAATGAAGGACAAACAAGACGAAGAACA<br>ACGAACTAGGCGGATGATGAGGACTAAGATGAGGATGCGGAGGATGAGACGGACG<br>CGACGCAAGATGCGCCGGAAAATGTCTCCCGCCCGGCCAAGGACGTCTTGTCGGGA<br>AGCCTGTTTGCAGGGCTGGACCGAAGCAGCTTACGAAGAAGCAGAAGACAATTGT<br>CGGCGAATGATGAGAACGAAGGCTGCTTACGTGCTTAACTATGGAGTGTGCTTCTG<br>CGCTGCCTATTTCTGCGGAGATGAGAACATTCTGGTG |
| 27 | CALR JAK2-<br>2x9mer Transgene<br>only without leader<br>sequence DNA for<br>expression in<br>MVA and Gad20 | ATGAAGGACAAACAAGACGAAGAACAACGAACTAGGCGGATGATGAGGACTAAG<br>ATGAGGATGCGGAGGATGAGACGGACGCGACGCAAGATGCGCCGGAAAATGTCTC<br>CCGCCCGGCCAAGGACGTCTTGTCGGGAAGCCTGTTTGCAGGGCTGGACCGAAGCA<br>GCTTACGAAGAAGCAGAAGACAATTGTCGGCGAATGATGAGAACGAAGGCTGCTT<br>ACGTGCTTAACTATGGAGTGTGCTTCTGCGCTGCCTATTTCTGCGGAGATGAGAAC<br>ATTCTGGT |
| 28 | JAK2 Epitope2-<br>AAY-JAK2<br>Epitope 2 | FCGDENILVAAYFCGDENILV |
| 29 | TCE | MGQKEQIHTLQKNSERMSKQLTRSSQAV |
| 30 | TCE<br>polynucleotide | ATGGGCCAGAAGGAACAGATTCATACGCTTCAGAAAAATTCTGAACGAATGTCAA<br>AGCAATTGACACGAAGTTCTCAGGCAGTA |
| 31 | TCE_CALR_JAK<br>2-2x9mer | MGQKEQIHTLQKNSERMSKQLTRSSQAVMKDKQDEEQRTRRMMRTKMRMRRMRRT<br>RRKMRRKMSPARPRTSCREACLQGWTEAAYEEAEDNCRRMMRTKAAYVLNYGVCFC<br>AAYFCGDENILV |
| 32 | P7.5 promoter | GATCACTAATTCCAAACCCACCCGCTTTTTATAGTAAGTTTTTCACCCATAAATAAT<br>AAATACAATAATTAATTTCTCGTAAAAGTAGAAAATATATTCTAATTTATTGCACG<br>GTAAGGAAGTAGAATCATAAAGAACAGTGACGGATC |
| 33 | Polynucleotide<br>sequence of the<br>full self-replicating<br>RNA plasmid | TAATACGACTCACTATAGATAGGCGGCGCATGAGAGAAGCCCAGACCAATTACCTA<br>CCCAAATAGGAGAAAGTTCACGTTGACATCGAGGAAGACAGCCCATTCCTCAGAG<br>CTTTGCAGCGGAGCTTCCCGCAGTTTGAGGTAGAAGCCAAGCAGGTCACTGATAAT<br>GACCATGCTAATGCCAGAGCGTTTTCGCATCTGGCTTCAAAACTGATCGAAACGGA<br>GGTGGACCCATCCGACACGATCCTTGACATTGGAATAGTCAGCATAGTACATTTCA<br>TCTGACTAATACTACAACACCACCACCATGAATAGAGGATTCTTTAACATGCTCGG<br>CCGCCGCCCCTTCCCGGCCCCCACTGCCATGTGGAGGCCGCGGAGAAGGAGGCAG<br>GCGGCCCCGGGAAGCGGAGCTACTAACTTCAGCCTGCTGAAGCAGGCTGGAGACG<br>TGGAGGAGAACCCTGGACCTGAGAAAGTTCACGTTGACATCGAGGAAGACAGCCC<br>ATTCCTCAGAGCTTTGCAGCGGAGCTTCCCGCAGTTTGAGGTAGAAGCCAAGCAGG<br>TCACTGATAATGACCATGCTAATGCCAGAGCGTTTTCGCATCTGGCTTCAAAACTG<br>ATCGAAACGGAGGTGGACCCATCCGACACGATCCTTGACATTGGAAGTGCGCCCGC<br>CCGCAGAATGTATTCTAAGCACAAGTATCATTGTATCTGTCCGATGAGATGTGCGG<br>AAGATCCGGACAGATTGTATAAGTATGCAACTAAGCTGAAGAAAACTGTAAGGA<br>ATAACTGATAAGGAATTGGACAAGAAAATGAAGGAGCTCGCCGCCGTCATGAGC<br>GACCCTGACCTGGAAACTGAGACTATGTGCCTCACGACGACGAGTCGTGTCGCTA<br>CGAAGGGCAAGTCGCTGTTTACCAGGATGTATACGCGGTTGACGGACCGACAAGTC<br>TCTATCACCAAGCCAATAAGGGAGTTAGAGTCGCCTACTGGATAGGCTTTGACACC<br>ACCCCTTTTATGTTTAAGAACTTGGCTGGAGCATATCCATCATACTCTACCAACTGG<br>GCCGACGAAACCGTGTTAACGGCTCGTAACATAGGCCTATGCAGCTCTGACGTTAT<br>GGAGCGGTCACGTAGAGGGATGTCCATTCTTAGAAAGAAGTATTTGAAACCATCCA<br>ACAATGTTCTATTCTCTGTTGGCTCGACCATCTACCACGAGAAGAGGGACTTACTG |

SEQUENCE LISTING

| SEQ ID NO: | Epitope | Sequence |
|---|---|---|
| | | AGGAGCTGGCACCTGCCGTCTGTATTTCACTTACGTGGCAAGCAAAATTACACATG |
| | | TCGGTGTGAGACTATAGTTAGTTGCGACGGGTACGTCGTTAAAAGAATAGCTATCA |
| | | GTCCAGGCCTGTATGGGAAGCCTTCAGGCTATGCTGCTACGATGCACCGCGAGGGA |
| | | TTCTTGTGCTGCAAAGTGACAGACACATTGAACGGGGAGAGGGTCTCTTTTCCCGT |
| | | GTGCACGTATGTGCCAGCTACATTGTGTGACCAAATGACTGGCATACTGGCAACAG |
| | | ATGTCAGTGCGGACGACGCGCAAAAACTGCTGGTTGGGCTCAACCAGCGTATAGTC |
| | | GTCAACGGTCGCACCCAGAGAAACACCAATACCATGAAAAATTACCTTTTGCCCGT |
| | | AGTGGCCCAGGCATTTGCTAGGTGGGCAAAGGAATATAAGGAAGATCAAGAAGAT |
| | | GAAAGGCCACTAGGACTACGAGATAGACAGTTAGTCATGGGGTGTTGTTGGGCTTT |
| | | TAGAAGGCACAAGATAACATCTATTTATAAGCGCCCGGATACCCAAACCATCATCA |
| | | AAGTGAACAGCGATTTCCACTCATTCGTGCTGCCCAGGATAGGCAGTAACACATTG |
| | | GAGATCGGGCTGAGAACAAGAATCAGGAAAATGTTAGAGGAGCACAAGGAGCCGT |
| | | CACCTCTCATTACCGCCGAGGACGTACAAGAAGCTAAGTGCGCAGCCGATGAGGCT |
| | | AAGGAGGTGCGTGAAGCCGAGGAGTTGCGCGCAGCTCTACCACCTTTGGCAGCTGA |
| | | TGTTGAGGAGCCCACTCTGGAAGCCGATGTCGACTTGATGTTACAAGAGGCTGGGG |
| | | CCGGCTCAGTGGAGACACCTCGTGGCTTGATAAAGGTTACCAGCTACGATGGCGAG |
| | | GACAAGATCGGCTCTTACGCTGTGCTTTCTCCGCAGGCTGTACTCAAGAGTGAAAA |
| | | ATTATCTTGCATCCACCCTCTCGCTGAACAAGTCATAGTGATAACACACTCTGGCCG |
| | | AAAAGGGCGTTATGCCGTGGAACCATACCATGGTAAAGTAGTGGTGCCAGAGGGA |
| | | CATGCAATACCCGTCCAGGACTTTCAAGCTCTGAGTGAAAGTGCCACCATTGTGTA |
| | | CAACGAACGTGAGTTCGTAAACAGGTACCTGCACCATATTGCCACACATGGAGGAG |
| | | CGCTGAACACTGATGAAGAATATTACAAAACTGTCAAGCCCAGCGAGCACGACGG |
| | | CGAATACCTGTACGACATCGACAGGAAACAGTCGTCAAGAAAGAACTAGTCACT |
| | | GGGCTAGGGCTCACAGGCGAGCTGGTGGATCCTCCCTTCCATGAATTCGCCTACGA |
| | | GAGTCTGAGAACACGACCAGCCGCTCCTTACCAAGTACCAACCATAGGGGTGTATG |
| | | GCGTGCCAGGATCAGGCAAGTCTGGCATCATTAAAAGCGCAGTCACCAAAAAAGA |
| | | TCTAGTGGTGAGCGCCAAGAAAGAAAACTGTGCAGAAATTATAAGGGACGTCAAG |
| | | AAAATGAAAGGGCTGGACGTCAATGCCAGAACTGTGGACTCAGTGCTCTTGAATGG |
| | | ATGCAAACACCCCGTAGAGACCCTGTATATTGACGAAGCTTTTGCTTGTCATGCAG |
| | | GTACTCTCAGAGCGCTCATAGCCATTATAAGACCTAAAAAGGCAGTGCTCTGCGGG |
| | | GATCCCAAACAGTGCGGTTTTTTTAACATGATGTGCCTGAAAGTGCATTTTAACCAC |
| | | GAGATTTGCACACAAGTCTTCCACAAAAGCATCTCTCGCCGTTGCACTAAATCTGTT |
| | | GACTTCGGTCGTCTCAACCTTGTTTTACGACAAAAAAATGAGAACGACGAATCCGA |
| | | AAGAGACTAAGATTGTGATTGACACTACCGGCAGTACCAAACCTAAGCAGGACGA |
| | | TCTCATTCTCACTTGTTTCAGAGGGTGGGTGAAGCAGTTGCAAATAGATTACAAAG |
| | | GCAACGAAATAATGACGGCAGCTGCCTCTCAAGGGCTGACCCGTAAAGGTGTGTAT |
| | | GCCGTTCGGTACAAGGTGAATGAAAATCCTCGTACGCACCCCACCTCTGAACATGT |
| | | GAACGTCCTACTGACCCGCACGGAGGACCGCATCGTGTGGAAAACACTAGCCGGC |
| | | GACCCATGGATAAAAACACTGACTGCCAAGTACCCTGGGAATTTCACTGCCACGAT |
| | | AGAGGAGTGGCAAGCAGAGCATGATGCCATCATGAGGCACATCTTGGAGAGACCG |
| | | GACCCTACCGACGTCTTCCAGAATAAGGCAAACGTGTGTTGGGCCAAGGCTTTAGT |
| | | GCCGGTGCTGAAGACCGCTGGCATAGACATGACCACTGAACAATGGAACACTGTG |
| | | GATTATTTTGAAACGGACAAAGCTCACTCAGCAGAGATAGTATTGAACCAACTATG |
| | | CGTGAGGTTCTTTGGACTCGATCTGGACTCCGGTCTATTTTCTGCACCCACTGTTCC |
| | | GTTATCCATTAGGAATAATCACTGGGATAACTCCCCGTCGCCTAACATGTACGGGC |
| | | TGAATAAAGAAGTGGTCCGTCAGCTCTCTCGCAGGTACCCACAACTGCCTCGGGCA |
| | | GTTGCCACTGGAAGAGTCTATGACATGAACACTGGTACACTGCGCAATTATGATCC |
| | | GCGCATAAACCTAGTACCTGTAAACAGAAGACTGCCTCATGCTTTAGTCCTCCACC |
| | | ATAATGAACACCCACAGAGTGACTTTTCTTCATTCGTCAGCAAATTGAAGGGCAGA |
| | | ACTGTCCTGGTGGTCGGGGAAAAGTTGTCCGTCCCAGGCAAAATGGTTGACTGGTT |
| | | GTCAGACCGGCCTGAGGCTACCTTCAGAGCTCGGCTGGATTTAGGCATCCCAGGTG |
| | | ATGTGCCCAAATATGACATAATATTTGTTAATGTGAGGACCCCATATAAATACCAT |
| | | CACTATCAGCAGTGTGAAGACCATGCCATTAAGCTTAGCATGTTGACCAAGAAAGC |
| | | TTGTCTGCATCTGAATCCCGGCGGAACCTGTGTCAGCATAGGTTATGGTTACGCTGA |
| | | CAGGGCCAGCGAAAGCATCATTGGTGCTATAGCGCGGCAGTTCAAGTTTTCCCGGG |
| | | TATGCAAACCGAAATCCTCACTTGAAGACGGAAGTTCTGTTTGTATTCATTGGG |
| | | TACGATCGCAAGGCCCGTACGCACAATCCTTACAAGCTTTCATCAACCTTGACCAA |
| | | CATTTATACAGGTTCCAGACTCCACGAAGCCGGATGTGCACCCTCATATCATGTGG |
| | | TGCGAGGGGATATTGCCACGGCCACCGAAGGAGTGATTATAAATGCTGCTAACAGC |
| | | AAAGGACAACCTGGCGGAGGGGTGTGCGGAGCGCTGTATAAGAAATTCCCGGAAA |
| | | GCTTCGATTTACAGCCGATCGAAGTAGGAAAAGCGCGACTGGTCAAAGGTGCAGCT |
| | | AAACATATCATTCATGCCGTAGGACCAAACTTCAACAAAGTTTCGGAGGTTGAAGG |
| | | TGACAAACAGTTGGCAGAGGCTTATGAGTCCATCGCTAAGATTGTCAACGATAACA |
| | | ATTACAAGTCAGTAGCGATTCCACTGTTGTCCACCGGCATCTTTTCCGGGAACAAA |
| | | GATCGACTAACCCAATCATTGAACCATTTGCTGACAGCTTTAGACACCACTGATGC |
| | | AGATGTAGCCATATACTGCAGGGACAAGAAATGGGAAATGACTCTCAAGGAAGCA |
| | | GTGGCTAGGAGAGAAGCAGTGGAGGAGATATGCATATCCGACGACTCTTCAGTGA |
| | | CAGAACCTGATGCAGAGCTGGTGAGGGTGCATCCGAAGAGTTCTTTGGCTGGAAGG |
| | | AAGGGCTACAGCACAAGCGATGGCAAAACTTTCTCATATTTGGAAGGGACCAAGTT |
| | | TCACCAGGCGGCCAAGGATATAGCAGAAATTAATGCCATGTGGCCCGTTGCAACGG |
| | | AGGCCAATGAGCAGGTATGCATGTATATCCTCGGAGAAAGCATGAGCAGTATTAG |
| | | GTCGAAATGCCCCGTCGAAGAGTCGGAAGCCTCCACACCACCTAGCACGCTGCCTT |
| | | GCTTGTGCATCCATGCCATGACTCCAGAAAGAGTACAGCGCCTAAAAGCCTCACGT |
| | | CCAGAACAAATTACTGTGTGCTCATCCTTTCCATTGCCGAAGTATAGAATCACTGGT |

SEQUENCE LISTING

| SEQ ID NO: | Epitope | Sequence |
|---|---|---|
| | | GTGCAGAAGATCCAATGCTCCCAGCCTATATTGTTCTCACCGAAAGTGCCTGCGTA
TATTCATCCAAGGAAGTATCTCGTGGAAACACCACCGGTAGACGAGACTCCGGAGC
CATCGGCAGAGAACCAATCCACAGAGGGGACACCTGAACAACCACCACTTATAAC
CGAGGATGAGACCAGGACTAGAACGCCTGAGCCGATCATCATCGAAGAGGAAGAA
GAGGATAGCATAAGTTTGCTGTCAGATGGCCCGACCCACCAGGTGCTGCAAGTCGA
GGCAGACATTCACGGGCCGCCCTCTGTATCTAGCTCATCCTGGTCCATTCCTCATGC
ATCCGACTTTGATGTGGACAGTTTATCCATACTTGACACCCTGGAGGGAGCTAGCG
TGACCAGCGGGGCAACGTCAGCCGAGACTAACTCTTACTTCGCAAAGAGTATGGAG
TTTCTGGCGCGACCGGTGCCTGCGCCTCGAACAGTATTCAGGAACCCTCCACATCC
CGCTCCGCGCACAAGAACACCGTCACTTGCACCCAGCAGGGCCTGCTCGAGAACCA
GCCTAGTTTCCACCCCGCCAGGCGTGAATAGGGTGATCACTAGAGAGGAGCTCGAG
GCGCTTACCCCGTCACGCACTCCTAGCAGGTCGGTCTCGAGAACCAGCCTGGTCTC
CAACCCGCCAGGCGTAAATAGGGTGATTACAAGAGAGGAGTTTGAGGCGTTCGTA
GCACAACAACAATGACGGTTTGATGCGGGTGCATACATCTTTTCCTCCGACACCGG
TCAAGGGCATTTACAACAAAAATCAGTAAGGCAAACGGTGCTATCCGAAGTGGTGT
TGGAGAGGACCGAATTGGAGATTTCGTATGCCCCGCGCCTCGACCAAGAAAAAGA
AGAATTACTACGCAAGAAATTACAGTTAAATCCCACACCTGCTAACAGAAGCAGAT
ACCAGTCCAGGAAGGTGGAGAACATGAAAGCCATAACAGCTAGACGTATTCTGCA
AGGCCTAGGGCATTATTTGAAGGCAGAAGGAAAAGTGGAGTGCTACCGAACCCTG
CATCCTGTTCCTTTGTATTCATCTAGTGTGAACCGTGCCTTTTCAAGCCCCAAGGTC
GCAGTGGAAGCCTGTAACGCCATGTTGAAAGAGAACTTTCCGACTGTGGCTTCTTA
CTGTATTATTCCAGAGTACGATGCCTATTTGGACATGGTTGACGGAGCTTCATGCTG
CTTAGACACTGCCAGTTTTTGCCCTGCAAAGCTGCGCAGCTTTCCAAAGAAACACT
CCTATTTGGAACCCACAATACGATCGGCAGTGCCTTCAGCGATCCAGAACACGCTC
CAGAACGTCCTGGCAGCTGCCACAAAAAGAAATTGCAATGTCACGCAAATGAGAG
AATTGCCCGTATTGGATTCGGCGGCCTTTAATGTGGAATGCTTCAAGAAATATGCG
TGTAATAATGAATATTGGGAAACGTTTAAAGAAAACCCCATCAGGCTTACTGAAGA
AAACGTGGTAAATTACATTACCAAATTAAAAGGACCAAAAGCTGCTGCTCTTTTTG
CGAAGACACATAATTTGAATATGTTGCAGGACATACCAATGGACAGGTTTGTAATG
GACTTAAAGAGAGACGTGAAAGTGACTCCAGGAACAAAACATACTGAAGAACGGC
CCAAGGTACAGGTGATCCAGGCTGCCGATCCGCTAGCAACAGCGTATCGTGCGGA
ATCCACCGAGAGCTGGTTAGGAGATTAAATGCGGTCCTGCTTCCGAACATTCATAC
ACTGTTTGATATGTCGGCTGAAGACTTTGACGCTATTATAGCCGAGCACTTCCAGCC
TGGGGATTGTGTTCTGGAAACTGACATCGCGTCGTTTGATAAAAGTGAGGACGACG
CCATGGCTCTGACCGCGTTAATGATTCTGGAAGACTTAGGTGTGGACGCAGAGCTG
TTGACGCTGATTGAGGCGGCTTTCGGCGAAATTTCATCAATACATTTGCCCACTAAA
ACTAAATTTAAATTCGGAGCCATGATGAAATCTGGAATGTTCCTCACACTGTTTGTG
AACACAGTCATTAACATTGTAATCGCAAGCAGAGTGTTGAGAGAACGGCTAACCG
GATCACCATGTGCAGCATTCATTGGAGATGACAATATCGTGAAAGGAGTCAAATCG
GACAAATTAATGGCAGACAGGTGCGCCACCTGGTTGAATATGGAAGTCAAGATTAT
AGATGCTGTGGTGGGCGAGAAAGCGCCTTATTTCTGTGGAGGGTTTATTTTGTGTG
ACTCCGTGACCGGCACAGCGTGCCGTGTGGCAGACCCCCTAAAAAGGCTGTTTAAG
CTTGGCAAACCTCTGGCAGCAGACGATGAACATGATGATGACAGGAGAAGGGCAT
TGCATGAAGAGTCAACACGCTGGAACCGAGTGGGTATTCTTTCAGAGCTGTGCAAG
GCAGTAGAATCAAGGTATGAAACCGTAGGAACTTCCATCATAGTTATGGCCATGAC
TACTCTAGCTAGCAGTGTTAAATCATTCAGCTACCTGAGAGGGGCCCCTATAACTCT
CTACGGCTAACCTGAATGGACTACGACATAGTCTAGTCCGCCAAGATATCGGCGCG
CCGTTTAAACGGCCGGCCTTAATTAAGTAACGATACAGCAGCAATTGGCAAGCTGC
TTACATAGAACTCGCGGCGATTGGCATGCCGCTTTAAAATTTTTATTTTATTTTTCTT
TTCTTTTCCGAATCGGATTTTGTTTTTAATATTTCAAAAAAAAAAAAAAAAAAAAA
AAAAAAAAAAAAAAAAAACCCTCTCTAAACGGAGGGGTTTTTTTCAGCGTAACTG
GACTGGCCACAGTTAGGCGGCCGCGCATGTTCATCATCAGTAACCCGTATCGTGAG
CATCCTCTCTCGTTTCATCGGTATCATTACCTCCATGAACAGAAATCCCCCTTACAC
GGAGGCATCAGTGACCAAACAGGAAAAAACCGCCCTTAACATGGCCGCTTTATCA
GAAGCCAGACATTAACGCTTCTGGAGAAACTCAACGAGCTGGACGCGGATGAACA
GGCAGACATCTGTGAATCGCTTCACGACCACGCTGATGAGCTTTACCGCAGCTGCC
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGTC
AGCGGGTGTTGGCGGGTGTCGGGGCGCAGCCATGACCCAGTCACGTAGCGATAGC
GGAGTGTATACTGGCTTAACTATGCGGCATCAGAGCAGATTGTACTGAGAGTGCAC
CATATGCGGTGTGAAATACCGCACAGATGCGTAAGGAGAAAATACCGCATCAGGC
GCTCGCTTCCTCGCTCACTGACTCGCTGCGCTCGGTCGTTCGGCTGCGGCGAGCGGT
ATCAGCTCACTCAAAGGCGGTAATACGGTTATCCACAGAATCAGGGGATAACGCA
GGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCG
ACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGT |

SEQUENCE LISTING

| SEQ ID NO: | Epitope | Sequence |
|---|---|---|
| | | TTGCAAGCAGCAGATTACGCGCAGAAAAAAGGATCTCAAGAAGATCCTTTGATCT<br>TTTCTACGGGGTCTGACGCTCAGTGGAACGAAAACTCACGTTAAGGGATTTTGGTC<br>ATGAGATTATCAAAAAGGATCTTCACCTAGATCCTTTTAAATTAAAAATGAAGTTTT<br>AAATCAATCTAAAGTATATATGAGTAAACTTGGTCTGACAGTTATTAGAAAAATTC<br>ATCCAGCAGACGATAAAACGCAATACGCTGGCTATCCGGTGCCGCAATGCCATACA<br>GCACCAGAAAACGATCCGCCCATTCGCCGCCCAGTTCTTCCGCAATATCACGGGTG<br>GCCAGCGCAATATCCTGATAACGATCCGCCACGCCCAGACGGCCGCAATCAATAAA<br>GCCGCTAAAACGGCCATTTTCCACCATAATGTTCGGCAGGCACGCATCACCATGGG<br>TCACCACCAGATCTTCGCCATCCGGCATGCTCGCTTTCAGACGCGCAAACAGCTCT<br>GCCGGTGCCAGGCCCTGATGTTCTTCATCCAGATCATCCTGATCCACCAGGCCCGCT<br>TCCATACGGGTACGCGCACGTTAATACGATGTTTCGCCTGATGATCAAACGGACA<br>GGTCGCCGGGTCCAGGGTATGCAGACGACGCATGGCATCCGCCATAATGCTCACTT<br>TTTCTGCCGGCGCCAGATGGCTAGACAGCAGATCCTGACCCGGCACTTCGCCCAGC<br>AGCAGCCAATCACGGCCCGCTTCGGTCACCACATCCAGCACCGCCGCACACGGAAC<br>ACCGGTGGTGGCCAGCCAGCTCAGACGCGCCGCTTCATCCTGCAGCTCGTTCAGCG<br>CACCGCTCAGATCGGTTTTCACAAACAGCACCGGACGACCCTGCGCGCTCAGACGA<br>AACACCGCCGCATCAGAGCAGCCAATGGTCTGCTGCGCCCAATCATAGCCAAACAG<br>ACGTTCCACCCACGCTGCCGGGCTACCCGCATGCAGGCCATCCTGTTCAATCATACT<br>CTTCCTTTTTCAATATTATTGAAGCATTTATCAGGGTTATTGTCTCATGAGCGGATA<br>CATATTTGAATGTATTTAGAAAAATAAACAAATAGGGGTTCCGCGCACATTTCCCC<br>GAAAAGTGCCACCTGACGTCTAAGAAACCATTATTATCATGACATTAAGCATCCGC<br>CTTTCGTTTTATTTGACCATGTTGGTATG |
| 34 | T7 terminator | AACCCCTCTCTAAACGGAGGGGTTTTTT |
| 35 | AmpR promoter | CGCGGAACCCCTATTTGTTTATTTTTCTAAATACATTCAAATATGTATCCGCTCATG<br>AGACAATAACCCTGATAAATGCTTCAATAATATTGAAAAAGGAAGAGT |
| 36 | 26S promoter | CTCTCTACGGCTAACCTGAATGGA |
| 37 | T7 promoter | TAATACGACTCACTATAG |
| 38 | Poly A site | AAAAAAAAAAAAAAAAAAAAAAAAAAAAAAAAAAAAAA |
| 39 | Alpha 5' replication sequence from nsP1 | TAGGAGAAAGTTCACGTTGACATCGAGGAAGACAGCCCATTCCTCAGAGCTTTGCA<br>GCGGAGCTTCCCGCAGTTTGAGGTAGAAGCCAAGCAGGTCACTGATAATGACCATG<br>CTAATGCCAGAGCGTTTTCGCATCTGGCTTCAAAACTGATCGAAACGGAGGTGGAC<br>CCATCCGACACGATCCTTGACATTGGA |
| 40 | DLP | ATAGTCAGCATAGTACATTTCATCTGACTAATACTACAACACCACCACCATGAATA<br>GAGGATTCTTTAACATGCTCGGCCGCCGCCCCTTCCCGGCCCCCACTGCCATGTGGA<br>GGCCGCGGAGAAGGAGGCAGGCGGCCCCG |
| 41 | P2A | GGAAGCGGAGCTACTAACTTCAGCCTGCTGAAGCAGGCTGGAGACGTGGAGGAGA<br>ACCCTGGACCT |
| 42 | Bon | CGCAGCCATGACCCAGTCACGTAGCGATAGCGGAGTGTATACTGGCTTAACTATGC<br>GGCATCAGAGCAGATTGTACTGAGAGTGCACCATATGCGGTGTGAAATACCGCACA<br>GATGCGTAAGGAGAAAATACCGCATCAGG |
| 43 | DLP nsp ORF | ATGAATAGAGGATTCTTTAACATGCTCGGCCGCCGCCCCTTCCCGGCCCCCACTGCC<br>ATGTGGAGGCCGCGGAGAAGGAGGCAGGCGGCCCCGGGAAGCGGAGCTACTAACT<br>TCAGCCTGCTGAAGCAGGCTGGAGACGTGGAGGAGAACCCTGGACCTGAGAAAGT<br>TCACGTTGACATCGAGGAAGACAGCCCATTCCTCAGAGCTTTGCAGCGGAGCTTCC<br>CGCAGTTTGAGGTAGAAGCCAAGCAGGTCACTGATAATGACCATGCTAATGCCAGA<br>GCGTTTTCGCATCTGGCTTCAAAACTGATCGAAACGGAGGTGGACCCATCCGACAC<br>GATCCTTGACATTGGAAGTGCGCCCGCCCGCAGAATGTATTCTAAGCACAAGTATC<br>ATTGTATCTGTCCGATGAGATGTGCGGAAGATCCGGACAGATTGTATAAGTATGCA<br>ACTAAGCTGAAGAAAACTGTAAGGAAATAACTGATAAGGAATTGGACAAGAAAA<br>TGAAGGAGCTCGCCGCCGTCATGAGCGACCCTGACCTGGAAACTGAGACTATGTGC<br>CTCCACGACGACGAGTCGTGTCGCTACGAAGGGCAAGTCGCTGTTTACCAGGATGT<br>ATACGCGGTTGACGGACCGACAAGTCTCTATCACCAAGCCAATAAGGGAGTTAGA<br>GTCGCCTACTGGATAGGCTTTGACACCACCCCTTTTATGTTTAAGAACTTGGCTGGA<br>GCATATCCATCATACTCTACCAACTGGGCCGACGAAACCGTGTTAACGGCTCGTAA<br>CATAGGCCTATGCAGCTCTGACGTTATGGAGCGGTCACGTAGAGGGATGTCCATTC<br>TTAGAAAGAAGTATTTGAAACCATCCAACAATGTTCTATTCTCGTTGGCTCGACCA<br>TCTACCACGAGAAGAGGGACTTACTGAGGAGCTGGCACCTGCCGTCTGTATTTCAC<br>TTACGTGGCAAGCAAATTACACATGTCGGTGTGAGACTATAGTTAGTTGCGACGG<br>GTACGTCGTTAAAAGAATAGCTATCAGTCCAGGCCTGTATGGGAAGCCTTCAGGCT<br>ATGCTGCTACGATGCACCGCGAGGGATTCTTGTGCTGCAAAGTGACAGACACATTG<br>AACGGGGAGAGGGTCTCTTTTCCCGTGTGCACGTATGTGCCAGCTACATTGTGTGA<br>CCAAATGACTGGCATACTGGCAACAGATGTCAGTGCGGACGACGCGCAAAAACTG<br>CTGGTTGGGCTCAACCAGCGTATAGTCGTCAACGGTCGCACCCAGAGAAACACCAA<br>TACCATGAAAAATTACCTTTTGCCCGTAGTGGCCCAGGCATTTGCTAGGTGGGCAA |

SEQUENCE LISTING

| SEQ ID NO: | Epitope | Sequence |
|---|---|---|
| | | AGGAATATAAGGAAGATCAAGAAGATGAAAGGCCACTAGGACTACGAGATAGACA GTTAGTCATGGGGTGTTGTTGGGCTTTTAGAAGGCACAAGATAACATCTATTTATA AGCGCCCGGATACCCAAACCATCATCAAAGTGAACAGCGATTTCCACTCATTCGTG CTGCCCAGGATAGGCAGTAACACATTGGAGATCGGGCTGAGAACAAGAATCAGGA AAATGTTAGAGGAGCACAAGGAGCCGTCACCTCTCATTACCGCCGAGGACGTACA AGAAGCTAAGTGCGCAGCCGATGAGGCTAAGGAGGTGCGTGAAGCCGAGGAGTTG CGCGCAGCTCTACCACCTTTGGCAGCTGATGTTGAGGAGCCCACTCTGGAAGCCGA TGTCGACTTGATGTTACAAGAGGCTGGGGCCGGCTCAGTGGAGACACCTCGTGGCT TGATAAAGGTTACCAGCTACGATGGCGAGGACAAGATCGGCTCTTACGCTGTGCTT TCTCCGCAGGCTGTACTCAAGAGTGAAAAATTATCTTGCATCCACCCTCTCGCTGAA CAAGTCATAGTGATAACACACTCTGGCCGAAAAGGGCGTTATGCCGTGGAACCATA CCATGGTAAAGTAGTGGTGCCAGAGGGACATGCAATACCCGTCCAGGACTTTCAAG CTCTGAGTGAAAGTGCCACCATTGTGTACAACGAACGTGAGTTCGTAAACAGGTAC CTGCACCATATTGCCACACATGGAGGAGCGCTGAACACTGATGAAGAATATTACAA AACTGTCAAGCCCAGCGAGCACGACGGCGAATACCTGTACGACATCGACAGGAAA CAGTGCGTCAAGAAAGAACTAGTCACTGGGCTAGGGCTCACAGGCGAGCTGGTGG ATCCTCCCTTCCATGAATTCGCCTACGAGTCTGAGAACACGACCAGCCGCTCCTT ACCAAGTACCAACCATAGGGGTGTATGGCGTGCCAGGATCAGGCAAGTCTGGCATC ATTAAAAGCGCAGTCACCAAAAAAGATCTAGTGGTGAGCGCCAAGAAAGAAACT GTGCAGAAATTATAAGGGACGTCAAGAAAATGAAAGGGCTGGACGTCAATGCCAG AACTGTGGACTCAGTGCTCTTGAATGGATGCAAACACCCCGTAGAGACCCTGTATA TTGACGAAGCTTTTGCTTGTCATGCAGGTACTCTCAGAGCGCTCATAGCCATTATAA GACCTAAAAAGGCAGTGCTCTGCGGGATCCCAAACAGTGCGGTTTTTTTAACATG ATGTGCCTGAAAGTGCATTTTAACCACGAGATTTGCACACAAGTCTTCCACAAAAG CATCTCTCGCCGTTGCACTAAATCTGTGACTTCGGTCGTCTCAACCTTGTTTTACGA CAAAAAAATGAGAACGACGAATCCGAAAGAGACTAAGATTGTGATTGACACTACC GGCAGTACCAAACCTAAGCAGGACGATCTCATTCTCACTTGTTTCAGAGGGTGGGT GAAGCAGTTGCAAATAGATTACAAAGGCAACGAAATAATGACGGCAGCTGCCTCT CAAGGGCTGACCCGTAAAGGTGTGTATGCCGTTCGGTACAAGGTGAATGAAAATCC TCTGTACGCACCCCACCTCTGAACATGTGAACGTCCTACTGACCCGCACGGAGGACC GCATCGTGTGGAAAACACTAGCCGGCGACCCATGGATAAAAACACTGACTGCCAA GTACCCTGGGAATTTCACTGCCACGATAGAGGAGTGGCAAGCAGAGCATGATGCC ATCATGAGGCACATCTTGGAGAGACCGGACCCTACCGACGTCTTCCAGAATAAGGC AAACGTGTGTTGGGCCAAGGCTTTAGTGCCGGTGCTGAAGACCGCTGGCATAGACA TGACCACTGAACAATGGAACACTGTGGATTATTTTGAAACGGACAAAGCTCACTCA GCAGAGATAGTATTGAACCAACTATGCGTGAGGTTCTTTGGACTCGATCTGGACTC CGGTCTATTTTCTGCACCCACTGTTCCGTTATCCATTAGGAATAATCACTGGGATAA CTCCCCGTCGCCTAACATGTACGGGCTGAATAAAGAAGTGGTCCGTCAGCTCTCTC GCAGGTACCCACAACTGCCTCGGGCAGTTGCCACTGGAAGAGTCTATGACATGAAC ACTGGTACACTGCGCAATTATGATCCGCGCATAAACCTAGTACCTGTAAACAGAAG ACTGCCTCATGCTTTAGTCCTCCACCATAATGAACACCCACAGAGTGACTTTTCTTC ATTCGTCAGCAAATTGAAGGGCAGAACTGTCCTGGTGGTCGGGGAAAAGTTGTCCG TCCCAGGCAAAATGGTTGACTGGTTGTCAGACCGGCCTGAGGCTACCTTCAGAGCT CGGCTGGATTTAGGCATCCCAGGTGATGTGCCCAAATATGACATAATATTTGTTAA TGTGAGGACCCCATATAAATACCATCACTATCAGCAGTGTGAAGACCATGCCATTA AGCTTAGCATGTTGACCAAGAAAGCTTGTCTGCATCTGAATCCCGGCGGAACCTGT GTCAGCATAGGTTATGGTTACGCTGACAGGGCCAGCGAAAGCATCATTGGTGCTAT AGCGCGGCAGTTCAAGTTTTCCCGGGTATGCAAACCGAAATCCTCACTTGAAGAGA CGGAAGTTCTGTTTGTATTCATTGGGTACGATCGCAAGGCCCGTACGCACAATCCTT ACAAGCTTTCATCAACCTTGACCAACATTTATACAGGTTCCAGACTCCACGAAGCC GGATGTGCACCCTCATATCATGTGGTGCGAGGGGATATTGCCACGGCCACCGAAGG AGTGATTATAAATGCTGCTAACAGCAAAGGACAACCTGGCGGAGGGTGTGCGGA GCGCTGTATAAGAAATTCCCGGAAAGCTTCGATTTACAGCCGATCGAAGTAGGAAA AGCGCGACTGGTCAAAGGTGCAGCTAAACATATCATTCATGCCGTAGGACCAAACT TCAACAAAGTTTCGGAGGTTGAAGGTGACAAACAGTTGGCAGAGGCTTATGAGTCC ATCGCTAAGATTGTCAACGATAACAATTACAAGTCAGTAGCGATTCCACTGTTGTC CACCGGCATCTTTTCCGGGAACAAAGATCGACTAACCCAATCATTGAACCATTTGC TGACAGCTTTAGACACCACTGATGCAGATGTAGCCATATACTGCAGGGACAAGAAA TGGGAAATGACTCTCAAGGAAGCAGTGGCTAGGAGAGAAGCAGTGGAGGAGATAT GCATATCCGACGACTCTTCAGTGACAGAACCTGATGCAGAGCTGGTGAGGGTGCAT CCGAAGAGTTCTTTGGCTGGAAGGAAGGCTACAGCACAAGCGATGGCAAAACTT TCTCATATTTGGAAGGGACCAAGTTTCACCAGGCGGCCAAGGATATAGCAGAAATT AATGCCATGTGGCCCGTTGCAACGGAGGCCAATGAGCAGGTATGCATGTATATCCT CGGAGAAAGCATGAGCAGTATTAGGTCGAAATGCCCCGTCGAAGAGTCGGAAGCC TCCACACCACCTAGCACGCTGCCTTGCTTGTGCATCCATGCCATGACTCCAGAAAG AGTACAGCGCCTAAAAGCCTCACGTCAGAACAAATTACTGTGTGCTCATCCTTTC CATTGCCGAAGTATAGAATCACTGGTGTGCAGAAGATCCAATGCTCCCAGCCTATA TTGTTCTCACCGAAAGTGCCTGCGTATATTCATCCAAGGAAGTATCTCGTGGAAAC ACCACCGGTAGACGAGACTCCGGAGCCATCGGCAGAGAACCAATCCACAGAGGGG ACACCTGAACAACCACCACTTATAACCGAGGATGAGACCAGGACTAGAACGCCTG AGCCGATCATCATCGAAGAGGAAGAAGAGGATAGCATAAGTTTGCTGTCAGATGG CCCGACCCACCAGGTGCTGCAAGTCGAGGCAGACATTCACGGGCCGCCCTCTGTAT CTAGCTCATCCTGGTCCATTCCTCATGCATCCGACTTTGATGTGGACAGTTTATCCA TACTTGACACCCTGGAGGGAGCTAGCGTGACCAGCGGGGCAACGTCAGCCGAGAC |

| SEQ ID NO: | Epitope | Sequence |
|---|---|---|
| | | TAACTCTTACTTCGCAAAGAGTATGGAGTTTCTGGCGCGACCGGTGCCTGCGCCTC<br>GAACAGTATTCAGGAACCCTCCACATCCCGCTCCGCGCACAAGAACACCGTCACTT<br>GCACCCAGCAGGGCCTGCTCGAGAACCAGCCTAGTTTCCACCCCGCCAGGCGTGAA<br>TAGGGTGATCACTAGAGAGGAGCTCGAGGCGCTTACCCCGTCACGCACTCCTAGCA<br>GGTCGGTCTCGAGAACCAGCCTGGTCTCCAACCCGCCAGGCGTAAATAGGGTGATT<br>ACAAGAGAGGAGTTTGAGGCGTTCGTAGCACAACAACAATGA |
| 44 | nsP2 | GGCTCAGTGGAGACACCTCGTGGCTTGATAAAGGTTACCAGCTACGATGGCGAGGA<br>CAAGATCGGCTCTTACGCTGTGCTTTCTCCGCAGGCTGTACTCAAGAGTGAAAAAT<br>TATCTTGCATCCACCCTCTCGCTGAACAAGTCATAGTGATAACACACTCTGGCCGA<br>AAAGGGCGTTATGCCGTGGAACCATACCATGGTAAAGTAGTGGTGCCAGAGGGAC<br>ATGCAATACCCGTCCAGGACTTTCAAGCTCTGAGTGAAAGTGCCACCATTGTGTAC<br>AACGAACGTGAGTTCGTAAACAGGTACCTGCACCATATTGCCACACATGGAGGAGC<br>GCTGAACACTGATGAAGAATATTACAAAACTGTCAAGCCCAGCGAGCACGACGGC<br>GAATACCTGTACGACATCGACAGGAAACAGTGCGTCAAGAAAGAACTAGTCACTG<br>GGCTAGGGCTCACAGGCGAGCTGGTGGATCCTCCCTTCCATGAATTCGCCTACGAG<br>AGTCTGAGAACACGACCAGCCGCTCCTTACCAAGTACCAACCATAGGGGTGTATGG<br>CGTGCCAGGATCAGGCAAGTCTGGCATCATTAAAAGCGCAGTCACCAAAAAAGAT<br>CTAGTGGTGAGCGCCAAGAAAGAAAACTGTGCAGAATTATAAGGGACGTCAAGA<br>AAATGAAAGGGCTGGACGTCAATGCCAGAACTGTGGACTCAGTGCTCTTGAATGGA<br>TGCAAACACCCCGTAGAGACCCTGTATATTGACGAAGCTTTTGCTTGTCATGCAGG<br>TACTCTCAGAGCGCTCATAGCCATTATAAGACCTAAAAAGGCAGTGCTCTGCGGGG<br>ATCCCAAACAGTGCGGTTTTTTTAACATGATGTGCCTGAAAGTGCATTTTAACCACG<br>AGATTTGCACACAAGTCTTCCACAAAAGCATCTCTCGCCGTTGCACTAAATCTGTG<br>ACTTCGGTCGTCTCAACCTTGTTTTACGACAAAAAAATGAGAACGACGAATCCGAA<br>AGAGACTAAGATTGTGATTGACACTACCGGCAGTACCAAACCTAAGCAGGACGAT<br>CTCATTCTCACTTGTTTCAGAGGGTGGGTGAAGCAGTTGCAAATAGATTACAAAGG<br>CAACGAAATAATGACGGCAGCTGCCTCTCAAGGGCTGACCCGTAAAGGTGTGTATG<br>CCGTTCGGTACAAGGTGAATGAAAATCCTCTGTACGCACCCACCTCTGAACATGTG<br>AACGTCCTACTGACCCGCACGGAGGACCGCATCGTGTGGAAAACACTAGCCGGCG<br>ACCCATGGATAAAAACACTGACTGCCAAGTACCCTGGGAATTTCACTGCCACGATA<br>GAGGAGTGGCAAGCAGAGCATGATGCCATCATGAGGCACATCTTGGAGAGACCGG<br>ACCCTACCGACGTCTTCCAGAATAAGGCAAACGTGTGTTGGGCAAGGCTTTAGTG<br>CCGGTGCTGAAGACCGCTGGCATAGACATGACCACTGAACAATGGAACACTGTGG<br>ATTATTTTGAAACGGACAAAGCTCACTCAGCAGAGATAGTATTGAACCAACTATGC<br>GTGAGGTTCTTTGGACTCGATCTGGACTCCGGTCTATTTTCTGCACCCACTGTTCCG<br>TTATCCATTAGGAATAATCACTGGGATAACTCCCCGTCGCCTAACATGTACGGGCT<br>GAATAAAGAAGTGGTCCGTCAGCTCTCTCGCAGGTACCCACAACTGCCTCGGGCAG<br>TTGCCACTGGAAGAGTCTATGACATGAACACTGGTACACTGCGCAATTATGATCCG<br>CGCATAAACCTAGTACCTGTAAACAGAAGACTGCCTCATGCTTAGTCCTCCACCA<br>TAATGAACACCCACAGAGTGACTTTTCTTCATTCGTCAGCAAATTGAAGGGCAGAA<br>CTGTCCTGGTGGTCGGGGAAAAGTTGTCCGTCCCAGGCAAAATGTTGACTGGTTG<br>TCAGACCGGCCTGAGGCTACCTTCAGAGCTCGGCTGGATTTAGGCATCCCAGGTGA<br>TGTGCCCAAATATGACATAATATTTGTTAATGTGAGGACCCCATATAAATACCATC<br>ACTATCAGCAGTGTGAAGACCATGCCATTAAGCTTAGCATGTTGACCAAGAAAGCT<br>TGTCTGCATCTGAATCCCGGCGGAACCTGTGTCAGCATAGGTTATGGTTACGCTGA<br>CAGGGCCAGCGAAAGCATCATTGGTGCTATAGCGCGGCAGTTCAAGTTTTCCCGGG<br>TATGCAAACCGAAATCCTCACTTGAAGACGGAAGTTCTGTTTGTATTCATTGGG<br>TACGATCGCAAGGCCCGTACGCACAATCCTTACAAGCTTTTCATCAACCTTGACCAA<br>CATTTATACAGGTTCCAGACTCCACGAAGCCGGATGT |
| 45 | nsP4 | TACATCTTTTCCTCCGACACCGGTCAAGGGCATTTACAACAAAAATCAGTAAGGCA<br>AACGGTGCTATCCGAAGTGGTGTTGGAGAGGACCGAATTGGAGATTTCGTATGCCC<br>CGCGCCTCGACCAAGAAAAAGAAGAATTACTACGCAAGAAATTACAGTTAAATCC<br>CACACCTGCTAACAGAAGCAGATACCAGTCCAGGAAGGTGGAGAACATGAAAGCC<br>ATAACAGCTAGACGTATTCTGCAAGGCCTAGGGCATTATTTGAAGGCAGAAGGAA<br>AAGTGGAGTGCTACCGAACCCTGCATCCTGTTCCTTTGTATTCATCTAGTGTGAACC<br>GTGCCTTTTCAAGCCCCAAGGTCGCAGTGGAAGCCTGTAACGCCATGTTGAAAGAG<br>AACTTTCCGACTGTGGCTTCTTACTGTATTATTCCAGAGTACGATGCCTATTTGGAC<br>ATGGTTGACGGAGCTTCATGCTGCTTAGACACTGCCAGTTTTTGCCCTGCAAAGCTG<br>CGCAGCTTTCCAAAGAAACACTCCTATTTGGAACCCACAATACGATCGGCAGTGCC<br>TTCAGCGATCCAGAACACGCTCCAGAACGTCCTGGCAGCTGCCACAAAAGAAATT<br>GCAATGTCACGCAAATGAGAGAATTGCCCGTATTGGATTCGGCGGCCTTTAATGTG<br>GAATGCTTCAAGAAATATGCCGTGTAATAATGAATATTGGGAAACGTTTAAAGAAAA<br>CCCCATCAGGCTTACTGAAGAAAACGTGGTAAATTACATTACCAAATTAAAAGGAC<br>CAAAAGCTGCTGCTCTTTTTTGCGAAGACACATAATTTGAATATGTTGCAGGACATA<br>CCAATGGACAGGTTTGTAATGGACTTAAAGAGAGACGTGAAAGTGACTCCAGGAA<br>CAAAAACATACTGAAGAACGGCCAAGGTACAGGTGATCCAGGCTGCCGATCCGCT<br>AGCAACAGCGTATCTGTGCGGAATCCACCGAGAGCTGGTTAGGAGATTAAATGCG<br>GTCCTGCTTCCGAACATTCATACACTGTTTGATATGTCGGCTGAAGACTTTGACGCT<br>ATTATAGCCGAGCACTTCCAGCCTGGGGATTGTGTTCTGGAAACTGACATCGCGTC<br>GTTTGATAAAAGTGAGGACGACGCCATGGCTCTGACCGCGTTAATGATTCTGGAAG<br>ACTTAGGTGTGGACGCAGAGCTGTTGACGCTGATTGAGGCGGCTTTCGGCGAAATT<br>TCATCAATACATTTGCCCACTAAAACTAAATTTAAATTCGGAGCCATGATGAAATC |

| SEQ ID NO: | Epitope | Sequence |
|---|---|---|
| | | TGGAATGTTCCTCACACTGTTTGTGAACACAGTCATTAACATTGTAATCGCAAGCA<br>GAGTGTTGAGAGAACGGCTAACCGGATCACCATGTGCAGCATTCATTGGAGATGAC<br>AATATCGTGAAAGGAGTCAAATCGGACAAATTAATGGCAGACAGGTGCGCCACCT<br>GGTTGAATATGGAAGTCAAGATTATAGATGCTGTGGTGGGCGAGAAAGCGCCTTAT<br>TTCTGTGGAGGGTTTATTTTGTGTGACTCCGTGACCGGCACAGCGTGCCGTGTGGCA<br>GACCCCCTAAAAAGGCTGTTTAAGCTTGGCAAACCTCTGGCAGCAGACGATGAACA<br>TGATGATGACAGGAGAAGGGCATTGCATGAAGAGTCAACACGCTGGAACCGAGTG<br>GGTATTCTTTCAGAGCTGTGCAAGGCAGTAGAATCAAGGTATGAAACCGTAGGAAC<br>TTCCATCATAGTTATGGCCATGACTACTCTAGCTAGCAGTGTTAAATCATTCAGCTA<br>CCTGAGAGGGGCCCCTATAACTCTCTACGGC |
| 46 | nsP3 | GCACCCTCATATCATGTGGTGCGAGGGGATATTGCCACGGCCACCGAAGGAGTGAT<br>TATAAATGCTGCTAACAGCAAAGGACAACCTGGCGGAGGGGTGTGCGGAGCGCTG<br>TATAAGAAATTCCCGGAAAGCTTCGATTTACAGCCGATCGAAGTAGGAAAAGCGC<br>GACTGGTCAAAGGTGCAGCTAAACATATCATTCATGCCGTAGGACCAAACTTCAAC<br>AAAGTTTCGGAGGTTGAAGGTGACAAACAGTTGGCAGAGGCTTATGAGTCCATCGC<br>TAAGATTGTCAACGATAACAATTACAAGTCAGTAGCGATTCCACTGTTGTCCACCG<br>GCATCTTTTCCGGGAACAAAGATCGACTAACCCAATCATTGAACCATTTGCTGACA<br>GCTTTAGACACCACTGATGCAGATGTAGCCATATACTGCAGGGACAAGAAATGGG<br>AAATGACTCTCAAGGAAGCAGTGGCTAGGAGAGAAGCAGTGGAGGAGATATGCAT<br>ATCCGACGACTCTTCAGTGACAGAACCTGATGCAGAGCTGGTGAGGGTGCATCCGA<br>AGAGTTCTTTGGCTGGAAGGAAGGGCTACAGCACAAGCGATGGCAAAACTTTCTCA<br>TATTTGGAAGGGACCAAGTTTCACCAGGCGGCCAAGGATATAGCAGAAATTAATGC<br>CATGTGGCCCGTTGCAACGGAGGCCAATGAGCAGGTATGCATGTATATCCTCGGAG<br>AAAGCATGAGCAGTATTAGGTCGAAATGCCCCGTCGAAGAGTCGGAAGCCTCCAC<br>ACCACCTAGCACGCTGCCTTGCTTGTGCATCCATGCCATGACTCCAGAAAGAGTAC<br>AGCGCCTAAAAGCCTCACGTCCAGAACAAATTACTGTGTGCTCATCCTTTCCATTGC<br>CGAAGTATAGAATCACTGGTGTGCAGAAGATCCAATGCTCCCAGCCTATATTGTTC<br>TCACCGAAAGTGCCTGCGTATATTCATCCAAGGAAGTATCTCGTGGAAACACCACC<br>GGTAGACGAGACTCCGGAGCCATCGGCAGAGAACCAATCCACAGAGGGGACACCT<br>GAACAACCACCACTTATAACCGAGGATGAGACCAGGACTAGAACGCCTGAGCCGA<br>TCATCATCGAAGAGGAAGAAGAGGATAGCATAAGTTTGCTGTCAGATGGCCCGAC<br>CCACCAGGTGCTGCAAGTCGAGGCAGACATTCACGGGCCGCCCTCTGTATCTAGCT<br>CATCCTGGTCCATTCCTCATGCATCCGACTTTGATGTGGACAGTTTATCCATACTTG<br>ACACCCTGGAGGGAGCTAGCGTGACCAGCGGGGCAACGTCAGCCGAGACTAACTC<br>TTACTTCGCAAAGAGTATGGAGTTTCTGGCGCGACCGGTGCCTGCGCCTCGAACAG<br>TATTCAGGAACCCTCCACATCCCGCTCCGCACAAGAACACCGTCACTTGCACCC<br>AGCAGGGCCTGCTCGAGAACCAGCCTAGTTTCCACCCCGCCAGGCGTGAATAGGGT<br>GATCACTAGAGAGGAGCTCGAGGCGCTTACCCCGTCACGCACTCCTAGCAGGTCGG<br>TCTCGAGAACCAGCCTGGTCTCCAACCCGCCAGGCGTAAATAGGGTGATTACAAGA<br>GAGGAGTTTGAGGCGTTCGTAGCACAACAACAATGACGGTTTGATGCGGGTGCA |
| 47 | nsP1 | GAGAAAGTTCACGTTGACATCGAGGAAGACAGCCCATTCCTCAGAGCTTTGCAGCG<br>GAGCTTCCCGCAGTTTGAGGTAGAAGCCAAGCAGGTCACTGATAATGACCATGCTA<br>ATGCCAGAGCGTTTTCGCATCTGGCTTCAAAACTGATCGAAACGGAGGTGGACCCA<br>TCCGACACGATCCTTGACATTGGAAGTGCGCCCGCCCGCAGAATGTATTCTAAGCA<br>CAAGTATCATTGTATCTGTCCGATGAGATGTGCGGAAGATCCGGACAGATTGTATA<br>AGTATGCAACTAAGCTGAAGAAAAACTGTAAGGAAATAACTGATAAGGAATTGGA<br>CAAGAAAATGAAGGAGCTCGCCGCCGTCATGAGCGACCCTGACCTGGAAACTGAG<br>ACTATGTGCCTCCACGACGACGAGTCGTGTCGCTACGAAGGGCAAGTCGCTGTTTA<br>CCAGGATGTATACGCGGTTGACGGACCGACAAGTCTCTATCACCAAGCCAATAAGG<br>GAGTTAGAGTCGCCTACTGGATAGGCTTTGACACCACCCCTTTTATGTTTAAGAACT<br>TGGCTGGAGCATATCCATCATACTCTACCAACTGGGCCGACGAAACCGTGTTAACG<br>GCTCGTAACATAGGCCTATGCAGCTCTGACGTTATGGAGCGGTCACGTAGAGGGAT<br>GTCCATTCTTAGAAAGAAGTATTTGAAACCATCCAACAATGTTCTATTCTCTGTTGG<br>CTCGACCATCTACCACGAGAAGAGGGACTTACTGAGGAGCTGGCACCTGCCGTCTG<br>TATTTCACTTACGTGGCAAGCAAAATTACACATGTCGGTGTGAGACTATAGTTAGTT<br>GCGACGGGTACGTCGTTAAAAGAATAGCTATCAGTCCAGGCCTGTATGGGAAGCCT<br>TCAGGCTATGCTGCTACGATGCACCGCGAGGGATTCTTGTGCTGCAAAGTGACAGA<br>CACATTGAACGGGGAGAGGGTCTCTTTTCCCGTGTGCACGTATGTGCCAGCTACAT<br>TGTGTGACCAAATGACTGGCATACTGGCAACAGATGTCAGTGCGGACGACGCGCA<br>AAAACTGCTGGTTGGGCTCAACCAGCGTATAGTCGTCAACGGTCGCACCCAGAGAA<br>ACACCAATACCATGAAAAATTACCTTTTGCCCGTAGTGGCCCAGGCATTTGCTAGG<br>TGGGCAAAGGAATATAAGGAAGATCAAGAAGATGAAAGGCCACTAGGACTACGAG<br>ATAGACAGTTAGTCATGGGGTGTTGTTGGGCTTTTAGAAGGCACAAGATAACATCT<br>ATTTATAAGCGCCCGGATACCCAAACCATCATCAAAGTGAACAGCGATTTCCACTC<br>ATTCGTGCTGCCCAGGATAGGCAGTAACACATTGGAGATCGGGCTGAGAACAAGA<br>ATCAGGAAAATGTTAGAGGAGCACAAGGAGCCGTCACCTCTCATTACCGCCGAGG<br>ACGTACAAGAAGCTAAGTGCGCAGCCGATGAGGCTAAGGAGGTGCGTGAAGCCGA<br>GGAGTTGCGCGCAGCTCTACCACCTTTGGCAGCTGATGTTGAGGAGCCCACTCTGG<br>AAGCCGATGTCGACTTGATGTTACAAGAGGCTGGGGCC |

SEQUENCE LISTING

| SEQ ID NO: | Epitope | Sequence |
|---|---|---|
| 48 | KanR | ATGATTGAACAGGATGGCCTGCATGCGGGTAGCCCCGGCAGCGTGGGTGGAACGTCT<br>GTTTGGCTATGATTGGGCGCAGCAGACCATTGGCTGCTCTGATGCGGCGGTGTTTC<br>GTCTGAGCGCGCAGGGTCGTCCGGTGCTGTTTGTGAAAACCGATCTGAGCGGTGCG<br>CTGAACGAGCTGCAGGATGAAGCGGCGCGTCTGAGCTGGCTGGCCACCACCGGTGT<br>TCCGTGTGCGGCGGTGCTGGATGTGGTGACCGAAGCGGGCCGTGATTGGCTGCTGC<br>TGGGCGAAGTGCCGGGTCAGGATCTGCTGTCTAGCCATCTGGCGCCGGCAGAAAAA<br>GTGAGCATTATGGCGGATGCCATGCGTCGTCTGCATACCCTGGACCCGGCGACCTG<br>TCCGTTTGATCATCAGGCGAAACATCGTATTGAACGTGCGCGTACCCGTATGGAAG<br>CGGGCCTGGTGGATCAGGATGATCTGGATGAAGAACATCAGGGCCTGGCACCGGC<br>AGAGCTGTTTGCGCGTCTGAAAGCGAGCATGCCGGATGGCGAAGATCTGGTGGTGA<br>CCCATGGTGATGCGTGCCTGCCGAACATTATGGTGGAAAATGGCCGTTTTAGCGGC<br>TTTATTGATTGCGGCCGTCTGGGCGTGGCGGATCGTTATCAGGATATTGCGCTGGCC<br>ACCCGTGATATTGCGGAAGAACTGGGCGGCGAATGGGCGGATCGTTTTCTGGTGCT<br>GTATGGCATTGCGGCACCGGATAGCCAGCGTATTGCGTTTTATCGTCTGCTGGATG<br>AATTTTTCTAATAA |
| 49 | Rop | GTGACCAAACAGGAAAAAACCGCCCTTAACATGGCCCGCTTTATCAGAAGCCAGA<br>CATTAACGCTTCTGGAGAAACTCAACGAGCTGGACGCGGATGAACAGGCAGACAT<br>CTGTGAATCGCTTCACGACCACGCTGATGAGCTTTACCGCAGCTGCCTCGCGCGTTT<br>CGGTGATGACGGTGAAAACCTCTGA |
| 50 | 5' UTR | ATAGGCGGCGCATGAGAGAAGCCCAGACCAATTACCTACCCAAA |
| 51 | 3' UTR | ATACAGCAGCAATTGGCAAGCTGCTTACATAGAACTCGCGGCGATTGGCATGCCGC<br>TTTAAAATTTTTATTTTATTTTTCTTTTCTTTTCCGAATCGGATTTTGTTTTTAATATT<br>TC |
| 52 | CVM promoter with TetO sites | CCATTGCATACGTTGTATCCATATCATAATATGTACATTTATATTGGCTCATGTCCA<br>ACATTACCGCCATGTTGACATTGATTATTGACTAGTTATTAATAGTAATCAATTACG<br>GGGTCATTAGTTCATAGCCCATATATGGAGTTCCGCGTTACATAACTTACGGTAAAT<br>GGCCCGCCTGGCTGACCGCCCAACGACCCCCGCCCATTGACGTCAATAATGACGTA<br>TGTTCCCATAGTAACGCCAATAGGGACTTTCCATTGACGTCAATGGGTGGAGTATTT<br>ACGGTAAACTGCCCACTTGGCAGTACATCAAGTGTATCATATGCCAAGTACGCCCC<br>CTATTGACGTCAATGACGGTAAATGGCCCGCCTGGCATTATGCCCAGTACATGACC<br>TTATGGGACTTTCCTACTTGGCAGTACATCTACGTATTAGTCATCGCTATTACCATG<br>GTGATGCGGTTTTGGCAGTACATCAATGGGCGTGGATAGCGGTTTGACTCACGGGG<br>ATTTCCAAGTCTCCACCCCATTGACGTCAATGGGAGTTTGTTTTGGCACCAAAATCA<br>ACGGGACTTTCCAAAATGTCGTAACAACTCCGCCCCATTGACGCAAATGGGCGGTA<br>GGCGTGTACGGTGGGAGGTCTATATAAGCAGAGCTCTCCCTATCAGTGATAGAGAT<br>CTCCCTATCAGTGATAGAGATCGTCGACGAGCTCGTTTAGTGAACCGTCAGATCGC<br>CTGGAGACGCCATCCACGCTGTTTTGACCTCCATAGAAGACACCGGGACCGATCCA<br>GCCTCCGCGGCCGGGAACGGTGCATTGGAACGCGGATTCCCCGTGCCAAGAGTGA |
| 53 | BGH poly A | CTGTGCCTTCTAGTTGCCAGCCATCTGTTGTTTGCCCCTCCCCCGTGCCTTCCTTGAC<br>CCTGGAAGGTGCCACTCCCACTGTCCTTTCCTAATAAAATGAGGAAATTGCATCGC<br>ATTGTCTGAGTAGGTGTCATTCTATTCTGGGGGGTGGGGTGGGGCAGGACAGCAAG<br>GGGGAGGATTGGGAAGACAATAGCAGGCATGCTGGGGATGCGGTGGGCTCTATGG<br>CC |
| 54 | Ubiquitin leader seq | MQIFVKTLTGKTITLEVEPSDTIENVKAKIQDKEGIPPDQQRLIFAGKQLEDGRTLSDYNI<br>QKESTLHLVLRLRGV |

The invention claimed is:

1. A polynucleotide encoding a polypeptide comprising the epitope sequences of:

MKDKQDEEQRTRRMMRTKMRMRRMRRTRRKMRRKMSPARPRTSCREACLQGWTE; (SEQ ID NO: 1)

EEAEDNCRRMMRTK; (SEQ ID NO: 2)

VLNYGVCFC; (SEQ ID NO: 5)
and

FCGDENILV. (SEQ ID NO: 6)

2. The polynucleotide of claim 1, wherein the polynucleotide comprises:
the nucleic acid sequence of SEQ ID NO: 17;
the nucleic acid sequence of SEQ ID NO: 19;
the nucleic acid sequence of SEQ ID NO: 26; or
the nucleic acid sequence of SEQ ID NO: 27.

3. The polynucleotide of claim 1, further encoding a leader sequence at the N terminus selected from:

MACPGFLWALVISTCLEFSMA; (SEQ ID NO: 8)

MQIFVKTLTGKTITLEVEPSDTIENVKAKIQDKEGIPPDQQRLIFAGKQLEDGRTLSDYNIQKESTLHLVLRLRGV; (SEQ ID NO: 54)
and

MGQKEQIHTLQKNSERMSKQLTRSSQAV. (SEQ ID NO: 29)

4. The polynucleotide of claim 1, further comprising one or more polynucleotides encoding one or more linker sequences, wherein the epitope sequences are connected to each other by the one or more linker sequences.

5. The polynucleotide of claim 4, wherein the one or more linker sequences encoded by the polynucleotide are selected from AAY, RR, DPP, HHAA, HHA, HHL, RKSYL, RKSY, SSL, and REKR.

6. The polynucleotide of claim 4, wherein the one or more linker sequences encoded by the one or more polynucleotides comprise a protease cleavage site.

7. The polynucleotide of claim 1, wherein the polynucleotide encodes a polypeptide comprising:
the amino acid sequence of SEQ ID NO: 10;
the amino acid sequence of SEQ ID NO: 12; or
the amino acid sequence of SEQ ID NO: 31.

8. The polynucleotide of claim 7, wherein the polynucleotide encodes the amino acid sequence of SEQ ID NO: 12.

9. The polynucleotide of claim 8, wherein the polynucleotide comprises SEQ ID NO: 27.

10. The polynucleotide of claim 1, comprising:
nucleotides 1-162 of SEQ ID NO: 27;
nucleotides 172-213 of SEQ ID NO: 27;
nucleotides 223-249 of SEQ ID NO: 27; and
nucleotides 259-285 of SEQ ID NO: 27.

11. A vector comprising the polynucleotide of claim 1.

12. The vector of claim 11, wherein the vector is selected from an adenovirus vector, an alphaviral vector, a poxvirus vector, an adeno-associated virus vector, a retrovirus vector, a self-replicating RNA molecule, and a combination thereof.

13. The vector of claim 12, wherein the adenovirus vector is selected from hAd5, hAd7, hAd11, hAd26, hAd34, hAd35, hAd48, hAd49, hAd50, GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

14. The vector of claim 12, wherein the poxvirus vector is selected from smallpox virus vector, vaccinia virus vector, cowpox virus vector, monkeypox virus vector, Copenhagen vaccinia virus vector, New York Attenuated Vaccinia Virus (NYVAC) vector, and Modified Vaccinia Ankara (MVA) vector.

15. The vector of claim 12, wherein the vector is the adenovirus vector.

16. The vector of claim 12, wherein the vector is the self-replicating RNA molecule.

17. The vector of claim 11, wherein the vector is an Ad26 vector and wherein the polynucleotide encodes the polypeptide of SEQ ID NO: 10.

18. The vector of claim 11, wherein the vector is an MVA vector and wherein the polynucleotide encodes the polypeptide of SEQ ID NO: 31.

19. The vector of claim 11, wherein the vector is a GAd20 vector and wherein the polynucleotide encodes the polypeptide of SEQ ID NO: 31.

20. The vector of claim 11, wherein the vector is a self-replicating RNA molecule and wherein the polynucleotide encodes the polypeptide of SEQ ID NO: 12.

21. A vector comprising the polynucleotide of claim 8.

22. The vector of claim 21, wherein the polynucleotide comprises SEQ ID NO: 27.

23. The vector of claim 22, wherein the vector is an Ad26 vector or an MVA vector.

24. A pharmaceutical composition comprising the polynucleotide of claim 1.

25. A pharmaceutical composition comprising the vector of claim 11.

26. The pharmaceutical composition of claim 25, wherein the vector is selected from an Ad26 vector, an MVVA vector, a GAd20 vector, a self-replicating RNA molecule, or combinations thereof.

* * * * *